US011898146B2

(12) United States Patent
Shannon et al.

(10) Patent No.: US 11,898,146 B2
(45) Date of Patent: Feb. 13, 2024

(54) **APTAMERS AGAINST *CLOSTRIDIUM DIFFICILE*, COMPOSITIONS COMPRISING APTAMERS AGAINST *CLOSTRIDIUM DIFFICILE* AND METHODS OF USING THE SAME**

(71) Applicant: LIV PROCESS, INC., Ardmore, PA (US)

(72) Inventors: Ronald J. Shannon, Ardmore, PA (US); Gregory Penner, Toronto (CA)

(73) Assignee: LIV PROCESS, INC., Ardmore, PA (US)

( * ) Notice: Subject to any disclaimer, the term of this patent is extended or adjusted under 35 U.S.C. 154(b) by 197 days.

(21) Appl. No.: 17/111,067

(22) Filed: Dec. 3, 2020

(65) Prior Publication Data
US 2022/0177886 A1   Jun. 9, 2022

(51) Int. Cl.
*C12N 15/115* (2010.01)
*G01N 21/64* (2006.01)
*G01N 33/569* (2006.01)

(52) U.S. Cl.
CPC ....... *C12N 15/115* (2013.01); *G01N 21/6428* (2013.01); *G01N 33/56911* (2013.01); *C12N 2310/16* (2013.01); *C12N 2310/531* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 8,592,202 B2 | 11/2013 | Heyduk et al. | |
| 9,081,010 B2 | 7/2015 | Ochsner et al. | |
| 10,145,844 B2 | 12/2018 | Cameron et al. | |
| 11,001,847 B2 * | 5/2021 | Shannon | C12N 15/115 |
| 11,104,905 B2 * | 8/2021 | Shannon | C12Q 1/689 |
| 2004/0023266 A1 | 2/2004 | Vivekananda et al. | |
| 2008/0020939 A1 | 1/2008 | Stanton et al. | |
| 2009/0304683 A1 | 12/2009 | Dimitrov et al. | |
| 2010/0291100 A1 | 11/2010 | Macinga | |
| 2011/0287557 A1 | 11/2011 | Zhang et al. | |
| 2012/0231467 A1 | 9/2012 | Ochsner et al. | |
| 2012/0308569 A1 | 12/2012 | Chan et al. | |
| 2014/0230087 A1 | 8/2014 | Hartig et al. | |
| 2015/0056627 A1 | 2/2015 | Karkkainen et al. | |
| 2015/0346199 A1 | 12/2015 | Li et al. | |
| 2016/0143274 A1 | 5/2016 | Bingham et al. | |
| 2016/0330971 A1 | 11/2016 | Joseph | |
| 2017/0362307 A1 | 12/2017 | Ingber et al. | |
| 2018/0003712 A1 | 1/2018 | Haam et al. | |
| 2018/0271423 A1 | 9/2018 | Agarwal et al. | |
| 2019/0069836 A1 | 3/2019 | Hettrick | |
| 2019/0071714 A1 | 3/2019 | Li et al. | |
| 2020/0332296 A1 | 10/2020 | Kang et al. | |
| 2020/0385730 A1 | 12/2020 | Shannon et al. | |
| 2020/0385731 A1 | 12/2020 | Shannon et al. | |
| 2021/0332362 A1 * | 10/2021 | Shannon | C12Q 1/689 |
| 2022/0307029 A1 * | 9/2022 | Shannon | C12N 15/115 |

FOREIGN PATENT DOCUMENTS

| | | |
|---|---|---|
| CN | 111849994 A | 10/2020 |
| CN | 112557349 A | 3/2021 |
| GB | 2491117 A | 11/2012 |
| WO | 2004058146 A2 | 7/2004 |
| WO | 2010126670 A2 | 11/2010 |
| WO | 2014169344 A1 | 10/2014 |
| WO | 2018106945 A1 | 6/2018 |
| WO | 2021202440 A1 | 10/2021 |
| WO | 2021211921 A2 | 10/2021 |
| WO | 2022120004 A1 | 6/2022 |

OTHER PUBLICATIONS

Hong et al., "The spore coat protein CotE facilitates host colonization by Clostridium difficile", The Journal of Infectious Diseases, vol. 216, pp. 1452-1459. (Year 2017).
Ikanovic, M. et al., "Fluorescence Assay Based on Aptamer-Quantum Dot Binding to Bacillus thuringiensis Spores". Journal of Fluorescence. Jan. 31, 2007, vol. 17, pp. 193-199.
Calderon-Romero et al., "Clostridium difficile exosporium cysteine-rich proteins are essential for the morphogenesis of the exosporium layer, spore resistance, and affect C. difficile pathogenesis," PLOS Pathogens, Aug. 8, 2018, vol. 14, No. 8, e1007199, pp. 1-33.
Diaz-Gonzalez et al., "Protein Composition of the Outermost Exosporium-like Layer of Clostridium difficile 630 Spores," Journal of Proteomics, Jun. 18, 2015, vol. 123, pp. 1-13.
GenBank Accession No. LN034564.1, Create Date Oct. 7, 2014.
International Search Report and Written Opinion dated May 12, 2022 in corresponding International Patent Application No. PCT/US21/61531 (12 pages).
Chan et al., "Antisense Oligonucleotides: From Design to Therapeutic Application," Clinical and Experimental Pharmacology Physiology, 2006, vol. 33, No. 5-6, pp. 533-540.
Jang, Sung Key, "A '15-minute' quick diagnostic testing for newly emerging viruses introduced." Pohang University of Science and Technology, pp. 1-3, Mar. 23, 2020.
Johansson "Choosing Reporter-Quencher Pairs for Efficient Quenching Through Formation of Intramolecular Dimers," Fluorescent Energy Transfer Nucleic Acid Probes: Designs and Protocols, 2006, No. pp. 17-29.
Marras et al., "Efficiencies of Fluorescence Resonance Energy Transfer and Contact-mediated Quenching in Oligonucleotide Probes," Nucleic Acids Research, Nov. 1, 2002, vol. 30, No. 21, p. e122.

\* cited by examiner

*Primary Examiner* — Sean McGarry
(74) *Attorney, Agent, or Firm* — Greenberg Traurig, LLP; Chinh H. Pham; Natalie Salem

(57) ABSTRACT

Compositions comprising optimized aptamers capable of specifically binding to a surface protein of *Clostridium difficile* spore are provided. A method for detecting, enriching, separating, and/or isolating *Clostridium difficile* spores is provided.

26 Claims, 78 Drawing Sheets
Specification includes a Sequence Listing.

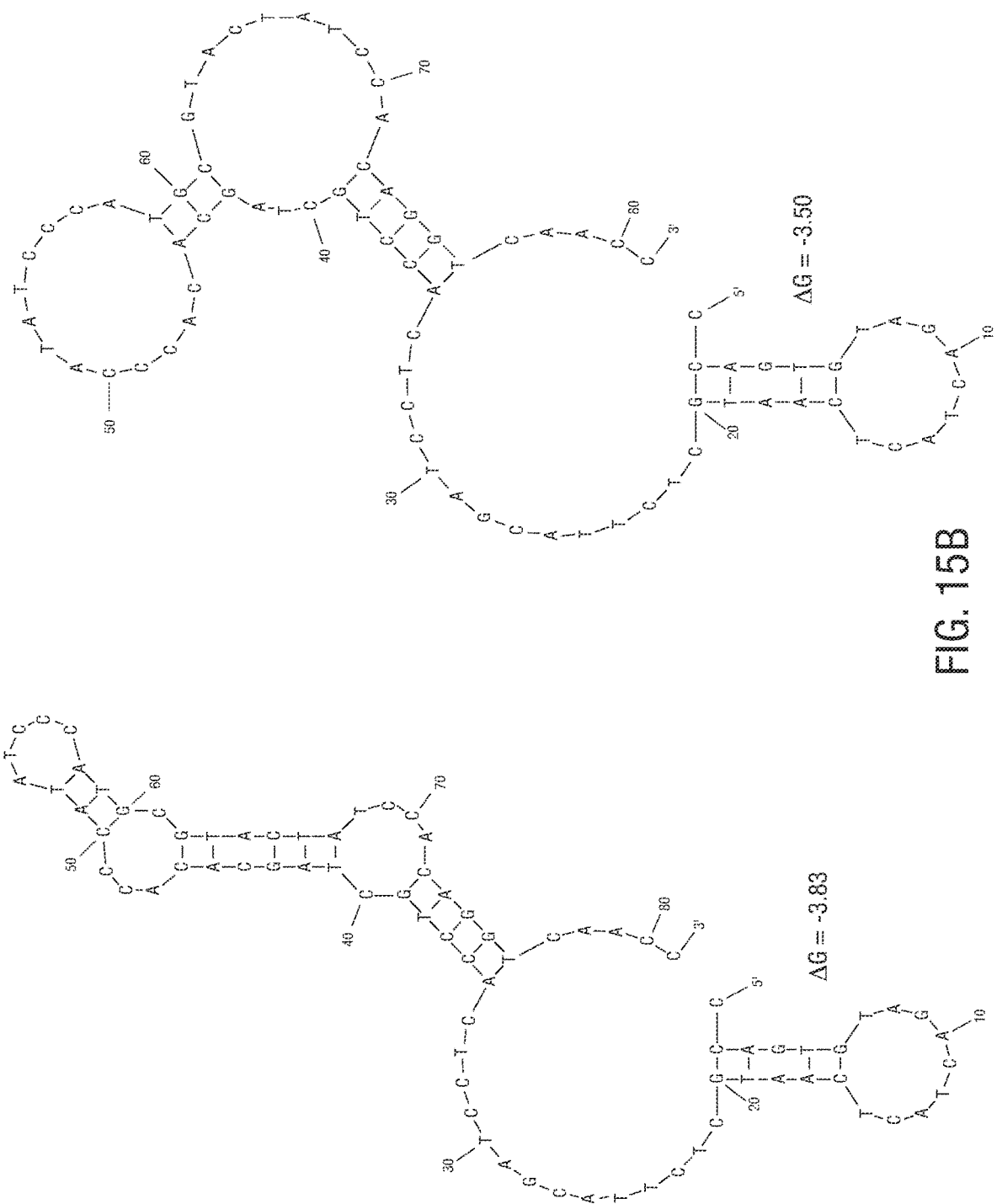

APTAMERS AGAINST *CLOSTRIDIUM DIFFICILE*, COMPOSITIONS COMPRISING APTAMERS AGAINST *CLOSTRIDIUM DIFFICILE* AND METHODS OF USING THE SAME

SEQUENCE LISTING

The instant application contains a Sequence Listing, submitted herewith which includes the file 193519-010400_SL.txt having the following size 33,903 bytes, which was created on Dec. 3, 2020, the contents of which are hereby incorporated by reference herein.

FIELD OF THE DISCLOSURE

Embodiments of the present disclosure relate to aptamers that specifically bind to a *Clostridium difficile* spore and methods of using the same. For example, embodiments of the disclosure relate to methods of detecting the presence, absence or amount of *C. difficile* bacteria e.g. spores in a sample using the aptamers described herein.

BACKGROUND

*Clostridium difficile* (also referred to as *C. difficile*) is a Gram-positive, anaerobic spore former and is an important nosocomial and community-acquired pathogenic bacterium. *C. difficile* infections (CDI) are a leading cause of infections worldwide with elevated rates of morbidity and mortality. Given the rise in antibiotic resistance and the potential mortality associated with *C. difficile* infection, control measures are of the highest importance.

SUMMARY

In some embodiments is provided an aptamer having a nucleic acid sequence that selectively binds to surface protein CdeM of a *Clostridium difficile* spore, the aptamer having a stem-loop structure comprising Loop(3)/Stem(4f)/Loop(5)/Stem(4r)/Loop(5)/Stem(2f)/Loop(1)/Stem(2f)/Loop(1)/Stem(5f)/Loop(5)/Stem(5r)/Loop(1)/Stem(2r)/Loop(1)/Stem(2r)/Loop(3). In some embodiments, the surface protein CdeM includes an amino acid sequence as set forth in SEQ ID NO: 19. In some embodiments, the aptamer comprises a nucleic acid sequence as set forth in SEQ ID NO: 55. In some embodiments, the aptamer comprises a nucleic acid sequence having at least 90% identity with SEQ ID NO: 55. In some embodiments, the aptamer is a single stranded DNA aptamer. In some embodiments, the aptamer comprises a fluorophore.

In some embodiments is provided a composition comprising the aptamer comprising a fluorophore and graphene oxide nanoparticles. In some embodiments, the composition includes an aqueous medium.

In some embodiments is provided a composition comprising two or more aptamers having a binding affinity to two or more epitopes of a surface protein of a *Clostridium difficile* spore or to two or more surface proteins of a *Clostridium difficile* spore, wherein the two or more aptamers have a stem-loop structure. In some embodiments, the surface protein is selected from the group consisting of CdeC, CdeM, CotA, CotE and CotE Chitinase. In some embodiments, the each of the two or more aptamers comprises a fluorophore. In some embodiments, the two or more aptamers comprise an aptamer having a nucleic acid sequence that selectively binds to surface protein CdeM of a *Clostridium difficile* spore, the aptamer having a stem-loop structure comprising Loop(3)/Stem(4f)/Loop(5)/Stem(4r)/Loop(5)/Stem(2f)/Loop(1)/Stem(2f)/Loop(1)/Stem(5f)/Loop(5)/Stem(5r)/Loop(1)/Stem(2r)/Loop(1)/Stem(2r)/Loop(3). In some embodiments, the two or more aptamers comprise a nucleic acid sequence as set forth in SEQ ID NOs: 27-39, 43-55. In some embodiments, the composition further comprises a first aptamer comprising a nucleic acid sequence as set forth in SEQ ID NO: 30, a second aptamer comprising a nucleic acid sequence as set forth in SEQ ID NO: 31 and a third aptamer comprising a nucleic acid sequence as set forth in SEQ ID NO: 55.

In some embodiments is provided a composition comprising two or more aptamers having a binding affinity to two or more epitopes of a surface protein of a *Clostridium difficile* spore or to two or more surface proteins of a *Clostridium difficile* spore, wherein the two or more aptamers have a stem-loop structure; (b) graphene oxide. In some embodiments, the graphene oxide is in the form of graphene oxide nanoparticles. In some embodiments, the protein is selected from the group consisting of CdeC, CdeM, CotA, CotE and CotE Chitinase. In some embodiments, the two or more aptamers comprise a fluorophore. In some embodiments, the two or more aptamers comprise a nucleic acid sequence as set forth in SEQ ID NOs: 27-39, 43-55. In some embodiments, the composition further comprises a first aptamer comprising a nucleic acid sequence as set forth in SEQ ID NO: 30, a second aptamer comprising a nucleic acid sequence as set forth in SEQ ID NO: 31 and a third aptamer comprising a nucleic acid sequence as set forth in SEQ ID NO: 55. In some embodiments, the composition comprises an aqueous medium.

In some embodiments is provided a method of visualizing *Clostridium difficile* spores on a surface, comprising: contacting a surface with a liquid composition comprising (a) at least one aptamer conjugated to a fluorophore, wherein the at least one aptamer has a stem-loop structure having a specific binding affinity for a surface protein of *Clostridium difficile* spore, wherein the surface protein is a spore coat surface protein or an exosporium layer protein; and (b) graphene oxide, wherein fluorophore is quenched by the association with the graphene oxide; and visualizing the presence or absence of *Clostridium difficile* spores on the surface, wherein fluorescence is visible when the at least one aptamer is bound to the surface protein of *Clostridium difficile* spores. In some embodiments, the at least one aptamer is not bound to the surface protein, the fluorophore is quenched and wherein when the aptamer binds to the surface protein, the fluorophore is not quenched. In some embodiments, the surface protein is CdeC, CdeM, CotA, CotE or CotE Chitinase. In some embodiments, the at least one aptamer comprises a nucleic acid sequence that selectively binds to surface protein CdeM of the *Clostridium difficile* spores, the aptamer having a stem-loop structure comprising Loop(3)/Stem(4f)/Loop(5)/Stem(4r)/Loop(5)/Stem(2f)/Loop(1)/Stem(2f)/Loop(1)/Stem(5f)/Loop(5)/Stem(5r)/Loop(1)/Stem(2r)/Loop(1)/Stem(2r)/Loop(3). In some embodiments, the composition comprises two or more aptamers having a binding affinity to two or more epitopes of a surface protein of the *Clostridium difficile* spores or to two or more surface proteins of the *Clostridium difficile* spores. In some embodiments, the graphene oxide is in the form of nanoparticles. In some embodiments, the fluorophore emits at a wavelength of between about 510 nm and 520 nm. In some embodiments, the method further comprises illuminating the surface with a light source. In some embodiments, the light from the light source has a predetermined wavelength, and the predetermined wavelength corresponds to a wavelength of light emitted by the fluorophore of the aptamer conjugate. In some embodiments, the light source is configured to produce light at a wavelength of between about 492 nm and 502 nm. In some embodiments, the method further comprises filtering the light produced by the light source such that light at a wavelength emitted by the fluorophore is filtered out. In some embodiments, the method comprises passing the light produced from the light source through a bandpass filter such that light at a wavelength emitted by the fluorophore is filtered out. In some embodiments, the method comprises passing the light produced from the light source through a circular polarizing filter such that light at a wavelength emitted by the fluorophore is filtered out. In some embodiments, the contacting comprises spraying. In some embodiments, the at least one aptamer comprises a nucleic acid sequence as set forth in SEQ ID NO: 55. In some embodiments, the at least one aptamer comprises a nucleic acid sequence having at least 90% identity with any one of the nucleic acid sequences as set forth in any of SEQ ID NOs: 27-39, 43-55.

BRIEF DESCRIPTION OF THE DRAWINGS

Embodiments of the present disclosure will be better understood when read in conjunction with the appended drawings. For the purposes of illustrating the disclosure, there are shown in the drawings embodiments which may be preferred. It is understood, however, that the disclosure is not limited to the precise arrangements and instrumentalities shown.

FIGS. 15A-15B show the predicted structures for the aptamer C.Diff F1 (SEQ ID NO: 1).

Figure 1A:
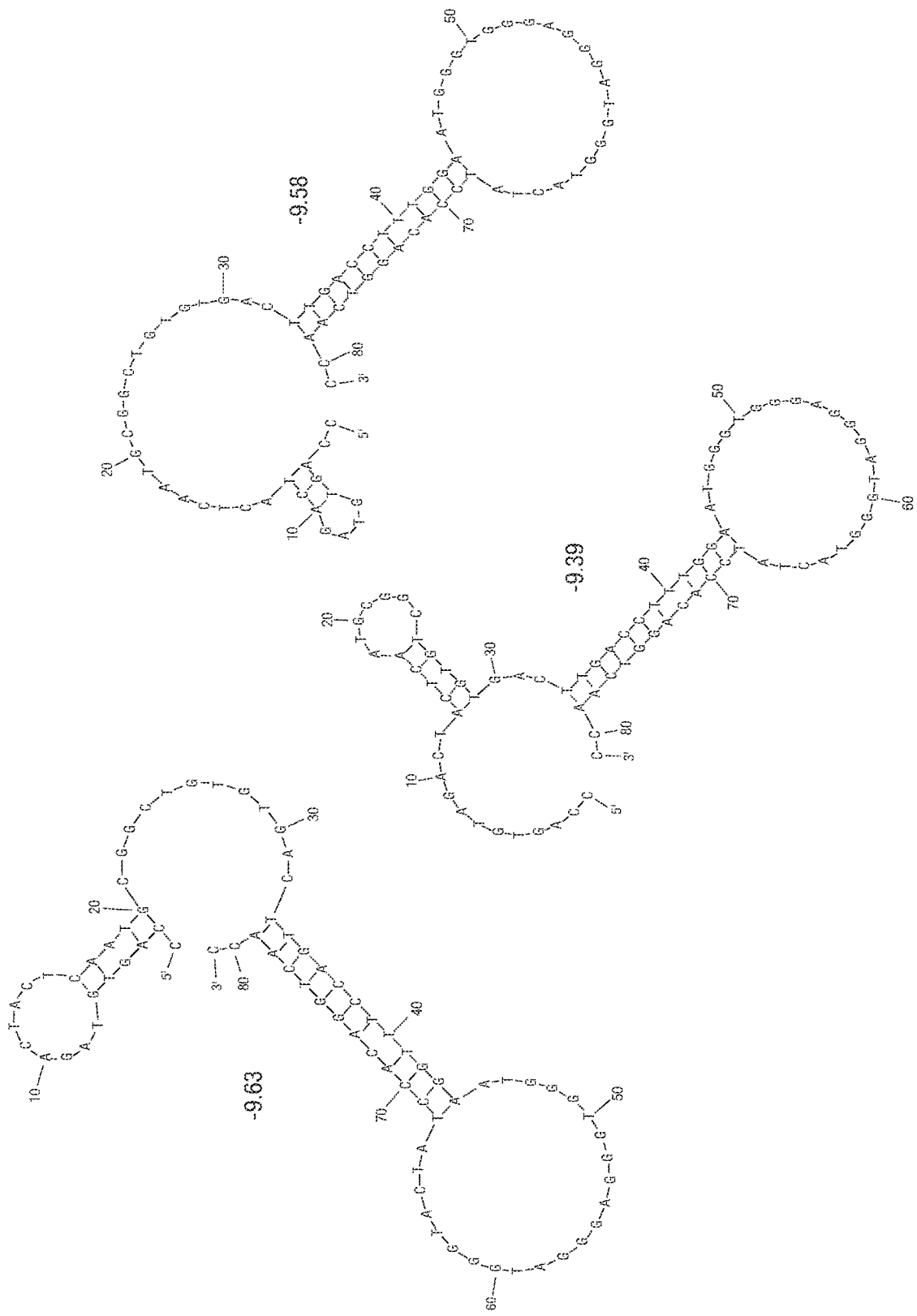
FIG. 1A shows structures predicted to be in flux at equilibrium at room temperature for the CotE H2 aptamer (SEQ ID NO: 11).

*Clostridium difficile* bacteria commonly affect older adults in hospitals or long-term care facilities. Subjects at greater risk of contracting *C. difficile* include but are not limited to those who have taken antibiotics, those with a compromised immune system, and those who have undergone abdominal or gastrointestinal surgery. For example, the mortality rate of *C. difficile* infection can be up to 25% in frail, elderly people in hospitals, and it has been postulated that antibiotic therapy disrupts normal gut microbiota, allowing *C. difficile* colonization and growth because it is naturally resistant to many drugs used to treat other infections, thereby enabling its toxin production.

An increase of *C. difficile* infections in subjects previously considered to be low-risk, for example, younger and otherwise healthy individuals without exposure to health care facilities, has also been seen in recent years. A new strain of *C. difficile*, Type 027, has recently been identified, which has been shown to produce more toxins than most other types of *C. difficile* causing a greater proportion of severe disease and apparent higher mortality.

First-line therapy for treating adults with CDI in the U.S. is vancomycin (125 mg, 4 times a day for 10 days) or fidaxomicin (200 mg, twice daily for 10 days) for both severe and non-severe CDI. In the UK, metronidazole (400 mg or 500 mg, 3 times daily for 10-14 days) is considered to be the first-line for treating first episodes of mild to moderate *C. difficile* infection; and, vancomycin (125 mg 4 times daily for 10-14 days) is considered for second episodes or if the infection is severe. An infection is defined as severe when there is a raised temperature or white cell count, rising creatinine, or signs or symptoms of severe colitis. Vancomycin may also be used in infections caused by the type 027 strain. If infection recurs, vancomycin or fidaxomicin (200 mg twice daily for 10 days) may be used. In some severe cases, a person might have to have surgery to remove the infected part of the intestines.

Spores from *C. difficile* are passed in feces and can be transmitted to food, surfaces and objects via unwashed hands. The spores can persist for weeks or months on surfaces and transmitted via contact with such surfaces.

Given the rise in antibiotic resistance and the potential mortality associated with *C. difficile* infection, control measures are of the highest importance. Current measures include healthcare providers such as nurses and doctors following protocols including:
a) Cleaning hands with soap and water or an alcohol-based hand rub before and after caring for every patient to prevent *C. difficile* and other germs from being passed from one patient to another on their hands.
b) Carefully cleaning hospital rooms and medical equipment that have been used for patients with CDI.
c) Giving patients antibiotics only when necessary.
d) Using Contact Precautions to prevent *C. difficile* from spreading to other patients. Contact Precautions mean:
   1) Whenever possible, keeping patients with *C. difficile* in a single room or in a room with another patient who has *C. difficile*.
   2) Wearing of gloves and a gown over clothing by healthcare providers while taking care of patients with *C. difficile*.
   3) Wearing of gloves and a gown by visitors.
   4) Removing of gloves and gown, and cleaning hands when leaving the room of a patient with *C. difficile*.
   5) Patients on Contact Precautions are asked to stay in their hospital rooms as much as possible. They can go to other areas of the hospital for treatments and tests.

Despite these preventative measures, *C. difficile* remains a significant healthcare issue and therefore there is a need for rapid identification of the presence of *C. difficile* in an environment in order to minimize its spread.

Embodiments disclosed herein may at least partially mitigate some of the problems identified in the prior art.

Embodiments disclosed herein may provide methods and products which have utility in the detection of *C. difficile*.

Further features of embodiments of the present disclosure are described below. The practice of embodiments of the present disclosure will employ, unless otherwise indicated, conventional techniques of molecular biology, microbiology, recombinant DNA technology and immunology, known to one of ordinary skill in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, 2nd ed., 2002, CRC Press; The Dictionary of Cell and Molecular Biology, 3rd ed., Academic Press; and the Oxford University Press, provide a person skilled in the art with a general dictionary of many of the terms used in this disclosure.

Units, prefixes and symbols are denoted in their Système International d' Unités (SI) accepted form. Numeric ranges are inclusive of the numbers defining the range. Unless otherwise indicated, amino acid sequences are written left to right in amino to carboxy orientation and nucleic acid sequences are written left to right in 5' to 3' orientation.

In the following, embodiments are explained in more detail by means of non-limiting examples. In the non-limiting, exemplary experiments, standard reagents and buffers free from contamination were used unless stated otherwise.

Embodiments comprise aptamers capable of specifically binding to *C. difficile*.

In certain embodiments, the *C. difficile* is a strain selected from SH11 (ribotype RT078), Type 027 and ATCC® 43598. In certain embodiments, the aptamer is capable of binding to a *C. difficile* spore of strain SH11. In certain embodiments, the aptamer is capable of binding to a *C. difficile* spore of strain Type 027. In certain embodiments, the aptamer is capable of binding to a *C. difficile* spore of strain ATCC® 43598.

Embodiments relate to aptamers which bind to a *C. difficile* spore. Embodiments comprise an aptamer that binds to a *C. difficile* spore coat protein.

*C. difficile* produces metabolically dormant spores. The spores comprise an outermost exosporium layer which may comprise a number of surface proteins. The exosporium layer may comprise one or more proteins selected from BclA1, BclA2, BclA3, CdeA, CdeB, CdeC and CdeM. Five coat proteins, cotA, cotB, cotCB, cotD, and cotE, were shown to be expressed on the outer coat layers of the spore.

One or more of these proteins may be a target of one or more aptamer herein, and binding to one or more of them by one or more aptamer herein may be a basis for a method of detecting *C. difficile* herein.

In some embodiments, the aptamer specifically binds to a *C. difficile* spore coat protein as listed in Table 1 below:

TABLE 1

| | |
|---|---|
| CotA | SEQ ID NO: 15 |
| Cot E | SEQ ID NO: 16 |
| CotEC | SEQ ID NO: 17 |
| CdeC | SEQ ID NO: 18 |
| CdeM | SEQ ID NO: 19 |

In some embodiments, the aptamer specifically binds to a target as defined herein. The term "target" as used herein is used to relate to a molecule selected from at least one of a *C. difficile* surface protein. In some embodiments, the target molecule is a target protein. In some embodiments, the term "target" as used herein is used to relate to a molecule selected from at least one of a *C. difficile* CotA protein, *C. difficile* CotE protein, *C. difficile* CdeC protein, *C. difficile* CdeM protein, *C. difficile* CotEC chitinase protein, and a *C. difficile* spore. As used herein, the terms "target protein" and "target peptide" are used interchangeably.

In some embodiments, the aptamer is selected against a whole *C. difficile* spore. Thus, in some embodiments, the aptamer selectively binds to a *C. difficile* spore.

In some embodiments, the aptamer specifically binds to a surface protein of the exosporium layer of the *C. difficile* spore (e.g. CdeC, CdeM). In some embodiments, the aptamer specifically binds to a coat protein of the *C. difficile* spore (e.g. CotA, CotE, CotEC).

In some embodiments, the target proteins can be naturally occurring target proteins or recombinant target proteins listed at Table 2 and may be a target of one or more aptamers described herein:

TABLE 2

| Target Protein | SEQ ID NO: |
|---|---|
| CotA | 15 |
| Cot E | 16 |
| rCotEC | 17 |
| CdeC | 18 |
| CdeM | 19 |
| rCotE (LS25) | 20 |

CdeC

In some embodiments, the aptamer specifically binds to a *C. difficile* CdeC protein. The amino acid sequence of CdeC is published under UniProtKB—Q18AS2 (Q18AS2_PEPD6) version 1 and is as set forth in SEQ ID NO: 18.

In some embodiments, the aptamer binds to an epitope of the CdeC protein which is conserved between *C. difficile* strains. Thus, in some embodiments, the aptamer is used to detect a plurality of *C. difficile* strains in a sample.

CdeM

In some embodiments, the aptamer selectively binds to an amino acid sequence of a *C. difficile* surface-bound CdeM protein. CdeM is a cysteine rich protein which is understood to be required for the morphogenesis of the coat and exosporium layer of spores. An amino acid sequence of a *C. difficile* protein is published under UniProtKB—A0A3T1GTU1 (A0A3T1GTU1_CLODI) (version 1) and as set forth in SEQ ID NO: 19.

In some embodiments, the aptamer binds to an epitope of the CdeM protein which is conserved between *C. difficile* strains. Thus, in some embodiments, the aptamer is used to detect a plurality of *C. difficile* strains in a sample.

In some embodiments, the spores comprise a spore coat. The spore coat may comprise a plurality of proteins including, but not limited to CotA and CotB for example.

CotA

In some embodiments, the aptamer specifically binds to a protein encoded by a *C. difficile* CotA gene. The protein may be referred to herein as either CotA or "spore coat assembly protein".

An amino acid sequence of CotA is published under UniProtKB Accession No. Q186G8 (Q186G8_PEPD6) version 1 and as set forth in SEQ ID NO: 15.

CotE and CotEC Chitinase

In some embodiments, the aptamer specifically binds to a *C. difficile* protein encoded by a CotE gene. An amino acid sequence of a CotE protein (also referred to as peroxiredoxin) is published under accession number UniProtKB—Q18BV5 (Q18BV5_PEPD6) and as set forth in SEQ ID NO: 16.

In some embodiments, aptamers were raised to a recombinant form of CotE referred to as "rCotE" (also referred to as LS25). The amino acid sequence of rCotE consists of amino acid residues N281-F712 (SEQ ID NO: 20). The recombinant protein comprises a chitinase domain and a sequence unique to CotE.

In some embodiments, the aptamer specifically binds to a recombinant *C. difficile* protein referred to as "rCotEC" (also referred to as AB45). The amino acid sequence of rCotEC consists of amino acid residues N381-F712 (SEQ ID NO: 17).

In some embodiments, the aptamers are selected against a tagged rCotEC protein, including but not limited to His-tagged rCotEC protein.

In some embodiments, the aptamers are selected against a tagged recombinant *C. difficile* protein including but not limited to His-tagged *C. difficile* protein. Other protein tags commonly used in the art to assist with protein purification may be used as well.

In some embodiments, the aptamer is selected against a whole *C. difficile* spore. Thus, in some embodiments, the aptamer selectively binds to a *C. difficile* spore.

In some embodiments, the aptamer specifically binds to an epitope in a *C. difficile* CotA protein.

In some embodiments, the aptamer specifically binds to an epitope in a *C. difficile* CotE protein.

In some embodiments, the aptamer specifically binds to an epitope in a *C. difficile* CdeC protein.

In some embodiments, the aptamer specifically binds to an epitope in a *C. difficile* CdeM protein.

In some embodiments, the aptamer specifically binds to an epitope in a *C. difficile* CotEC chitinase protein.

An aptamer binds "specifically" to a target as defined herein if the aptamer binds with preferential or high affinity to the target protein but does not bind or binds with only low affinity to other structurally related molecules (e.g. *Bacillus subtilis* spores.) In some embodiments, the dissociation constant for the target protein is in the micro-molar range. In some embodiments, the dissociation constant for the target protein is in the nano-molar (nM) range. In some embodiments, the dissociation constant for the target protein is in the pico-molar (pM) range. In some embodiments, the dissociation constant is about 0.1 nM or less. In some embodiments, the dissociation constant is about 0.1 nM to about 1 nM. In some embodiments, the dissociation constant is about 1 nM to about 10 nM. In some embodiments, the dissociation constant is about 10 nM to about 100 nM. In some embodiments, the dissociation constant is about 100 nM to about 1000 nM. Lower affinity binding may refer to binding that occurs at less affinity than to a target protein. The lower affinity binding may be selected from the range of less than 1 fold to 2 fold, less than 2 fold to 5 fold, less than 5 fold to 10 fold, less than 10 fold to 50 fold, less than 50 fold to 100 fold, less than 100 fold to 1000 fold, less than 1000 fold to 10000 fold, or less than 10000 fold to 100000 fold of binding to the target protein.

Aptamers

The aptamers described herein are small artificial ligands, comprising DNA, RNA or modifications thereof, capable of specifically binding to a target as defined herein with high affinity and specificity.

As used herein, "aptamer," "nucleic acid molecule," or "oligonucleotide" are used interchangeably to refer to a non-naturally occurring nucleic acid molecule that has a desirable action on a target as defined herein.

In some embodiments, the aptamers may be DNA aptamers. For example, the aptamers may be formed from single-stranded DNA (ssDNA). In some embodiments, the aptamers may be RNA aptamers. For example, the aptamers can be formed from single-stranded RNA (ssRNA).

In some embodiments, there is provided an aptamer comprising a nucleic acid sequence selected from a nucleic acid sequence as set forth in Table 3.

TABLE 3

Aptamer Sequences
Sequence

CCAGTGTAGACTACTCAATGCTCTTACGATCCTCACCTGCTAGCACACCC
ATATCCCATGCGTACTATCCACAGGTCAACC (SEQ ID NO: 1)

CCAGTGTAGACTACTCAATGCGGGTTGCGACATGGTGGTAAGAGCTCAGC
CCGTTCCCATAGTACTATCCACAGGTCAACC (SEQ ID NO: 2)

CCAGTGTAGACTACTCAATGCACGGCCTGTTCGTAAGACCCTTACAGACT
AGTTTTTCCCTGTACTATCCACAGGTCAACC (SEQ ID NO: 3)

CCAGTGTAGACTACTCAATGCCCTATTAGCTGTATCGATCCGTTTAGTCG
CTCCTCCGATAGTACTATCCACAGGTCAACC (SEQ ID NO: 4)

CCAGTGTAGACTACTCAATGCCTGGTAAATCGATGACCGCTGCCTCGCCT
GAGTAATCATCGTACTATCCACAGGTCAACC (SEQ ID NO: 5)

CCAGTGTAGACTACTCAATGCCGTGGACTGGTCGGGTTTGGATTCGGCAG
ATGAATCAGTAGTACTATCCACAGGTCAACC (SEQ ID NO: 6)

CCAGTGTAGACTACTCAATGCCTTGTAAGAAGAACAATCGCCGCTTCGCC
TGAATAGGTTCGTACTATCCACAGGTCAACC (SEQ ID NO: 7)

CCAGTGTAGACTACTCAATGCGGACCGTTGCCTCGCCCGAGTAATCCGCC
ATCGCCTTTCCGTACTATCCACAGGTCAACC (SEQ ID NO: 8)

CCAGTGTAGACTACTCAATGCTTAAGTTCTGGGGACACGTGATGAACGCA
TTTAATGGGGCGTACTATCCACAGGTCAACC (SEQ ID NO: 9)

CCAGTGTAGACTACTCAATGCCGTGGACTGGTCGGGTTTGGATTCGGCAG
ATGAATCACTAGTACTATCCACAGGTCAACC (SEQ ID NO: 10)

CCAGTGTAGACTACTCAATGCGGCTGTGTGACTTGACCTTTGGAATGGGT
GGGAGGGATGGGTACTATCCACAGGTCAACC (SEQ ID NO: 11)

CCAGTGTAGACTACTCAATGCGGTGTGGTGACCTTGACCTATGGAACCT
GGTTGTAGTACTATCCACAGGTCAACC (SEQ ID NO: 12)

CCAGTGTAGACTACTCAATGCTCGACATTTCCGCCCCGACGGCCCTCCT
AGTGATGGGGAGAGTACTATCCACAGGTCAACC (SEQ ID NO: 13)

CCAGTGTAGACTACTCAATGCCTTCCATTCACCTACCGAGCTAAGCGTT
CGACTTAGGTCTGTACTATCCACAGGTCAACC (SEQ ID NO: 14)

TABLE 3-continued

Aptamer Sequences
Sequence

ATCGATGACCGCTGCCTCGCCTGAGTAATCATCGTA
(SEQ ID NO: 23)

CCATACTCAATGCTCTTACGATCCTCATCAACC
(SEQ ID NO: 24)

CCAGTGTAGACTACTCAATGCTCTTACGATCCTCATCAACC
(SEQ ID NO: 25)

AGTGTAGACTACTCAATGCGGCTGGCCACAGGTCAACC
(SEQ ID NO: 26)

CTTGACCTTTGGAATGGGTGGGAGGGATGGGTACTATCCACAGGTCAACC
(SEQ ID NO: 27)

AATGGGTGGGAGGGATGGGTACTA (SEQ ID NO: 28)

CTTGACCTTTGGAATGGGTAGGGAGGGAGGGATACTATCCACAGGTCAAC
C (SEQ ID NO: 29)

CTTGACCTTTGGAATGGGTGGGAGGGAGGGTATCCACAGGTCAACC
(SEQ ID NO: 30)

ACTACTCAATGCTCGACATTTCCGCCCCGACGGCCCTCCTAGTGAGGGGA
GAGTAGA (SEQ ID NO: 31)

ACTACTCAATGCTCGACATTTCCGCCCCGACGGCCCTCCTAGTGATGGGG
AGAGTAGA (SEQ ID NO: 32)

ACTCAAGGCCGTGGACTGGTCGGGTTTGGATTCGGCAGATGAATCACT
(SEQ ID NO: 33)

ACTCAAGGCCGTGGACTGGTCGGGTTTGGAT (SEQ ID NO: 34)

ACCCGTGGGACTGGGTCGGGTCGGG (SEQ ID NO: 35)

AACTGCCTGGTAAATCGATGACCGCTGCCTCGCCTGAGTAATCATCGTAC
TATCCACAGGTC (SEQ ID NO: 36)

GTAAATCGATGACCGCTGCCTCGCCTGAGTAATCATCGTAC
(SEQ ID NO: 37)

ACTACTCAAACCCGTGGACTGGTCGGGTTTGGATTCGGCAGATGAATCAG
TAGAAA (SEQ ID NO: 38)

ACTACTCAATGCCGTGGACTGGTCGGGTTTGGAATCGGCAGATGAATCAG
TAGTAAA (SEQ ID NO: 39)

CCTACCGAGCTAAGCGTTCGACTTAGGTCTGTACT
(SEQ ID NO: 43)

CTCACCTGCTAGCACACCCATATCCCATGGGTACAATCCACAGGTCAA
(SEQ ID NO: 44)

CTCACCTGCTAGCACACCCACATCCCGTGCGTGCTATCCACAGGTGAA
(SEQ ID NO: 45)

AGTGCAGACTACTCAATGCACGGCCGGTTCGGAAGACCCTTCCAGACTAG
TTTTTCCCTGTACTAGTCCACCGGCTA (SEQ ID NO: 46)

AGTGCAGACTACTCAATGCACGGCCTGGTTCGTAAGACCCTTACCAGACT
(SEQ ID NO: 47)

CGGTTGCGACATGGTGGTAAGAGCTCAGCCCGTTCCCATAGTACTATCCA
CAGGTCAACCT (SEQ ID NO: 48)

CGGTTGCGACATGGTGGTAAGAGCTCAGCCCGTTCCCATAGTACTATCCA
CAGGTCGCAACCT (SEQ ID NO: 49)

CCCGTGTAGACTACTCAATGCGGGCTGCGACATGGTGGTAAGAGCTCAGC
CCGTTCCCATAGTACTATCCACGGGT (SEQ ID NO: 50)

CCCGTGTAGACTATTTTAGTACTATCCACGGG (SEQ ID NO: 51)

TGCGGGCTGCGACATGGTGGTAAGAGCTCAGCCCGTT
(SEQ ID NO: 52)

TABLE 3-continued

Aptamer Sequences
Sequence

ACCCAGGTGTAGGACGACTCAATGCCCTATTAGCTGTATCGATCCGTTTA
GTCGCTCCTCCGATAGTACCCTATCCACCAGGGA
(SEQ ID NO: 53)

ACCAGGTGGTAGACCTACTCACATGCCCTATTAGCGTGTATCGATCCGGT
TTAGTCCGCTTCGATAGTAGUCCCACCAGGA (SEQ ID NO: 54)

CTCAATGCCTTCCATTCACCTACCGAGCTAAGCGTTCGACTTAGGTCTGT
ACT (SEQ ID NO: 55)

Primer regions are indicated in bold and italic:

TABLE 4

| ID | Sequence | Target |
|---|---|---|
| C.diff_F1 | *CCAGTGTAGACTACTCAATGC* TCTTACGATCCTCACCTGCTA GCACACCCATATCCCATGC *GTACTATCCACAGGTCAACC* (SEQ ID NO: 1) | C.diff spores |
| C.diff_G1 | *CCAGTGTAGACTACTCAATGC* GGGTTGCGACATGGTGGTAAG AGCTCAGCCCGTTCCCATA *GTACTATCCACAGGTCAACC* (SEQ ID NO: 2) | C.diff spores |
| C.diff_E2 | *CCAGTGTAGACTACTCAATGC* ACGGCCTGTTCGTAAGACCCT TACAGACTAGTTTTTCCCT *GTACTATCCACAGGTCAACC* (SEQ ID NO: 3) | C.diff spores |
| Chitinase_D10 | *CCAGTGTAGACTACTCAATGC* CCTATTAGCTGTATCGATCCG TTTAGTCGCTCCTCCGATA *GTACTATCCACAGGTCAACC* (SEQ ID NO: 4) | CotEC Chitinase |
| Chitinase_D11 | *CCAGTGTAGACTACTCAATGC* CTGGTAAATCGATGACCGCTG CCTCGCCTGAGTAATCATC *GTACTATCCACAGGTCAACC* (SEQ ID NO: 5) | CotEC Chitinase |
| CdeC_D1 | *CCAGTGTAGACTACTCAATGC* CGTGGACTGGTCGGGTTTGGA TTCGGCAGATGAATCAGTA *GTACTATCCACAGGTCAACC* (SEQ ID NO: 6) | CdeC |
| Chitinase_H11 | *CCAGTGTAGACTACTCAATGC* CTTGTAAGAAGAACAATCGCC GCTTCGCCTGAATAGGTTC *GTACTATCCACAGGTCAACC* (SEQ ID NO: 7) | CotEC Chitinase |
| Chitinase_D7 | *CCAGTGTAGACTACTCAATGC* GGACCGTTGCCTCGCCCGAGT AATCGCCATCGCCTTTCC *GTACTATCCACAGGTCAACC* (SEQ ID NO: 8) | CotEC Chitinase |
| CotA_B1 | *CCAGTGTAGACTACTCAATGC* TTAAGTTCTGGGGACACGTGA TGAACGCATTTAATGGGGC *GTACTATCCACAGGTCAACC* (SEQ ID NO: 9) | CotA |

TABLE 4-continued

| ID | Sequence | Target |
|---|---|---|
| CotA_C1 | *CCAGTGTAGACTACTCAATGC* CGTGGACTGGTCGGGTTTGGA TTCGGCAGATGAATCACTA *GTACTATCCACAGGTCAACC* (SEQ ID NO: 10) | CotA |
| CotE_H2 | *CCAGTGTAGACTACTCAATGC* GGCTGTGTGACTTGACCTTTG GAATGGGTGGGAGGGATGG *GTACTATCCACAGGTCAACC* (SEQ ID NO: 11) | CotE |
| CotE_E2 | *ATCCACAGGTCAACCTACTCAATGC* GGTGTGGTGACCTTGACCTAT GGAACCTGGTTGTA *GTACTATCCACAGGTCAACC* (SEQ ID NO: 12) | CotE |
| CotE_D2 | *CCAGTGTAGACTACTCAATGC* TCGACATTTCCGCCCCGACGG CCCTCCTAGTGATGGGGAGA *GTACTATCCACAGGTCAACC* (SEQ ID NO: 13) | CotE |
| CdeM_E2 | *CCAGTGTAGACTACTCAATGC* CTTCCATTCACCTACCGAGCT AAGCGTTCGACTTAGGTCT *GTACTATCCACAGGTCAACC* (SEQ ID NO: 14) | CdeM |
| Chitinase_D11 | ATCGATGACCGCTGCCTCGCC TGAGTAATCATC*GTA* (SEQ ID NO: 23) | CotEC Chitinase |
| C.diff_F1 | CCATACTCAATGCTCTTACGA TCCTCATCAACC (SEQ ID NO: 24) | C.diff spores |
| C.diff_G1 | CCAGTGTAGACTACTCAATGC TCTTACGATCCTCATCAACC (SEQ ID NO: 25) | C.diff spores |
| CotE_H2 | AGTGTAGACTACTCAATGCGG CTGGCCACAGGTCAACC (SEQ ID NO: 26) | CotE |
| CotE_H2 | CTTGACCTTTGGAATGGGTGG GAGGGATGGGTACTATCCACA GGTCAACC (SEQ ID NO: 27) | CotE |
| CotE_H2 | AATGGGTGGGAGGGATGGGTA CTA (SEQ ID NO: 28) | CotE |
| CotE_H2 | CTTGACCTTTGGAATGGGTAG GGAGGGAGGGATACTATCCAC AGGTCAACC (SEQ ID NO: 29) | CotE |
| CotE_H2 | CTTGACCTTTGGAATGGGTGG GAGGGAGGGTATCCACAGGTC AACC (SEQ ID NO: 30) | CotE |

TABLE 4-continued

| ID | Sequence | Target |
|---|---|---|
| CotE_D2 | ACTACTCAATGCTCGACATTT CCGCCCCGACGGCCCTCCTAG TGAGGGGAGAGTAGA (SEQ ID NO: 31) | CotE |
| CotE_D2 | ACTACTCAATGCTCGACATTT CCGCCCCGACGGCCCTCCTAG TGATGGGGAGAGTAGA (SEQ ID NO: 32) | CotE |
| CotA_C1 | ACTCAAGGCCGTGGACTGGTC GGGTTTGGATTCGGCAGATGA ATCACT (SEQ ID NO: 33) | CotA |
| CotA_C1 | ACTCAAGGCCGTGGACTGGTC GGGTTTGGAT (SEQ ID NO: 34) | CotA |
| CotA_C1 | ACCCGTGGGACTGGGTCGGGT CGGG (SEQ ID NO: 35) | CotA |
| Chitinase_D11 | AACTGCCTGGTAAATCGATGA CCGCTGCCTCGCCTGAGTAAT CATCGTACTATCCACAGGTC (SEQ ID NO: 36) | CotEC Chitinase |
| Chitinase_D11 | GTAAATCGATGACCGCTGCCT CGCCTGAGTAATCATCGTAC (SEQ ID NO: 37) | CotEC Chitinase |
| CdeC_D1 | ACTACTCAAACCCGTGGACTG GTCGGGTTTGGATTCGGCAGA TGAATCAGTAGAAA (SEQ ID NO: 38) | CdeC |
| CdeC_D1 | ACTACTCAATGCCGTGGACTG GTCGGGTTTGGAATCGGCAGA TGAATCAGTAGTAAA (SEQ ID NO: 39) | CdeC |
| CdeM_E2 | CCTACCGAGCTAAGCGTTCGA CTTAGGTCTGTACT (SEQ ID NO: 43) | CdeM |
| C.diff_F1 | CTCACCTGCTAGCACACCCAT ATCCCATGGGTACAATCCACA GGTCAA (SEQ ID NO: 44) | C.diff spores |
| C.diff_F1 | CTCACCTGCTAGCACACCCAC ATCCCGTGCGTGCTATCCACA GGTGAA (SEQ ID NO: 45) | C.diff spores |
| C.diff_E2 | AGTGCAGACTACTCAATGCAC GGCCGGTTCGGAAGACCCTTC CAGACTAGTTTTTCCCTGTAC TAGTCCACCGGCTA (SEQ ID NO: 46) | C.diff spores |
| C.diff_E2 | AGTGCAGACTACTCAATGCAC GGCCTGGTTCGTAAGACCCTT ACCAGACT (SEQ ID NO: 47) | C.diff spores |
| C.diff_G1 | CGGTTGCGACATGGTGGTAAG AGCTCAGCCCGTTCCCATAGT ACTATCCACAGGTCAACCT (SEQ ID NO: 48) | C.diff spores |
| C.diff_G1 | CGGTTGCGACATGGTGGTAAG AGCTCAGCCCGTTCCCATAGT ACTATCCACAGGTCGCAACCT (SEQ ID NO: 49) | C.diff spores |
| C.diff_G1 | CCCGTGTAGACTACTCAATGC GGGCTGCGACATGGTGGTAAG AGCTCAGCCCGTTCCCATAGT ACTATCCACGGGT (SEQ ID NO: 50) | C.diff spores |
| C.diff_G1 | CCCGTGTAGACTATTTTAGTA CTATCCACGGG (SEQ ID NO: 51) | C.diff spores |
| C.diff_G1 | TGCGGGCTGCGACATGGTGGT AAGAGCTCAGCCCGTT (SEQ ID NO: 52) | C.diff spores |
| Chitinase_D10 | ACCCAGGTGTAGGACGACTCA ATGCCCTATTAGCTGTATCGA TCCGTTTAGTCGCTCCTCCGA TAGTACCCTATCCACCAGGGA (SEQ ID NO: 53) | CotEC Chitinase |
| Chitinase_D10 | ACCAGGTGGTAGACCTACTCA CATGCCCTATTAGCGTGTATC GATCCGGTTTAGTCCGCTTCG ATAGTAGUCCCACCAGGA (SEQ ID NO: 54) | CotEC Chitinase |
| CdeM_E2 | CTCAATGCCTTCCATTCACCT ACCGAGCTAAGCGTTCGACTT AGGTCTGTACT (SEQ ID NO: 55) | CdeM |

In some embodiments, the aptamers are RNA aptamers and comprise a sequence in which one or some or all of the deoxyribonucleotides in any of the sequences set forth in SEQ ID NO. 1 to 14 and SEQ ID NO: 23 to 39 and SEQ ID NO: 43 to 55 are substituted for their equivalent ribonucleotide residues AMP, GMP, UMP or CMP.

The aptamers of embodiments of the disclosure may comprise modified nucleic acids as described herein.

In some embodiments, the aptamers of the disclosure are prepared using principles of in vitro selection known in the art, that include iterative cycles of target binding, partitioning and preferential amplification of target binding sequences. Selection may be performed using immobilized target proteins. Immobilization may include, but is not limited to, immobilization to a solid surface. In a non-limiting example, the solid surface may be beads. In a non-limiting example, the solid surface may be magnetic beads.

Non-limiting examples of amplification methods include polymerase chain reaction (PCR), ligation amplification (or ligase chain reaction, LCR), strand displacement amplification, nucleic acid sequence-based amplification, and amplification methods based on the use of Q-beta replicase. In a non-limiting embodiment, at least one type of aptamer may be immobilized on a solid surface during amplification. Each of these exemplary methods is well known in the art.

In some embodiments, the aptamers are selected from a nucleic acid molecule library such as a single-stranded DNA or RNA nucleic acid molecule library. The aptamers may be selected from a "universal aptamer selection library" that is designed such that any selected aptamers need little to no adaptation to convert into any of the listed assay formats.

Once selected, the aptamer may be further modified before being used e.g. to remove one or both primer sequences and/or parts of the randomized sequence not required for target binding.

Typically, aptamers of the embodiments of the disclosure comprise a first primer region (e.g. at the 5' end), a second primer region (e.g. at the 3' end), or both. The primer regions may serve as primer binding sites for PCR amplification of the library and selected aptamers.

The skilled person would understand different primer sequences can be selected depending, for example, on the starting library and/or aptamer selection protocol. In some embodiments, the primer comprises or consists of a nucleic acid sequence of SEQ ID NO: 21 and/or 22. In some embodiments, aptamers may comprise SEQ ID NO: 21 and/or 22. In other embodiments, any one of one to all of the nucleotides disclosed by SEQ ID NO: 21 or 22 may be modified. The primer region length may also be varied.

In some embodiments, the primers are as shown in Table 5

TABLE 5

| | |
|---|---|
| CCAGTGTAGACTACTCAATGC (primer) | SEQ ID NO: 21 |
| GTACTATCCACAGGTCAACC (primer) | SEQ ID NO: 22 |

The first primer region and/or second region may comprise a detectable label as described herein. As used herein the terms "detectable label" and "detectable moiety" are used interchangeably. In some embodiments, the first and/or second primer region may be fluorescently labelled. Non-limiting examples of fluorescent labels include but are not limited to fluorescein, green fluorescent protein (GFP), yellow fluorescent protein, cyan fluorescent protein, and others. In some embodiments, a fluorescein label is used. In some embodiments, other forms of detecting the primer may be used, including but not limited to phosphate ($PO_4$) labelling, isotope labelling, electrochemical sensors, colorimetric biosensors, and others.

In some embodiments, the aptamers of the disclosure comprise or consist of a nucleic acid sequence selected from any one of SEQ ID NOs: 1 to 14.

In some embodiments, aptamers of the disclosure comprise or consist of a nucleic acid sequence having at least 85%, at least 90%, at least 95%, at least 96%, at least 97%, at least 98%, at least 99% or more sequence identity to the nucleotide sequence of any one of SEQ ID NOs: 1 to 14 or SEQ ID NOs: 23 to 39 or SEQ ID Nos: 43 to 55.

As used herein, "sequence identity" refers to the percentage of nucleotides in a candidate sequence that are identical with the nucleotides in said sequences after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, CLUSTALW or Megalign (DNASTAR) software. For example, % nucleic acid sequence identity values can be generated using sequence comparison computer programs found on the European Bioinformatics Institute website (www.ebi.ac.uk).

As used herein, when describing the percent identity of a nucleic acid, such as an aptamer, the sequence of which is at least, for example, about 90% identical to a reference nucleotide sequence, it is intended that the nucleic acid sequence is identical to the reference sequence except that the nucleic acid sequence may include up to ten-point mutations (e.g. substitution, deletion, insertion) per each 100 nucleotides of the reference nucleic acid sequence. These mutations may occur at the 5' or 3' terminal positions of the reference nucleotide sequence or anywhere between those 5' or 3' terminal positions, interspersed either individually among nucleotides in the reference sequence or in one or more contiguous groups within the reference sequence.

In some embodiments, aptamers comprise, consist essentially of, or consist of a minimal effective fragment of SEQ ID NOs: 1 to 14 or SEQ ID NOs: 23 to 39 or SEQ ID Nos: 43 to 55. Herein, a "minimal effective fragment" is understood to mean a fragment (e.g. portion) of the full-length aptamer capable of binding to a target as defined herewith with the same or improved affinity as compared to the full-length aptamer. A minimal effective fragment may compete for binding to a target as defined herein with the full-length aptamer.

In some embodiments, the aptamers comprise, consist essentially of, or consist of at least 10 contiguous nucleic acid residues of any of the sequences as set forth in any one of SEQ ID NOs: 1 to 14 or SEQ ID NOs: 23 to 39 or SEQ ID NOs: 43 to 55 and show equivalent or improved binding to the target molecule. In some embodiments, the aptamers of the disclosure comprise, consist essentially of, or consist of at least 10 contiguous nucleic acid residues of any of the sequences as set forth in any one of SEQ ID NOs: 1 to 14 or SEQ ID NOs: 23 to 39 or SEQ ID NOs: 43 to 55 and show adequate binding to the target molecule. Adequate binding includes binding to target molecule that occurs with affinity and specificity as described herein, or an affinity and/or specificity of binding less than that of the full-length aptamer sequence above but still capable of delivering a report of the presence of its respective target.

In some embodiments, an aptamer of the disclosure comprises, consists essentially of, or consists of at least 10 contiguous nucleotides of any of the sequences as set forth in any one of SEQ ID NOs: 1 to 14 or SEQ ID NOs: 23 to 39 or SEQ ID Nos: 43 to 55.

In some embodiments, an aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 1. The aptamer may comprise, consist essentially of, or consist of any span of contiguous nucleotides from SEQ ID NO: 1, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 2. The aptamer may comprise, consist essentially of, or consist of any span of contiguous nucleotides from SEQ ID NO: 2, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 3. The aptamer may comprise, consist essentially of, or consist of any span of contiguous nucleotides from SEQ ID NO: 3, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 4. The aptamer may comprise, consist essentially of, or consist of any span of contiguous nucleotides from SEQ ID NO: 4, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 5. The aptamer may comprise, consist essentially of, or consist of any span of contiguous nucleotides from SEQ ID NO: 5, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 6. The aptamer may comprise, consist essentially of, or consist of any span of contiguous nucleotides from SEQ ID NO: 6, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 7. The aptamer may comprise, consist essentially of, or consist of any span of contiguous nucleotides from SEQ ID NO: 7, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 8. The aptamer may comprise, consist essentially of, or consist of any span of contiguous nucleotides from SEQ ID NO: 8, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 9. The aptamer may comprise, consist essentially of, or consist of any span of contiguous nucleotides from SEQ ID NO: 9, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 10. The aptamer may comprise, consist essentially of, or consist of any span of contiguous nucleotides from SEQ ID NO: 10, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 11. The aptamer may comprise, consist essentially of, or consist of any span of contiguous nucleotides from SEQ ID NO: 11, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or 76 contiguous nucleotides in the nucleic acid sequence of SEQ ID NO: 12. The aptamer may comprise, consist essentially of, or consist of any span of contiguous nucleotides from SEQ ID NO: 12, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82 nucleotides in the nucleic acid sequence of SEQ ID NO: 13. The aptamer may comprise, consist essentially of, or consist of any span of contiguous nucleotides from SEQ ID NO: 13, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 14. The aptamer may comprise, consist essentially of, or consist of any span of contiguous nucleotides from SEQ ID NO: 14, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, or 36 contiguous nucleotides in the nucleic acid sequence of SEQ ID NO: 23. The aptamer may comprise, consist essentially of, or consist of any span of contiguous nucleotides from SEQ ID NO: 23, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32 or 33 contiguous nucleotides in the nucleic acid sequence of SEQ ID NO: 24. The aptamer may comprise, consist essentially of, or consist of any span of contiguous nucleotides from SEQ ID NO: 24, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 contiguous nucleotides in the nucleic acid sequence of SEQ ID NO: 25. The aptamer may comprise, consist essentially of, or consist of any span of contiguous nucleotides from SEQ ID NO: 25, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, or 38 contiguous nucleotides in the nucleic acid sequence of SEQ ID NO: 26. The aptamer may comprise, consist essentially of, or consist of any span of contiguous nucleotides from SEQ ID NO: 26, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides in the nucleic acid sequence of SEQ ID NO: 27. The aptamer may comprise, consist essentially of, or consist of any span of contiguous nucleotides from SEQ ID NO: 27, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, or 24 contiguous nucleotides in the nucleic acid sequence of SEQ ID NO: 28. The aptamer may comprise, consist essentially of, or consist of any span of contiguous nucleotides from SEQ ID NO: 28, where the span has a length chosen in one nucleotide increments from 15 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 contiguous nucleotides in the nucleic acid sequence of SEQ ID NO: 29. The aptamer may comprise, consist essentially of, or consist of any span of contiguous nucleotides from SEQ ID NO: 29, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 contiguous nucleotides in the nucleic acid sequence of SEQ ID NO: 30. The aptamer may comprise, consist essentially of, or consist of any span of contiguous nucleotides from SEQ ID NO: 30, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 contiguous nucleotides in the nucleic acid sequence of SEQ ID NO: 31. The aptamer may comprise, consist essentially of, or consist of any span of contiguous nucleotides from SEQ ID NO: 31, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, or 58 contiguous nucleotides in the nucleic acid sequence of SEQ ID NO: 32. The aptamer may comprise, consist essentially of, or consist of any span of contiguous nucleotides from SEQ ID NO: 32, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 contiguous nucleotides in the nucleic acid sequence of SEQ ID NO: 33. The aptamer may comprise, consist essentially of, or consist of any span of contiguous nucleotides from SEQ ID NO: 33, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, or 31 contiguous nucleotides in the nucleic acid sequence of SEQ ID NO: 34. The aptamer may comprise, consist essentially of, or consist of any span of contiguous nucleotides from SEQ ID NO: 34, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, or 25 contiguous nucleotides in the nucleic acid sequence of SEQ ID NO: 35. The aptamer may comprise, consist essentially of, or consist of any span of contiguous nucleotides from SEQ ID NO: 35, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 contiguous nucleotides in the nucleic acid sequence of SEQ ID NO: 36. The aptamer may comprise, consist essentially of, or consist of any span of contiguous nucleotides from SEQ ID NO: 36, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 contiguous nucleotides in the nucleic acid sequence of SEQ ID NO: 37. The aptamer may comprise, consist essentially of, or consist of any span of contiguous nucleotides from SEQ ID NO: 37, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 contiguous nucleotides in the nucleic acid sequence of SEQ ID NO: 38. The aptamer may comprise, consist essentially of, or consist of any span of contiguous nucleotides from SEQ ID NO: 38, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 contiguous nucleotides in the nucleic acid sequence of SEQ ID NO: 39. The aptamer may comprise, consist essentially of, or consist of any span of contiguous nucleotides from SEQ ID NO: 39, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 contiguous nucleotides in the nucleic acid sequence of SEQ ID NO: 42. The aptamer may comprise, consist essentially of, or consist of any span of contiguous nucleotides from SEQ ID NO: 42, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, or 35 contiguous nucleotides in the nucleic acid sequence of SEQ ID NO: 43. The aptamer may comprise, consist essentially of, or consist of any span of contiguous nucleotides from SEQ ID NO: 43, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 contiguous nucleotides in the nucleic acid sequence of SEQ ID NO: 44. The aptamer may comprise, consist essentially of, or consist of any span of contiguous nucleotides from SEQ ID NO: 44, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 contiguous nucleotides in the nucleic acid sequence of SEQ ID NO: 45. The aptamer may comprise, consist essentially of, or consist of any span of contiguous nucleotides from SEQ ID NO: 45, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 contiguous nucleotides in the nucleic acid sequence of SEQ ID NO: 46. The aptamer may comprise, consist essentially of, or consist of any span of contiguous nucleotides from SEQ ID NO: 46, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 contiguous nucleotides in the nucleic acid sequence of SEQ ID NO: 47. The aptamer may comprise, consist essentially of, or consist of any span of contiguous nucleotides from SEQ ID NO: 47, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 contiguous nucleotides in the nucleic acid sequence of SEQ ID NO: 48. The aptamer may comprise, consist essentially of, or consist of any span of contiguous nucleotides from SEQ ID NO: 48, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 contiguous nucleotides in the nucleic acid sequence of SEQ ID NO: 49. The aptamer may comprise, consist essentially of, or consist of any span of contiguous nucleotides from SEQ ID NO: 49, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or 76 contiguous nucleotides in the nucleic acid sequence of SEQ ID NO: 50. The aptamer may comprise, consist essentially of, or consist of any span of contiguous nucleotides from SEQ ID NO: 50, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, or 32 contiguous nucleotides in the nucleic acid sequence of SEQ ID NO: 51. The aptamer may comprise, consist essentially of, or consist of any span of contiguous nucleotides from SEQ ID NO: 51, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, or 37 contiguous nucleotides in the nucleic acid sequence of SEQ ID NO: 52. The aptamer may comprise, consist essentially of, or consist of any span of contiguous nucleotides from SEQ ID NO: 52, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84 contiguous nucleotides in the nucleic acid sequence of SEQ ID NO: 53. The aptamer may comprise, consist essentially of, or consist of any span of contiguous nucleotides from SEQ ID NO: 53, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 54. The aptamer may comprise, consist essentially of, or consist of any span of contiguous nucleotides from SEQ ID NO: 54, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, or 53 contiguous nucleotides in the nucleic acid sequence of SEQ ID NO: 55. The aptamer may comprise, consist essentially of, or consist of any span of contiguous nucleotides from SEQ ID NO: 55, where the span has a length chosen in one nucleotide increments from 10 nucleotides to full length.

In some embodiments, these sequences relate to aptamer fragments with equivalent, suitable, or improved binding to a target protein as described herein as compared to full-length aptamer.

In some embodiments, aptamers comprise, consist essentially of, or consist of a nucleic acid sequence comprising at least about 10, 15, 20, 25, 30, 35, 40, 45, 50, 51, 52, 53, 54, 55, 60 or more consecutive nucleotides of a sequence having at least 85%, at least 90%, at least 95%, at least 96%, at least 97%, at least 98%, at least 99% or more identity with any of SEQ ID NOs: 1 to 14 or SEQ ID NOs: 23 to 39 or SEQ ID Nos: 43-55. In this context the term "about" typically means the referenced nucleotide sequence length plus or minus 10% of that referenced length.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence having at least 85% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 85% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 85% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 85% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 85% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 85% or more identity with SEQ ID NO: 27. In some embodiments, aptamers comprise, consist essentially of, or consist of a nucleic acid sequence comprising at least about 10, 15, 20, or more consecutive nucleotides of a sequence having at least 85% or more identity with SEQ ID NO: 28. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 85% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 85% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 85% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 85% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 85% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 85% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 85% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 85% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 85% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 85% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 85% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 85% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 85% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 85% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 85% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 85% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 85% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 85% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 85% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 85% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 85% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 85% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 85% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 85% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence having at least 90% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 90% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 90% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 90% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 90% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 27. In some embodiments, aptamers comprise, consist essentially of, or consist of a nucleic acid sequence comprising at least about 10, 15, 20, or more consecutive nucleotides of a sequence having at least 90% or more identity with SEQ ID NO: 28. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 90% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 90% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 90% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 90% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 90% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 90% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 90% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 90% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 90% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 90% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 90% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 90% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 90% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 90% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 90% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 90% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 90% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 90% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 90% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence having at least 95% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 95% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 95% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 95% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 95% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 27. In some embodiments, aptamers comprise, consist essentially of, or consist of a nucleic acid sequence comprising at least about 10, 15, 20, or more consecutive nucleotides of a sequence having at least 95% or more identity with SEQ ID NO: 28. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 95% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 95% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 95% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 95% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 95% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 95% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 95% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 95% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 95% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 95% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 95% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 95% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 95% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 95% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 95% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 95% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 95% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 95% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 95% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence having at least 96% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 96% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 96% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 96% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 96% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 27. In some embodiments, aptamers comprise, consist essentially of, or consist of a nucleic acid sequence comprising at least about 10, 15, 20, or more consecutive nucleotides of a sequence having at least 96% or more identity with SEQ ID NO: 28. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 96% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 96% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 96% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 96% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 96% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 96% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 96% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 96% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 96% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 96% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 96% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 96% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 96% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 96% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 96% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 96% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 96% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 96% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 96% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80, 85 or more consecutive nucleotides of a sequence having at least 97% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 97% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 97% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 97% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 97% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 27. In some embodiments, aptamers comprise, consist essentially of, or consist of a nucleic acid sequence comprising at least about 10, 15, 20, or more consecutive nucleotides of a sequence having at least 97% or more identity with SEQ ID NO: 28. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 97% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 97% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 97% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 97% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 97% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 97% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 97% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 97% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 97% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 97% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 97% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 97% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 97% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 97% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 97% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 97% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 97% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 97% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 97% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence having at least 98% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 98% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 98% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 98% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 98% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 27. In some embodiments, aptamers comprise, consist essentially of, or consist of a nucleic acid sequence comprising at least about 10, 15, 20, or more consecutive nucleotides of a sequence having at least 98% or more identity with SEQ ID NO: 28. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 98% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 98% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 98% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 98% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 98% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 98% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 98% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 98% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 98% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 98% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 98% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 98% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 98% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 98% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 98% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 98% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 98% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 98% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 98% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence having at least 99% or more identity with any of SEQ ID NOs: 1 to 14. In some embodiments, aptamers comprise, consist essentially of, or consist of a nucleic acid sequence comprising at least about 10, 15, 20, 25, 30, 35, or more consecutive nucleotides of a sequence having at least 99% or more identity with SEQ ID NO: 23. In some embodiments, aptamers comprise, consist essentially of, or consist of a nucleic acid sequence comprising at least about 10, 15, 20, 25, 30, or more consecutive nucleotides of a sequence having at least 99% or more identity with SEQ ID NO: 24. In some embodiments, aptamers comprise, consist essentially of, or consist of a nucleic acid sequence comprising at least about 10, 15, 20, 25, 30, 35, 40, or more consecutive nucleotides of a sequence having at least 99% or more identity with SEQ ID NO: 25. In some embodiments, aptamers comprise, consist essentially of, or consist of a nucleic acid sequence comprising at least about 10, 15, 20, 25, 30, 35, or more consecutive nucleotides of a sequence having at least 99% or more identity with SEQ ID NO: 26. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 27. In some embodiments, aptamers comprise, consist essentially of, or consist of a nucleic acid sequence comprising at least about 10, 15, 20, or more consecutive nucleotides of a sequence having at least 99% or more identity with SEQ ID NO: 28. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 29. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 30. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 99% or more identity with SEQ ID NO: 31. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 99% or more identity with SEQ ID NO: 32. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 33. In some embodiments, aptamers comprise, consist essentially of, or consist of a nucleic acid sequence comprising at least about 10, 15, 20, 25, 30, or more consecutive nucleotides of a sequence having at least 99% or more identity with SEQ ID NO: 34. In some embodiments, aptamers comprise, consist essentially of, or consist of a nucleic acid sequence comprising at least about 10, 15, 20, 25, or more consecutive nucleotides of a sequence having at least 99% or more identity with SEQ ID NO: 35. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 99% or more identity with SEQ ID NO: 36. In some embodiments, aptamers comprise, consist essentially of, or consist of a nucleic acid sequence comprising at least about 10, 15, 20, 25, 30, 35, 40, or more consecutive nucleotides of a sequence having at least 99% or more identity with SEQ ID NO: 37. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 99% or more identity with SEQ ID NO: 38. In some embodiments, aptamers comprise, consist essentially of, or consist of a nucleic acid sequence comprising at least about 10, 15, 20, 25, 30, 35, 40, 45, 50, 55, or more consecutive nucleotides of a sequence having at least 99% or more identity with SEQ ID NO: 39. In some embodiments, aptamers comprise, consist essentially of, or consist of a nucleic acid sequence comprising at least about 10, 15, 20, 25, 30, or more consecutive nucleotides of a sequence having at least 99% or more identity with SEQ ID NO: 43. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 44. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 45. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 99% or more identity with SEQ ID NO: 46. In some embodiments, aptamers comprise, consist essentially of, or consist of a nucleic acid sequence comprising at least about 10, 15, 20, 25, 30, 35, 40, 45, or more consecutive nucleotides of a sequence having at least 99% or more identity with SEQ ID NO: 47. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 99% or more identity with SEQ ID NO: 48. In some embodiments, aptamers comprise, consist essentially of, or consist of a nucleic acid sequence comprising at least about 10, 15, 20, 25, 30, 35, 40, 45, 50, 55, 60, or more consecutive nucleotides of a sequence having at least 99% or more identity with SEQ ID NO: 49. In some embodiments, aptamers comprise, consist essentially of, or consist of a nucleic acid sequence comprising at least about 10, 15, 20, 25, 30, 35, 40, 45, 50, 55, 60, 65, 70, 75, or more consecutive nucleotides of a sequence having at least 99% or more identity with SEQ ID NO: 50. In some embodiments, aptamers comprise, consist essentially of, or consist of a nucleic acid sequence comprising at least about 10, 15, 20, 25, 30, or more consecutive nucleotides of a sequence having at least 99% or more identity with SEQ ID NO: 51. In some embodiments, aptamers comprise, consist essentially of, or consist of a nucleic acid sequence comprising at least about 10, 15, 20, 25, 30, 35, or more consecutive nucleotides of a sequence having at least 99% or more identity with SEQ ID NO: 52. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 99% or more identity with SEQ ID NO: 53. In some embodiments, aptamers comprise, consist essentially of, or consist of a nucleic acid sequence comprising at least about 10, 15, 20, 25, 30, 35, 40, 45, 50, 55, 60, 65, 70, 75, 80, or more consecutive nucleotides of a sequence having at least 99% or more identity with SEQ ID NO: 54. In some embodiments, aptamers comprise, consist essentially of, or consist of a nucleic acid sequence comprising at least about 10, 15, 20, 25, 30, 35, 40, 45, 50, or more consecutive nucleotides of a sequence having at least 99% or more identity with SEQ ID NO: 55.

In some embodiments, aptamers comprise, consist essentially of, or consist of a nucleic acid sequence comprising at least about 10, 15, 20, 25, 30, 35, 40, 45, 50, 55, 60, 65, 70, 75, 80 or more consecutive nucleotides of a sequence comprising any one of SEQ ID NOs: 1 to 14.

In some embodiments, aptamers comprise, consist essentially of, or consist of a nucleic acid sequence comprising at least about 10 or more consecutive nucleotides of a sequence comprising SEQ ID NO: 23. In some embodiments, aptamers comprise, consist essentially of, or consist of a nucleic acid sequence comprising at least about 10 or more consecutive nucleotides of a sequence comprising SEQ ID NO: 24. In some embodiments, aptamers comprise, consist essentially of, or consist of a nucleic acid sequence comprising at least about 10 or more consecutive nucleotides of a sequence comprising SEQ ID NO: 25. In some embodiments, aptamers comprise, consist essentially of, or consist of a nucleic acid sequence comprising at least about 10 or more consecutive nucleotides of a sequence comprising SEQ ID NO: 26. In some embodiments, aptamers comprise, consist essentially of, or consist of a nucleic acid sequence comprising at least about 10 or more consecutive nucleotides of a sequence comprising SEQ ID NO: 27. In some embodiments, aptamers comprise, consist essentially of, or consist of a nucleic acid sequence comprising at least about 20 or more consecutive nucleotides of a sequence comprising SEQ ID NO: 28. In some embodiments, aptamers comprise, consist essentially of, or consist of a nucleic acid sequence comprising at least about 10 or more consecutive nucleotides of a sequence comprising SEQ ID NO: 29. In some embodiments, aptamers comprise, consist essentially of, or consist of a nucleic acid sequence comprising at least about 10 or more consecutive nucleotides of a sequence comprising SEQ ID NO: 30. In some embodiments, aptamers comprise, consist essentially of, or consist of a nucleic acid sequence comprising at least about 10 or more consecutive nucleotides of a sequence comprising SEQ ID NO: 31. In some embodiments, aptamers comprise, consist essentially of, or consist of a nucleic acid sequence comprising at least about 10 or more consecutive nucleotides of a sequence comprising SEQ ID NO: 32. In some embodiments, aptamers comprise, consist essentially of, or consist of a nucleic acid sequence comprising at least about 10 or more consecutive nucleotides of a sequence comprising SEQ ID NO: 33. In some embodiments, aptamers comprise, consist essentially of, or consist of a nucleic acid sequence comprising at least about 10 or more consecutive nucleotides of a sequence comprising SEQ ID NO: 34. In some embodiments, aptamers comprise, consist essentially of, or consist of a nucleic acid sequence comprising at least about 20 or more consecutive nucleotides of a sequence comprising SEQ ID NO: 35. In some embodiments, aptamers comprise, consist essentially of, or consist of a nucleic acid sequence comprising at least about 10 or more consecutive nucleotides of a sequence comprising SEQ ID NO: 36. In some embodiments, aptamers comprise, consist essentially of, or consist of a nucleic acid sequence comprising at least about 10 or more consecutive nucleotides of a sequence comprising SEQ ID NO: 37. In some embodiments, aptamers comprise, consist essentially of, or consist of a nucleic acid sequence comprising at least about 10 or more consecutive nucleotides of a sequence comprising SEQ ID NO: 38. In some embodiments, aptamers comprise, consist essentially of, or consist of a nucleic acid sequence comprising at least about 10 or more consecutive nucleotides of a sequence comprising SEQ ID NO: 39. In some embodiments, aptamers comprise, consist essentially of, or consist of a nucleic acid sequence comprising at least about 10 or more consecutive nucleotides of a sequence comprising SEQ ID NO: 43. In some embodiments, aptamers comprise, consist essentially of, or consist of a nucleic acid sequence comprising at least about 10 or more consecutive nucleotides of a sequence comprising SEQ ID NO: 44. In some embodiments, aptamers comprise, consist essentially of, or consist of a nucleic acid sequence comprising at least about 10 or more consecutive nucleotides of a sequence comprising SEQ ID NO: 45. In some embodiments, aptamers comprise, consist essentially of, or consist of a nucleic acid sequence comprising at least about 10 or more consecutive nucleotides of a sequence comprising SEQ ID NO: 46. In some embodiments, aptamers comprise, consist essentially of, or consist of a nucleic acid sequence comprising at least about 10 or more consecutive nucleotides of a sequence comprising SEQ ID NO: 47. In some embodiments, aptamers comprise, consist essentially of, or consist of a nucleic acid sequence comprising at least about 10 or more consecutive nucleotides of a sequence comprising SEQ ID NO: 48. In some embodiments, aptamers comprise, consist essentially of, or consist of a nucleic acid sequence comprising at least about 10 or more consecutive nucleotides of a sequence comprising SEQ ID NO: 49. In some embodiments, aptamers comprise, consist essentially of, or consist of a nucleic acid sequence comprising at least about 10 or more consecutive nucleotides of a sequence comprising SEQ ID NO: 50. In some embodiments, aptamers comprise, consist essentially of, or consist of a nucleic acid sequence comprising at least about 10 or more consecutive nucleotides of a sequence comprising SEQ ID NO: 51. In some embodiments, aptamers comprise, consist essentially of, or consist of a nucleic acid sequence comprising at least about 10 or more consecutive nucleotides of a sequence comprising SEQ ID NO: 52. In some embodiments, aptamers comprise, consist essentially of, or consist of a nucleic acid sequence comprising at least about 10 or more consecutive nucleotides of a sequence comprising SEQ ID NO: 53. In some embodiments, aptamers comprise, consist essentially of, or consist of a nucleic acid sequence comprising at least about 10 or more consecutive nucleotides of a sequence comprising SEQ ID NO: 54. In some embodiments, aptamers comprise, consist essentially of, or consist of a nucleic acid sequence comprising at least about 10 or more consecutive nucleotides of a sequence comprising SEQ ID NO: 55.

The aptamers may comprise natural or non-natural nucleotides and/or base derivatives (or combinations thereof). In some embodiments, the aptamers comprise one or more modifications such that they comprise a chemical structure other than deoxyribose, ribose, phosphate, adenine (A), guanine (G), cytosine (C), thymine (T), or uracil (U). The aptamers may be modified at the nucleobase, at the sugar or at the phosphate backbone.

In some embodiments, the aptamers comprise one or more modified nucleotides. Exemplary modifications include for example nucleotides comprising an alkylation, arylation or acetylation, alkoxylation, halogenation, amino group, or another functional group. Examples of modified nucleotides include, but are not limited to, 2'-fluoro ribonucleotides, 2'-NH$_2$—, 2'-OCH$_3$— and 2'-O-methoxyethyl ribonucleotides, which are used for RNA aptamers.

The aptamers may be wholly or partly phosphorothioate or DNA, phosphorodithioate or DNA, phosphoroselenoate or DNA, phosphorodiselenoate or DNA, locked nucleic acid (LNA), peptide nucleic acid (PNA), N3'-P5'phosphoramidate RNA/DNA, cyclohexene nucleic acid (CeNA), tricyclo DNA (tcDNA) or spiegelmer, or the phosphoramidate morpholine (PMO) components or any other modification known to those skilled in the art (see also Chan et al., Clinical and Experimental Pharmacology and Physiology (2006) 33, 533-540).

Some of the modifications may allow the aptamers to be stabilized against nucleic acid-cleaving enzymes. In the stabilization of the aptamers, a distinction can generally be made between the subsequent modification of the aptamers and the selection with already modified RNA/DNA. The stabilization may not affect the affinity of the modified RNA/DNA aptamers but may prevent the rapid decomposition of the aptamers in an organism, biological solutions, or solutions, by RNases/DNases. An aptamer is referred to as stabilized if the half-life of the aptamer in the sample (e.g. biological medium, organism, solution) is greater than one minute, greater than one hour, or greater than one day. The aptamers may be modified with reporter molecules, which may enable detection of the labelled aptamers. Reporter molecules may also contribute to increased stability of the aptamers.

Aptamers form a three-dimensional structure that depends on their nucleic acid sequence. The three-dimensional structure of an aptamer may arise due to Watson and Crick intramolecular base pairing, Hoogsteen base pairing (quadruplex), wobble-pair formation, or other non-canonical base interactions. In some embodiments, the three-dimensional structure enables aptamers, analogous to antigenantibody binding, to bind target structures accurately. A nucleic acid sequence of an aptamer may, under defined conditions, have a three-dimensional structure that is specific to a defined target structure.

Embodiments comprise competitive aptamers that compete for binding to a target protein as defined herein with aptamers as described herein. Embodiments comprise competitive aptamers that compete for binding to a target protein as defined herein with the aptamers set forth in any one of SEQ ID NOs: 1 to 14 or SEQ ID NOs: 23 to 39, or SEQ ID Nos: 43 to 55, or with aptamers having a nucleic acid sequence having at least 85%, at least 90%, at least 95%, at least 96%, at least 97%, at least 98%, at least 99% sequence identity to the nucleotide sequence of any one of SEQ ID NOs: 1 to 14 or SEQ ID NOs: 23 to 39 or SEQ ID Nos: 43 to 55. Embodiments comprise competitive one or more aptamers that compete for binding to a target protein as defined herein with one or more of the aptamers described above. In some embodiments, competition assays may be used identify a competitive aptamer that competes for binding to a target protein as defined herein. In an exemplary, non-limiting, competition assay, an immobilized target protein as defined herein is incubated in a solution comprising a first labelled aptamer that binds to a target protein as defined herein and a second unlabeled aptamer that is being tested for its ability to compete with the first aptamer for binding to a target protein as defined herein. As a control, an immobilized target protein as defined herein may be incubated in a solution comprising the first labelled aptamer but not the second unlabeled aptamer. After incubation under conditions permissive for binding of the first aptamer to a target protein as defined herein excess unbound aptamer may be removed, and the amount of label associated with immobilized target protein as defined herein measured. If the amount of label associated with immobilized target as defined herein is substantially reduced in the test sample relative to the control sample, then that indicates that the second aptamer is competing with the first aptamer for binding to a target protein as defined herein.

Optimization of Aptamers

Full length aptamer sequences have the capacity to form multiple three dimensional configurations (also referred herein as "shape") at room temperature. These three dimensional configurations are in flux, based on an energy landscape among possible configurations. Structural elements of the aptamers are responsible for binding to the target. In some embodiments, truncation of the aptamer sequences and changing of the sequences to stabilize the structural elements responsible for binding can improve aptamer performance by reducing the energy landscape of the optimized aptamer such that only the configuration that binds to the target is present, or at least by increasing the probability of such configurations (and thus presence over time).

Compositions

Aspects of the disclosure relate to a composition comprising two or more aptamers or combination comprising two or more aptamers. Embodiments relate to a composition or combination comprising two or more aptamers, wherein each of the two or more aptamers are independently selected from an aptamer which comprises or consists essentially of a nucleic acid sequence selected from the group consisting of: SEQ. ID. No: 1; SEQ. ID. No: 2; SEQ. ID. No: 3; SEQ. ID. No: 4; SEQ. ID. No: 5; SEQ. ID. No: 6; SEQ. ID. No: 7; SEQ. ID. No: 8; SEQ. ID. No: 9; SEQ. ID. No: 10; SEQ. ID. No: 11; SEQ. ID. No: 12; SEQ. ID. No: 13; SEQ. ID. No: 14; SEQ. ID. No: 23; SEQ. ID. No: 24; SEQ. ID. No: 25; SEQ. ID. No: 26; SEQ. ID. No: 27; SEQ. ID. No: 28; SEQ. ID. No: 29; SEQ. ID. No: 30; SEQ. ID. No: 31; SEQ. ID. No: 32; SEQ. ID. No: 33; SEQ. ID. No: 34; SEQ. ID. No: 35; SEQ. ID. No: 36; SEQ. ID. No: 37; SEQ. ID. No: 38; SEQ. ID. No: 39; SEQ. ID. No: 43; SEQ. ID. No: 44; SEQ. ID. No: 45; SEQ. ID. No: 46; SEQ. ID. No: 47; SEQ. ID. No: 48; SEQ. ID. No: 49; SEQ. ID. No: 50; SEQ. ID. No: 51; SEQ. ID. No: 52; SEQ. ID. No: 53; SEQ. ID. No: 54; and SEQ. ID. No: 55; or an aptamer comprising or consisting essentially of a nucleic acid sequence which has at least 90%, e.g. 95%, 96%, 97%, 98%, 99% sequence identity with any of SEQ. ID. No. 1 to 14, 23 to 39 and 43 to 55.

Embodiments relate to a composition or combination comprising two or more aptamers wherein one of the two or more aptamers comprises or consists essentially of a nucleic acid sequence as set forth in SEQ. ID. No. 55 and the composition or combination further comprises one or more aptamers which comprise or consist essentially of a nucleic acid sequence as set forth in SEQ. ID. No. 1 to 14, 23 to 39 and 43 to 54.

Embodiments relate to a composition or combination comprising three or more aptamers, wherein each aptamer is independently selected from an aptamer which comprises or consists essentially of a nucleic acid sequence as set forth in SEQ. ID. No. 1 to 14 and 23 to 39 and 43 to 55.

Embodiments relate to a composition or combination which comprises or consists essentially of a nucleic acid sequence as set forth in SEQ. ID. No. 55 and which further comprises two or more aptamers which are independently selected from an aptamer which comprises or consists essentially of a nucleic acid sequence as set forth in SEQ. ID. No. 1 to 14, 23 to 39 and 43 to 54.

Embodiments relate to a composition or combination of three or more aptamers, wherein each aptamer comprises or consists essentially of a nucleic acid sequence as set forth in 1 to 14, 23 to 39 and 43 to 55 or an aptamer comprising or consisting essentially of a nucleic acid sequence which has at least 90%, e.g. 95%, 96%, 97%, 98%, 99% sequence identity with any of SEQ. ID. No. 1 to 14, 23 to 39 and 43 to 55.

Embodiments relate to a composition or combination comprising two or more aptamers wherein one of the two or more aptamers comprises or consist essentially of a nucleic acid sequence as set forth in SEQ. ID. No. 1 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 2 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 3 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 4 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 5 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 6 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 7 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 8 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 9 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 10 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 11 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 12 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 13 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 14 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 23 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 24 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 25 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 26 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 27 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 28 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 29 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 30 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 31 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 32 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 33 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 34 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 35 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 36 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 37 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 38 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 39 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 43 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 44 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 45 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 46 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 47 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 48 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 49 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 50 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 51 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 52 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 53 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 54 and optionally wherein a second of the two or more aptamers comprises or consist essentially of a nucleic acid sequence as set forth in SEQ. ID. No. 55.

Embodiments relate to a composition or combination which comprise the following aptamers: CotE H2.1.2 (SEQ ID NO: 30); CotE D2.1 (SEQ ID NO: 31); CotA C1.1 (SEQ ID NO: 33); and CotEC Chitinase (SEQ ID NO: 36).

Support

In some embodiments, the target peptide or protein is attached to a support. In a non-limiting example, the support may be a solid support. Non-limiting examples of a solid support include a membrane or a bead. In some embodiments, the support may be a two-dimensional support. A non-limiting example of a two-dimensional support is a microplate. In some embodiments, the support may be a three-dimensional support. A non-limiting example of a three-dimensional support is a bead. In some embodiments, the support may comprise at least one magnetic bead.

In some embodiments, the protein comprises a polyhistidine tag (His tag) tag (e.g. hexa-histidine tag) at its N- or C-termini. For example, the protein can be a recombinant protein having Histidine residues at its C-terminus or its N-terminus. In some embodiments, the His-tagged protein can be immobilized onto a support carrying a histidine binding agent. For example, the His-tagged protein can be immobilized to a support having nickel nitrilotriacetic acid (Ni-NTA).

In some embodiments, the support may comprise at least one nanoparticle. A non-limiting example of a nanoparticle is a gold nanoparticle or the like. In yet further embodiments, the support may comprise a microtiter or other assay plate, a strip, a membrane, a film, a gel, a chip, a microparticle, a nanofiber, a nanotube, a micelle, a micropore, a nanopore, or a biosensor surface. In some embodiments, the biosensor surface may be a probe tip surface, a biosensor flow-channel, or similar.

In some embodiments, the support comprises a membrane. Non-limiting examples of a membrane include a nitrocellulose, a polyethylene (PE), a polytetrafluoroethylene (PTFE), a polypropylene (PP), a cellulose acetate (CA), a polyacrylonitrile (PAN), a polyimide (PI), a polysulfone (PS), a polyethersulfone (PES) membrane or an inorganic membrane comprising aluminum oxide ($Al_2O_3$), silicon oxide ($SiO_2$), and/or zirconium oxide ($ZrO_2$). Non-limiting examples of materials from which a support may be made include inorganic polymers, organic polymers, glasses, organic and inorganic crystals, minerals, oxides, ceramics, metals, especially precious metals, carbon, and semiconductors. In some embodiments, the organic polymer is a polymer based on polystyrene. Biopolymers, including but not limited to cellulose, dextran, agar, agarose and Sephadex, which may be functionalized in particular as nitrocellulose or cyanogen bromide Sephadex, may be polymers in a support.

Detectable Labels

In some embodiments, the aptamers of the disclosure are used to detect and/or quantify the amount of a target as defined herein in a sample. Typically, the aptamers comprise a detectable label. Any label capable of facilitating detection and/or quantification of the aptamers may be used herein. Non-limiting examples of detectable labels are described below.

In some embodiments, the detectable label is a fluorescent moiety, e.g. a fluorescent compound (also referred herein as fluorophore). In some embodiments, the aptamer comprises a fluorescent and a quencher compound. Fluorescent and quencher compounds are known in the art. See, for example, Mary Katherine Johansson, Methods in Molecular Biol. 335: Fluorescent Energy Transfer Nucleic Acid Probes: Designs and Protocols, 2006, Didenko, ed., Humana Press, Totowa, NJ, and Marras et al., 2002, Nucl. Acids Res. 30, e122 (incorporated by reference herein).

In some embodiments, the detectable label is FAM. In some embodiments, the FAM-label is conjugated to the 5' end or the 3' end of the aptamer. One of ordinary skill in the art would understand that the label may be located at any suitable position within the aptamer.

In some embodiments, the aptamer comprises a FAM fluorophore at its 5' end. In some embodiments, the aptamer is synthesized by incorporating phosphoramidite one at a time into the nucleic acid chain and the FAM-labeled phosphoramidite is incorporated through the synthesis process. In some embodiments, the FAM fluorophore is attached at the 5' end of the aptamer via a linker. In some embodiments, the detectable label is attached to an aptamer described herein via a moiety selected from a thiol group, an amine group, an azide, six-carbon linker, and an aminoallyl group and combinations thereof. In some embodiments, the FAM label can be incorporated into the aptamer using a forward primer with a FAM on the 5' end. In some embodiments, the aptamer can be prepared by solid phase synthesis with the FAM label already in place, attached to the 5' end as in the primer.

Moieties that result in an increase in detectable signal when in proximity of each other may also be used herein, for example, as a result of fluorescence resonance energy transfer ("FRET"); suitable pairs include but are not limited to fluorescein and tetramethylrhodamine; rhodamine 6G and malachite green, and FITC and thiosemicarbazole, to name a few.

In some embodiments, the detectable label is and/or comprises a moiety selected from at least one of the following non-limiting examples: a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, and a liposome.

In some embodiments, the detectable label is a fluorescent protein such as Green Fluorescent Protein (GFP) or any other fluorescent protein known to those skilled in the art.

In some embodiments, the detectable label is an enzyme. For example, the enzyme may be selected from horseradish peroxidase, alkaline phosphatase, urease, $\beta$-galactosidase or any other enzyme known to those skilled in the art.

In some embodiments, the nature of the detection will be dependent on the detectable label used. For example, the label may be detectable by virtue of its color e.g. gold nanoparticles. A color can be detected quantitatively by an optical reader or camera e.g. a camera with imaging software.

In some embodiments, the detectable label is a fluorescent label e.g. a quantum dot. In such embodiments, the detection means may comprise a fluorescent plate reader, strip reader or similar, which is configured to record fluorescence intensity.

In some embodiments in which the detectable label is an enzyme label, non-limiting detection means may, for example, be colorimetric, chemiluminescence and/or electrochemical (including, but not limited to using an electrochemical detector). Electrochemical sensing may be through conjugation of a redox reporter (including, but not limited to methylene blue or ferrocene) to one end of the aptamer and a sensor surface to the other end. A change in aptamer conformation upon target binding may change the distance between the reporter and sensor to provide a readout.

In some embodiments, the detectable label may further comprise enzymes, including but not limited to, horseradish peroxidase (HRP), Alkaline phosphatase (APP) or similar, to catalytically turnover a substrate to give an amplified signal.

Embodiments comprise a complex (e.g. conjugate) comprising aptamers of the disclosure and a detectable molecule. Typically, the aptamers of the disclosure are covalently or physically conjugated to a detectable molecule.

In some embodiments, the detectable molecule is a visual, optical, photonic, electronic, acoustic, opto-acoustic, mass, electrochemical, electro-optical, spectrometric, enzymatic, or otherwise physically, chemically or biochemically detectable label.

In some embodiments, the detectable molecule is detected by luminescence, UV/VIS spectroscopy, enzymatically, electrochemically or radioactively. Luminescence refers to the emission of light. For example, photoluminescence, chemiluminescence and bioluminescence are used for detection of the label. In photoluminescence or fluorescence, excitation occurs by absorption of photons. Exemplary fluorophores include, but are not limited to, bisbenzimidazole, fluorescein, acridine orange, Cy5, Cy3 or propidium iodide, which can be covalently coupled to aptamers, tetramethyl-6-carboxyrhodamine (TAMRA), Texas Red (TR), rhodamine, Alexa Fluor dyes (et al. Fluorescent dyes of different wavelengths from different companies).

In some embodiments, the detectable molecule is a colloidal metallic particle, including but not limited to a gold nanoparticle, colloidal non-metallic particle, quantum dot, organic polymer, latex particle, nanofiber (carbon nanofiber, as a non-limiting example), nanotube (carbon nanotube, as a non-limiting example), dendrimer, protein or liposome with signal-generating substances. Colloidal particles may be detected colorimetrically.

In some embodiments, the detectable molecule is an enzyme. In some embodiments, the enzyme may convert substrates to colored products. Examples of the enzyme include but are not limited to peroxidase, luciferase, 8-galactosidase or alkaline phosphatase. For example, the colorless substrate X-gal is converted by the activity of 8-galactosidase to a blue product whose color is visually detected.

In some embodiments, the detection molecule is a radioactive isotope. The detection may also be carried out by means of radioactive isotopes with which the aptamer is labelled, including but not limited to $^3H$, $^{14}C$, $^{32}P$, 33P, 35S or $^{125}I$. In some embodiments, scintillation counting may be conducted, and thereby the radioactive radiation emitted by the radioactively labelled aptamer target complex is measured indirectly. A scintillator substance is excited by the isotope's radioactive emissions. During the transition of the scintillation material, back to the ground state, the excitation energy is released again as flashes of light, which are amplified and counted by a photomultiplier.

In some embodiments, the detectable molecule is selected from digoxigenin and biotin. Thus, the aptamers may also be labelled with digoxigenin or biotin, which are bound for example by antibodies or streptavidin, which may in turn carry a label, such as an enzyme conjugate. The prior covalent linkage (conjugation) of an aptamer with an enzyme can be accomplished in several known ways.

In some embodiments, detection of aptamer binding may also be achieved through labelling of the aptamer with a radioisotope in an RIA (radioactive immunoassay), preferably with $^{125}I$, or by fluorescence in a FIA (fluoroimmunoassay) with fluorophores. In some embodiments, the fluorophore is fluorescein or fluorescein isothiocyanate (FITC).

Embodiments comprise methods for detecting the presence, absence or amount of a target as defined herein in a sample. In the methods, the sample may be interacted (i.e. contacted) with an aptamer as described herein. For example, the sample and aptamers as described herein may be incubated under conditions sufficient for at least a portion of the aptamer to bind to a target as defined herein in the sample.

A person skilled in the art will understand that the conditions required for binding to occur between the aptamers described herein and a target as defined herein. In some embodiments, the sample and aptamer may be incubated at temperatures between about 4° C. and about 40° C. In some embodiments, the sample and aptamer may be incubated at temperatures between about 20° C. and about 37° C. In some embodiments, the sample and aptamer may be incubated at or about 22° C. The incubation temperature may be selected from the range of 4° C. to less than 20° C., 20° C. to less than 22° C., 22° C. to less than 24° C., 24° C. to less than 26° C., 26° C. to less than 28° C., 28° C. to less than 30° C., 30° C. to less than 32° C., 32° C. to less than 34° C., 34° C. to less than 36° C., 36° C. to 37° C., and 37° C. to 40° C. In some embodiments, the sample and aptamer may be diluted to different concentrations (e.g. at least about 1%, 5%, 10%, 20%, 25%, 30%, 40%, 50%, 60%, 70% 80% v/v or more) with a buffer (exemplary buffers include but are not limited to PBS). The diluted concentrations may be selected from the range of 1% to less than 5%, 5% to less than 10%, 10% to less than 20%, 20% to less than 30%, 30% to less than 40%, 40% to less than 50%, 50% to less than 60%, 60% to less than 70%, 70% to less than 80%, or 80% to less than 90%. In some embodiments, the aptamer concentration before dilution may be from 100 nM to 50 µM. In some embodiments, the aptamer concentration before dilution may be selected from the range of 100 nM to 500 nM, 500 nM to 1 µM, 1 µM to 2 µM, 2 µM to 5 µM, 5 µM to 1 µM, 10 µM to 15 µM, 15 µM to 20 µM, 2 µM to 30 µM, 30 µM to 4 µM, 40 µM to 50 µM, 50 µM to 60 µM, 60 µM to 70 µM, 70 µM to 80 µM, 8 µM to 90 µM, 90 µM to 100 µM. In some embodiments, the aptamer concentration before dilution may be a concentration selected from the ranges described herein in. The selected value may be selected from 0.1 µM increment concentrations in a range herein. In some embodiments, the aptamer concentration before dilution may be 2 µM. In some embodiments, the sample and aptamer may be incubated whilst shaking and/or mixing. In some embodiments, the sample and aptamer are incubated for at least 1 minute, at least 5 minutes, at least 15 minutes, at least 1 hour, or more. The sample and aptamer may be incubated for 1 minute to less than 5 minutes, 5 minutes to less than 15 minutes, 15 minutes to less than one hour, one hour to less than 24 hours, 24 hours to less than 48 hours.

In some embodiments, binding of the aptamer and a target as defined leads to formation of an aptamer-target complex. The binding or binding event may be detected, for example, visually, optically, photonically, electronically, acoustically, opto-acoustically, by mass, electrochemically, electro-optically, spectrometrically, enzymatically or otherwise chemically, biochemically or physically as described herein.

The binding of aptamer and the target may be detected using any suitable technique. As discussed above, for example, binding of the aptamer and the target may be detected using a biosensor. In some embodiments, binding of the aptamer and the target is detected using the non-limiting examples of SPR, RIfS, BLI, LFD or ELONA as described herein.

In some embodiments, the aptamer can be attached to the surface of the biosensor using a biotin group. In some embodiments, the biotin group is attached at the 5' end or the 3' end of the aptamer. In some embodiments, the surface of the biosensor has an avidin/streptavidin attached thereto and the immobilization of the aptamer to the surface of the biosensor is via biotin-avidin interaction. In some embodiments, the surface of the biosensor is coated with avidin/streptavidin.

In some embodiments, the aptamer is linked to a fluorescent moiety. In some embodiments, the aptamer is an aptamer conjugate comprising an aptamer conjugated with a fluorescent moiety. In some embodiments the fluorophore is at the 5' end or the 3' end of the aptamer. In some embodiments, the aptamer is associated with an antisense oligonucleotide having a fluorophore. In some embodiments the fluorophore is at the 5' end or the 3' end of the aptamer. In some embodiments the antisense oligonucleotide is complementary to the 5' end or 3' end of the aptamer. In some embodiments, the fluorophore is at the 5' end or the 3' end of the antisense oligonucleotide.

In some embodiments, the aptamers are modified to form secondary and/or tertiary conformation to improve the binding affinity of the aptamer to the target molecule.

It should be appreciated that a given aptamer may exist in dynamic equilibrium among many possible shapes or conformations. These structures can be in flux amongst each other. The binding affinity of the aptamer to the target protein is dependent on the structure of the aptamers. In some embodiments, the aptamer structure comprises one or more stem and loop.

To optimize binding effectiveness of a given structure to a target protein, it is desirable if the structure of the selected aptamer is not in flux with other structures (for example in different environments) but is the structure which is predominantly present. As such, although the aptamers are selected using an affinity-based selection assay as described herein, further optimization may be required to achieve the desired binding affinity to the target protein. The predicted conformation(s)/structure(s) of each aptamer can be obtained in silico from the primary sequence. In some embodiments, the primary structure of the aptamers can be engineered (e.g. substitution, deletion) to stabilize the secondary structures or tertiary structures. In some embodiments, the aptamers can be truncated to stabilize the secondary structures.

In some embodiments the aptamers are selected using an affinity-based selection assay, the predicted conformations is obtained in silico, the primary sequence is optimized (e.g. truncation/deletion, substitutions, etc.) so that the optimized aptamer exhibits the optimized conformation and is stabilized. The resulting optimized aptamers have fewer structures that are in flux, or exhibit a range or difference among structures in flux that is less than the non-optimized aptamers. These optimized aptamers can be retested for binding effectiveness in order to determine whether the structure that was stabilized is the desired structure that binds to the target protein.

An aptamer may have a secondary structure having at least two complementary regions of the same nucleic acid strand that base-pair to form a double helix (referred to herein as a "stem"). A stem as described herein may be referred to by the position, in a 5' to 3' direction on the aptamer, of the 5' side of the stem (i.e., the stem sequence closer to the 5' terminus of the aptamer), relative to the 5' side of additional stems present on the aptamer.

For example, stem 1 may refer to the stem sequence that is closest to the 5' terminus of the aptamer, its complementary stem sequence, or both stem sequences collectively. Similarly, stem 2 may refer to the next stem sequence that is positioned 3' relative to stem 1, its complementary stem sequence, or both stem sequences collectively. In some cases, the aptamers of the disclosure have one or more stems. For example, the aptamers of the disclosure can have 1, 2, 3 or ore stems. Each additional stem may be referred to by its position, in a 5' to 3' direction, on the aptamer, as described above. For example, stem 2 may be positioned 3' relative to stem 1 on the aptamer, stem 3 may be positioned 3' relative to stem 2 on the aptamer, and so on. A stem may be adjacent to an unpaired region. An unpaired region may be present at a terminus of the aptamer or at an internal region of the aptamer.

A stem as described herein may be referred to by its position in a 5' to 3' direction on the aptamer. A stem as described herein may be referred to by its length (1, 2, 3 4, 5, 6 or more base pairs). For example, stem (4f) refers 5' side of a 4 base pairs stem structure. Stem (4r) refers 3' side of a 4 base pairs stem structure.

As used herein, the term "loop" generally refers to an internal unpaired region of an aptamer. The term "loop" generally refers to any unpaired region of an aptamer that is flanked on both the 5' end and the 3' end by a stem region. In some cases, a loop sequence may be adjacent to a single base-paired stem, such that the loop and stem structure together resemble a hairpin. In such cases, generally the primary sequence of the aptamer contains a first stem sequence adjacent to the 5' end of the loop sequence and a second stem sequence adjacent to the 3' end of the loop sequence; and the first and second stem sequences are complementary to each other.

A loop as described herein may be referred to by its position in a 5' to 3' direction on the aptamer. A loop as described herein may be referred to by its length (1, 2, 3 4, 5, 6 or more nucleotides). For example, a loop (4) refers to a loop structure having 4 nucleotides.

The term "stem-loop" as used herein generally refers to the secondary structure of an aptamer of the disclosure having at least one stem and at least one loop. In some cases, a stem-loop secondary structure includes structures having two stems, which may include a terminal stem, an internal loop, an internal stem, and a terminal loop. A "terminal stem" as used herein generally refers to a stem that encompasses both the 5' and/or 3' terminus of the aptamer. In some cases, a "terminal stem" is bordered at one or both termini by a "tail" comprising one or more unpaired nucleotides. For example, a terminal stem present in the aptamer may be bordered by a tail of one or more unpaired nucleotides (or other structures) at its 5' end. Similarly, a terminal stem present in the aptamer may be bordered by a tail of one or more unpaired nucleotides (or other structures) at its 3' end. In some cases, a stem-loop secondary structure includes structures having more than two stems. Unless otherwise stated, when an aptamer includes more than one stem and/or more than one loop, the stems and loops are numbered consecutively in ascending order from the 5' end to the 3' end of the primary nucleotide sequence.

In some embodiments, the structure formed starting with a double stranded stem at position 17 of SEQ ID NO: 14 and ending with another double stranded stem at position 63 of SEQ ID NO: 14 is suspected of being the core structure enabling this aptamer to bind to the CdeM target. This structure could be described as: Loop(3)/Stem(4f)/Loop(5)/Stem(4r)/Loop(5)/Stem(2f)/Loop(1)/Stem(2f)/Loop(1)/Stem(5f)/Loop(5)/Stem(5r)/Loop(1)/Stem(2r)/Loop(1)/Stem(2r)/Loop(3).

Where the term stem refers to a double stranded structure and loop refers to a single stranded structure, the terms 'f' and 'r' refer to 5' side of a double stranded structure and the 3' side respectively.

Two truncated, optimized aptamers were created—one starting at position 14 and ending at position 66 (named Em2.1, SEQ ID NO: 55), and one starting at position 32 and ending at position 66 (named Em2.2, SEQ ID NO: 43).

The aptamer Em2.1 assumes that all of the stem and loop structures described above are necessary for binding to CdeM protein.

The aptamer Em2.2 was designed based on the assumption that only the following substructure was necessary for binding to CdeM protein: Loop(3)/Stem(2f)/Loop(1)/Stem(2f)/Loop(1)/Stem(5f)/Loop(6)/Stem(5r)/Loop(1)/Stem(2r)/Loop(1)/Stem(2r)/Loop(3).

In some embodiments, the aptamer of the disclosure may have one or more stem and one or more loops as depicted in FIG. 1A-FIG. 26, for example.

The structure of the nucleic acid molecule may be shown by way of structural characters. The structural character may be indicative of a structural attribute, i.e., paired or unpaired, of the corresponding nucleotide. For each structural character of a paired character type there will be a corresponding structural character of a complementary paired character type in the structure string. Thus, the structure string may include a plurality of structural characters for each of the character types to define the structure of the nucleic acid molecule. For example, the character can be a three letter alphabet. For example, the characters can be the dot-bracket notation used for RNA consisting in a balanced parentheses string composed by a three-character alphabet {.,(,)}, that can be unambiguously converted in the RNA secondary structure (see for example, Mattei E. et al., Nucleic Acids Res. 2014 Jun. 1; 42(10): 6146-6157). Its characters code for an unpaired base '.', an open base pair (BP) '(' and a closed BP ')'.

For example, for sequence CTCAATGCCTTCCATTCACCTACCGAGCTAAGCGTTCGACTTAGGTCTGTACT (SEQ ID NO: 55) the code will be
. . . (((( . . . )))) . . . (((.(.(((( . . . ))))).)).)) . . .

In some embodiments, the aptamer is an aptamer beacon that undergoes a conformational change when the aptamer binds to the target protein and the detection of the binding of the aptamer to the target protein relies on the conformational change of the aptamer.

In some embodiments, the aptamer conjugate is an aptamer comprising a fluorescent moiety at a first end of the aptamer and a quencher moiety at a second end of the aptamer. In some embodiments, the aptamer comprises a loop, a first nucleic acid segment that is complementary to a second nucleic acid segment, wherein the first segment and the second segment forms a stem portion when the first segment and the second segment are hybridized, wherein the first segment of the aptamer comprises a fluorophore and the second segment of the aptamer comprises a quencher.

In some embodiments, antisense oligonucleotides can be designed to hybridize to the first segment, the second segment or combination thereof and to disrupt the stem and loop structure of the aptamers. For example, the antisense oligonucleotides can be complementary to the 5' end, the 3' end, the 5' end and the 3' end of or any relevant sequence of the aptamer. In some embodiments, two antisense oligonucleotides are provided, wherein the first antisense oligonucleotide comprises a fluorophore and hybridizes to the first segment of the aptamer, the second antisense comprises a quencher and hybridizes to the second segment of the aptamer.

In some embodiments, the quencher comprises a "dark" quencher. In some embodiments, the quencher comprises a Black Hole Quencher® (BHQ). For example, the 3' end of the antisense oligonucleotides can be linked to a Black Hole Quencher®.

In some embodiments, the antisense oligonucleotides act competitively with the binding of the aptamer to the target protein.

In some embodiments, upon binding of the aptamer to the target protein, the aptamer undergoes a conformation change, altering the distance between the fluorophore and the quencher, resulting in the emission of a fluorescent signal.

In some embodiments, two or more different aptamers are provided configured to bind to two or more different target proteins in a sample, each aptamer comprising a different fluorophore.

Kits

Embodiments also provide a kit for detecting and/or quantifying *C. difficile*, wherein the kit comprises one or more aptamers as described herein. Typically, the kit also comprises a detectable molecule as described herein.

Embodiments provide a kit that further comprises a light source as described herein. In some embodiments, the kit may further comprise a bandpass filter as described herein. In some embodiments, the kit may comprise viewing goggles or glasses or the like as described herein. In some embodiments, the kit comprises:

a) A solution comprising aptamers having a detection molecule conjugated thereto e.g. a fluorophore capable of emitting at a wavelength of between about 485-515 nm. In some embodiments, the fluorophore is capable of emitting at a wavelength with a peak of 517 and being excited at a peak of between about 490-505 nm. In some embodiments, the fluorophore is capable of being excited at a peak of 495 nm. In some embodiments the fluorophore is capable of emitting at a wavelength of about 505 nm:

b) A light source. In some embodiments, the light source produces light having a wavelength of between about 485-515 nm. In some embodiments, the light source produces light having a wavelength of between about 490-505 nm:

c) A bandpass filter. In some embodiment, the bandpass filter is a 590 nm bandpass filter; in some embodiments, the bandpass filter is about 590 nm; and d) Viewing goggles. In some embodiments, the viewing goggles are orange viewing goggles. In some embodiments, the viewing goggles have a bandpass filter. In some embodiments, the viewing goggles have a BP590 bandpass filter.

e) Circular polarizing filter. In some embodiments the base fluorescence level (fluorescence observed in the absence of spores is visible with the viewing goggles but not through the combination of the viewing goggles and the circular polarizing filter. The fluorescence in the presence of the spores is visible through both the viewing goggles and the circular polarizing filter.

In some embodiments, the kit may further comprise a bandpass filter as described herein. In some embodiments, the kit may comprise viewing goggles or glasses or the like as described herein. In some embodiments, the kit comprises:

a) A solution comprising aptamers having a detection molecule conjugated thereto e.g. a fluorophore capable of emitting at a wavelength of between about 485-515 nm; and graphene oxide. In some embodiments, the fluorophore is capable of emitting at a wavelength with a peak of 517 and being excited at a peak of between about 490-505 nm. In some embodiments, the fluorophore is capable of being excited at a peak of 495 nm. In some embodiments the fluorophore is capable of emitting at a wavelength of about 505 nm;

b) A light source. In some embodiments, the light source produces light having a wavelength of between about 485-515 nm. In some embodiments, the light source produces light having a wavelength of between about 490-505 nm;

c) A bandpass filter. In some embodiment, the bandpass filter is a 590 nm bandpass filter: in some embodiments, the bandpass filter is about 590 nm; and d) Viewing goggles. In some embodiments, the viewing goggles are orange viewing goggles. In some embodiments, the viewing goggles have a bandpass filter. In some embodiments, the viewing goggles have a BP590 bandpass filter.

e) Circular polarizing filter. In some embodiments the base fluorescence level (fluorescence observed in the absence of spores is visible with the viewing goggles but not through the combination of the viewing goggles and the circular polarizing filter. The fluorescence in the presence of the spores is visible through both the viewing goggles and the circular polarizing filter.

In some embodiments, the kit further comprises instructions for use in accordance with any of the methods described herein.

The kit may comprise further components for the reaction intended by the kit or the method to be carried out, for example components for an intended detection of enrichment, separation and/or isolation procedures. Non-limiting examples include buffer solutions, substrates for a color reaction, dyes or enzymatic substrates. In the kit, the aptamer may be provided in a variety of forms, including but not limited to being pre-immobilized onto a support (e.g. solid support), freeze-dried, or in a liquid medium.

A kit herein may be used for carrying out any method described herein. It will be appreciated that the parts of the kit may be packaged individually in vials or in combination in containers or multi-container units. Typically, manufacture of the kit follows standard procedures which are known to the person skilled in the art. USES In some embodiments, method of detecting *C. difficile*, e.g. *C. difficile* spores, using the aptamers described herein, is provided. The method may comprise interacting the sample with an aptamer described herein and detecting the presence, absence, and/or amount of *C. difficile*. The method may be for detecting the presence, absence, and/or amount of *C. difficile* spores in a sample using a detection method including, but not limited to, photonic detection, electronic detection, acoustic detection, electrochemical detection, electro-optic detection, enzymatic detection, chemical detection, biochemical detection, or physical detection.

In some embodiments, the method is for detecting the presence, absence, or amount of *C. difficile*, e.g. *C. difficile* spores, on a surface. In some embodiments, the aptamers and method provided may have utility in detecting *C. difficile* on surfaces in hospital and healthcare facilities. Non-limiting examples of surfaces may include bed linen, medical equipment, clothing, floors, walls, and the like. In a non-limiting example, the aptamers of the present disclosure may be used to detect the presence, absence, and/or amount of *C. difficile*, e.g. *C. difficile* spores, on a patient's body.

In some embodiments, the aptamers may be for use in detecting *C. difficile*, e.g. *C. difficile* spores, in a sample previously obtained from a surface as described herein.

In some embodiments, the aptamers of the disclosure may be used to detect whole *C. difficile* spores. In some embodiments, the aptamers may be used to detect *C. difficile* proteins as described herein.

In some embodiments, the aptamers may be used to detect *C. difficile* spores or proteins in real-time. Following detection and/or quantification of *C. difficile*, action may be taken to kill and/or remove the spores. Non-limiting examples of such action may include washing or destruction of bed linen, and/or cleaning of surfaces including but not limited to medical equipment, beds, walls, floors, and the like. Measures such as isolation of patients and enforcement of stringent hygiene protocols may also be taken.

In some embodiments, the aptamers of the disclosure are for use in a method of detecting the presence or absence of *C. difficile* spores or *C. difficile* spore proteins using a light source. In certain embodiments, there is provided a method of detecting the presence or absence of *C. difficile* spores comprising:

Providing an aptamer conjugate comprising an aptamer described herein, wherein the aptamer is conjugated to a detectable moiety. In some embodiments, the detectable moiety is a fluorescent moiety;

Contacting the aptamer conjugate with a location of interest, wherein the location of interest may comprise *C. difficile* spores;

Incubating the aptamer conjugate at the location of interest for a predetermined period of time to allow the aptamer conjugate to bind to a *C. difficile* spore if present;

Optionally washing the location of interest to remove any unbound aptamer conjugates; and Visualizing the aptamer conjugate bound to a *C. difficile* spore.

Graphene Oxide

In some embodiments, a composition comprising one or more aptamer conjugates and graphene oxide (GO) is provided. Graphene oxide self-assembles into two-dimensional sheets in an aqueous environment (See He et al., Chemical Physical Letters, Volume 287, Issues 1-2, 24 Apr. 1998, Pages 53-56). See FIG. 32. In some embodiments, the composition is a suspension. In some embodiments, the composition comprises a buffer. In some embodiments, the composition further comprises a blocking agent to minimize or eliminate non-specific binding. In some embodiments, the blocking agent includes, but is not limited to, polyethylene glycol (PEG) (including polymeric chain of various lengths), Tween (e.g., Tween 20, Tween 40, Tween 80), nucleic acid (e.g. oligonucleotides, sheared salmon sperm DNA), polyvinyl pyrrolidine or any blocking agent known in the art.

In some embodiments, are provided fluorescently labeled aptamers in combination with graphene oxide to enable surface detection of *Clostridium difficile*. Without being bound to any particular theory, the labeled aptamers bind aspecifically to graphene oxide (GO) and the proximity of the fluorophore label on the aptamer to the GO surface results in fluorescence quenching. The introduction of a mixture of aptamer and graphene oxide to a target molecule or a sample comprising a target molecule that the aptamer binds to results in a change in the equilibrium formed between the aptamer and GO, such that less aptamer is bound to GO, and more aptamer is bound to the target. The fluorescence of the aptamer bound to the target is not quenched, or at least not quenched to the same degree that it was when the aptamer was bound to GO.

In some embodiments, this aptamer/GO mixture can be used for the detection of a visual change on a surface. In some embodiments, no fluorescence is visible/detected when an aptamer/GO equilibrated mixture is sprayed onto a surface where no *Clostridium difficile* spores are present. In some embodiments, fluorescence is observed/detected in the presence of *C. difficile* spores.

An equilibrated mixture of aptamer/GO refers to a mixture of aptamer/GO having a relative fluorescence that does not change over time. In some embodiments, this equilibration can be achieved 24 hours after the aptamer(s) and GO are mixed.

In some embodiments, the composition comprises one or more different aptamers having a binding affinity to the same *Clostridium difficile* spore protein. In some embodiments, the composition comprises one or more different aptamers having a binding affinity to one or more different *Clostridium difficile* spore proteins. In some embodiments, each aptamer can comprise a different detectable moiety.

In some embodiments, the detectable moiety comprises a fluorescent moiety and visualization comprises visualizing and/or measuring the level of fluorescence. In some embodiments, the detectable moiety comprises biotin having a binding affinity for streptavidin protein conjugates, such as streptavidin/horseradish peroxidase and visualization comprises visualizing using a colorimetric reaction. In some embodiments, the detectable moiety gold nanoparticles conjugated to the aptamer and visualization comprises visualizing using a colorimetric assay. In some embodiment, the detectable moiety comprises a quantum dot, that fluoresces.

Graphene oxide is prepared from graphene by the exposure of graphene to oxygen donor sources such as $NaNO_3$, $H_2SO_4$, $H_3PO_4$ and $KMnO_4$. In some embodiments, the graphene oxide comprises an oxygen content of about 36%. In some embodiments, the graphene oxide comprises an oxygen content greater than 36%. In some embodiments, the graphene oxide comprises an oxygen content of about 44-45%.

The graphene oxide once formed self-assembles into two-dimensional sheets of varying sizes. In some embodiments, the total surface area of the graphene oxide is about 736.6 $m^2/g$. In some embodiments, the total surface area of the graphene oxide is a function of the amount of graphene oxide used. In some embodiments, the amount of graphene oxide used is optimized based on the level of fluorescence quenching. Without being bound to the theory, determination of the appropriate amount of GO to be used for a desired level of aptamer quenching can be a consideration of the total surface area of the GO in the solution. In some embodiments, the workable range is defined as a function of the desired quenching range, given the need to visualize fluorescence in the presence of the virus and not in the absence. In some embodiments, a fluorescence level of 150 to 190 relative fluorescence units on a Tecan Safire 2 fluorometer with a GAIN setting of 118 can be employed.

In some embodiments, the graphene oxide is in the form of nanoparticles. In some embodiments, the average size of the nanoparticles is 10 to 500 nm.

Aptamers (APT) adhere to the graphene oxide (GO) sheets based on Van der Waals forces and hydrogen bonds.

In some embodiments, when a detectable moiety such as a fluorescent moiety is conjugated to the aptamer, the fluorescence of the fluorescent moiety is quenched by the association with the graphene oxide surface.

In some embodiments, in the presence of a target surface protein of *Clostridium difficile* spore for which the aptamer binds with a binding affinity greater than binding affinity to the graphene oxide, the aptamer is "displaced" from the graphene oxide surface and becomes bound to the target protein. In some embodiments, the aptamer binds with a binding affinity that is twice, ten, twenty, thirty, forty, fifty, sixty, seventy, eighty, ninety, hundred greater, five hundred, thousand times or more than binding affinity to the graphene oxide. In some embodiments, the aptamer binds with a binding affinity that is between 2 and 1000 fold, between 10 and 1000 fold, between 50 and 1000 fold, between 100 and 1000 fold, between 2 and 100 fold, between 10 and 100 fold, between 50 and 100 fold, between 100 and 200 fold, between 100 and 500 fold, between 100 and 1,000 fold, than binding affinity to the graphene oxide. When the aptamer is "displaced" from the graphene due to its specific binding to the target protein, fluorescence is emitted. A minimum of two times, the most preferred enablement would be 100 fold, an acceptable range would be between 10 and 1000 fold.

Without being bound to the theory, in physical terms, the aptamer is not displaced (dynamically binding and unbinding rapidly) and a relationship between the aptamer and the graphene oxide surface can be described by the following linked differential equations.

$$Dx1=-a*x1*x2+b*x3$$

$$Dx2=-a*x1*x2+b*x3$$

$$Dx3=a*x1*x2-b*x3$$

wherein x1 corresponds to the concentration of aptamer, x2 corresponds to the concentration of graphene oxide, x3 corresponds to the concentration of the complex aptamer-graphene oxide and "D" stands for derivative as a function of time. D is the derivative of their concentrations over time, and 'a' and 'b' are the on and off binding rates for complex formation.

These equations describe the movement of the system towards an equilibrium. At equilibrium, the system is not static, the molecules are still associating and disassociating at the same rate, it is just that the overall measurement of the system results in no changes in expression of fluorescence.

As such, the introduction of a further element [T] for concentration of a target protein that the aptamer binds to, displaces this equilibrium such that the concentration of Aptamer/GO is decreased in relation to the amount of Aptamer/T formed.

As such, a new system of equations can be elaborated as follows:

$$Dx1=-a*x1*x2+b*x3-c*x1*x4+d*x5$$

$$Dx2=-a*x1*x2+b*x3$$

$$Dx3=a*x1*x2-b*x3$$

$$Dx4=-c*x1*x4+d*x5$$

$$Dx5=c*x1*x4-d*x5$$

wherein x1 corresponds to the concentration of aptamer, x2 corresponds to the concentration of graphene oxide, x3 corresponds to the concentration of the complex aptamer-graphene oxide, x4 corresponds to the concentration of target, x5 corresponds to the concentration of the complex between the free target and the aptamer, 'c' and 'd' are the on and off rates for complex formation between the aptamer and the target.

When d/c is a lower number than b/a, equilibrium will shift towards a higher amount of x5 and a lower amount of x3 resulting in the expression of fluorescence.

In some embodiments, the methods provided herein allow for a limit of detection of 25 nM or more.

In some embodiments, the aptamer to target protein ratio may play a role in enhancing the signal at lower concentrations. Without being bound to the theory, this is because at lower concentrations of aptamer, a lower amount of target protein may be needed to make a significant change in recovery (or proportional change). In some embodiments, using lower amount of aptamer may help in detecting concentration lower than about 25 nM, for example about 10 pM or about 100 fM.

In some embodiments, there is provided a method of detecting the presence or absence of *C. difficile* spores comprising:

Providing one or more aptamer conjugates comprising one or more aptamers described herein, wherein the aptamer is conjugated to a detectable moiety.

Combining the aptamer conjugates with a pre-determined concentration of graphene oxide;

Contacting the aptamer conjugates-graphene oxide combination with a sample to be tested;

Visualizing the detectable moiety of the aptamer conjugate bound to a *C. difficile* spore protein.

In some embodiments, the visualizing step comprises imaging the sample. In some embodiments, the visualizing step comprises measuring the level of fluorescence. In some embodiments, the visualizing step comprises comparing the fluorescence level to a negative control sample. In some embodiments, the method does not comprise a washing step.

In some embodiments, the method further comprises the step of incubating the aptamer conjugates with the sample for a predetermined period of time to allow the aptamer conjugate to bind to a *C. difficile* spore if present.

In some embodiments, the sample is contacted first with a blocking agent and subsequently with a with the combination of aptamer conjugates-graphene oxide.

In some embodiments, the sample is a solid surface.

In some embodiments, the sample comprises a surface. In some embodiments, the sample comprises a human, e.g. a patient's body, or a sample obtained from a subject suspected of having or diagnosed with a *Clostridium difficile* infection. In some embodiments, the sample comprises an object located in a hospital environment.

In some embodiments, the methods comprises spraying, immersing, adding an aliquot of the solution directly either by pouring, or swabbing, or with a pipetting device to a sample with the composition comprising one or more aptamer conjugates and graphene oxide. In some embodiments, the methods comprise fogging, vaporizing, or coating, etc.

Visualization

In some embodiments, visualizing the aptamer conjugate comprises illuminating the location with a light source. In some embodiments, the light source produces light at a predetermined wavelength, wherein the predetermined wavelength corresponds to a wavelength of light emitted by the detectable moiety of the aptamer conjugate.

In some embodiments, the step of visualizing the location may be performed in ambient light or in dark conditions.

In some embodiments, the method further comprises filtering the light produced by the light source.

In some embodiments, the method further comprises imaging (e.g. photographing) the location and detecting the presence or absence of *C. difficile* spores.

In some embodiments, the method of detecting *C. difficile* may comprise applying one or more of the aptamers of the disclosure to a location suspected of comprising *C. difficile* spores. Following a predetermined period of time sufficient to permit the aptamer binding to *C. difficile* spores, the location may be washed one or more times to remove any unbound aptamer. The method may then comprise a set of conditions for illuminating the location using a light source.

In some embodiments, the light source may be in the form of a forensic light source. In some embodiments, the light source may be in the form of a Polilight® Flare.

In some embodiments, the light source may be capable of switching between different wavelengths, each wavelength being suited to a specific interchangeable filter. The forensic light source may be in the form of a LED, laser, Pohlight® or the like. In some embodiments, the light source is a handheld light source. In some embodiments, the handheld light source may be a Polilight Flare+2, which is a battery operated, handheld LED light source, available from e.g. Rofin Forensic.

Aptly, each Polilight Flare "torch" may produce light within a specified wavelength range. For example, in some embodiments, the light source may produce light at a wavelength of between about 360 nm-385 nm (UV light). In some embodiments, the light source may produce light at a wavelength of between about 405 nm-420 nm. In some embodiments, the light source may produce light at a wavelength of between about 435 nm-465 nm. In some embodiments, the light source may produce light at a wavelength of between about 485 nm-515 nm. In some embodiments, the light source may produce light at a wavelength of between about 490 nm-505 nm. In some embodiments, the light source may produce light at a wavelength of between about 510 nm-545 mu. In some embodiments, the light source may produce light at a wavelength of between about 530 nm-560 nm. In some embodiments, the light source may produce light at a wavelength of between about 585 nm-605 nm. In some embodiments, the light source may produce light at a wavelength of between about 615 nm-635 nm. In some embodiments, the light source m ay produce light at a wavelength of between about 400 nm-700 nm. In some embodiments, the light source may produce light at a wavelength of between about 835 nm-865 nm. In some embodiments, the light source may produce light at a wavelength of between about 935 nm-965 nm.

In some embodiments, the light source used may be compatible with a detectable molecule conjugated to the aptamer. In some embodiments, the aptamer is conjugated to a detection molecule. In some embodiments, the detection molecule may be a fluorophore which emits in a spectral range which corresponds to the output of the light source. In some embodiments, the aptamer may be conjugated to a fluorophore which emits at; a wavelength of about 505 nm. In some embodiments, the light source produces light having a wavelength of about 505 nm.

In some embodiments, the method may comprise the use of a bandpass filter in combination with the light source. The bandpass filter may be configured to transmit light of a certain wavelength band and reject stray light outside the predetermined wavelength band. In some embodiments, the light source is configured to produce narrow bands of light having center wavelengths of 365 nm, 415 nm, 450 nm, 505 nm, 530 nm, 545 nm, 620 nm, and 850 nm. In some embodiments, the light source is configured to produce narrow bands of light having a center wavelength of 505 nm, in addition to white light wavelengths. In some embodiments, the bandpass filter is a 590 nm bandpass filter.

In some embodiments, the method may further comprise visualizing the location with viewing goggles, glasses, or the like. In some embodiments, the viewing goggles are of a color which corresponds to the color of light produced by the light source and emitted by the detection molecule conjugated to the aptamer. In some embodiments, the goggles are orange and thus are suitable for use in combination with a light source which produces light having a wavelength of between about 485 nm-515 nm, e.g. 505 nm, and an aptamer which comprises a detection molecule that emits at a wavelength of approximately 505 nm.

In some embodiments, the fluorescence can be observed visually. In some embodiments, the fluorescence can be observed with an instrument. In some embodiments, the instrument is a fluorometer. In some embodiments, the fluorometer can be calibrated so as to allow for the observation of the signal at a predetermined wavelength and/or at a predetermined intensity.

In an aspect, the disclosure relates to the development of aptamers which bind to *Clostridium difficile* and methods of using the same. In an aspect, the disclosure relates to aptamers which specifically bind to a *C. difficile* spore. The aptamers may specifically bind to a *C. difficile* protein; e.g. a surface protein. The molecule that an aptamer binds to may be referred to as a target molecule. Further details of the target molecules are provided herein.

Unexpectedly, the present inventors have identified aptamers which are capable of identifying *C. difficile* spores.

In embodiments, the disclosure provides an aptamer capable of specifically binding to a *Clostridium difficile* protein.

In embodiments, the *Clostridium difficile* protein is a surface protein of *Clostridium difficile* spore. In embodiments, the *Clostridium difficile* protein is a spore coat surface protein or an exosporium layer protein.

In embodiments the *Clostridium difficile* protein selected from CdeC, CdeM, CotA, CotE and CotE Chitinase.

In embodiments the *Clostridium difficile* protein is a CdeC protein having an amino acid sequence as set forth in SEQ ID NO: 18.

In embodiments the *Clostridium difficile* protein is a CdeM protein having an amino acid sequence as set forth in SEQ ID NO: 19.

In embodiments the *Clostridium difficile* protein is a CotA, protein having an amino acid sequence as set forth in SEQ ID NO: 15.

In embodiments the *Clostridium difficile* protein is a CotE, protein having an amino acid sequence as set forth in SEQ ID NO: 16.

In embodiments the *Clostridium difficile* protein is a CotE Chitinase protein having an amino acid sequence as set forth in SEQ ID NO: 17.

In embodiments the aptamer comprises or consists of:
a) a nucleic acid sequence selected from any one of the nucleic acid sequences as set forth in any of SEQ ID NOs: 1-14, 27-39, 43-55;
b) a nucleic acid sequence having at least 85%, for example 90%, 95%, 96%, 97%, 98%, or 99% identity with any one of the nucleic acid sequence the nucleic acid sequences as set forth in any of SEQ ID NOs: 1-14, 27-39, 43-55;
c) a nucleic acid sequence having at least about 10 consecutive nucleotides of any one the nucleic acid sequences as set forth in any of SEQ ID NOs: 1-14, 27-39, 43-55;
d) a nucleic acid sequence having at least about 10 consecutive nucleotides of a sequence having at least 85% identity with any one of SEQ ID NOs: 1-14 27-30, 43-55;
e) a nucleic acid sequence of SEQ ID NO: 55;
f) a nucleic acid sequence having a fragment extending from position 28 to position 64 of SEQ ID NO: 5, also known as SEQ ID NO: 23; or
g) a nucleic acid sequence having a fragment extending from position 28 to position 64 of SEQ ID NO: 5, also known as SEQ ID NO: 23 having at least 85% identity with SEQ ID NO: 23.

In embodiments the aptamer is a single stranded DNA aptamer.

In embodiments, there is provided an aptamer that competes for binding to a *Clostridium difficile* protein with the aptamer as described herein.

In embodiments the aptamer comprises a detectable label.

In embodiments the detectable label is and/or comprises a moiety selected from a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, and a liposome. In some embodiments, the detectable label is a fluorophore, a quantum dot, a colloidal metallic particle, or a colloidal non-metallic particle. In some embodiments, the detectable label is attached to an aptamer described herein via a moiety selected from a thiol group, an amine group, an azide and an aminoallyl group and combinations thereof.

In an aspect of the present disclosure, there is provided a complex comprising an aptamer of any preceding claim and a detectable molecule.

In an aspect of the present disclosure, there is provided a composition comprising at least one aptamer, wherein at least one of the aptamers is as described herein wherein the composition optionally comprises at least one of water, salts, one or more buffer herein, a detergent, and BSA. In an aspect of the present disclosure, there is provided a composition comprising at least one aptamer and graphene oxide, wherein at least one of the aptamers is as described herein wherein the composition optionally comprises at least one of water, salts, one or more buffer herein, a detergent, and BSA. In some embodiments, the composition is a solution.

In an aspect of the present disclosure, there is provided a composition comprising at least one aptamer having a nucleic acid sequence as set forth in SEQ ID NO: 1, 2, 3, 4, 5, 6, 7, 8, 9, 10, 11, 12, 13, 14, 23, 24, 25, 26, 27, 28, 29, 30, 31, 32, 33, 34, 35, 36, 37, 38, 39, 43, 44, 45, 46, 47, 48, 49, 50, 51, 52, 53, 54, or 55, wherein the composition optionally comprises at least one of water, salts, one or more buffer herein, a detergent, and BSA.

In an aspect of the present disclosure, there is provided a biosensor or test strip comprising an aptamer as described herein.

In an aspect of the present disclosure, there is provided an apparatus for detecting the presence, absence or level of *Clostridium difficile* in a sample, the apparatus comprising:
i. a support; and
ii. an aptamer as described herein.

In embodiments, the apparatus is for detecting the presence, absence or level of *Clostridium difficile* spores in a sample.

In embodiments, the sample can be a sample previously obtained from a subject suspected of having or diagnosed with a *Clostridium difficile* infection. In embodiments, the sample can be an object located in a hospital environment, for example bedding, furniture, building structures.

In embodiments, the support is a bead, a microtiter or other assay plate, a strip, a membrane, a film, a gel, a chip, a microparticle, a nanoparticle, a nanofiber, a nanotube, a micelle, a micropore, a nanopore or a biosensor surface.

In embodiments, the apparatus is suitable for surface plasmon resonance (SPR), biolayer interferometry (BLI), lateral flow assay and/or enzyme-linked oligonucleotide assay (ELONA).

In an aspect of the present disclosure, there is provided a use of an aptamer a complex, a biosensor or test strip, a composition or apparatus as described herein for detecting, enriching, separating and/or isolating *Clostridium difficile*. In certain embodiments, the use is for specifically detecting, enriching, separating and/or isolating *Clostridium difficile* spores.

In an aspect of the present disclosure, there is provided a method of detecting the presence, absence or amount of *Clostridium difficile* in a sample, the method comprising: interacting the sample with an aptamer, a complex, or a composition as described herein; and detecting the presence, absence or amount of *Clostridium difficile*.

In some embodiments, the method is for detecting the presence, absence or amount of *Clostridium difficile* spores in a sample.

In some embodiments, the presence, absence or amount of *Clostridium difficile* is detected by photonic detection, electronic detection, acoustic detection, electrochemical detection, electro-optic detection, enzymatic detection, chemical detection, biochemical detection or physical detection.

In an aspect of the present disclosure, there is provided a kit for detecting and/or quantifying *Clostridium difficile* the kit comprising an aptamer as described herein.

EXAMPLES

In the following, the disclosure will be explained in more detail by means of non-limiting examples of specific embodiments. In the example experiments, standard reagents and buffers free from contamination are used.

Example 1—Aptamer Selection

Target Information

Aptamers were selected against several protein targets of *C. difficile*. The targets were as follows:
1. CdeC, a protein which has a molecular weight (MW) of 46,000 Da. Stored in a buffer with the following composition:
   20 mM HEPES-Na, pH 7.9, 5% glycerol, 200 mM NaCl, 0.2 mM $CaCl_2$, 0.1% Triton X114
   Concentration: 0.75 mg mL-1
2. CdeM a protein having a MW of 25,000 Da. Storage Buffer: 20 mM HEPES-Na, pH 7.9, 5% glycerol, 200 mM NaCl, 0.2 mM $CaCl_2$), 0.1% Triton X114
   Concentration: 0.50 mg mL-1
3. CotA-His6 a protein with a MW of 34,900 Da Ext. Co: 27695 in water
   Storage Buffer: 20 mM HEPES, 5% glycerol, 200 mM NaCl, 1 mM DTT Concentration: 4.17 mg mL-1
4. rCotE, N281-F712, Molecular Weight: 48,000 Da,
   Storage Buffer: 20 mM HEPES-Na, pH 7.9, 5% glycerol, 200 mM NaCl, 0.2 mM $CaCl_2$), 0.1% Triton X114
   Concentration: ~0.8 mg $mL^{-1}$
5. SPG-HU58. Non-pathogenic spores. Storage buffer: Sterile $dH_2O$
   Concentration: $1 \times 10^7$ CFU pure spores in 0.5 mL sterile water Preparation for Aptamer Selection The protein targets were each analyzed using a Nanodrop to generate a series of UV spectra, to confirm concentration and aggregation state of the targets (data not shown). Analysis of the UV spectra for the supplied CdeC, CdeM and CotE show clear signs of aggregation or multimerization. CotA and CotEC Chitinase show slight signs of aggregation. It is considered that some proteins may multimerize.

In addition, the targets were subjected to a 'Buffer Screen' with a panel of selection buffers. Binding of the aptamer library to beads immobilized with each target or blank beads were compared (data not shown). The buffer for each target which promoted greater interaction between the aptamer library and the target was identified and selected for future use in the selection process.

Non-limiting, exemplary buffers may be broadly similar for all of the targets. In some embodiments, the buffer may be a Tris buffer. In some embodiments, the pH may be approximately 7.4 to 7.6. In some embodiments, the ionic strength may be approximately 100 mM. Non-limiting examples of salts included in the buffer are $MgCl_2$ and $CaCl_2$). In some embodiments, the buffer may comprise detergents, including but not limited to Tween. In some embodiments, the buffer may comprise bovine serum albumin (BSA) or other stabilizers known in the art.

The buffers are as follows:
CdeC—50 mM Tris pH 7.6, 2.5 mM $MgCl_2$, 2.5 mM $CaCl_2$), 85 mM KOAc, 0.01% Tween 20, 0.01% BSA.
CdeM—50 mM Tris pH 7.6, 2.5 mM $MgCl_2$, 2.5 mM $CaCl_2$, 85 mM NaCl, 0.01% Tween 20, 0.01% BSA.
CotA—50 mM Tris pH 7.4, 5 mM $MgCl_2$, 1 mM $CaCl_2$), 77.5 mM NaCl, 4.5 mM KCl, 0.01% Tween 20, 0.01% BSA.
CotE—50 mM Tris pH 7.6, 2.5 mM $MgCl_2$, 2.5 mM $CaCl_2$), 28 mM $K_2SO_4$, 0.01% Tween 20, 0.01% BSA
rCotE Chitinase—50 mM Tris pH 7.4, 5 mM $MgCl_2$, 1 mM $CaCl_2$, 77.5 mM NaCl, 4.5 mM KCl, 0.01% Tween 20, 0.01% BSA.

Polyclonal Aptamer Selection

The selection protocol was broadly as followed:

His-tagged target protein were each loaded on to Ni-NTA coated magnetic beads and incubated for 1 hour in PBS. Loaded beads were washed and quantified, and used in aptamer selection.

The aptamer library was incubated with respective targets for one hour with constant mixing at room temperature in a selection buffer as identified in the buffer screen and shown above.

Target protein and bound aptamers were eluted using imidazole. Recovered material was subsequently purified to remove imidazole and amplified to create the enriched library for the subsequent selection round.

The process was repeated using increasing stringency from one selection round to the next.

The buffer conditions identified in the upfront screens were used for the first two rounds of in vitro selection. Subsequent rounds were conducted using a variety of different selection 'pressures'. The population from the best performing condition in each selection round was taken forward to the subsequent selection round. The amount of aptamer recovered during selection was quantified.

Aptamer library recovery from the target-loaded beads (blue, on left side of each data set) gradually increased with sequential rounds of selection. Any fall in recovery generally coincided with the introduction of an increase in stringency during that round of selection. The best target: negative ratio (recovery from target-loaded beads vs. recovery from blank beads) was obtained in round 7 (R7) for targets CotA, CdeC, CdeM and CotEC Chitinase, and in R10 for target CotE, respectively. Each of these aptamer populations was then taken forward to a biophysical assay to confirm enrichment of target binding species.

Biophysical Characterization

Biolayer Interferometry (BLI) was used to assess the binding of each aptamer population to their respective targets. The target proteins were immobilized on separate Biolayer Interferometry sensor probes. The loaded probes were then incubated with the naïve aptamer library or the respective aptamer populations to monitor and compare the interactions.

BLI was performed at room temperature using the same buffer as those used during the selection. BLI probes were loaded with target protein in 1×PBS for 180 seconds. Subsequently the naïve aptamer library or respective aptamer populations were incubated for 300 seconds. The aptamers were then dissociated for 300 seconds in selection buffer.

The refined aptamer populations that have undergone the aptamer selection process described herein generally had improved binding to their respective targets compared to the unselected naïve library (some better than others). The immobilized targets showed little to no interaction with unrefined naïve aptamer population. Binding was seen between the immobilized targets and the respective refined aptamer populations. Rapid association of the respective aptamer pool was seen for immobilized CotA, CotE and CotEC Chitinase (signals at ~480-780 sec). Both aptamer pools for CdeC and CdeM showed slower association to their respective targets. The bound aptamer populations did not appear to show significant dissociation from their targets (signals at 780-1080 sec).

Spore Selection

The refined aptamer populations described above were taken into 'spore-based selection' using *Clostridium difficile* spores as 'positive target.' *Bacillus subtilis* spores were used as a 'negative target' (counter selection) to reduce non-specific binding to spore surfaces. Four subsequent rounds of spore-based selection (rounds S1-S4) were performed. The amount of aptamer recovered during these selection rounds was quantified.

After 4 consecutive rounds of spore-based selection (S1-S4); the five aptamer populations, selected against CotA, CdeC, CdeM, and CotE, all showed enhanced binding to the *Clostridium difficile* spores ('positive') compared to *Bacillus subtilis* spores ('negative'). This indicated further refinement of each of the aptamer populations in the context of the spore 'coat'.

Selectivity Profiling

The refined aptamer populations isolated against recombinant CotA, CdeC, CdeM, CotE and CotEC Chitinase, and subsequently further refined by spore-based selection; were fluorescently labelled and incubated with either *Clostridium difficile* spores or *Bacillus subtilis* spores. Unbound material was removed by washing, before imaging the spores by epifluorescence microscopy.

Four of the isolated aptamer populations appeared to bind preferentially to the *Clostridium difficile* spores compared to the *Bacillus subtilis* spores. These aptamer populations included CotA, CdeC, CdeM and CotE, respectively.

Conclusion

The reported data shows the following:

Biolayer interferometry data shows that the refined aptamer populations selected against CotA, CdeC, CdeM, CotE and CotEC Chitinase proteins, interacted with their respective immobilized target. Interactions were a result of selection process (not simply through non-specific binding) as the 'Naïve' population did not show such interaction.

Epifluorescence microscopy data showed that four of the aptamer populations had preferential binding to *Clostridium difficile* spores compared to *Bacillus subtilis* spores. These aptamer populations were isolated against CotA, CdeC, CdeM and CotE and subsequently refined by spore-based selection using *C. difficile* spores ('positive') and *B. subtilis* spores ('negative').

Aptamer populations isolated for CotEC Chitinase showed binding to both *Clostridium difficile* and *Bacillus subtilis* spores after 3 rounds of spore-based selection. No binding was seen for *C. difficile* after the 4th spore-based selection round.

Example 2—Monoclonal Aptamer Isolation

The refined pools were taken forwards for monoclonal isolation. All aptamers were purified (after elution) and resuspended and stored in water. Before use in selections or binding assays, aptamers were diluted in a final concentration 1×buffer. Individual aptamer clones were isolated and screened by BLI using aptamer concentrations of 0.5 µM, 1 µM, or 2 µM. Again, the target was immobilized onto a Biolayer Interferometry sensor probe and then incubated with each aptamer clone.

The selected monoclonal aptamers had improved binding to their respective targets compared to the unselected naïve library. The immobilized targets showed little to no interaction with unrefined naïve aptamer population. Binding was seen between the immobilized targets and the respective selected monoclonal aptamers.

Rapid association of the monoclonal aptamers was seen for immobilized CdeM, CdeC, CotE and CotEC Chitinase (signals at ~60-240 sec). The bound monoclonal aptamers did not appear to show significant dissociation from CotEC Chitinase, CotA and CdeC. There was a higher rate of dissociation of the monoclonal aptamer from CdeM and CotE for the specific monoclonal aptamer pools used in this example (signals at ~240-420 sec); however, rapid association for their respective immobilized target protein occurred as described herein.

Both selected monoclonal aptamers for CotA showed slower association to their respective target but very little dissociation of the bound aptamers.

The naïve library control for the CotE aptamers showed a slight association. This was considered to be an anomalous result that has no effect on the integrity of the data.

Biolayer Interferometry showed that the selected monoclonal aptamers selected against CotA, CdeC, CdeM, CotE and CotEC Chitinase proteins, interacted with their respective immobilized target. Interactions are a result of selection process (not simply through non-specific binding) as the 'naïve' population showed no such interaction.

Example 3: Detection

The ability of the CotE H2 aptamer to visualise *Clostridium difficile* SH11 bacterial spores on stainless-steel and gown surfaces, in ambient light and dark conditions was assessed.

Materials and Methods

*Clostridium difficile* purified spore suspensions used in this study are listed in Table 6. *C. difficile* suspensions were provided by SporeGen® and stored at 4° C. upon arrival.

TABLE 6

Test organisms

| | Ribotype | Format | Description | In test concentration (CFUmL−1) |
|---|---|---|---|---|
| *C. difficile* | RT078 (SH11) | Wild type | Purified spore suspension | 1 × 107 ± 5 × 106 |

Test agents used throughout the study are described in Table 7. The CotE H2 aptamer and TbKst buffer were provided by Aptamer Group.

TABLE 7

Test agents

| Test agent name | Format | Description | In-test aptamer concentration (μM) |
|---|---|---|---|
| Negative control 1 | Solid surface | Stainless-steel or gown surface only | N/A |
| Negative control 2 | Liquid | *C. difficile* SH11 spores only | N/A |
| Negative control 3 | Liquid | Horse blood only | N/A |
| Positive control 4 | Liquid | CotE H2 aptamer in TbKst buffer | 10 |
| CotE H2 + SH11 | Liquid | CotE H2 aptamer in TbKst buffer incubated with *C. difficile* SH11 spores | 10 |

Equipment:
UKAS calibrated pipettes—Sartorius, UK Eppendorf 5452
Minispin Centrifuge—Eppendorf, DE
Polilight® Flare+2 forensic lights (wavelength 505 nm)—Rofin,
UK Stainless-steel table
Hospital gown surface
Canon EOS 2000D camera—
590 nm wavelength filter, Midwest Optical Systems, Inc.
Media:
Nuclease free water—provided by Aptamer Group
TbKst buffer—provided by Aptamer Group. The buffer solution contains 50 mM Tris
pH 7.6, 2.5 mM $MgCl_2$, 2.5 mM $CaCl_2$), 28 mM $K_2SO_4$, 0.01% Tween, 0.01% BSA.
Clinell sporicidal wipes—GAMA healthcare,
UK 70% isopropyl alcohol (IPA)—Fisher Scientific,
UK—1% Virkon solution—Scientific Laboratory Supplies, UK Method Assessment of the ability of the CotE H2 aptamer to detect *Clostridium difficile* SH11 bacterial spores on stainless-steel and gown surfaces, in ambient light and dark conditions.

CotE H2 aptamer and *Clostridium difficile* SH11 binding procedure:

Prior to testing, the CotE H2 aptamer was folded in nuclease free water by heating to 95° C. for 5 minutes. The CotE H2 aptamer was immediately cooled to 2° C. on ice. An inoculum of *C. difficile* SH11 bacterial spores was prepared to 1×107 CFUmL−1 from stock solution in nuclease free water. Once folded, 20 μL of the *C. difficile* SH11 spore suspension was added to 20 μL of 20 μM of folded CotE H2 aptamer to obtain a final concentration of 10 μM. The aptamers comprise a FAM fluorophore incorporated at the 5' end via a linker.

The aptamer-spore suspension was mixed and vortexed for 5 seconds to obtain a homogenous suspension and incubated for 1 hour at room temperature. Following incubation, the aptamer-spore suspension was washed by centrifugation to remove unbound CotE H2 aptamer. One hundred microliters of TbKst buffer was added to the aptamer-spore suspension and centrifuged at 12,100×g (13,000 rpm) for 10 minutes. The supernatant liquid was discarded. The aptamer-spore pellet was resuspended in 100 μL of TbKst buffer and vortexed for 10 minutes to obtain a homogenous suspension. For negative control 4 (CotE H2 aptamer in TbKst buffer without spores), 10 μL of TbKst buffer was added to 10 μL of 20 μM of folded CotE H2 aptamer to obtain a final concentration of 10 μM.

Detection of Bacterial Spores from *Clostridium difficile* SH11 on Stainless-Steel and Gown Surfaces in Ambient Light and Dark Conditions A stainless-steel surface was cleaned sequentially with sporicidal wipes, 1% Virkon™ solution and 70% isopropyl alcohol (IPA). Following cleaning, the surface was rinsed with water. The surface was divided into five 10×10 cm samples labelled S1-S5. Sample S1 was untreated to act as a clean surface control for the stainless-steel surface (negative control 1). Five×5 μL aliquots of the negative control 2 (*C. difficile* SH11 spores only), negative control 3 (horse blood only), positive control 4 (CotE H2 aptamer at 10 μM in TbKst buffer) and the aptamer-spore suspension were pipetted onto samples S2, S3, S4 and S5 respectively. The surface was allowed to dry at room temperature for 1 hour. Following drying, the fluorescence of the aptamer-spore suspension was assessed in ambient light and dark conditions, with and without the Polilight® Flare+2 forensic light (505 nm). Images of the fluorescence were taken with a Canon EOS 2000D with and without a 590 nm bandpass filter. Autofluorescence of the negative controls was also assessed. The test was repeated on hospital gown surfaces.

Results

Assessment of the Ability of the CotE H2 Aptamer to Detect *Clostridium difficile* SH11 Bacterial Spores on Stainless-Steel and Gown Surfaces, in Ambient Light and Dark Conditions:

Stainless-Steel Surface:

Ambient Light, without Polilight® Flare+2 Forensic and without 590 nm Bandpass Filter No visible fluorescence was observed for all the test samples without the exposure to Polilight® Flare+2 forensic light (505 nm) and the 590 nm bandpass filter in ambient light conditions.

Ambient Light, with Polilight® Flare+2 Forensic and without 590 Nm Bandpass Filter Visible reflection of the Polilight® Flare+2 forensic light caused by the stainless-steel surface was observed for test sample when exposed to Polilight® Flare+2 forensic light (505 nm) without the 590 nm bandpass filter in ambient light conditions. Visible reflection of the test sample was also observed within the samples containing *C. difficile* SH11 spores, horse blood, CotE H2 aptamer at 10 µM, and the combination of CotE H2 aptamer 10 µM and *C. difficile* SH11 spores.

Ambient Light, with Polilight® Flare+2 Forensic and with 590 nm Bandpass Filter

No visible reflection of the Polilight® Flare+2 forensic light caused by the stainless-steel surface was observed when exposed to Polilight® Flare+2 forensic light (505 nm) when using the 590 nm bandpass filter in ambient light conditions. No visible autofluorescence was observed on the samples containing the stainless-steel surface, *C. difficile* SH11 spores, or horse blood. Fluorescence was observed within the sample containing CotE H2 aptamer at 10 µM. No visible fluorescence was observed within the sample containing the combination of CotE H2 aptamer 10 µM and *C. difficile* SH11 spores.

Dark Conditions, with Polilight® Flare+2 Forensic and with 590 nm Bandpass Filter Some visible reflection of the Polilight® Flare+2 forensic light caused by the stainless-steel surface was observed for all the test samples when exposed to Polilight Flare+2 forensic light (505 nm) with the 590 nm bandpass filter in dark conditions. Minimal autofluorescence was observed within the samples containing the stainless-steel surface, *C. difficile* SH11 spores, or horse blood. Some autofluorescence was also observed from particles present on the surface. Fluorescence was observed on the stainless-steel surface, within the sample containing CotE H2 aptamer at 10 µM. Fluorescence was also observed with the sample containing the combination of CotE H2 aptamer 10 µM and *C. difficile* SH11 spores.

Gown Surface

Ambient Light, without Polilight® Flare+2 Forensic and without 590 nm Bandpass Filter No fluorescence was observed for the gown surface test samples without the exposure to Polilight® Flare+2 forensic light (505 nm) and the 590 nm bandpass filter in ambient light conditions.

Ambient Light, with Polilight® Flare+2 Forensic and without 590 Nm Bandpass Filter No visible fluorescence was observed for the test samples on the gown surface when exposed to Polilight® Flare+2 forensic light (505 nm) when observed without the 590 nm bandpass filter in ambient light conditions. Visible reflection of the Polilight® Flare+2 forensic light caused by the gown surface was observed for test samples when exposed to Polilight® Flare+2 forensic light (505 nm) without the 590 nm bandpass filter in ambient light conditions. Visible reflection of test samples was also observed within the samples containing *C. difficile* SH11 spores, horse blood, CotE H2 aptamer at 10 µM, and the combination of CotE H2 aptamer 10 µM and *C. difficile* SH11 spores.

Ambient Light, with Polilight® Flare+2 Forensic and with 590 nm Bandpass Filter

Bright green/yellow fluorescence was observed within the sample containing CotE H2 aptamer at 10 µM and, visible fluorescence was observed within the sample containing the combination of CotE H2 aptamer 10 µM and *C. difficile* SH11 spores. No visible reflection of the Polilight® Flare+2 forensic light was observed on the gown surfaces when they were exposed to Polilight® Flare+2 forensic light (505 nm) and observed with the 590 nm bandpass filter in ambient light conditions.

Dark Conditions, with Polilight® Flare+2 Forensic and with 590 nm Bandpass Filter Bright fluorescence was observed within the sample containing CotE H2 aptamer at 10 µM. Fluorescence was observed within the sample containing the combination of CotE H2 aptamer 10 µM and *C. difficile* SH11 spores. No autofluorescence was observed within the samples containing the gown surface, *C. difficile* SH11 spores or horse blood.

Discussion

*C. difficile* is an anaerobic spore-forming microorganism and is considered a leading cause of infections worldwide, with elevated rates of morbidity. A method of visual identification of *C. difficile* spore contamination in the health care environment would allow improved cleaning procedures.

The assessment of fluorescence for the stainless-steel showed that fluorescence was detected only under dark conditions. The assessment of fluorescence for the gown surface showed that fluorescence of the CotE H2 aptamer in combination with *C. difficile* SH11 spores was detected under both ambient light and dark conditions. The intensity of the fluorescence observed on the gown surface in response to the presence of the combination CotE H2 aptamer and *C. difficile* SH11 spores under ambient light conditions was lower than intensity of the fluorescence under dark conditions. No visible reflection or autofluorescence was detected on the gown surface controls, but a high amount of reflection was observed on stainless-steel samples.

Example 4: Minimal Binding Fragments

A fragment of the chitinase D11 aptamer (SEQ ID NO: 5) was found to bind to *C. difficile* spores. The fragment extended from position 28 to position 64 of SEQ ID NO: 5. This sequence is also shown in SEQ ID NO: 23. Binding was identified using an ELISA-type assay in which a biotinylated fragment of SEQ ID NO: 23 was used in a similar manner to a primary antibody. A streptavidin-HRP conjugate was used as a secondary binding partner.

Several fragments of the *C. diff*-F1 aptamer (SEQ ID NO: 1) were found to bind to *C. difficile* spores. The sequence for the minimal fragment, *C diff*-F1-f10, is 5'-CCATACTCAATGCTCTTACGATCCTCATCAACC-3', and is 33 bases long (SEQ ID NO: 24). The fragment comprises 23 contiguous nucleotides extending from position 12 to position 35 of SEQ ID NO: 1.

Several fragments of the *C. diff*-G1 aptamer (SEQ ID NO: 2) were found to bind to *C. difficile* spores. The sequence for the minimal fragment, *C diff*-G1-f6, is 5'-CCAGTGTAGACTACTCAATGCTCTTACGATCCTCATCAACC-3', and is 41 bases long (SEQ ID NO: 25). The fragment comprises 21 contiguous nucleotides extending from position 1 to position 21 of Seq ID NO: 2.

Several fragments of the CotE-H2 aptamer (SEQ ID NO: 11) were found to bind to *C. difficile* spores. The sequence for the minimal fragment, CotE-H2-f4, is 5'-AGTGTAGACTACTCAATGCGGCTGGCCACAGGTCAACC-3', and is 40 bases long (SEQ ID NO: 26). The sequence comprises 24 contiguous nucleotides from the 5' end and 13 contiguous nucleotides from the 3' end of SEQ ID NO: 11 (with an internal truncation of 42 nucleotides from SEQ ID NO: 11) which were combined with an additional guanine bridge.

In a single point ELISA assay, the minimal fragments *C diff*-F1-f10, *C diff*-G1-f6, and CotE-H2-f4 each displayed preferential binding to spores from *C. difficile* over *B. sub.* (approximately two-fold).

Several fragments of the CotE-H2 aptamer (SEQ ID NO: 11) were found to bind to *C. difficile* spores. The sequence for the minimal fragment, CotE H2.1, is 5'-CTTGACCTTTGGAATGGGTGGGAGG-GATGGGTACTATCCACAGGTCAAC-3', and is 50 bases long (SEQ ID NO: 27). The sequence comprises 50 contiguous nucleotides of SEQ ID NO: 11.

Several fragments of the CotE-H2 aptamer (SEQ ID NO: 11) were found to bind to *C. difficile* spores. The sequence for the minimal fragment, CotE H2.2, is 5'-AATGGGTGG-GAGGGATGGGTACTA-3', and is 24 bases long (SEQ ID NO: 28). The sequence comprises 24 contiguous nucleotides of SEQ ID NO: 11.

Several fragments of the CotE-H2 aptamer (SEQ ID NO: 11) were found to bind to *C. difficile* spores. The sequence for the minimal fragment, CotE H2.1.1, is 5'-CTTGACCTTTGGAATGGGTAGGGAGGGAGGGA-TACTATCCACAGGTCAACC 3', and is 51 bases long (SEQ ID NO: 29). The sequence comprises 51 contiguous nucleotides of SEQ ID NO: 11.

Several fragments of the CotE-H2 aptamer (SEQ ID NO: 11) were found to bind to *C. difficile* spores. The sequence for the minimal fragment, CotE H2.1.2, is 5'-CTTGACCTTTGGAATGGGTGGGAGG-GAGGGTATCCACAGGTCAACC-3', and is 46 bases long (SEQ ID NO: 30). The sequence comprises 46 contiguous nucleotides of SEQ ID NO: 11.

Several fragments of the CotE-D2 aptamer (SEQ ID NO: 13) were found to bind to *C. difficile* spores. The sequence for the minimal fragment, CotE D2.1, is 5'-ACTACT-CAATGCTCGACAT-TTCCGCCCCGACGGCCCTCCTAGTGAGGGGAGAG TAGA-3', and is 57 bases long (SEQ ID NO: 31). The sequence comprises 57 contiguous nucleotides of SEQ ID NO: 13.

Several fragments of the CotE-D2 aptamer (SEQ ID NO: 13) were found to bind to *C. difficile* spores. The sequence for the minimal fragment, CotE D2.2, is 5'-ACTACT-CAATGCTCGACAT-TTCCGCCCCGACGGCCCTCCTAGTGATGGGGAGA GTAGA-3', and is 58 bases long (SEQ ID NO: 32). The sequence comprises 58 contiguous nucleotides of SEQ ID NO: 13.

Several fragments of the CotA-C1 aptamer (SEQ ID NO: 10) were found to bind to *C. difficile* spores. The sequence for the minimal fragment, CotA C1.1, is 5'-ACT-CAAGGCCGTGGACTGGTCGGGTTTGGATTCGGCA-GATGAATCACT-3', and is 48 bases long (SEQ ID NO: 33). The sequence comprises 48 contiguous nucleotides of SEQ ID NO: 10.

Several fragments of the CotA-C1 aptamer (SEQ ID NO: 10) were found to bind to *C. difficile* spores. The sequence for the minimal fragment, CotA C1.2, is 5'-ACT-CAAGGCCGTGGACTGGTCGGGTTTGGAT-3', and is 31 bases long (SEQ ID NO: 34). The sequence comprises 31 contiguous nucleotides of SEQ ID NO: 10.

Several fragments of the CotA-C1 aptamer (SEQ ID NO: 10) were found to bind to *C. difficile* spores. The sequence for the minimal fragment, CotA C1.3, is 5'-ACCCGTGGGACTGGGTCGGGTCGGG-3', and is 25 bases long (SEQ ID NO: 35). The sequence comprises 25 contiguous nucleotides of SEQ ID NO: 10.

Several fragments of the CotE Chitinase-D11 aptamer (SEQ ID NO: 5) were found to bind to *C. difficile* spores. The sequence for the minimal fragment, CotE Chitinase-D11.1, is 5'-AACTGCCTGGTAAATCGATGACCGC-TGCCTCGCCTGAGTAATCATCGTACTATCCACAGG-TC-3', and is 62 bases long (SEQ ID NO: 36). The sequence comprises 62 contiguous nucleotides of SEQ ID NO: 5.

Several fragments of the CotE Chitinase-D11 aptamer (SEQ ID NO: 5) were found to bind to *C. difficile* spores. The sequence for the minimal fragment, CotE Chitinase-D11.2, is 5'-GTAAATCGATGACCGCTGCCTCGCCT-GAGTAATCATCGTAC-3', and is 41 bases long (SEQ ID NO: 37). The sequence comprises 41 contiguous nucleotides of SEQ ID NO: 5.

Several fragments of the CdeC-D1 aptamer (SEQ ID NO: 6) were found to bind to *C. difficile* spores. The sequence for the minimal fragment, CdeC-D1.1, is 5'-ACTACT-CAAACCCGTGGACTGGTCGGGTTTGGATTCGGCA-GATGAATCAGTAG AAA-3', and is 56 bases long (SEQ ID NO: 38). The sequence comprises 56 contiguous nucleotides of SEQ ID NO: 6.

Several fragments of the CdeC-D1 aptamer (SEQ ID NO: 6) were found to bind to *C. difficile* spores. The sequence for the minimal fragment, CdeC-D1.2, is 5'-ACTACT-CAATGCCGTGGACTGGTCGGGTTTGGAATCGGCA-GATGAATCAGTAG TAAA-3', and is 57 bases long (SEQ ID NO: 39). The sequence comprises 57 contiguous nucleotides of SEQ ID NO: 6.

Example 5: Aptamer Binding to Proteins

The binding affinity, as reported by the equilibrium dissociation constant ($K_D$), was determined for several aptamers and proteins (performed under contract by NeoVentures Biotechnology Inc. (London, Ontario, Canada)).

For CotE D2, CotE H2 and CotEC chitinase, aptamers were spotted on a gold surface at a concentration of 5 μM in PBS at a volume of approximately 10 nL in triplicate. Negative aptamers of the same length as the positive aptamers were spotted in the same manner, also in triplicate. Protein was then injected over the chip at a volume of 200 μL, with a flow rate of 50 μL/min in a Horiba (OpenPlex) surface plasmon resonance imaging (SPRi) instrument. Resonance due to binding was obtained by subtracting total resonance on the negative sequences from total resonance on the positive sequences. Disassociation values were computed with the following equation: dx/dt~−kd*x, wherein dx/dt is the derivative of resonance values as a function of time and x is the resonance value for any given time point. Association values were computed with the following equation: dx/dt~ka*c*Rmax−(ka*c+kd)*x, where x is the resonance due to binding at specific time points, c is the concentration of injectant, and Rmax is the maximum resonance observed.

For CotA C1, the protein was immobilized on a hydrogel chip with EDC-mediated conjugation between primary amines on the protein (side chains on residues) and carboxylic acid groups on the surface of the chip. A protein of similar size was immobilized in the same manner as a negative control. The variation in concentration for this data is in the amount of aptamer injected. For CdeC D1, the protein was received as aggregated, insoluble balls of protein. The binding assay was performed by incubating fluorescently labeled aptamers (FAM) with the protein, and then spinning the tubes down in a microcentrifuge to remove unbound. The pellet was resuspended in selection buffer and spun down again. Bound aptamers were eluted by adding 6 M urea, and spinning again, retaining the supernatant. The aptamers were cleaned up with PCR cleanup columns and the fluorescence was read on a Tecan Sapphire II fluorometer. Excitation was at 497 nm, and emission was at 515 nm. The amount of fluorescence measured in the eluant was divided by the total amount of fluorescence of all fractions.

For aptamer CotE H2 (SEQ ID NO: 11), the $K_D$ was determined to be 1.43E-07 (at 250 nM protein), 9.16E-08 (at 125 nM protein), and 8.47E-08 (at 62.5 nM protein), respectively. For aptamer CotE D2 (SEQ ID NO: 13), the $K_D$ was determined to be greater than 250 nM. For aptamer CotA C1 (SEQ ID NO: 10), the $K_D$ was determined to be 6.874E-09 (at 250 nM protein injected). For aptamer CotEC Chitinase D11 (SEQ ID NO: 5), the $K_D$ was determined to be 2.54E-07 (at 500 nM protein), 2.35E-07 (at 750 nM protein), and 2.75E-07 (at 1000 nM protein), respectively. For aptamer CdeC D1 (SEQ ID NO: 6), the $K_D$ was not determined due to protein aggregation.

Example 6: Optimization of Aptamers

Optimization of aptamers included the design of sequences for each aptamer. Full-length aptamers retain full primer recognition sequences as well as random sequences. The secondary structure of these sequences can be predicted and substructures within the aptamers as the potential core sequence responsible for the capacity to bind can be identified. Full length aptamers will be in flux between different possible shapes at room temperature. It is probable that only certain of these shapes will present substructures that bind to the target for which the aptamer was selected to bind. If the appropriate shape is not being presented by the aptamer at the time that the aptamer collides with such a target epitope then it is possible that an instance of the aptamer binding to the target could be missed. As such, aptamers can be optimized by identifying a core set of nucleotides responsible for a given substructure. This core set of contiguous nucleotides can be used to predict whether they are expected to form the same substructure that they form within the full-length aptamer. If they do not, or if they are still in flux among a large number of possible shapes, nucleotide substitutions may be introduced that favor the formation of the desired substructure.

Figure 1B:
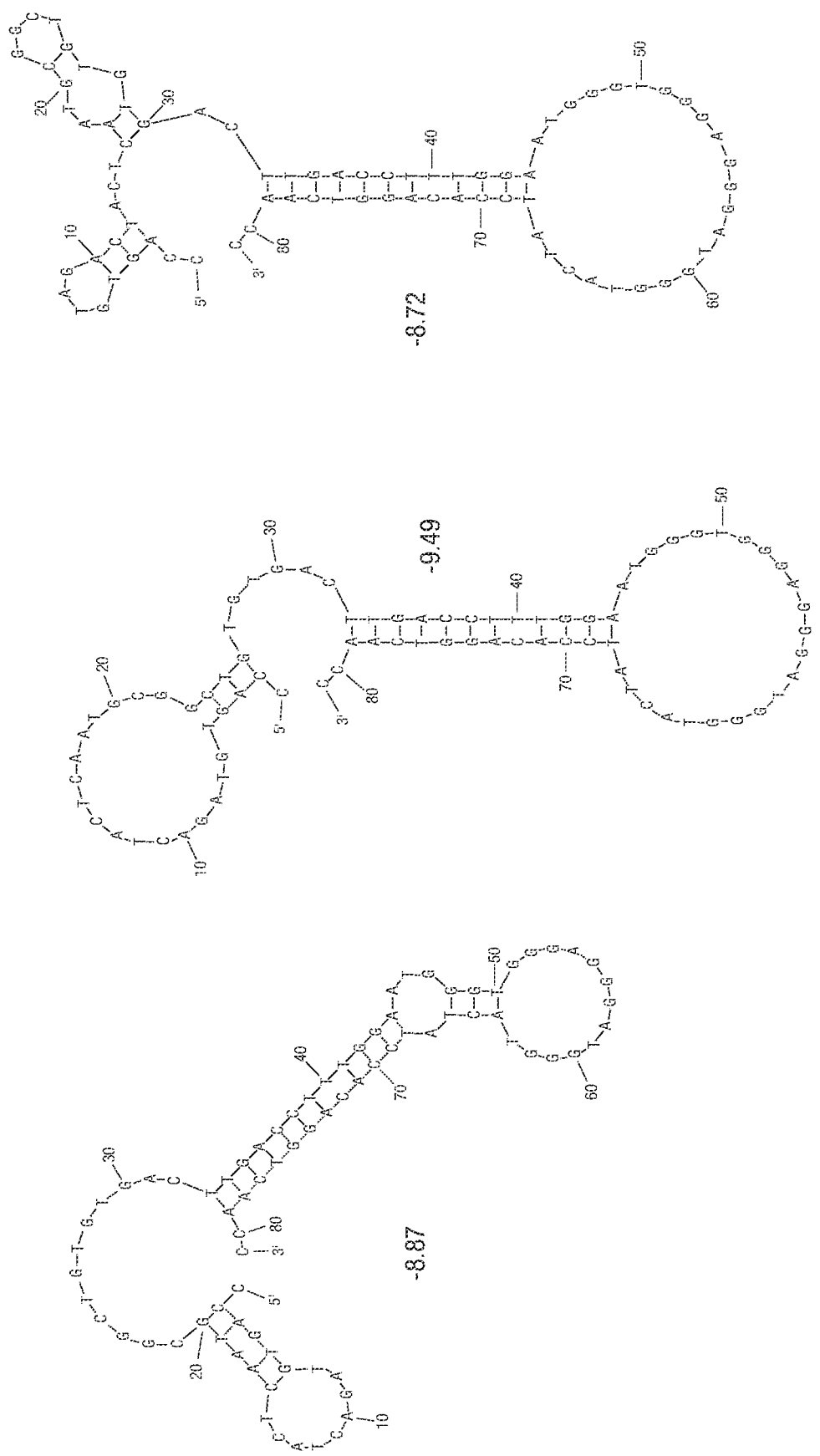
FIG. 1B shows structures predicted to be in flux at equilibrium at room temperature for the CotE H2 aptamer (SEQ ID NO: 11).
Figure 1C:
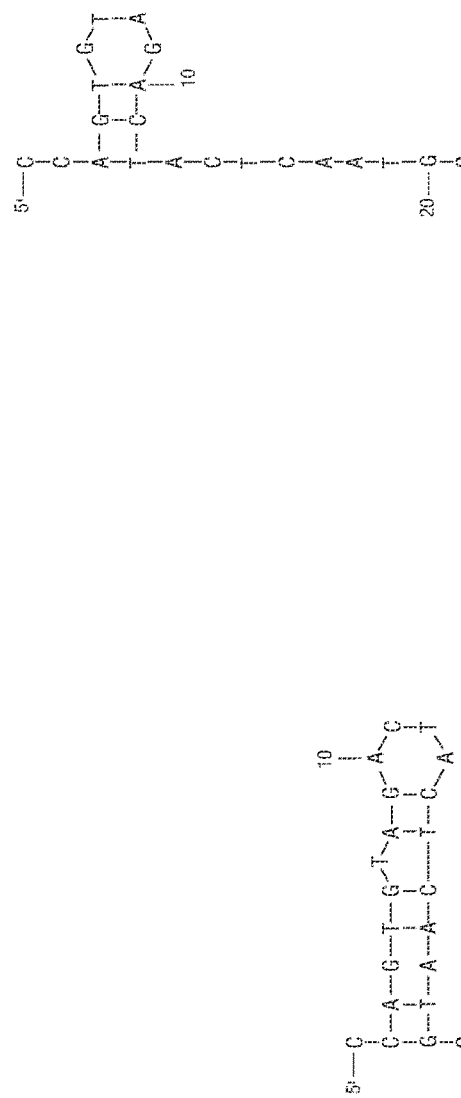
FIG. 1C shows structures predicted to be in flux at equilibrium at room temperature for the CotE H2 aptamer (SEQ ID NO: 11).
Figure 1C:
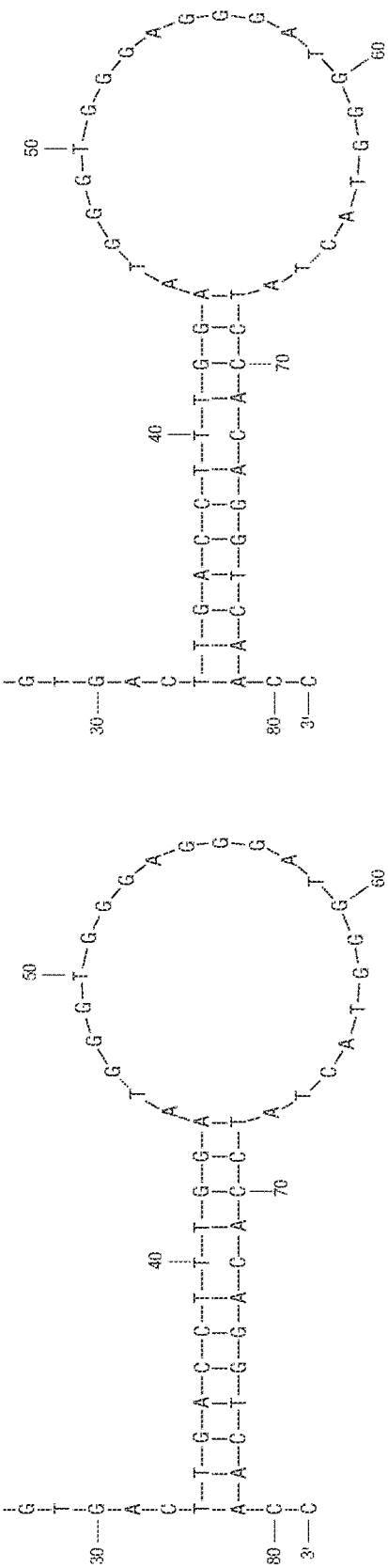
Figure 2:
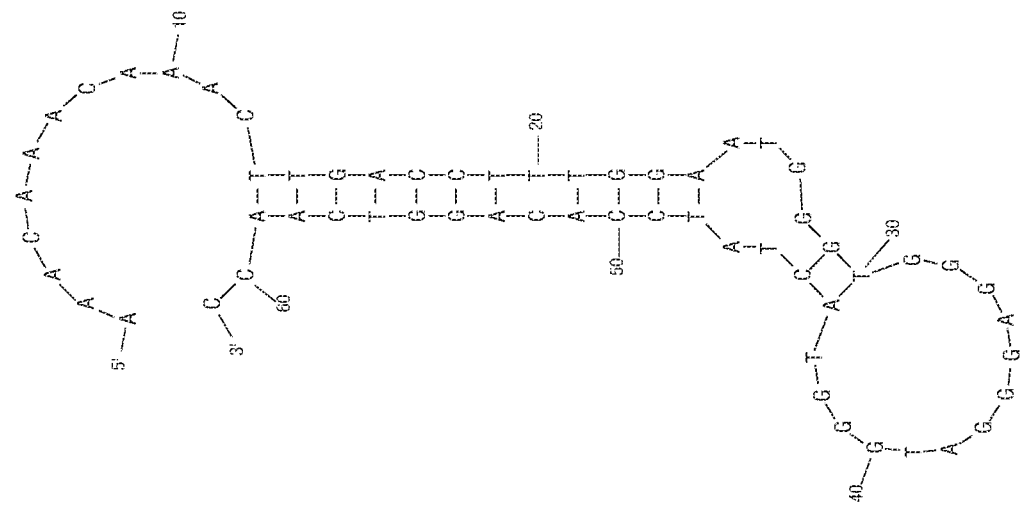
FIG. 2 shows the predicted structures for the aptamer CotE H2.1 (SEQ ID NO: 27).
Figure 2:
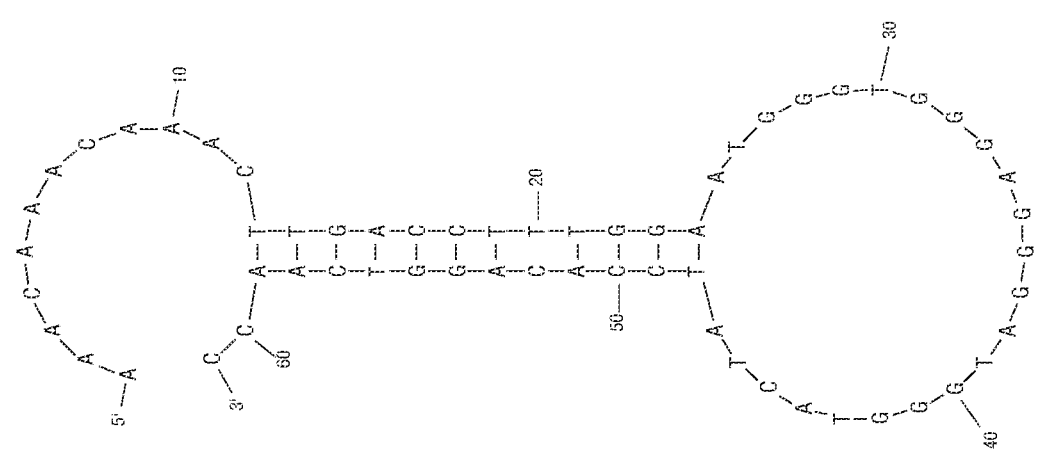
Figure 3:
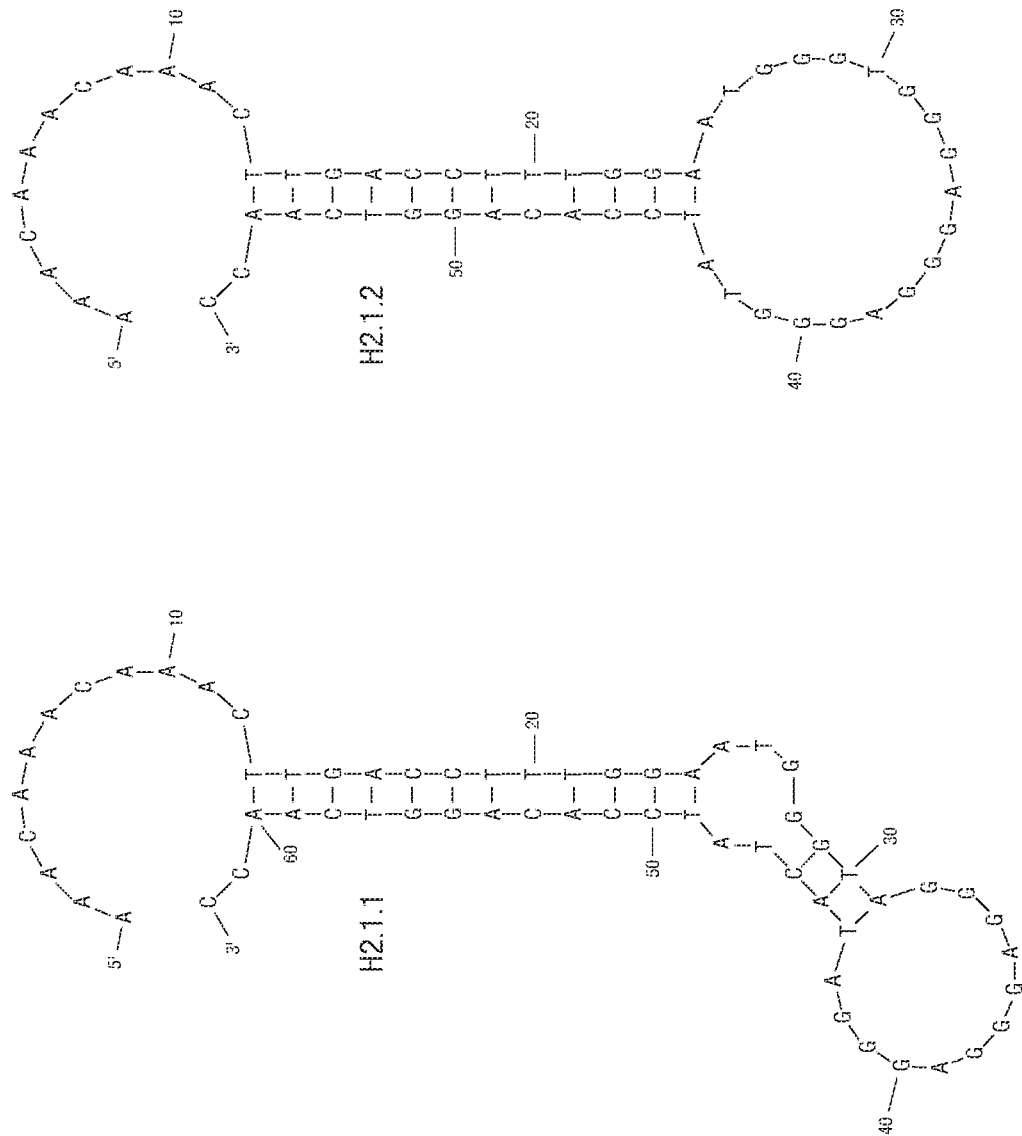
FIG. 3 shows the predicted structure for the aptamers CotE H2.1.1 (SEQ ID NO: 29) and aptamer CotE H2.1.2 (SEQ ID NO: 30).

H2 CotE: The original aptamer sequence was SEQ ID NO: 11, which binds to the CotE protein from *C. difficile*. The aptamer has the capacity to form many different shapes at room temperature with slight variations in free energy ($\Delta G$) as shown in FIGS. 1A, 1B and 1C. Aptamers were designed to reduce the variation in shape and to decrease the overall length of the aptamer. The predicted aptamer shapes for the first, H2.1 (SEQ ID NO: 27), are shown in FIG. 2. Of note, the open loop of aptamer H2.1 contains four repeats of three guanidine (G) nucleotides, which are required for the formation of a G-quartet structure in single stranded DNA. A second aptamer, H2.2 (SEQ ID NO: 28) was designed to test whether these four G repeat units were acting alone as a G-quartet structure, as this aptamer was predicted to not form stable secondary structures other than a G-quartet structure.

The aptamers were synthesized with a 5' disulphide group (IDT DNA) and an AAACAAACAAA spacer nucleotide sequence on the 5' end for analysis by surface plasmon resonance imaging (SPRi). Each aptamer was spotted in triplicate at a concentration of 5 μM in a volume of approximately 10 μL on a gold surface. Negative oligonucleotides of similar size were also spotted in triplicate at the same concentration and volume. The remainder of the chip was blocked with thiolylated PEG molecules. CotE protein was injected over this surface in a Horiba OpenPlex SPRi instrument at a volume of 200 μL, and a flow rate of 200 μL.

The observed resonance for the negative aptamers was subtracted from the observed resonance from the positive aptamers thus removing resonance due to mass transfer and leaving only resonance due to binding.

For aptamer CotE H2 (SEQ ID NO: 11), the $K_D$ was determined to be 1.43E-07 (at 250 nM protein), 9.16E-08 (at 125 nM protein), and 8.47E-08 (at 62.5 nM protein), respectively. For aptamer CotE H2.1 (SEQ ID NO: 27), the $K_D$ was determined to be 3.02E-08 (at 250 nM protein), 1.60E-08 (at 125 nM protein), and 1.01E-08 (at 62.5 nM protein), respectively. For aptamer CotE H2.2 (SEQ ID NO: 28), the $K_D$ was determined to be greater than 250 nM. The truncation of aptamer CotE H2 (SEQ ID NO: 11) to CotE H2.1 (SEQ ID NO: 27) resulted in an improvement in binding of 4.74-, 5.71-, and 8.40-fold, respectively.

The predicted shape of the CotE H2.1 (SEQ ID NO: 27) exhibited the capacity for variance at room temperature, and therefore, additional sequences were designed by introducing nucleotide substitution, giving aptamer CotE H2.1.1 (SEQ ID NO: 29) and CotE H2.1.2 (SEQ ID NO: 30). The predicted shapes can be found in FIG. 3.

For aptamer CotE H2.1.1 (SEQ ID NO: 29), the $K_D$ was determined to be greater than 250 nM. For aptamer CotE H2.1.2 (SEQ ID NO: 30), the $K_D$ was determined to be 9.22E-09 (at 125 nM protein), and 6.14E-09 (at 62.5 nM protein), respectively, resulting in an improvement in binding of 9.9-, and 13.8-fold, respectively.

Figure 4A:
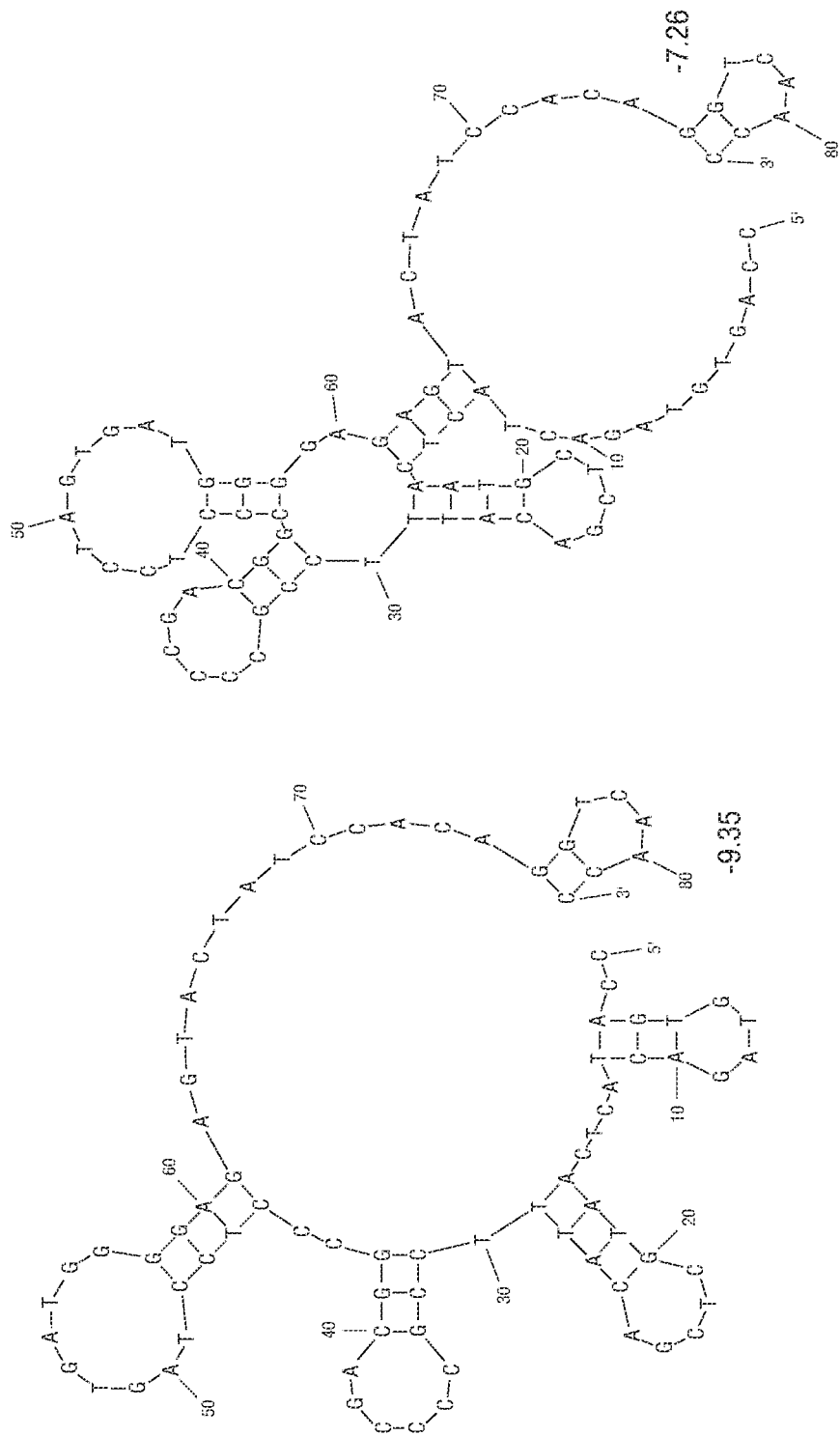
FIG. 4A shows the predicted structures for the aptamer CotE D2 (SEQ ID NO: 13).
Figure 4B:
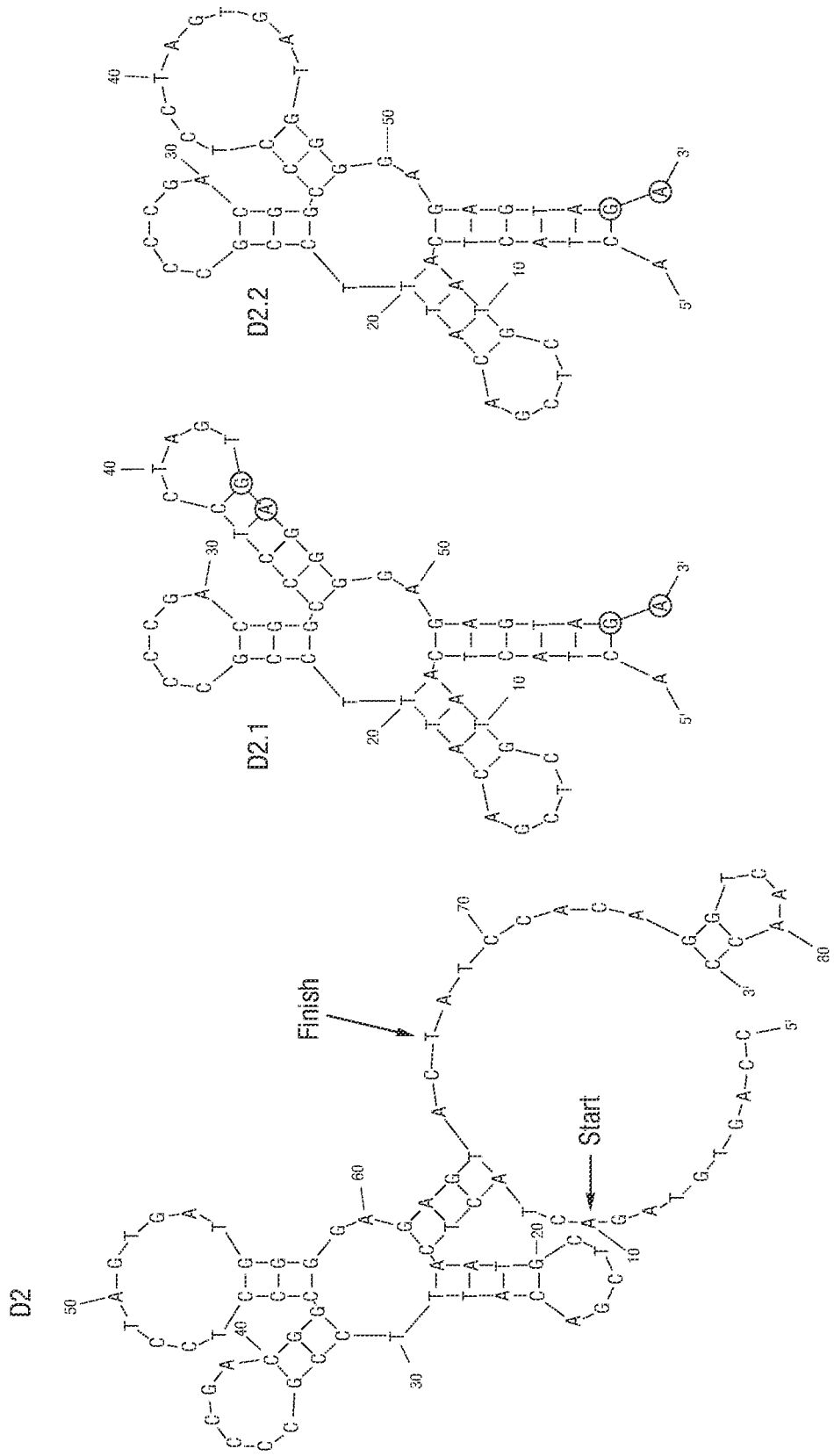
FIG. 4B shows the predicted structures for the aptamers CotE D2.1 (SEQ ID NO: 31) and CotE D2.2 (SEQ ID NO: 32).

D2 CotE: The original aptamer sequence was SEQ ID NO: 13, which binds to the CotE protein from *C. difficile*. The D2 CotE aptamer appeared to be stable, but the predicted stable structure contains very little secondary structure, as shown by the two structures in FIG. 4A. Two aptamers, D2.1 (SEQ ID NO: 31) and D2.2 (SEQ ID NO: 32), were designed based on the second structure, predicted to be the structure that is binding to the CotE protein, as shown in FIG. 4B.

For aptamer CotE D2 (SEQ ID NO: 13), the $K_D$ was determined to be greater than 250 nM. For aptamer CotE D2.1 (SEQ ID NO: 31), the $K_D$ was determined to be 3.41E-08 (at 500 nM protein). For aptamer CotE D2.2 (SEQ ID NO: 32), the $K_D$ was determined to be 2.07E-07 (at 500 nM protein).

Figure 5:
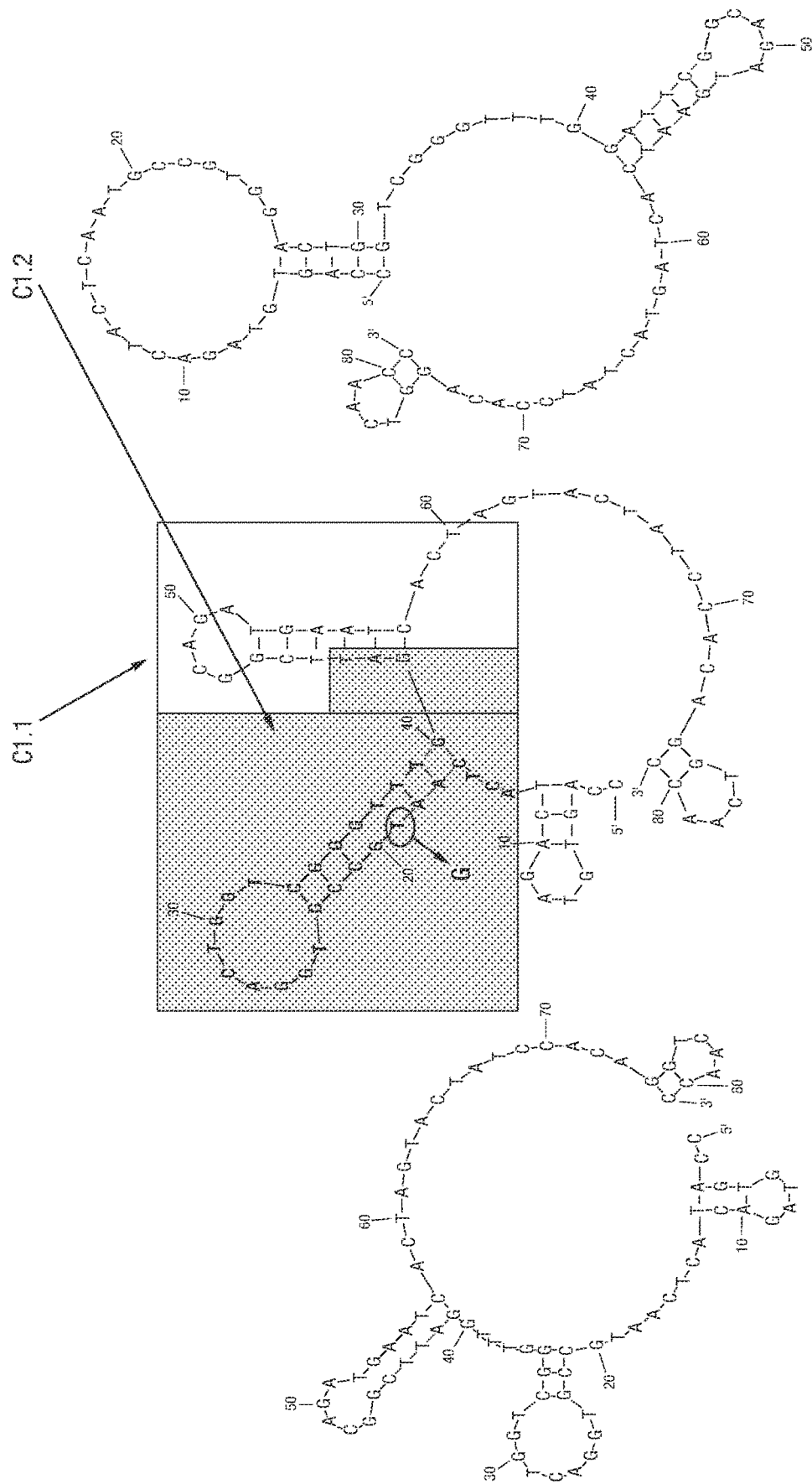
FIG. 5 shows the predicted structures for the aptamer CotA C1 (SEQ ID NO: 10), together with highlighted sections for aptamers CotA C1.1 (SEQ ID NO: 33) and CotA C1.2 (SEQ ID NO: 34).
Figure 6:
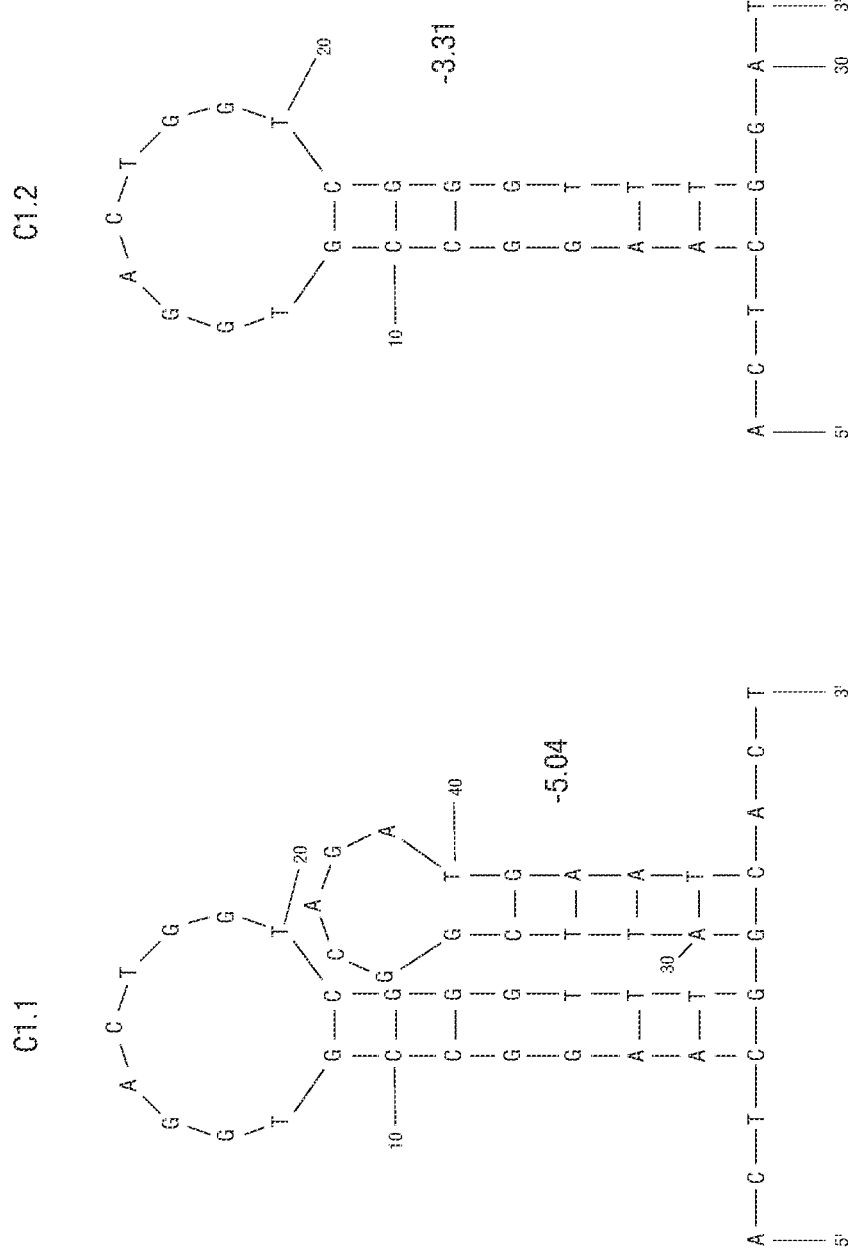
FIG. 6 shows the predicted structures for the CotA C1.1 (SEQ ID NO: 33) and CotA C1.2 (SEQ ID NO: 34) aptamers.

CotA C1: The original aptamer sequence was SEQ ID NO: 10, which binds to the CotA protein from *C. difficile*. The predicted secondary structures are shown in FIG. 5. There is variance regarding secondary structures (stem and loop configurations) that are predicted at room temperature under these salt conditions. These structures will be in flux amongst each other in such solutions at such temperatures. To optimize binding effectiveness of a given structure, it is desirable if the structure is not in flux with other structures but is the structure which is predominantly present. In some embodiments, the aptamers are engineered (e.g. substitution, deletion) to stabilize the secondary structures. In some embodiments, the aptamers can be truncated. The stability of these truncated structures with nucleotide substitutions was verified by in silico predictive analysis (DNAFold). Stabilization of the structure provided CotA C1.1 (SEQ ID NO: 33), and CotA C1.2 (SEQ ID NO: 34). The predicted structures for CotA C1.1 (SEQ ID NO: 33) and CotA C1.2 (SEQ ID NO: 34) can be found in FIG. 6. Optimization of potential G-quartet structure led to CotA C1.3 (SEQ ID NO: 35).

The binding analysis for the CotA protein was performed in a reverse orientation to that described for the CotE protein. Here, the protein was spotted on a hydrogel surface and aptamers were flowed over the hydrogel surface. Streptavidin was used as a negative control, spotted at the same concentration (5 µm).

For aptamer CotA C1 (SEQ ID NO: 10), the $K_D$ was determined to be 6.874E-09 (250 nM protein). For aptamer CotA C1.1 (SEQ ID NO: 33), the $K_D$ was determined to be 1.84E-08 (250 nM protein). For aptamer CotA C1.2 (SEQ ID NO: 34), the $K_D$ was determined to be 5.21E-08 (250 nM protein). For aptamer CotA C1.3 (SEQ ID NO: 35), the $K_D$ was determined to be 7.82E-08 (250 nM protein).

Figure 7A:
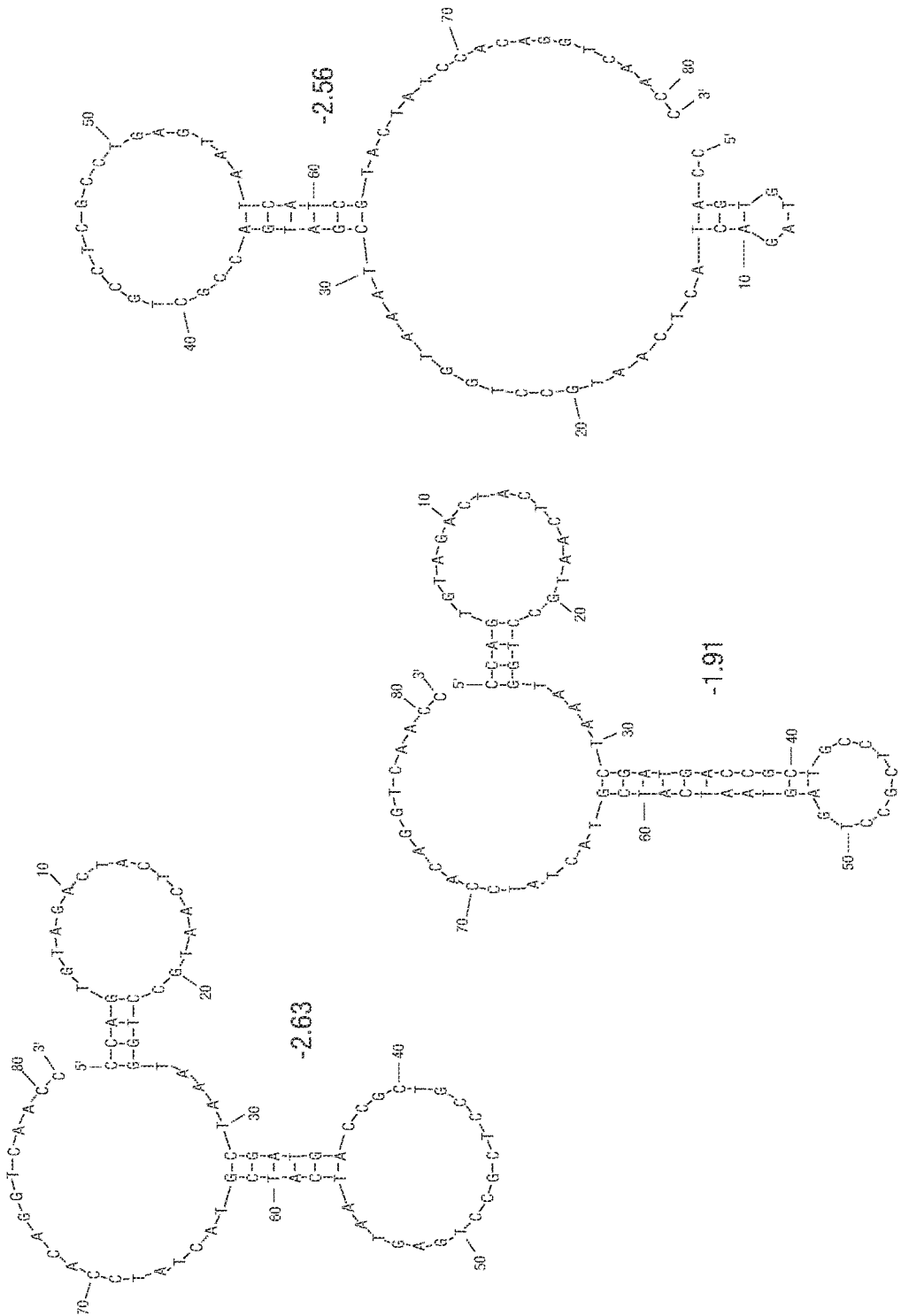
FIGS. 7A-7B show the predicted structures for the aptamer CotEC Chitinase D11 (SEQ ID NO: 5).
Figure 7B:
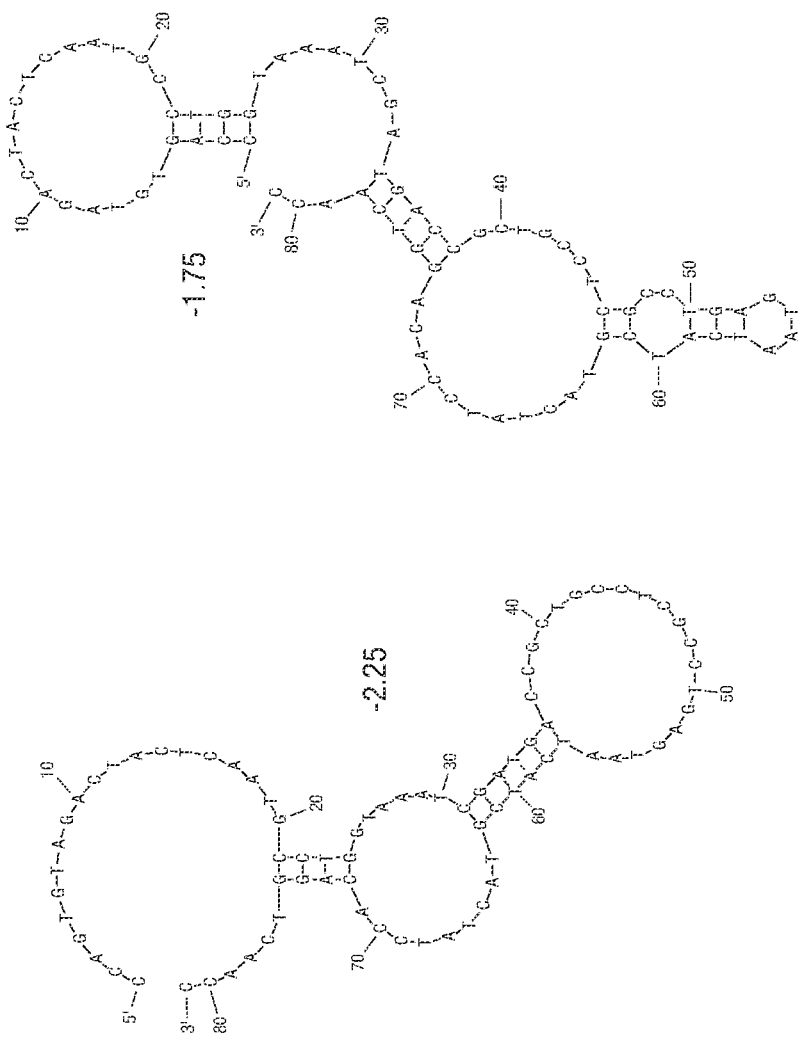
Figure 8:
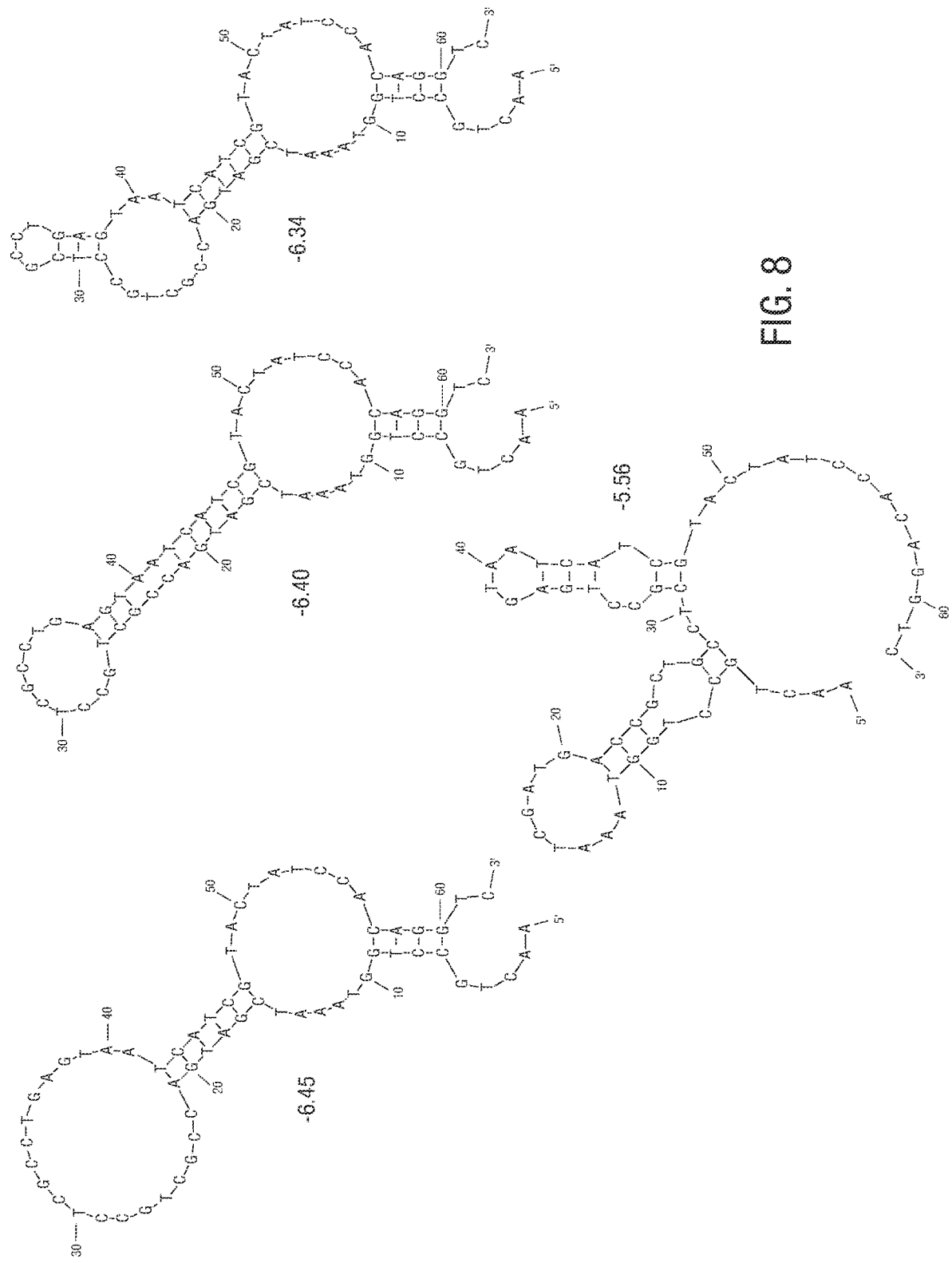
FIG. 8 shows the predicted structures for the aptamer CotEC Chitinase D11.1 (SEQ ID NO: 36).
Figure 9:
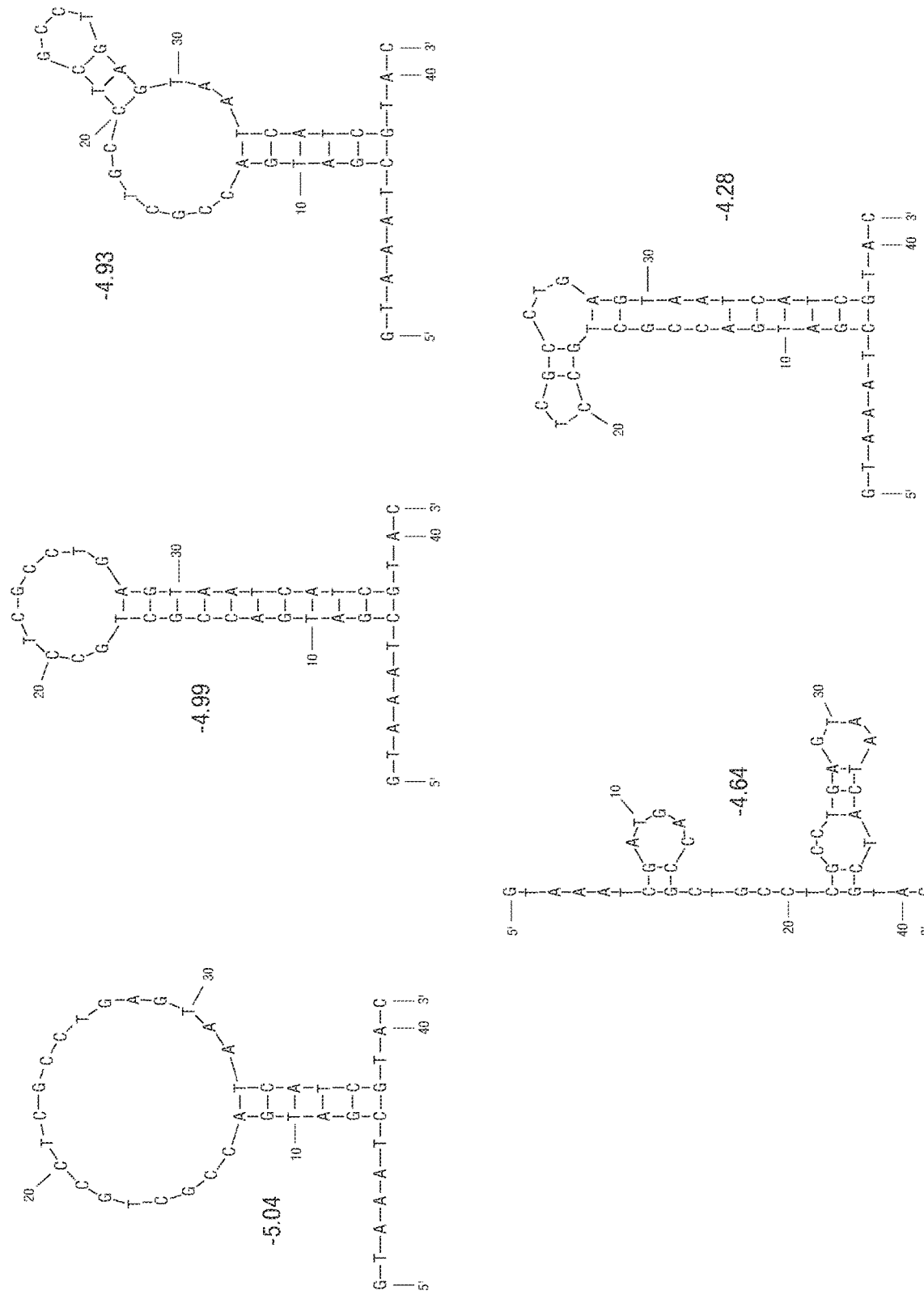
FIG. 9 shows the predicted structures for the aptamer CotEC Chitinase D11.2 (SEQ ID NO: 37).

D11 CotEC Chitinase: The original aptamer sequence was SEQ ID NO: 5, which binds to the CotEC Chitinase protein from *C. difficile*. The predicted secondary structures are shown in FIGS. 7A-7B. As the predicted shapes for this sequence were all relatively high in free energy, a high probability of flux is predicted. Two aptamers, D11.1 (SEQ ID NO: 36) and D11.2 (SEQ ID NO: 37), were designed to stabilize the predominant shape. The predicted shapes for these aptamers are shown in FIG. 8 for D11.1, and FIG. 9 for D11.2.

Surface plasmon resonance imaging (SPRi) analysis of binding was performed with the various aptamers immobilized on a surface while the protein was flowed over at various concentrations. For aptamer CotEC Chitinase D11 (SEQ ID NO: 5), the $K_D$ was determined to be 2.54E-07 (at 500 nM protein), 2.35E-07 (at 750 nM protein), and 2.75E-07 (at 1000 nM protein), respectively. For aptamer CotEC Chitinase D11.1 (SEQ ID NO: 36), the $K_D$ was determined to be 3.00E-07 (at 750 nM protein), and 2.9E-07 (at 1000 nM protein), respectively.

Figure 10:
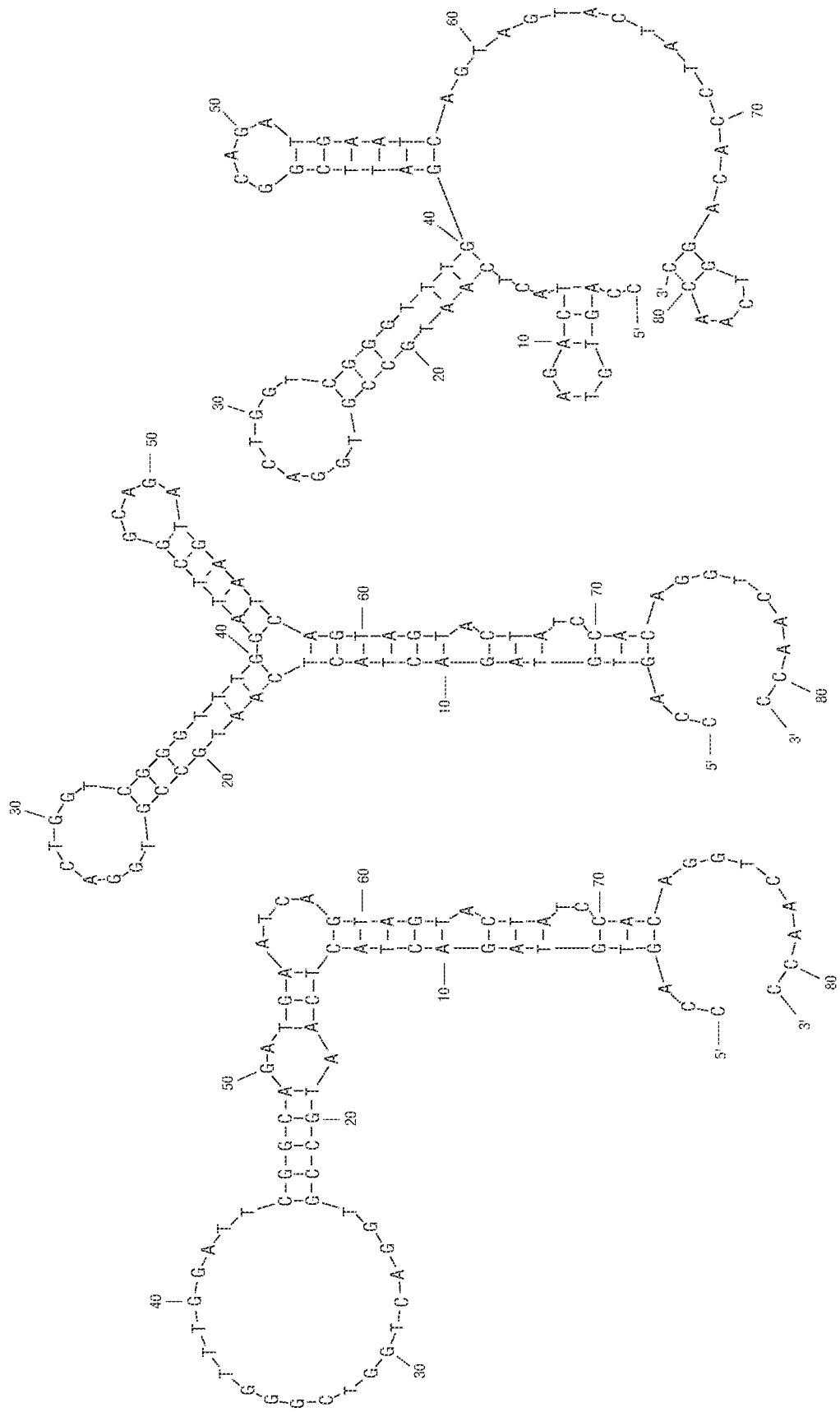
FIG. 10 shows the predicted structures for the aptamer CdeC D1 (SEQ ID NO: 6).
Figure 11:
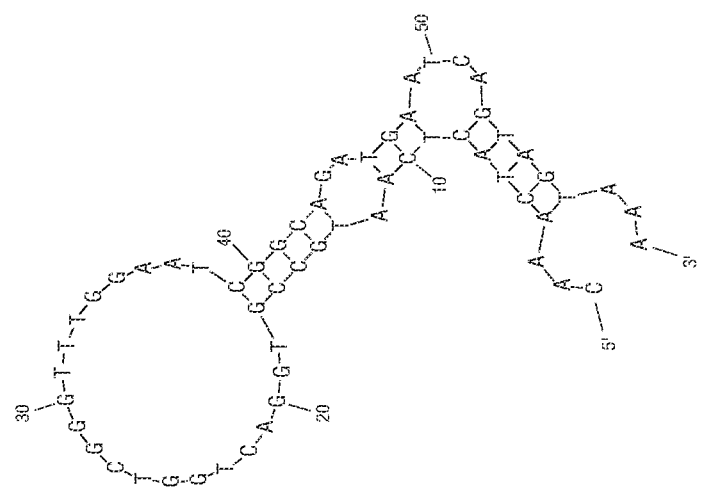
FIG. 11 shows the predicted structures for the aptamers CdeC D1.1 (SEQ ID NO: 38) and CdeC D1.2 (SEQ ID NO: 39).
Figure 11:
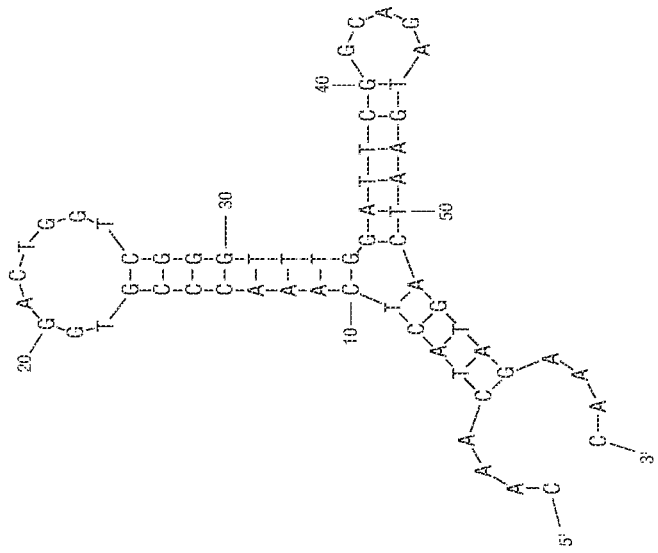

D1 CdeC: The original aptamer sequence was SEQ ID NO: 6, which binds to the CdeC protein from *C. difficile*. The predicted secondary structures are shown in FIG. 10. This aptamer exhibits a large variety of possible shapes with free energies that are close to one another. Two aptamers, D1.1 (SEQ ID NO: 38) and D1.2 (SEQ ID NO: 39), were designed to stabilize the structure observed in the analysis of the original sequence (FIG. 11). The CdeC protein self-aggregates in aqueous solutions making surface plasmon resonance analysis difficult. The protein forms large aggregates that are insoluble. The protein aggregates were combined as suspensions with the aptamers in solutions, allowed to incubate at room temperature for 15 min, and then spun down in a microcentrifuge to remove unbound aptamer. The complexes were washed with the appropriate selection buffer (50 mM Tris pH 7.6, 2.5 mM MgCl$_2$, 2.5 mM CaCl$_2$, 85 mM KOAc, 0.01% Tween 20, 0.01% BSA) once and the spin process was repeated. Finally, the bound aptamer was eluted from the protein structures with the addition of 6M urea. The protein aggregates were spun again, and this time the supernatant containing the eluted aptamers was retained. The aptamers were synthesized with a FAM label on the 5' end for this analysis.

For aptamer CdeC D1 (SEQ ID NO: 6), the $K_D$ was not determined due to protein aggregation. For aptamer CdeC D1.1 (SEQ ID NO: 38), the $K_D$ was not determined due to protein aggregation. For aptamer CdeC D1.2 (SEQ ID NO: 39), the $K_D$ was not determined due to protein aggregation. A relative comparison of aptamer binding was performed with 5000 nM fluorescently labeled (Fam) aptamers being incubated with 19 mL of a suspension of the aggregated protein. The mixture was allowed to incubate at room temperature for 15 min, and then spun down in a microcentrifuge to remove unbound aptamer. The complexes were washed with selection buffer once and the spin process was repeated. Finally, the bound aptamer was eluted from the protein structures with the addition of 6M urea. The protein aggregates were spun again, and this time, the supernatant containing the eluted fraction (previously bound aptamers) was retained. This binding analysis in terms of comparative fluorescence demonstrated that more CdeC D1.2 was bound to the same amount of aggregated CdeC protein than the full length aptamer sequence CdeC D1. While the amount of aggregated protein present was not known, the amount was the same for both aptamers and the results showed that the CdeC D1.2 aptamer binds with higher affinity to the CdeC protein than the original CdeC D1 aptamer. This was not true for the CdeC D1.1 aptamer, which exhibited less fluorescence and thus a lower binding affinity to this protein than the other two aptamers tested.

The aptamers can be optimized according to the following examples.

Figure 13:
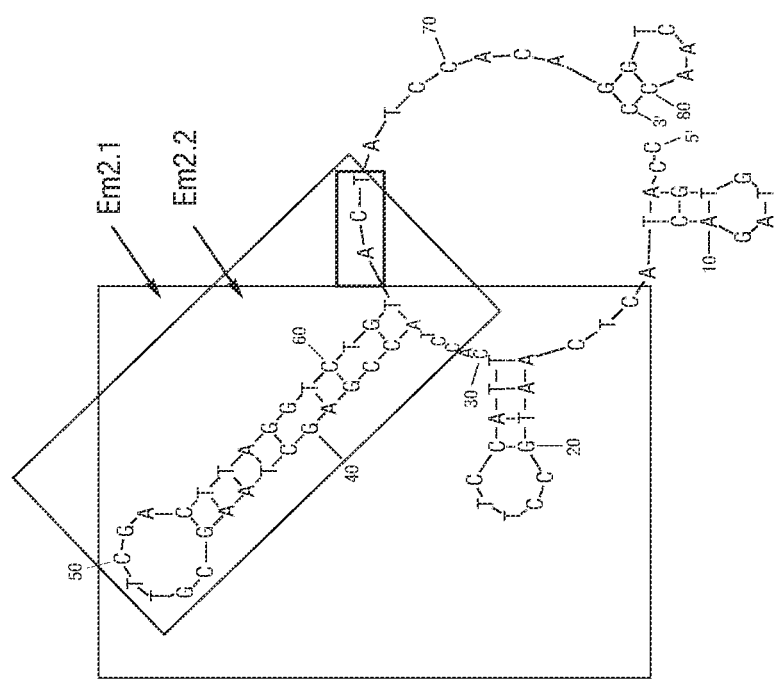
FIG. 13 shows the predicted structures for the aptamer CdeM E2/Em2 (SEQ ID NO: 14), together with highlighted sections for the aptamers CdeM E2.1/Em2.1 (SEQ ID NO: 55) and CdeM E2.2/Em2.2 (SEQ ID NO: 43).
Figure 14:
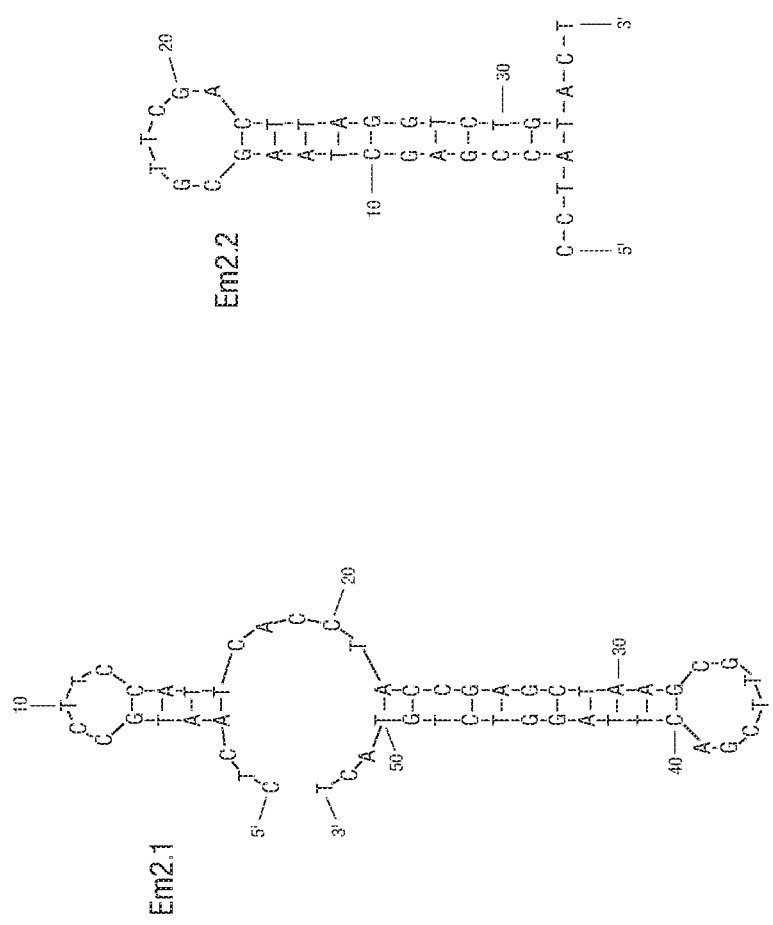
FIG. 14 shows the predicted structures for the aptamers CdeM E2.1/Em2.1 (SEQ ID NO: 55) and CdeM E2.2/Em2.2 (SEQ ID NO: 43).

CdeM E2/Em2: FIG. 13 shows the predicted structures for the aptamer CdeM E2/Em2 (SEQ ID NO: 14), together with highlighted sections for the aptamers CdeM E2.1/Em2.1 (SEQ ID NO: 55) and CdeM E2.2/Em2.2 (SEQ ID NO: 43), according to some embodiments of the disclosure. FIG. 14 shows the predicted structures for the aptamers CdeM E2.1 (SEQ ID NO: 55) and CdeM E2.2 (SEQ ID NO: 43).

Figure 15A:
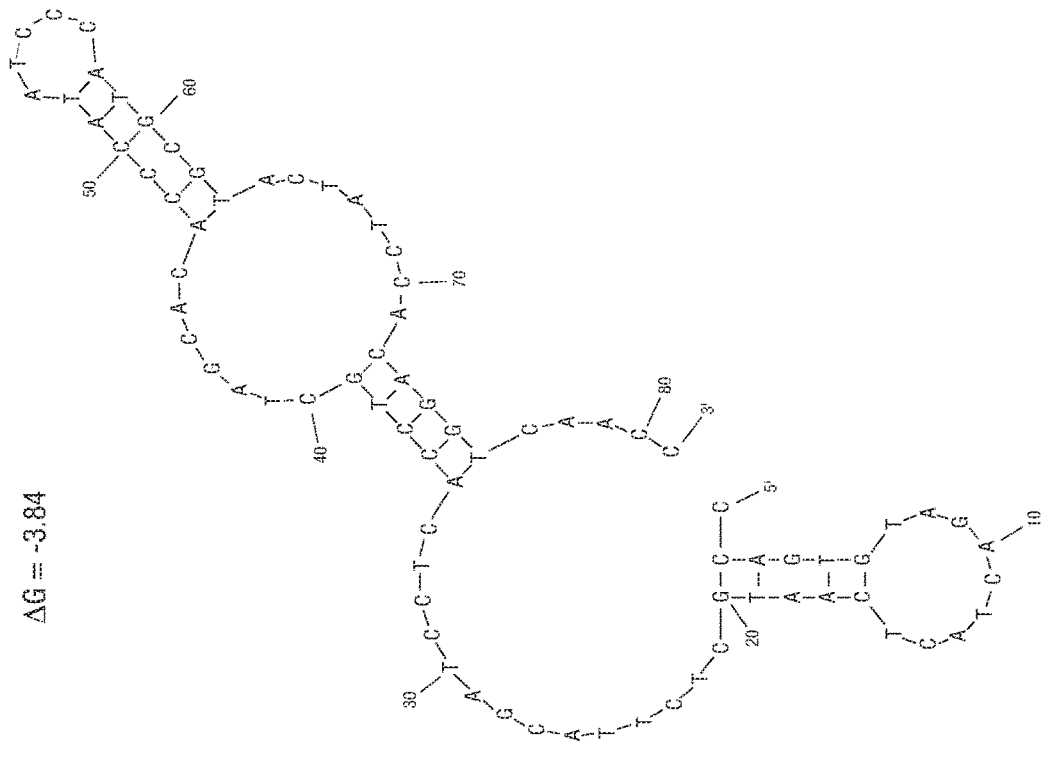
Figure 15A:
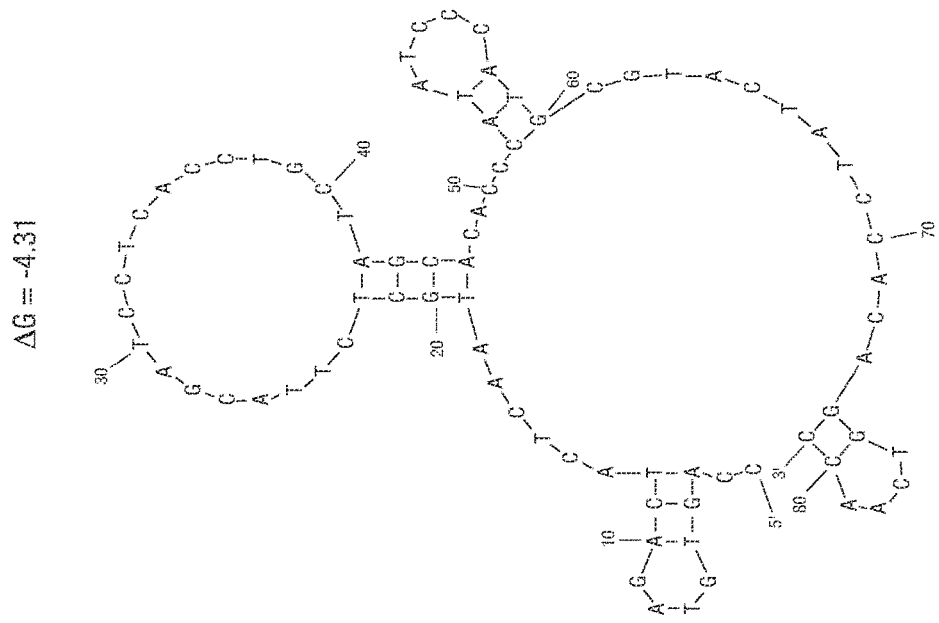
Figure 16:
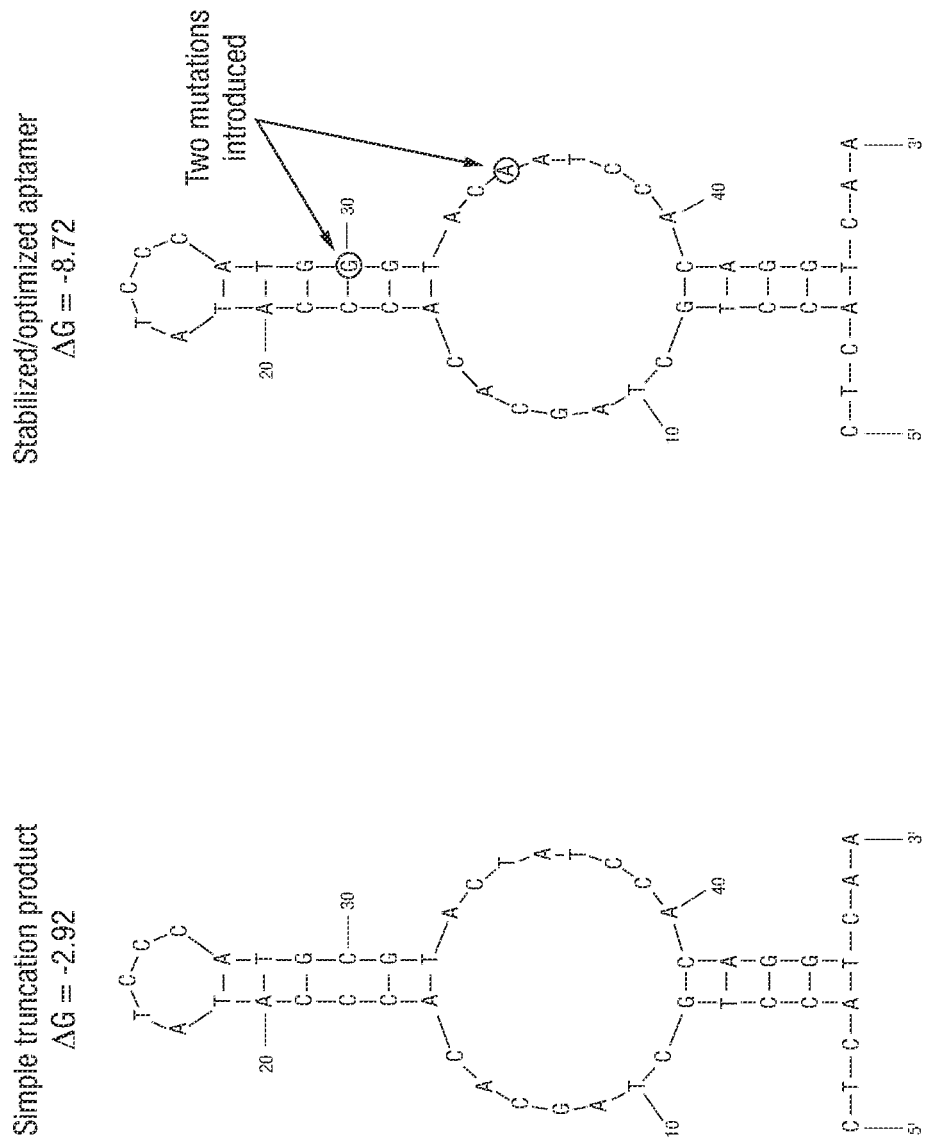
FIG. 16 shows the predicted structures for the aptamer C.Diff F1.1 (SEQ ID NO: 44).
Figure 17:
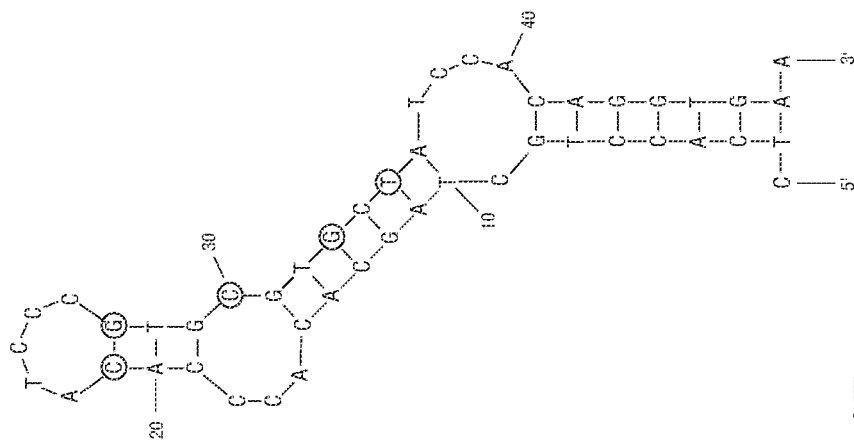
FIG. 17 shows the predicted structures for the aptamer C.Diff F1.2 (SEQ ID NO: 45).
Figure 17:
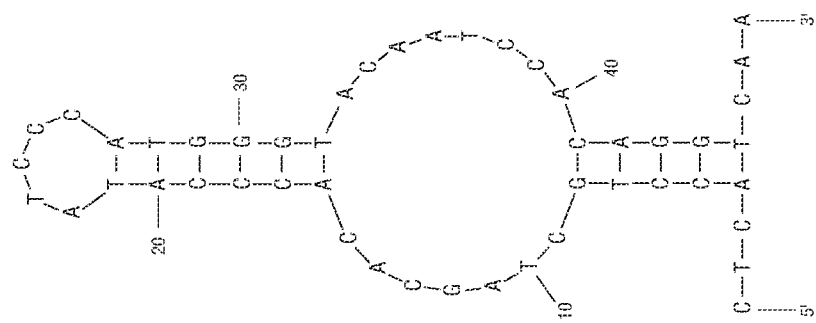
Figure 18:
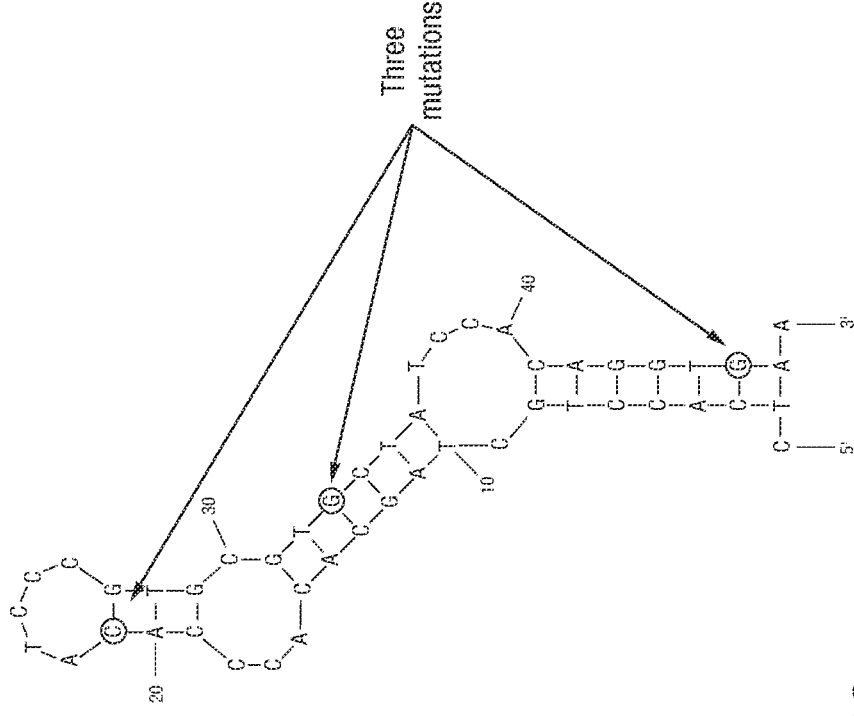
FIG. 18 shows the predicted structures for the aptamer C.Diff F1.2 (SEQ ID NO: 45).
Figure 18:
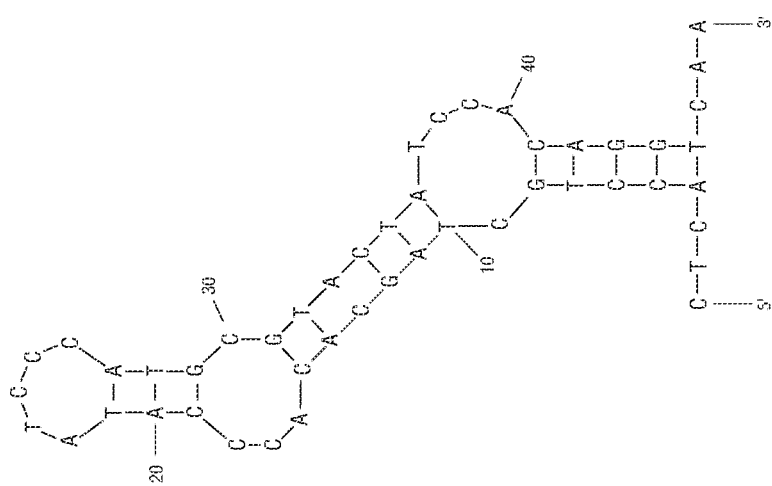

*C.Diff* F1: FIGS. 15A-15B show the predicted structures for the aptamer *C.Diff* F1 (SEQ ID NO: 1). FIG. 16 shows the predicted structures for the aptamer *C.Diff* F1.1 (SEQ ID NO: 44). FIG. 17 shows the predicted structures for the aptamer *C.Diff* F1.2 (SEQ ID NO: 45). FIG. 18 shows the predicted structures for the aptamer *C.Diff* F1.2 (SEQ ID NO: 45).

Figure 19:
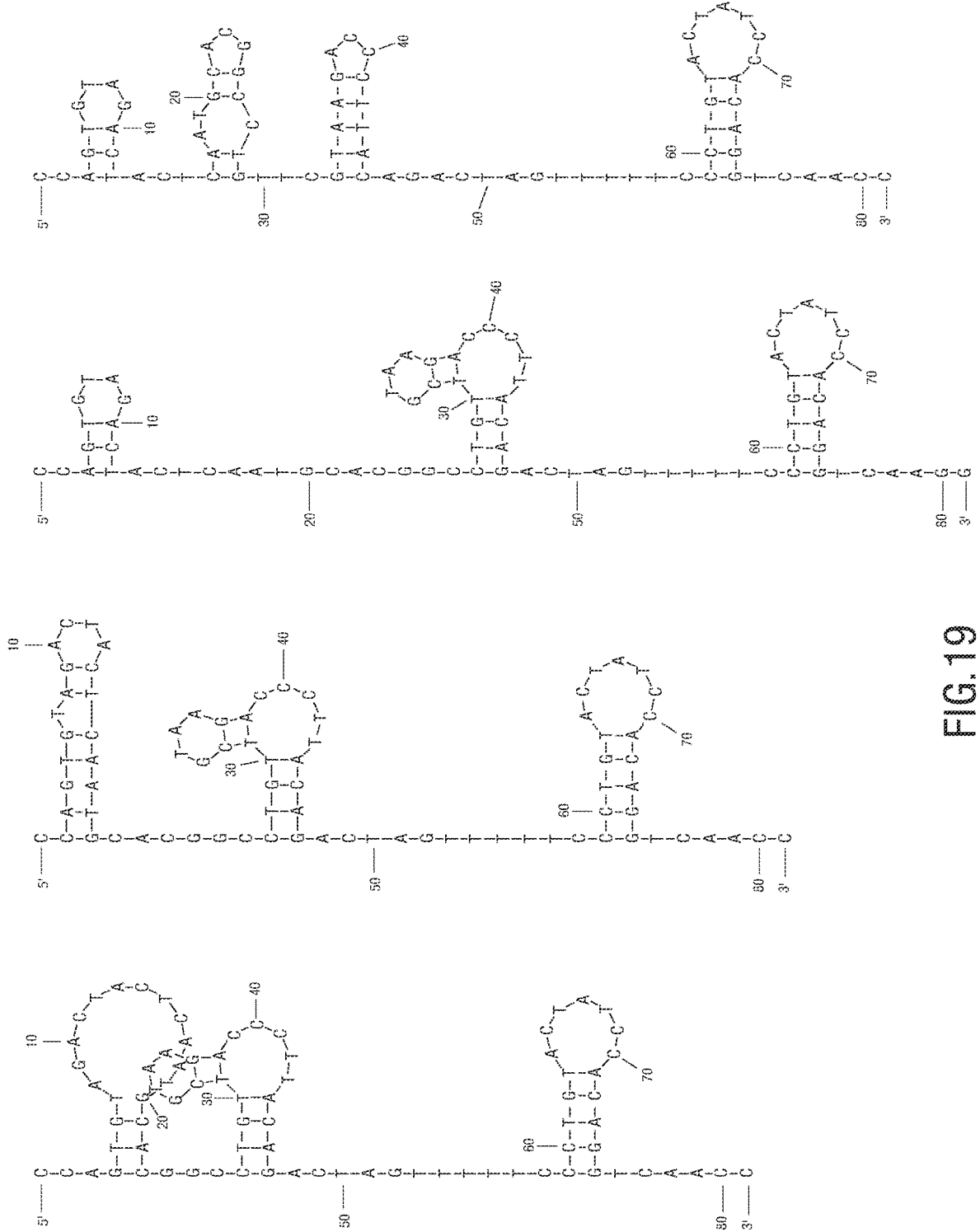
FIG. 19 shows the predicted structures for the aptamer C. diff E2 (SEQ ID NO: 3).
Figure 20:
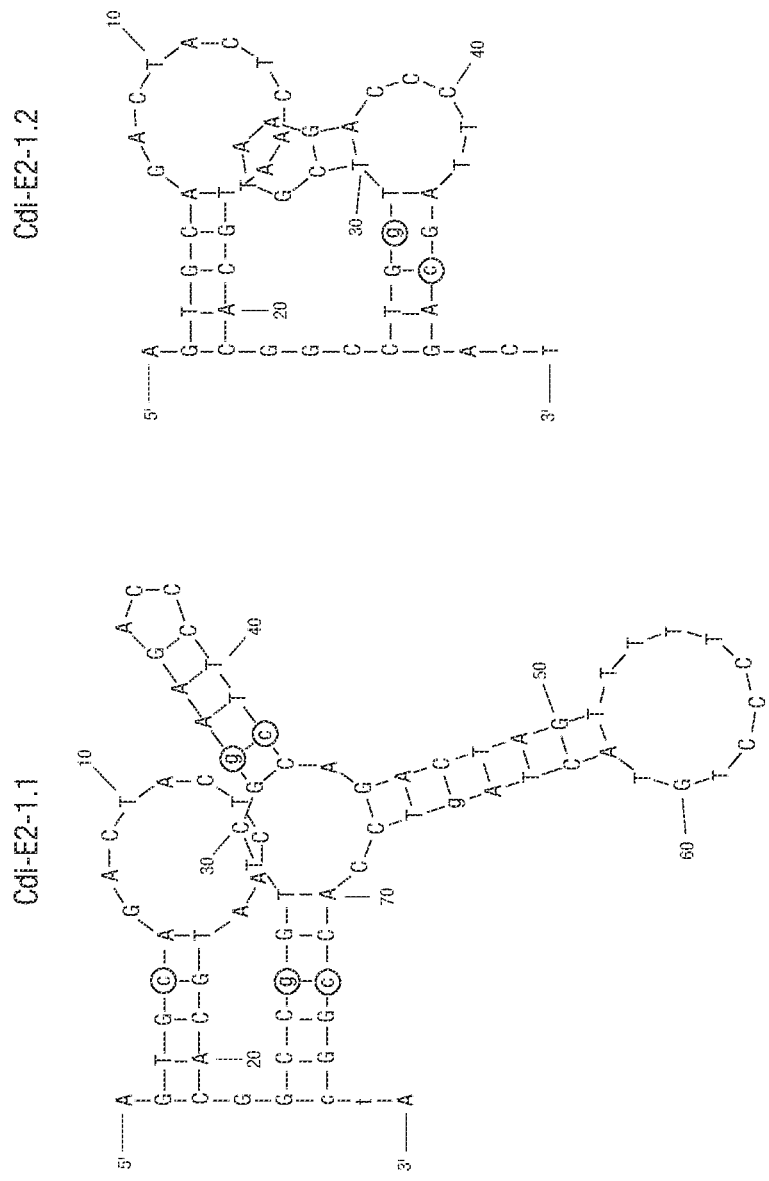
FIG. 20 shows the predicted structures for the aptamers C. diff E2-1.1 (SEQ ID NO: 46) and C. diff E2-1.2 (SEQ ID NO: 47).

*C.Diff* E2: FIG. 19 shows the predicted structures for the aptamer *C. diff* E2 (SEQ ID NO: 3). FIG. 20 shows the predicted structures for the aptamers *C. diff* E2-1.1 (SEQ ID NO: 46) and *C. diff* E2-1.2 (SEQ ID NO: 47).

Figure 21A:
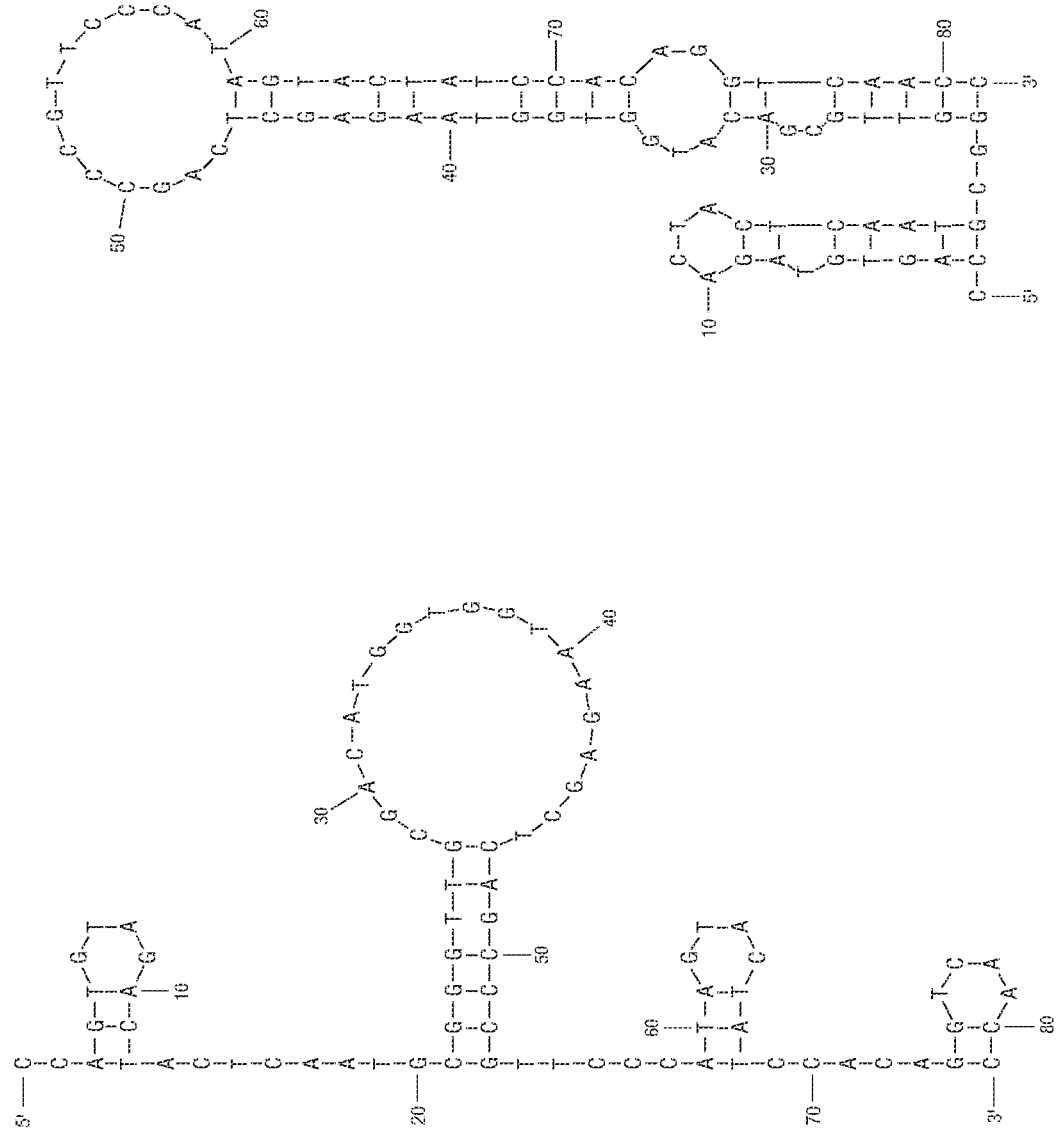
FIGS. 21A-21B show the predicted structures for the aptamer C. Diff G1 (SEQ ID NO: 2).
Figure 21B:
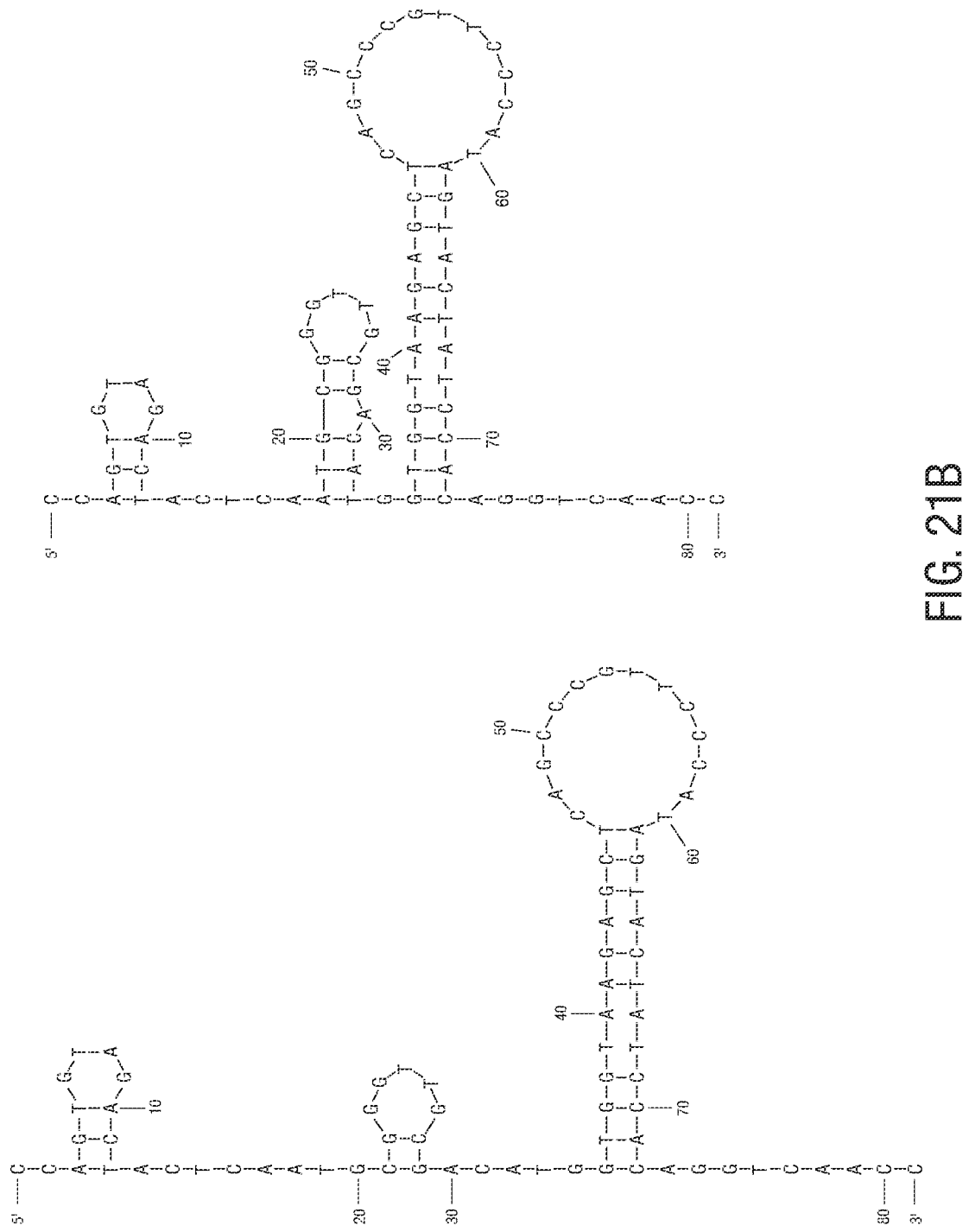
Figure 22:
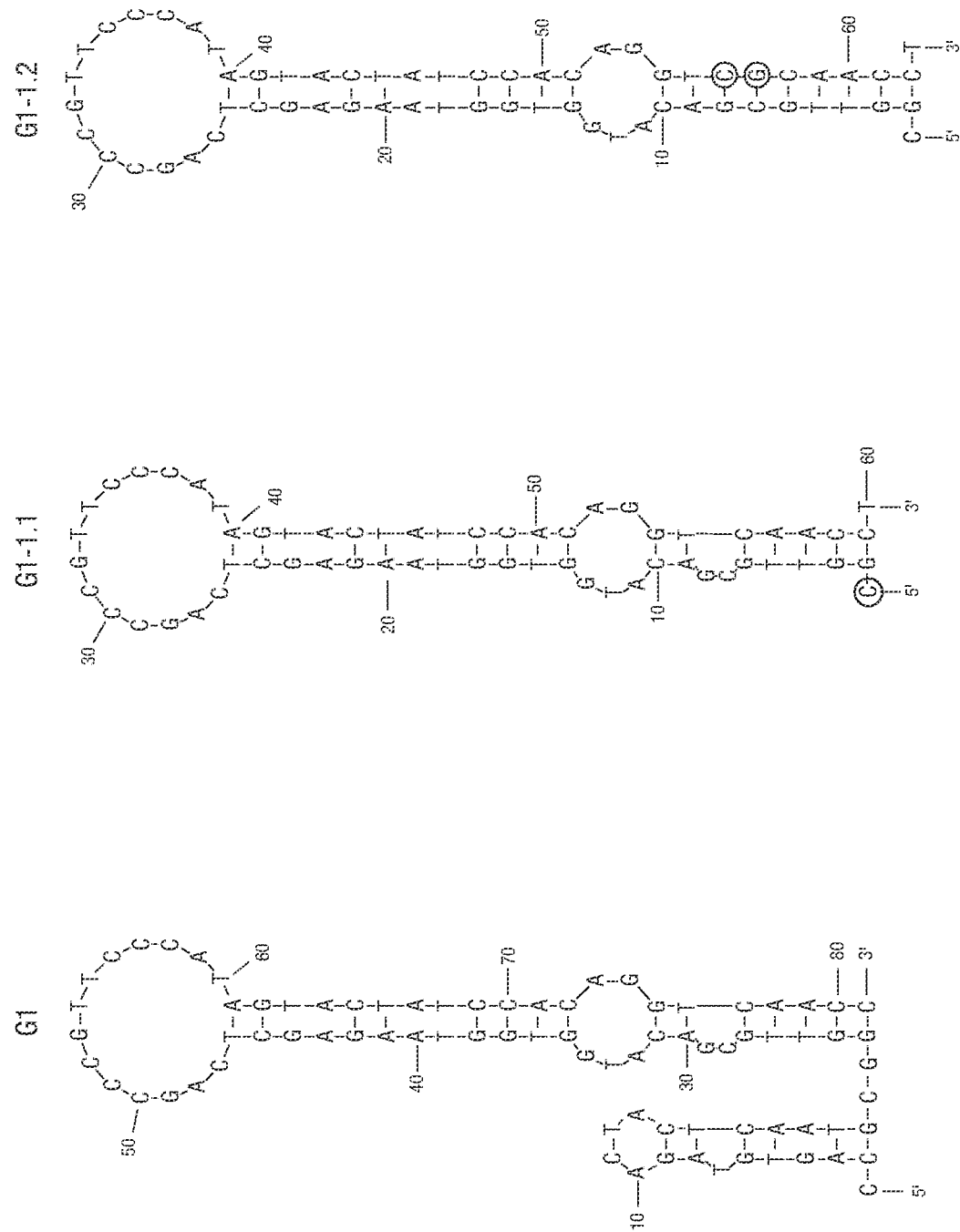
FIG. 22 shows the predicted structures for the aptamers C. Diff G1-1.1 (SEQ ID NO: 48) and C. Diff G1-1.2 (SEQ ID NO: 49).
Figure 23:
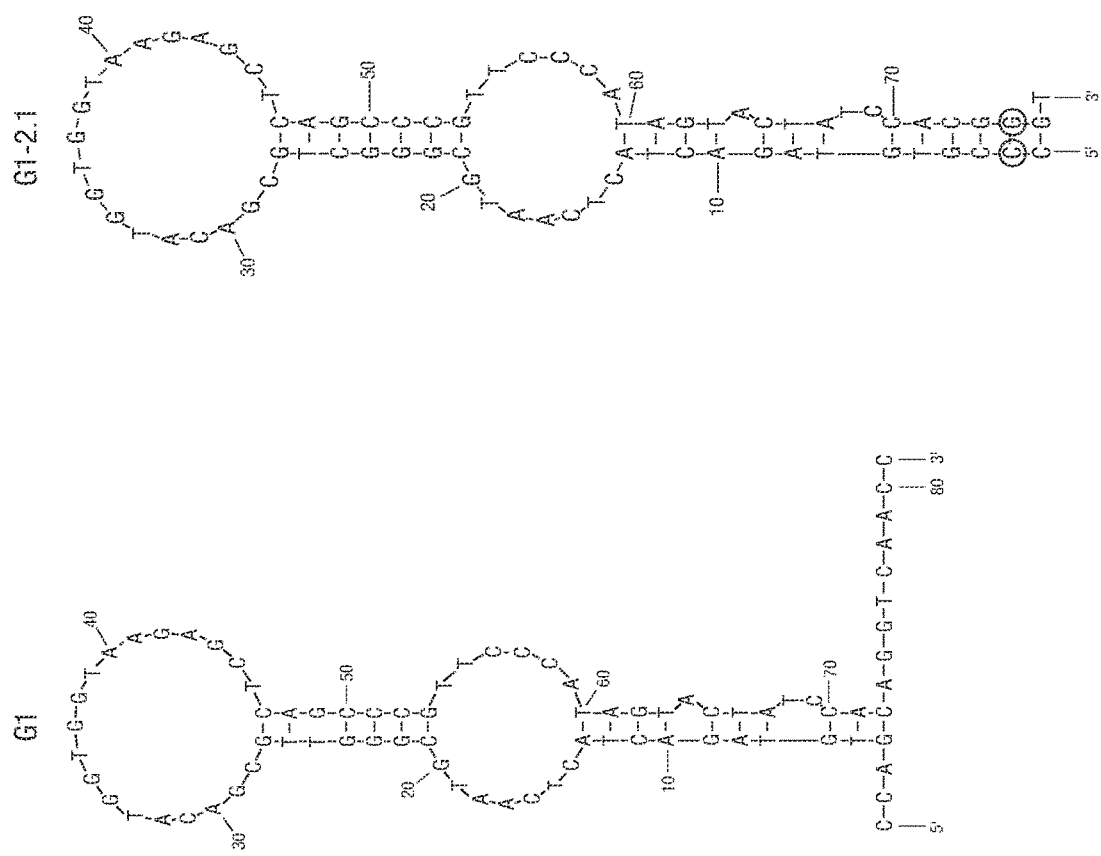
FIG. 23 shows the predicted structures for the aptamer C. Diff G1-2.1 (SEQ ID NO: 50).
Figure 24:
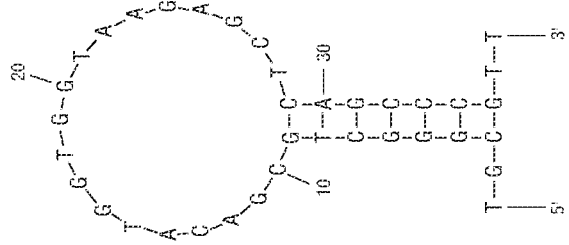
FIG. 24 shows the predicted structures for the aptamers C. Diff G1-2.1.1 (SEQ ID NO: 51) and C. Diff G1-2.1.2 (SEQ ID NO: 52).
Figure 24:
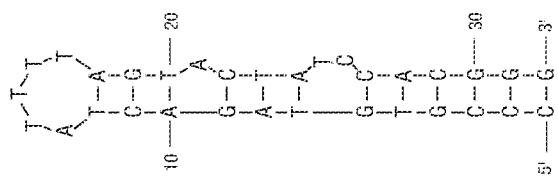

*C.Diff.* G1: FIGS. 21A-21B show the predicted structures for the aptamer *C.Diff* G1 (SEQ ID NO: 2). FIG. 22 shows the predicted structures for the aptamers *C.Diff* G1-1.1 (SEQ ID NO: 48) and *C.Diff* G1-1.2 (SEQ ID NO: 49). FIG. 23 shows the predicted structures for the aptamer *C.Diff* G1-2.1 (SEQ ID NO: 50). FIG. 24 shows the predicted structures for the aptamers *C.Diff* G1-2.1.1 (SEQ ID NO: 51) and *C.Diff* G1-2.1.2 (SEQ ID NO: 52).

Figure 25:
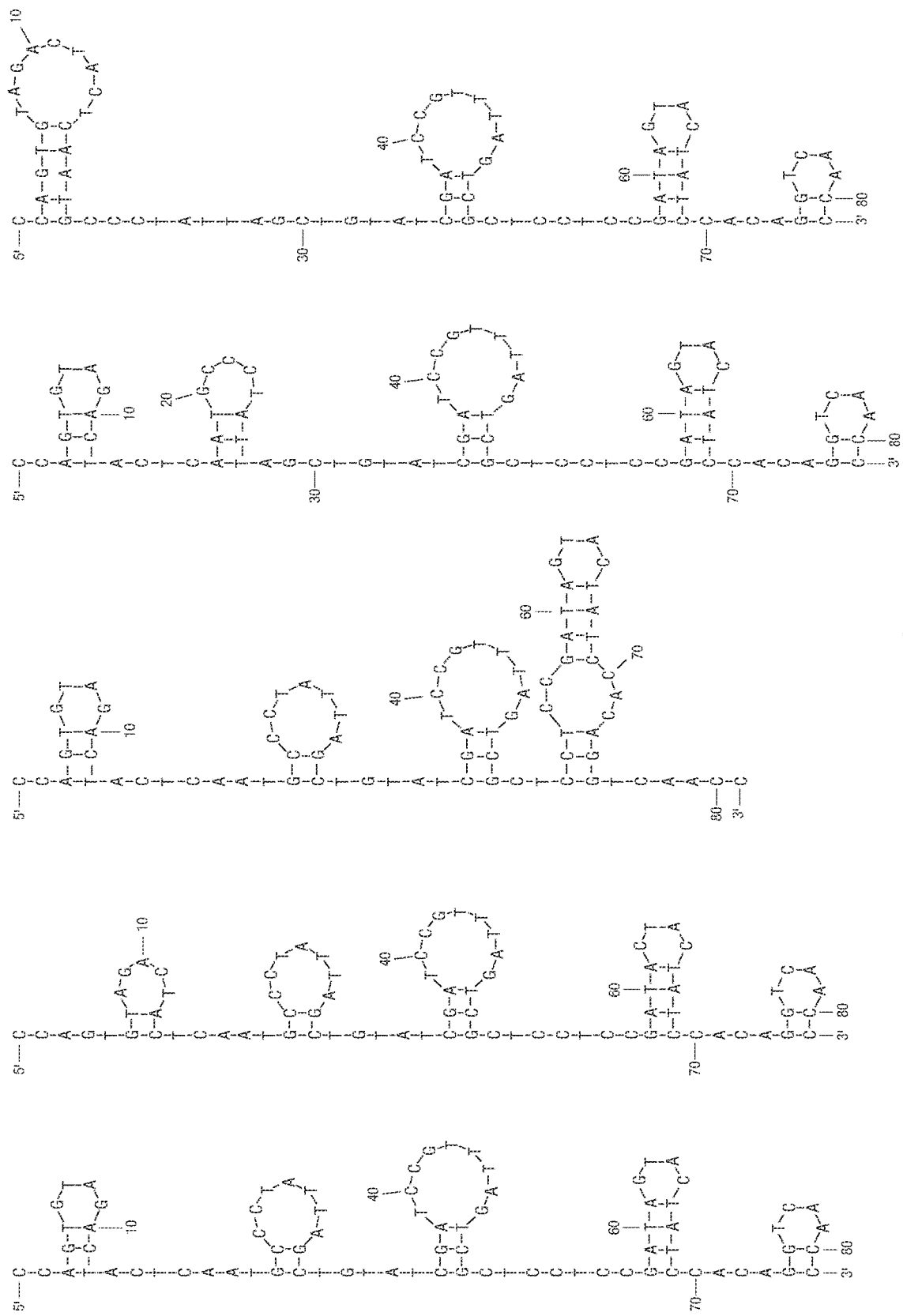
FIG. 25 shows the predicted structures for the aptamer CotEC Chitinase D10 (SEQ ID NO: 4).
Figure 26:
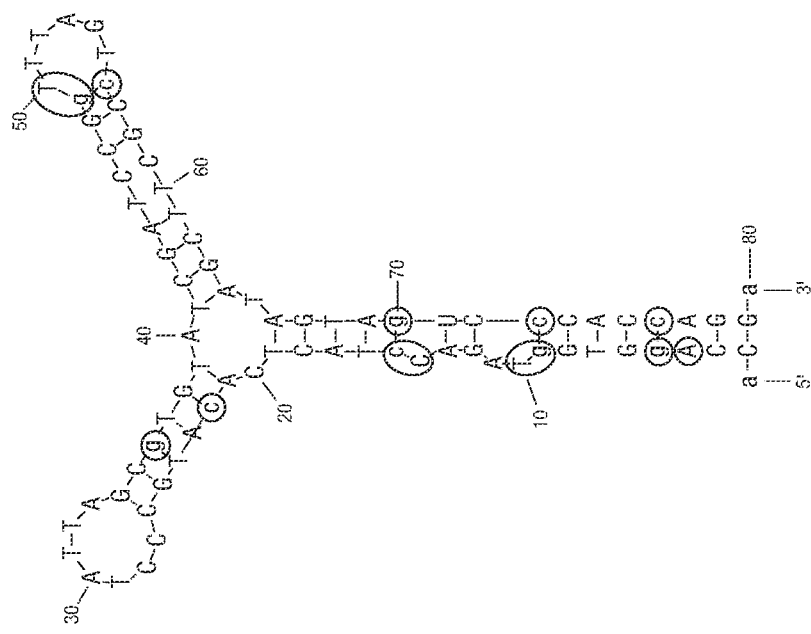
FIG. 26 shows the predicted structures for the aptamers CotEC Chitinase D10.1 (SEQ ID NO: 53) and CotEC Chitinase D10.2 (SEQ ID NO: 54).
Figure 26:
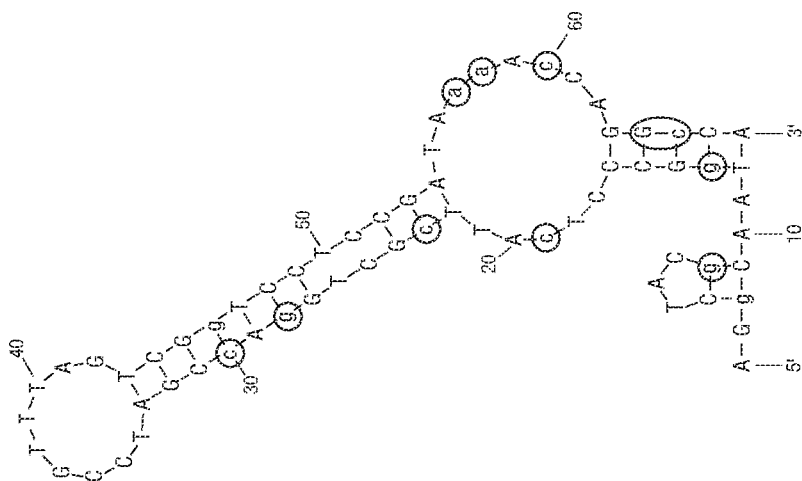

CotEC Chitinase D10: FIG. 25 shows the predicted structures for the aptamer CotEC Chitinase D10 (SEQ ID NO: 4). FIG. 26 shows the predicted structures for the aptamers CotEC Chitinase D10.1 (SEQ ID NO: 53) and CotEC Chitinase D10.2 (SEQ ID NO: 54).

Example 7: Beacon Design for the H2.1.2 Aptamer

The beacon detection concept involves the use of a first and a second labeled moieties either on separate oligonucleotides, or on the different portions of the same oligonucleotide: a first moiety is a fluorophore (fluorescent moiety), while the second moiety is a molecule that quenches the fluorophore (quenching moiety). The system is designed so that oligonucleotide hybridization, either between different elements of the same oligonucleotide, or separate oligonucleotides brings the quenching moiety into physical proximity with the fluorescent moiety, thus achieving maximum quenching. This hybridization event results in a decrease in the expression of fluorescence. For use in a detection system the hybridization event is in competition with the aptamer binding to a target molecule.

A beacon detection system has been designed and tested for the H2.1.2 aptamer (SEQ ID NO: 30).

Two antisense oligonucleotides have been designed to disrupt the stem structure of the H2.1.2 aptamer and thus act competitively with the binding of this aptamer to the CotE protein. The antisense sequences are:

H2.1.2as1:  CATTCCAAAGGTCAAG         (SEQ ID NO: 40)

H2.1.2as2:  CACACATTCCAAAAGGTCAAG    (SEQ ID NO: 41)

Figure 12:
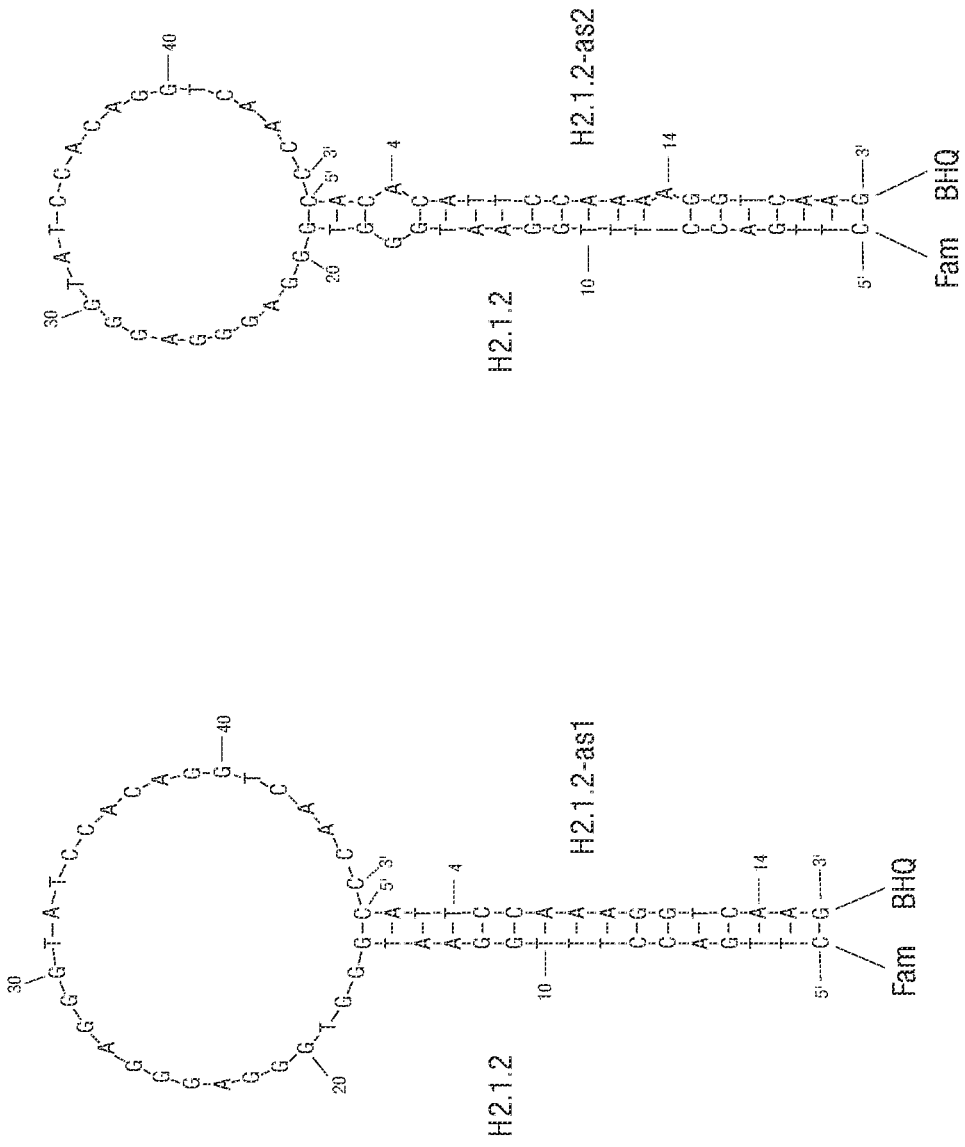
FIG. 12 shows the predicted structures for the H2.1.2 Black Hole Quencher® (BHQ)-containing antisense oligonucleotides, H2.1.2-as1 (SEQ ID NO: 40) and H2.1.2-as2 (SEQ ID NO: 41).

Each sequence has a Black Hole Quencher® (BHQ) on the 3' end. These sequences were designed to bind to the 5' end of the H2.1.2 aptamer as shown in FIG. 12.

Example 8: Detection of *Clostridium Difficile* Using Aptamer and Graphene Oxide Optimization of the Aptamer and GO Amounts:

The amount of aptamer and the amount of graphene oxide needed to quench the signal to maximize the observable change in fluorescence upon addition of target protein were optimized.

To a fixed concentration of FAM-labelled aptamer (H2.1.2), varying concentration of graphene oxide (GO) were added. To the aptamer-GO mix, 100 nM of the target protein (CotE) was added.

Following the protein addition, proportional change at any time point was calculated using the following equation:

$$\frac{\text{signal at a given time point} - \text{signal at the start of protein addition}}{\text{signal at the start of protein addition}}$$

Figure 33:
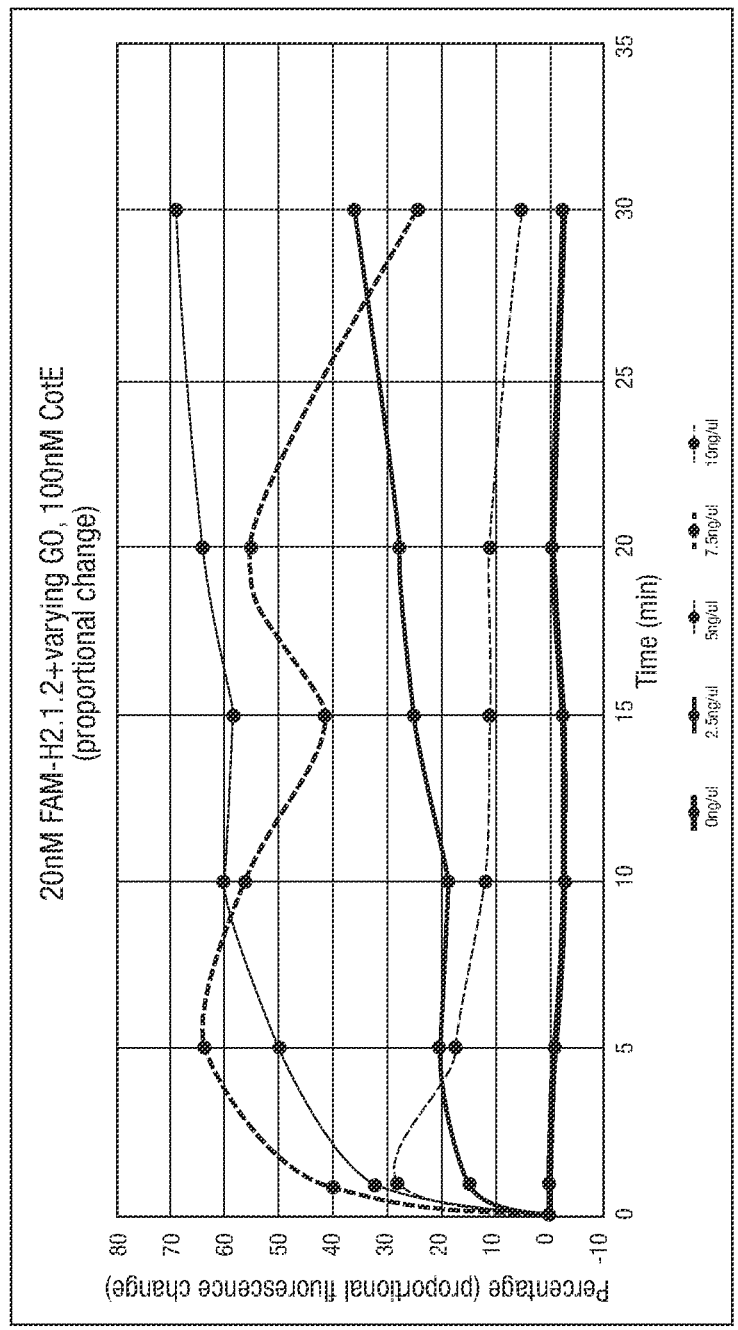
FIG. 33 is a graph showing the proportional change in recovery of the quenched signal following the addition of target protein.

FIG. 33 shows that based on the proportional change in quenched signal following the addition of target (CotE), 20 nM aptamer+5 ng/µL GO is the best combination.

For the combination 20 nM FAM-H2.1.2+5 ng/µL GO, 87% quenching was observed. More quenching was observed at higher concentration of GO, and the lower proportional recovery was attributed to aptamers not being released from the aptamer-GO mix even in presence of target due to an excess of GO surface.

Therefore, 20 nM aptamer+5 ng/µL was demonstrated as an example of an optimal combination.

At the optimal combination (20 nM aptamer+5 ng/µL GO), there was only 8% recovery of quenched fluorescence indicating that there was still room for optimization of the assay.

Effect of buffer on quenching and recovery:

In initial experiments, 20 mM Tris buffer without salts was used and no quenching of fluorescence was observed. The presence of salts is clearly required for aptamer adhesion to GO.

Two different buffers were tested:
1×SB: 10 mM HEPES, 120 mM NaCl, 5 mM KCl, 5 mM MgCl$_2$
1×BioV: 50 mM Tris, 77.5 mM NaCl, 4.5 mM KCl, 5 mM MgCl$_2$, 1 mM CaCl$_2$)

Figure 34:
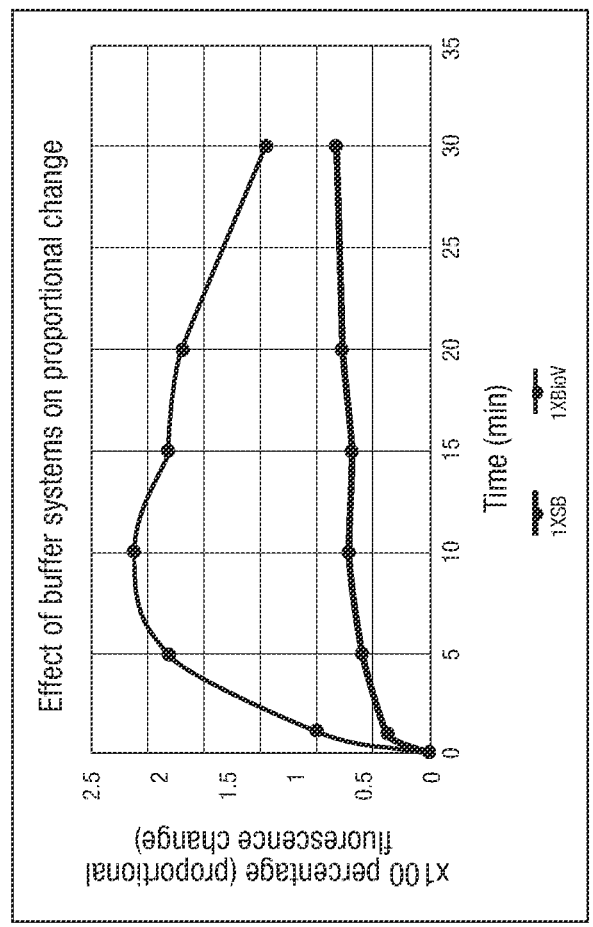
FIG. 34 is a graph showing the comparison of the recovery of quenched signal in different buffer systems.

FIG. 34 shows the comparison of the recovery of quenched signal in different buffer assays.

Using 20 nM FAM-H2.1.2 with 5 ng/µL GO, proportional change in quenched signal was observed following addition of 100 nM target (CotE).

Compared to the 1×SB, the 1×BioV buffer assay exhibited much better recovery of fluorescence in presence of the target. Therefore, in further experiments 1×BioV buffer systems was used for FAM-H2.1.2 aptamer.

Stability of the Assay:

To check upon the stability of the assay, the aptamer-GO mixture was incubated overnight, and then 100 nM of target was added.

Figure 35:
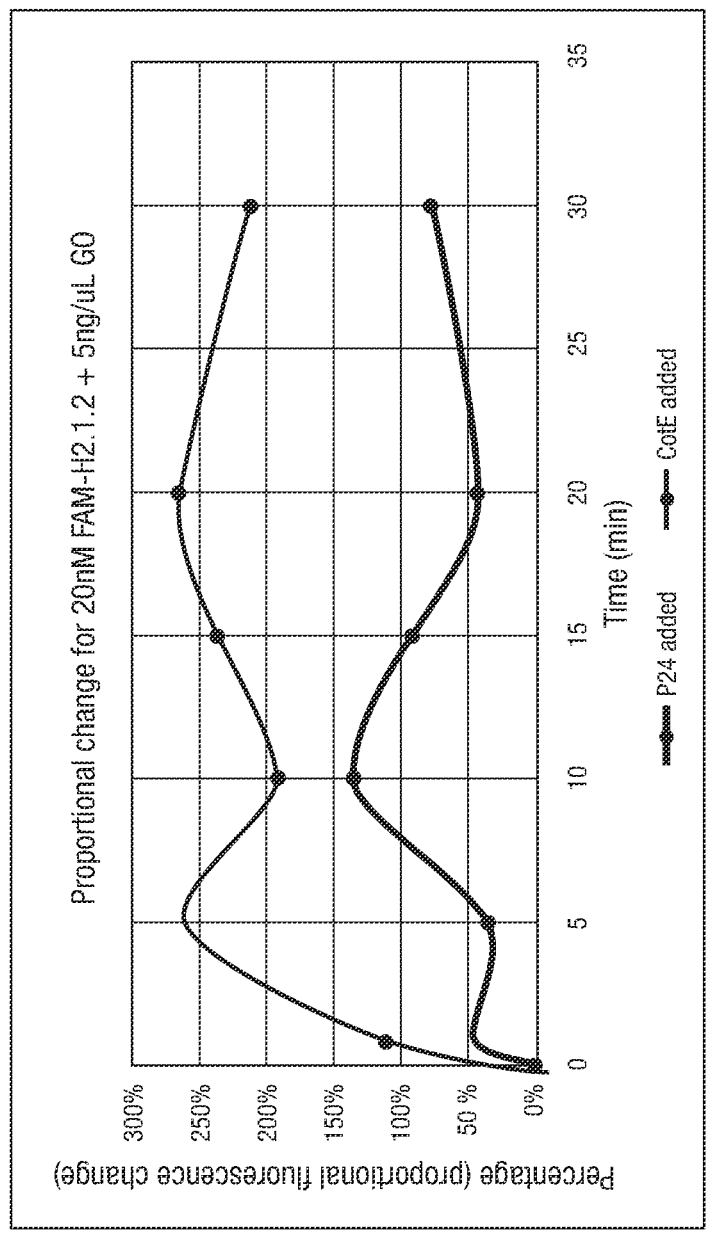
FIG. 35 is a graph showing the proportional change in recovery of quenched signals for aptamer-graphene oxide (GO) mix upon overnight incubation.

FIG. 35 shows the proportional change in recovery of quenched signals for overnight aptamer-GO mix. The results show that after overnight incubation the level of quenching did not change. Without being bound to the theory, once equilibrium has been reached in terms of quenching this equilibrium remains stable over longer periods e.g. days, weeks, etc.

Visualization:

A solution containing the aptamer with GO was added to the surface of a sample in order to directly visualize the presence of the target protein.

Different concentrations of fluorescent aptamers were tested. Fluorescent aptamers at a concentration of 200 nM or higher were easily visualized. In some embodiments, the excitation wavelength can be 495 nm. In some embodiments, the emission wavelength can be 517 nm.

Based on previous experiments, 8% of the original signal could be recovered. Scaling up to the level of concentrations so that the recovery could be visualized, the experiment aimed for the recovery equivalent to the signal from 200 nM aptamer. Since recovery was approximately at 10% of the original signal, therefore, 2 µM was the concentration of the aptamer that was used.

Figure 36:
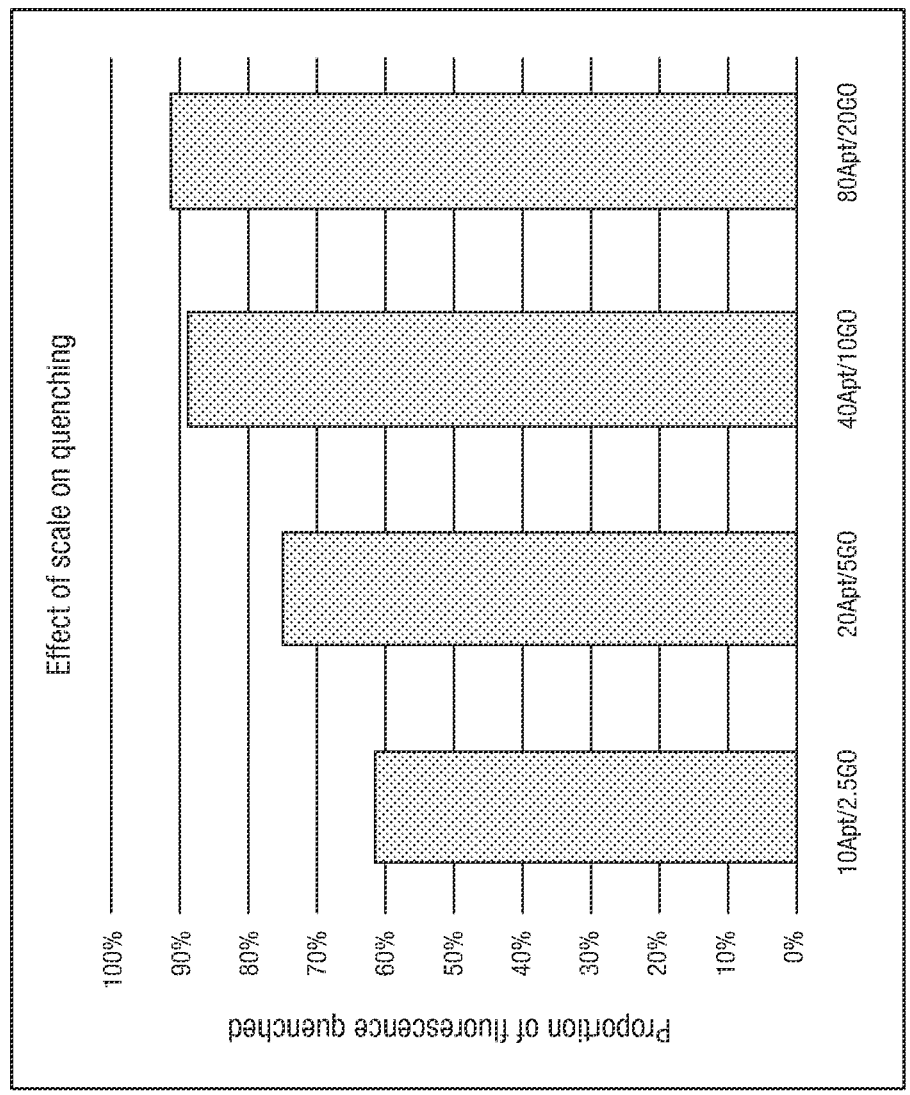
FIG. 36 is a bar graph showing the effect of quenching at different concentrations of aptamer while maintaining the same aptamer to GO ratio.

Before scaling up, the amount of signal that was quenched using same proportion of Aptamer and GO, but at different scales, was tested (see FIG. 36). FIG. 36 shows the quenching at different concentrations of aptamer while the aptamer to GO ratio was maintained. The results showed that the percent of quenching increased for the same proportion of the GO. Therefore, a much lower proportion of GO is needed at higher concentrations of aptamer to observe 80 to 90% quenching. 2 µM of FAM labelled CdeC D1.2 aptamer with 200 ng/µL of the graphene oxide (GO) was used. The resulting mixture is referred as "Aptamer-GO mix".

CdeC D1.2 aptamer is designed to specifically target the CdeC protein. CdeC protein most closely resembles the *C. difficile* spores in their attribute of clustering together.

The CdeC protein is expressed in the exosporium of *C. difficile* spores. Once the protein is purified it self-aggregates into large insoluble balls of protein that can visualized under a microscope.

Figure 37:
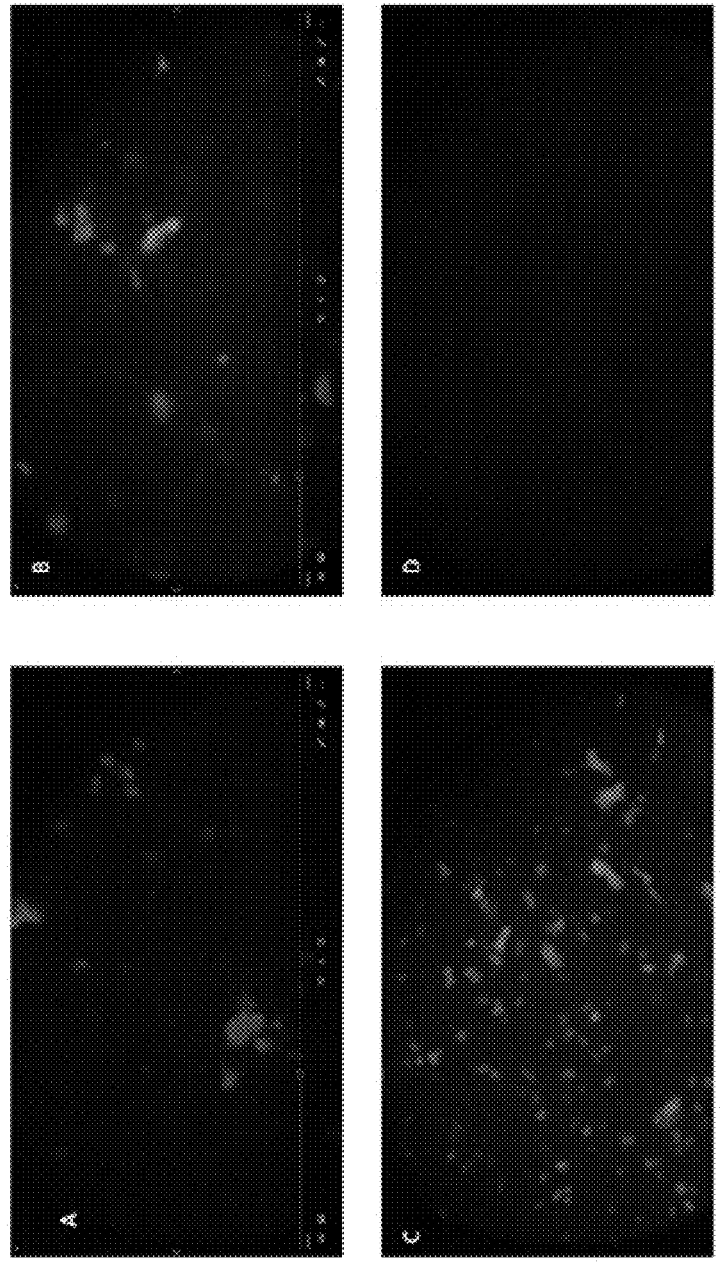
FIG. 37 is a series of four images showing the visualization of C. difficile protein balls without a wash step with a fluorescent aptamer. A, B, C are in the presence of CdeC proteins, D is in the absence of protein.

The method described herein was applied to detect CdeC protein aggregates under the microscope with the no-wash approach using a concentration of 2 µM Fain labeled aptamer (D1.2) for the proteins and 200 ng/µL of GO. CdeC protein balls were suspended in 4 µL of solution at a concentration of 5E9 particles/mL on a microscope slide and 10 µL of the aptamer/GO complex was added. FIG. 37 are images obtained of the aptamer attached to the protein balls after a minimum of five minutes after application of the Aptamer/GO mixture.

In presence of target protein, the Aptamer-GO mix releases the fluorescent labeled aptamers which then bind to the target proteins.

In presence of target protein, the background fluorescence fades out, leaving the stable fluorescent signal at precisely the locations where the target protein has clumped together (as observed under bright field microscope).

In absence of the protein, no such observation was evident. The background fluorescence fades out with no evident signal from the fluorescent aptamers, implying that the fluorescent signal from the aptamer was evident only in presence of the protein, due to the target protein capturing the fluorescent aptamer from the Aptamer-GO mix.

The efficacy of this assay against other *C. difficile* proteins, in particular the exosporium protein CotE, was also demonstrated.

Specificity:

The detection assay described herein was designed such that the quenched fluorescent signal is recovered only in the presence of the target protein and not in presence of non-target proteins (negative control).

Experiments were carried out a lower scale of Aptamer/GO concentration in order to conserve protein. At lower concentrations it was noted that more time is required for the quenching of aptamer fluorescence to equilibrate. At lower concentrations, a time of at least 150 minutes was required for stable quenching. As such, a composition of pre-mixed aptamer and can be used for the detection assay.

Figure 38:
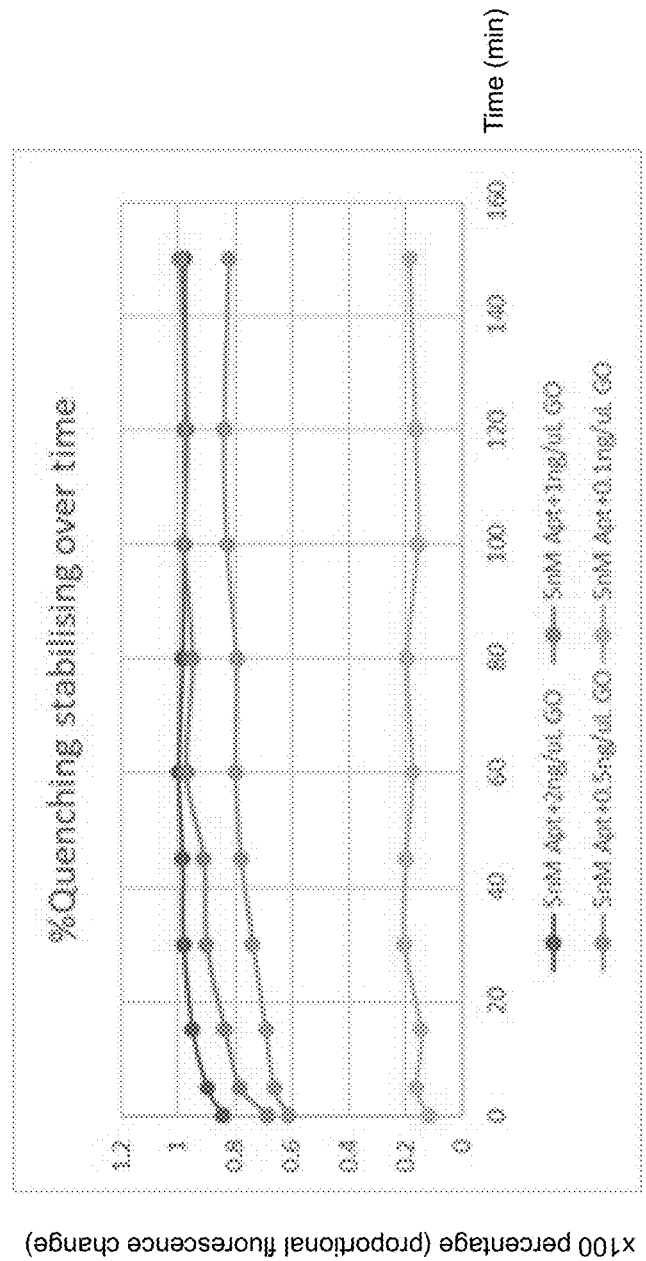
FIG. 38 is a graph showing the quenched signal for 5 nM FAM-H2.1.2 with different concentrations of GO, stabilizing over time.

FIG. 38 shows the quenched signal for 5 nM FAM-H2.1.2 with different GO, stabilizing over time.

The signal from 5 nM aptamer with 0.5 ng/μL GO exhibited 83% quenching and stabilized after 150 minutes. The 80% to 90% quenching can be used to record optimal proportional recovery following the addition of target proteins.

Once the quenched signal was stabilized, a fixed concentration of the target protein was added to the aptamer-GO mix (5 nM aptamer+0.5 ng/μL GO), and the recovery in quenched signal was recorded over time.

As negative control, a non-target protein at the same concentration (HIV cap protein P24) was added to the aptamer-GO mix.

In these experiments FAM-labelled H2.1.2 aptamer that was designed specifically to target CotE protein were used. FAM-labelled H2.1.2 aptamer was also tested in presence of P24 protein as negative control.

Figure 39:
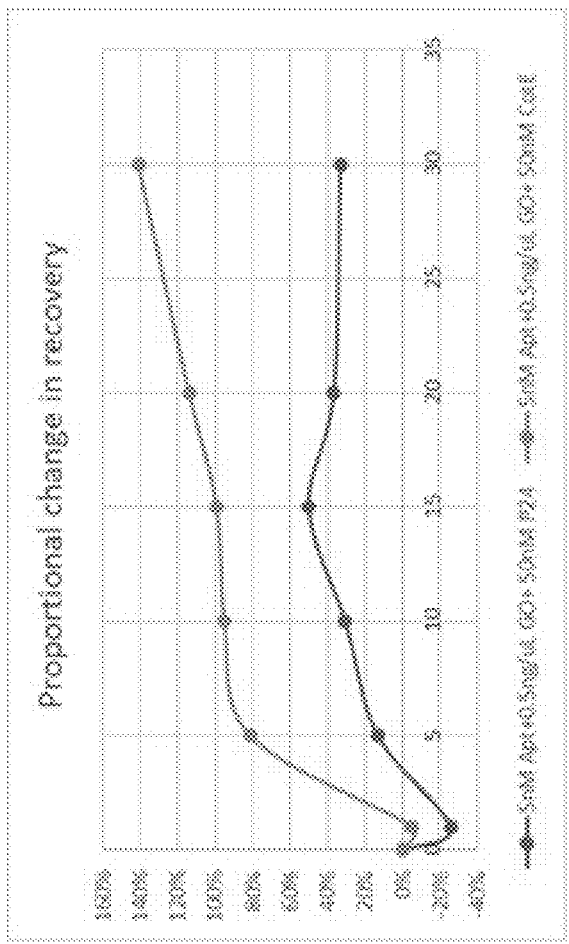
FIG. 39 is a graph showing the recovery in quenched signal of the aptamer-GO mix with 50 nM CotE vs with 50 nM P24.

FIG. 39 shows the proportional change in the recovery of the quenched signal of aptamer-GO mix in presence of 50 nM CotE (target) or the presence of 50 nM P24 (negative control).

To improve the consistency of the detection assay, the concentration of PEG to be used in the buffer system as blocking agent was optimized for minimizing aspecific interactions.

Using 0.005% PEG in the buffer system, and 5 nM Fam-H2.1.2 with 0.5 ng/μL GO, the recovery of quenched signal was recorded after adding 50 nM of target protein (CotE) and 50 nM negative control protein (P24).

Figure 40:
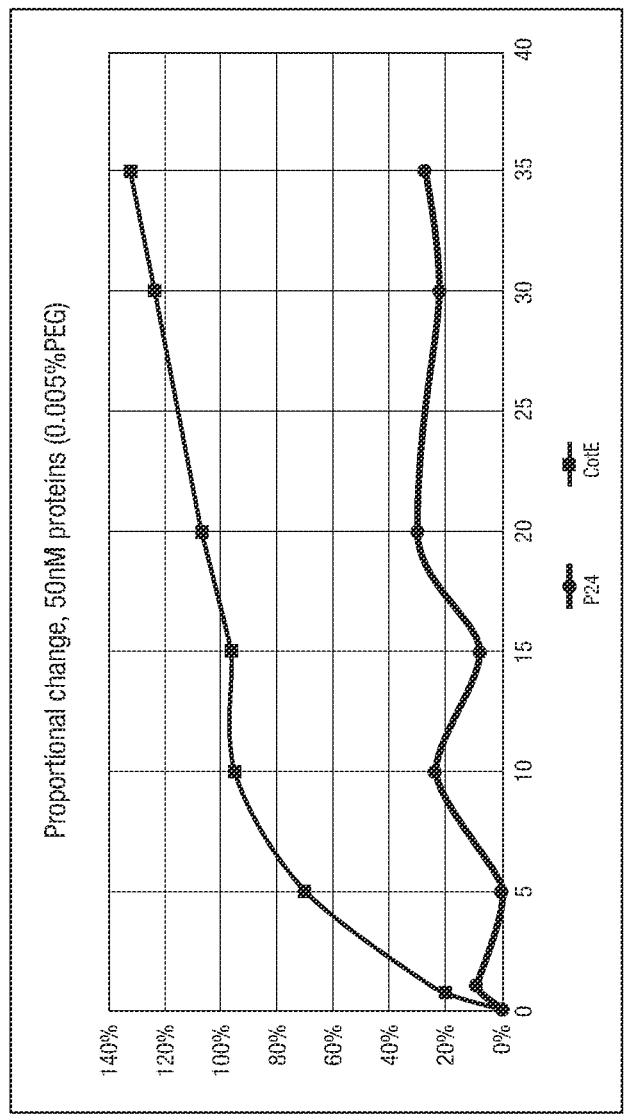
FIG. 40 is a graph showing the recovery in quenched signal of the aptamer-GO mix with 50 nM CotE vs 50 nM P24, in PEG.

FIG. 40 shows the recovery in quenched signal of aptamer-GO mix with 50 nM CotE vs 50 nM P24, in PEG. The results conclusively prove the specificity of the recovery of quenched signal of aptamer-GO mix in presence of the target protein.

Sensitivity:

A progressively lower amount of target protein and negative control protein were used to test the lowest concentration of the target protein the assay system could detect such that the signal recovery (proportional change) is distinguishable from the effects of aspecific recovery (observed in negative control).

The recovery of stabilized quenched signal of the aptamer-GO mix (5 nM FAM-H2.1.2+0.5 ng/μL GO) was tested in presence of varying concentrations of target protein (CotE) and compared with recovery in presence of same concentrations of negative control protein (P24).

Figure 41A:
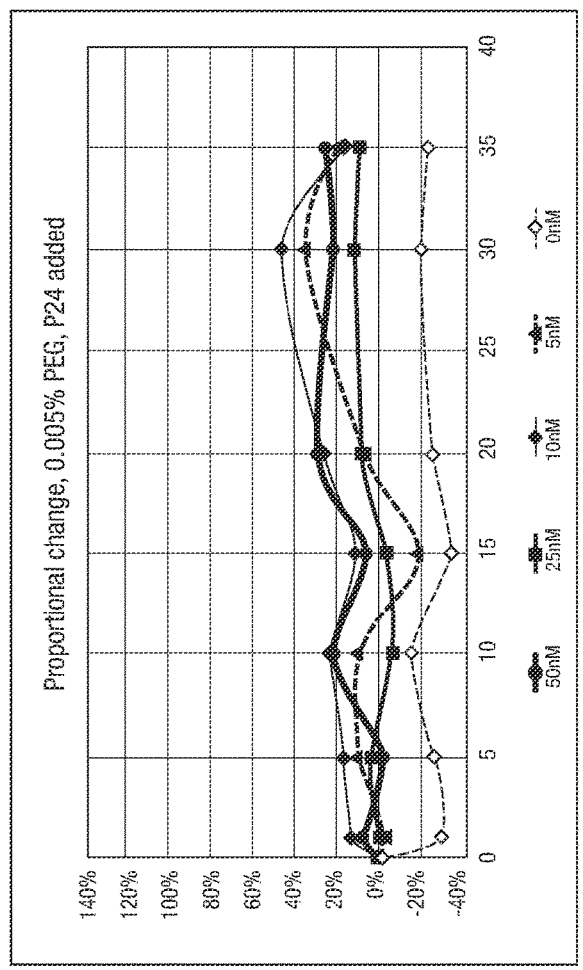
FIG. 41A and FIG. 41B are graphs showing the recovery in quenched signal of the aptamer-GO mix in varying concentrations of P24 negative control (FIG. 41A) and varying concentrations of CotE protein (FIG. 41B).
Figure 41B:
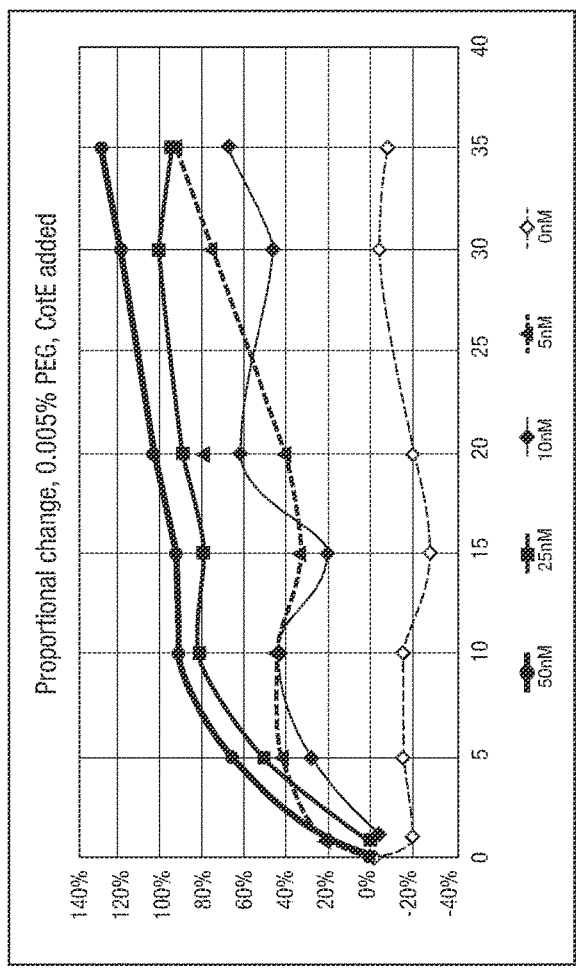

FIG. 41A shows the recovery in quenched signal of aptamer-GO mix in varying concentrations of P24 (negative control protein). FIG. 41B shows the recovery in quenched signal of aptamer-GO mix in varying concentrations of CotE (target protein).

As shown in FIGS. 41A-41B, the recovery is observable in as low as 5 nM-10 nM range for target (CotE) protein and the recovery is greater than aspecific recovery observed for same concentrations of P24 (negative control).

Figure 42:
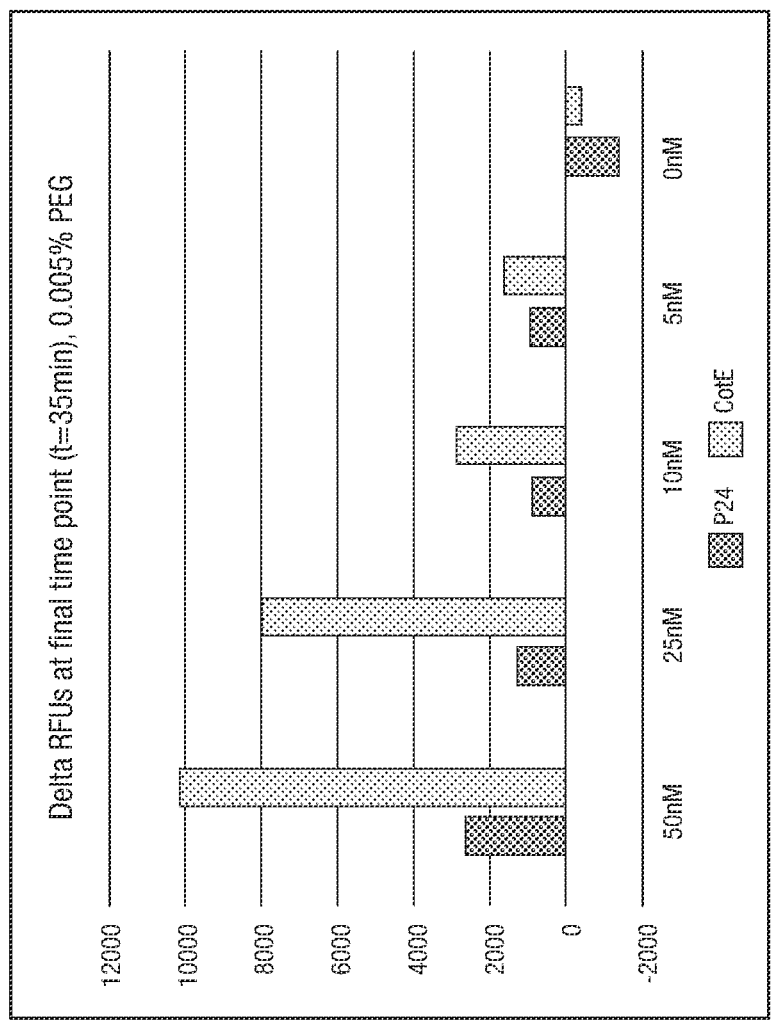
FIG. 42 is a bar graph showing the specific detection of low concentrations of CotE protein with aptamer/GO treatment after 35 min.

FIG. 42 shows a quantitation of the amount of fluorescence released from after exposure of varying concentrations of the CotE protein, or a negative control protein P24 (the cap protein from the HIV virus). To demonstrate maximum sensitivity, the concentration of aptamer was reduced to 5 nM, and the concentration of GO was reduced to 0.5 ng/μL. 0.005% polyethylene glycol was added as a blocking agent to enhance specificity. The experiment was performed with the H2.1.2 aptamer. This same data is provided in FIG. 34 as a function of time.

Figure 43:
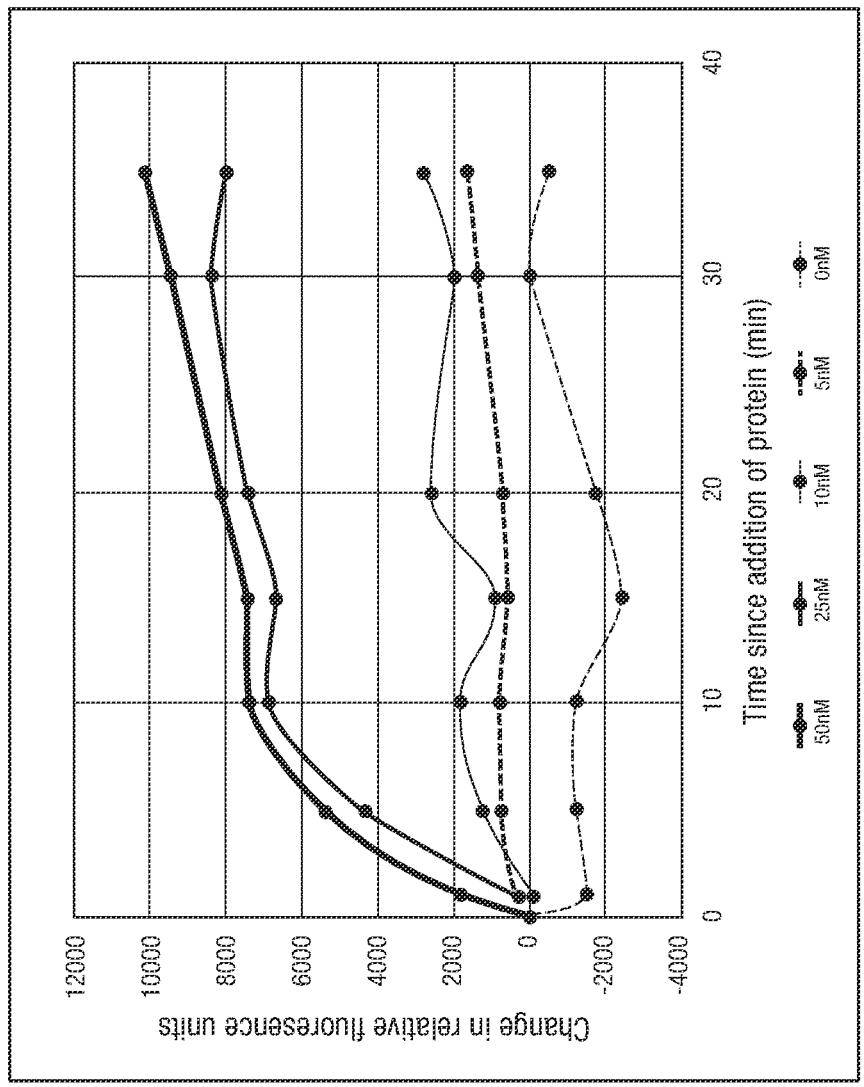
FIG. 43 is a graph showing the fluorescence response with the H2.1.2 aptamer in response to varying concentrations of the FAM-labeled H2.1.2 aptamer with varying CotE concentrations.

FIG. 43 shows the change in relative fluorescence units (RFU). FIG. 43 shows an increase in the fluorescent signal of the sample, following the addition of the protein. These results imply that in presence of 25 nM, 10 nM, 5 nM CotE detectable signal can be observed.

However, at concentrations below 25 nM, the detectable increase in fluorescence was less reliable compared to aspecific increase in fluorescent signal in presence of P24.

Figure 44A:
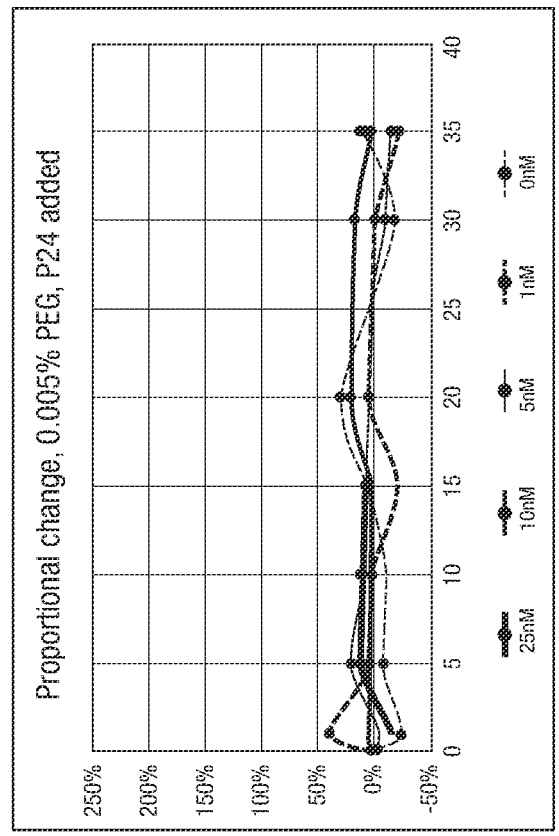
FIG. 44A and FIG. 44B are graphs showing the recovery in quenched signal of the aptamer-GO mix in varying concentrations of P24 negative control (FIG. 44A) and varying concentrations of CotE protein (FIG. 44B).
Figure 44B:
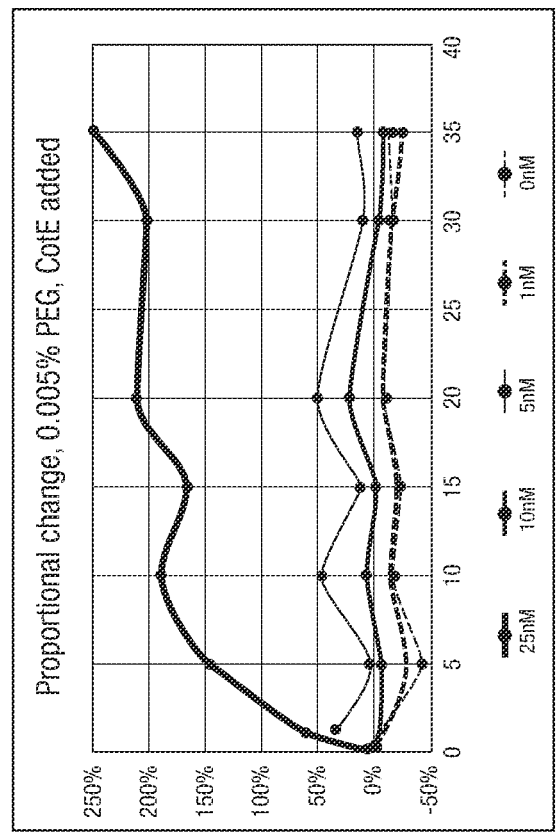

To check the consistency of the results, the experiments were repeated at lower aptamer concentrations (25 nM, 10 nM, 5 nM, 1 nM). See FIG. 44A showing the recovery in quenched signal of aptamer-GO mix in varying lower concentrations of P24 (negative control), and FIG. 44B showing the recovery in quenched signal of aptamer-GO mix in varying lower concentrations of CotE (target protein).

Figure 45:
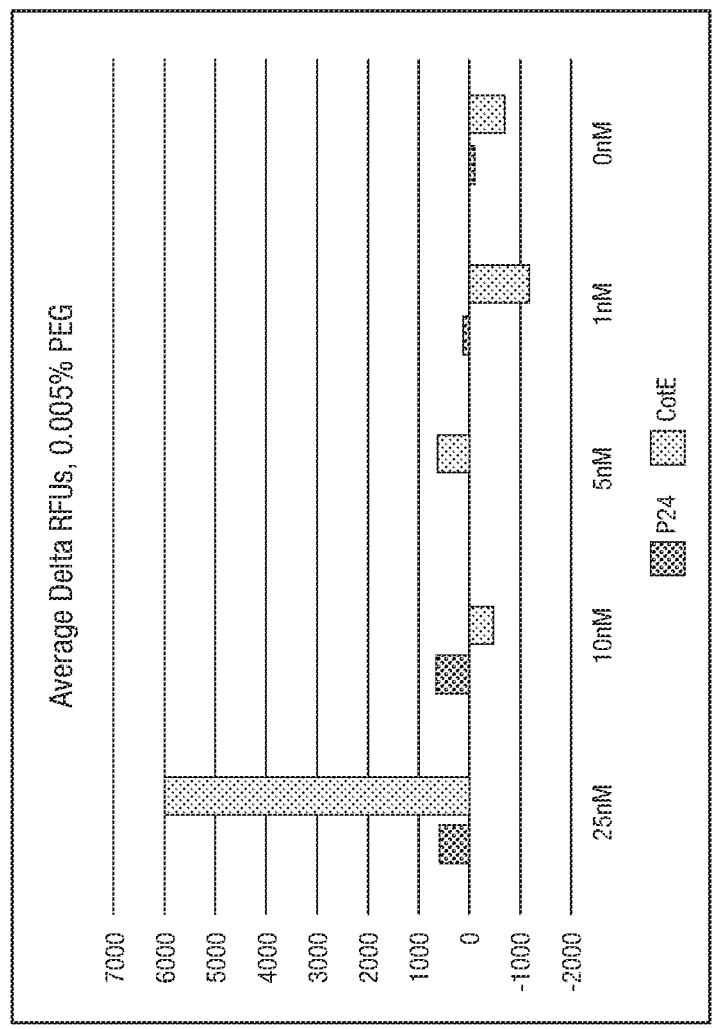
FIG. 45 is a bar graph showing the specific detection of low concentrations of the CotE protein with aptamer/GO treatment averaged across all time points.

The results show that concentration as low as 25 nM of target (CotE) can be consistently and reliably detected (FIG. 45). However, at concentration lower than 25 nM, the signal is not enough for it to be distinguishable from the observed aspecific signal.

Figure 46A:
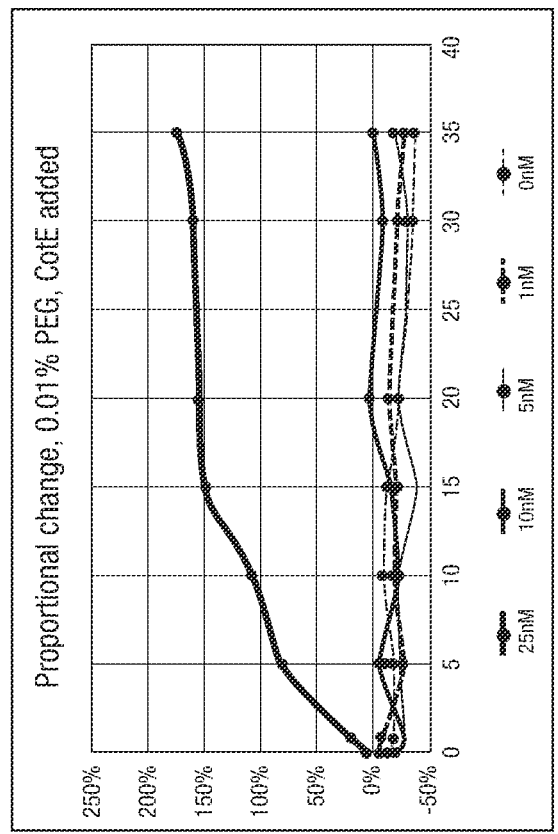
FIG. 46A and FIG. 46B are graphs showing the recovery in quenched signal of the aptamer-GO mix in varying concentrations of P24 negative control (FIG. 46A) and varying concentrations of CotE protein, both in the presence of 0.01% PEG.
Figure 46B:
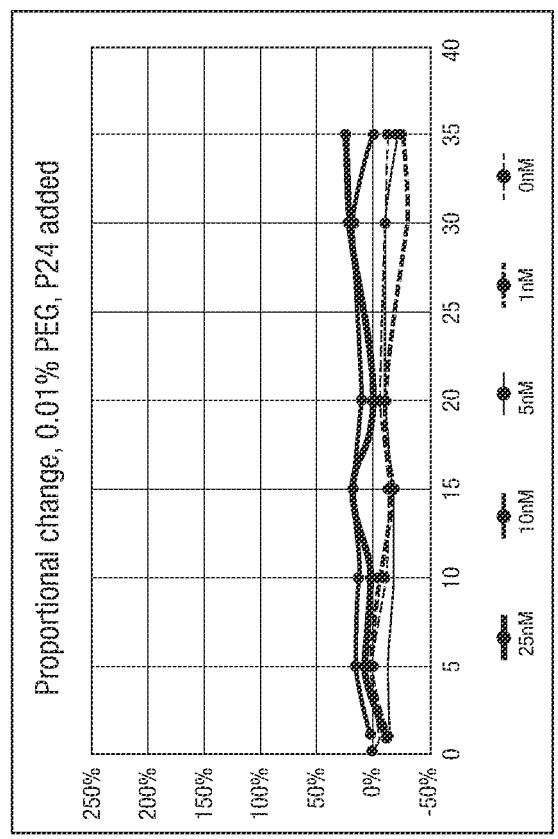

Using a higher concentrations of PEG (0.01%), FIG. 46A shows the recovery in quenched signal of aptamer-GO mix in varying lower concentrations of P24 (negative control) in presence of 0.01% PEG, and FIG. 46B shows the recovery in quenched signal of aptamer-GO mix in varying lower concentrations of CotE (target protein) in presence of 0.01% PEG.

Figure 47:
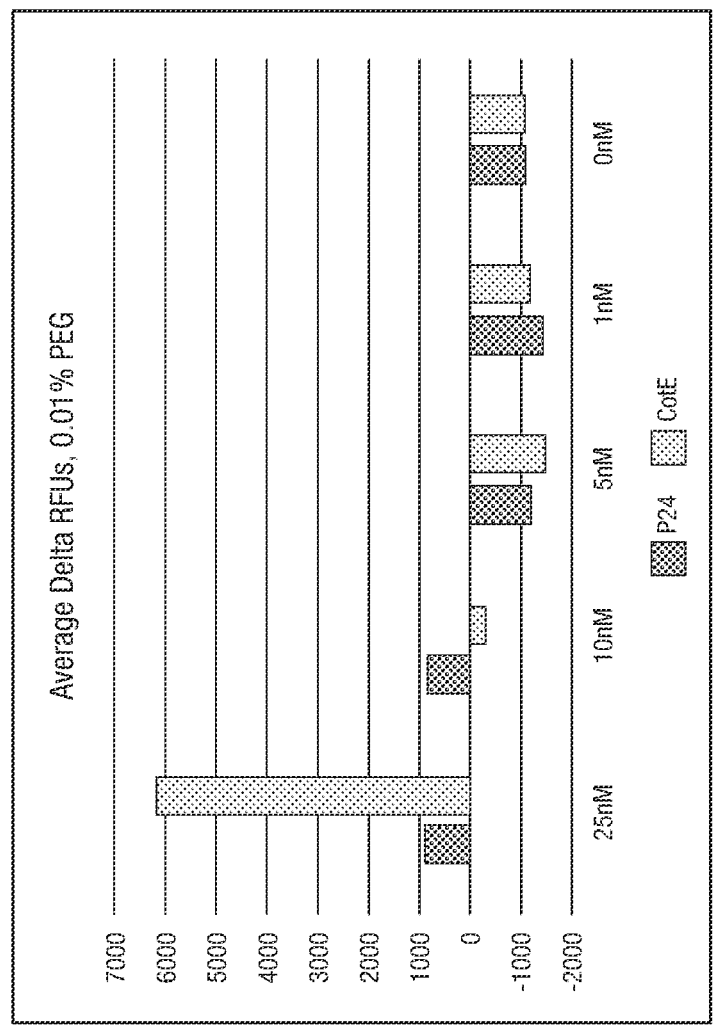
FIG. 47 is a bar graph showing the specific detection of low concentrations of the CotE protein with aptamer/GO treatment averaged across all time points, in 0.01% PEG.

FIG. 47 shows the specific detection of low concentrations of CotE protein with aptamer/GO treatment in 0.01% PEG.

Compared to the data for 0.005% PEG, results in 0.01% PEG show a similar trend. There are less inconsistencies among the samples with 0.01% PEG. Material:

Aptamer sequences labelled at their 5' ends with 6-FAM (Fluorescein) were purchased from Integrated DNA Technologies Inc. (USA). Sequences of the aptamers used in the study are:

```
a) FAM labelled CdeC D1.2 aptamer:
                              (SEQ ID NO: 39)
5'-FAM/CAA ACT ACT CAA TGC CGT GGA CTG GTC GGG TTT GGA ATC GGC AGA TGA ATC AGT AGT AAA/-3';
and b) FAM labelled H2.1.2 aptamer:
                              (SEQ ID NO: 30)
5'-FAM/CTT GAC CTT TGG AAT GGG TGG GAG GGA GGG

TAT CCA CAG GTC AAC C/-3'.
```

Graphene oxide was purchased from Sigma-Aldrich, in the form of dispersion in water at 4 mg/mL concentration (product no. 777676).

Recombinant HIV-1 p24 derived from *E. coli* (Code 212-10004) was purchased from RayBiotech (USA).

ally a consequence of physical light blocking on the part of the graphene oxide nanostructures, and that the subsequent slow quenching was a function of the aptamer binding aspecifically to GO. Table 8 provides the basis for this explanation.

TABLE 8

| GO concentration | 20 ng/uL | 40 ng/uL | 60 ng/uL | 80 ng/uL | 100 ng/uL | |
|---|---|---|---|---|---|---|
| | | | | | | Instantaneous quenching |
| a | 0.000001 | 0.000001 | 0.000001 | 0.000001 | 0.000001 | Aptamer concentration |
| b | 0.288638 | 0.553039 | 0.766777 | 0.907912 | 0.973818 | Filtering |
| c = a*b | 7.11E−07 | 4.47E−07 | 2.33E−07 | 9.21E−08 | 2.62E−08 | Apparent aptamer concentration |
| d = c/a | 0.711362 | 0.446961 | 0.233223 | 0.092088 | 0.026182 | Proportional fluorescence |
| | | | | | | Slow quenching |
| e = calculated | 6.07E−08 | 1.15E−07 | 1.63E−07 | 1.63E−07 | 2.45E−07 | Bound aptamer |
| f = a − e | 9.39E−07 | 8.85E−07 | 8.37E−07 | 8.37E−07 | 7.55E−07 | Real free aptamer |
| b | 0.288638 | 0.553039 | 0.766777 | 0.907912 | 0.973818 | Filtering |
| g = f*b | 6.68E−07 | 3.96E−07 | 1.95E−07 | 7.71E−08 | 1.98E−08 | Apparent aptamer concentration |
| h = g/a | 0.66817 | 0.553039 | 0.195236 | 0.077089 | 0.019758 | Proportional fluorescence |
| b | 0.288638 | 0.604288 | 0.766777 | 0.907912 | 0.973616 | Fast quenching |
| i = 1 − h | 0.33183 | 0.604288 | 0.804764 | 0.922911 | 0.980242 | Combined slow quenching |
| j = i − b | 0.043192 | 0.051249 | 0.037987 | 0.014999 | 0.006424 | Difference |

CotE protein at concentration of 1.5 mg/mL, and CdeC protein at concentration of 5E9 particles/mL were supplied by Biovector.

HEPES and Tris base were purchased from Fisher Scientific (Canada).

Tris, NaCl, KCl, $MgCl_2$, $CaCl_2$ and Poly (ethylene glycol) with average Mn of 300, were purchased from Sigma-Aldrich.

Figure 27:
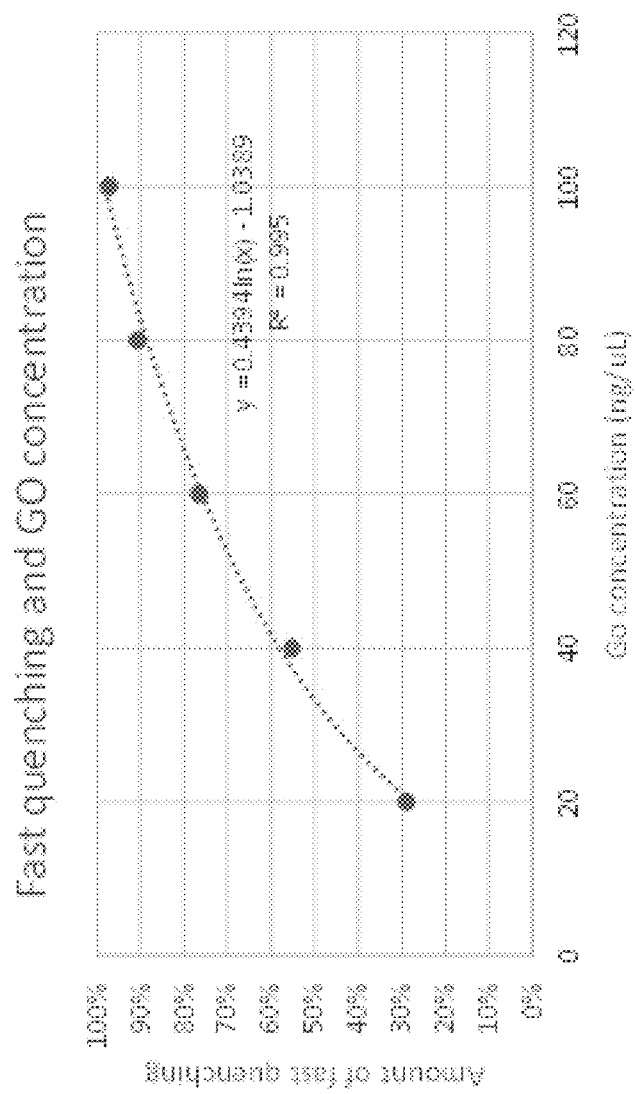
FIG. 27 is a graph of % of fast quenching versus graphene oxide (GO) concentration.

Example 9: Mathematical Basis for Aptamer-Graphene Oxide as a Basis for Surface Detection An equilibrated mixture of aptamer/GO refers to a mixture of aptamer/GO having a relative fluorescence that does not change over time. In some embodiments, this equilibration can be achieved 24 hours after the aptamer(s) and GO are mixed. In some embodiments, there is a very rapid initial quenching of fluorescence as illustrated in FIG. 27.

Varying amounts of GO were combined with 1 mM of the Em2.1 aptamer (SEQ ID NO: 55). Fluorescence was measured immediately before, and immediately after the addition of GO. Quenching level was determined by the equation:

1−(Fluorescence in absence of GO)/(Fluorescence in presence of GO)

for each mixture versus reference wells where no GO was added. This experiment was performed with duplicate treatments for each GO concentration. The surface was illuminated with a Phospho505 flashlight containing a filter that cut off wavelengths above 505 nm, and the surface was observed through a filter that cut off wavelengths below 505 nm.

Figure 28:
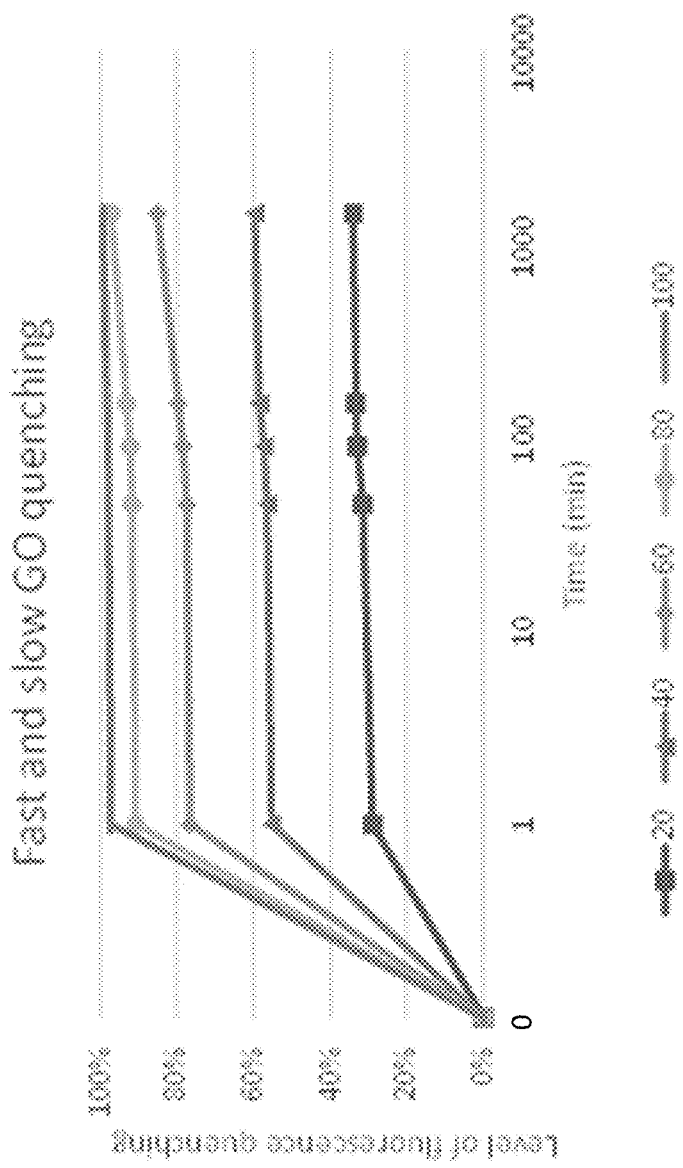
FIG. 28 is a graph of % of fluorescence quenching versus time for different GO concentrations (in ng/µL).
Figure 29:
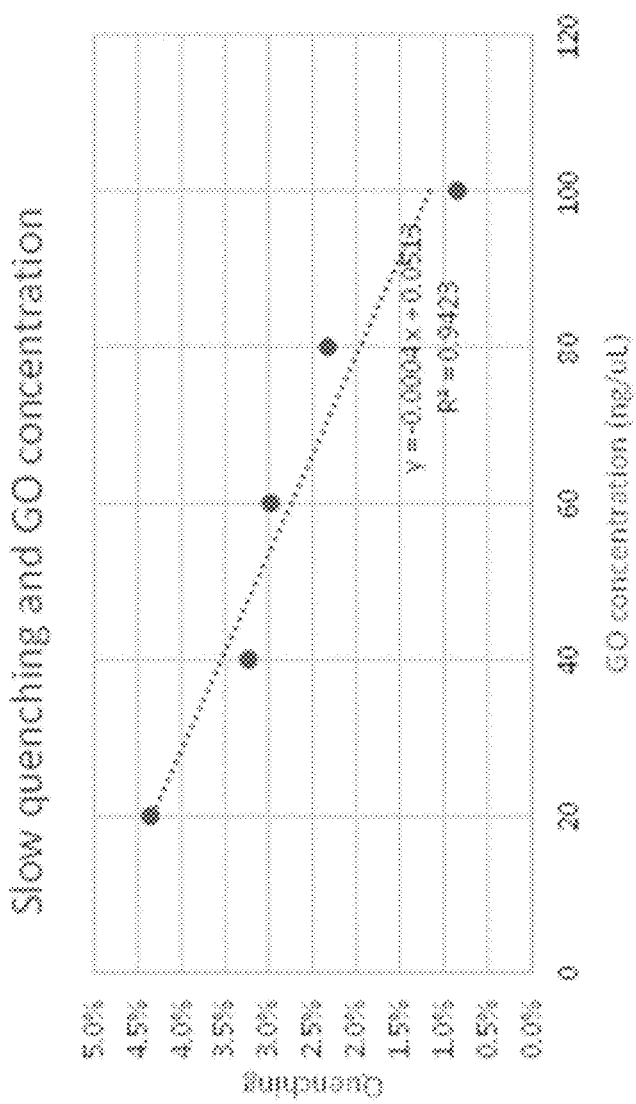
FIG. 29 is a graph of % of slow quenching versus graphene oxide (CO) concentration (in ng/µL).

Over the next several hours there was a slow change in quenching that continued to occur, as shown in FIG. 28. The slow GO quenching represented a lower proportional change to the overall quenching of fluorescence at higher concentrations of GO than at lower concentrations of GO, which is shown in FIG. 29.

Both of these effects can be explained mathematically by assuming that the fast quenching (instantaneous) was actu- The row 'b' was derived from the observed data in FIG. 27. This was the observed level of instantaneous quenching.

The calculation in row 'e' was based on the solution of the following set of linked differential equations.

$$dx1 = -a*x1*x2 + b*x3$$

$$dx2 = -a*x1*x2 + b*x3$$

$$dx3 = a*x1*x2 - b*x3$$

Where a=the kon value for the rate of formation of the aptamer/GO complex and was assumed to be 1E5 for this model, and b=the koff value for the disruption of the aptamer/GO complex and was assumed to be 3 for this model.

dx1=aptamer concentration (1E-6 M), dx2=GO concentration (ng/mL were converted directly to mM as in 20 ng/mL was equated to 2E-6 mM), and dx3=the complex between aptamer and GO.

The row 'g' provides the fit to the model in terms of how the effect of filtering (row b) affected the observation of fluorescence. This model shows that while there was actually much less aptamer bound over time with lower GO concentrations, the apparent increase in fluorescence was higher.

Figure 30:
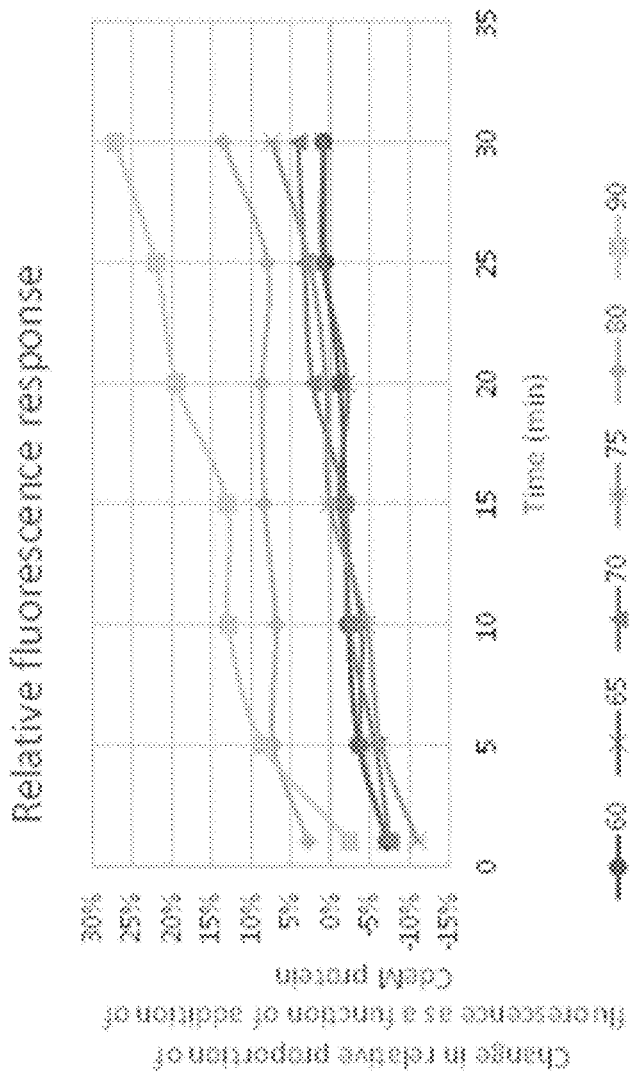
FIG. 30 is a graph of the change in relative proportion of fluorescence as a function of addition of CdeM protein versus time for different GO concentrations (in ng/µL).

Addition of Target Protein:

In a separate experiment, the effect of adding aggregated balls of CdeM protein (a protein target that is specific to *C. difficile*) to equilibrated mixtures of aptamer/GO was measured. The CdeM protein balls exhibited a filtering effect on the observation of fluorescence. The same amount of CdeM protein was loaded in each experiment, the amount of GO varied as shown in the legend in FIG. 30.

Two observations were made: (1) the relative fluorescence decreased immediately upon addition of the aggregated protein, and (2) the fluorescence response continued to increase over time for each GO concentration. The immediate drop in relative fluorescence was more pronounced at lower concentrations of GO, in keeping with an assumption that the CdeM protein balls also induced a fluorescence filtering effect. This effect was more pronounced as the filtering effect of the GO decreased because of lower GO concentration.

Without being bound to any particular theory, it is thought that in surface detection, the spores are on the surface and thus will minimally interfere with the transmission of excitation light to the fluorophore or with the transmission of emission light from the fluorophore.

The increase in relative proportion of fluorescence showed a clear response to the aptamer binding to the target protein, being released from the GO and fluorescence being expressed.

Figure 31:
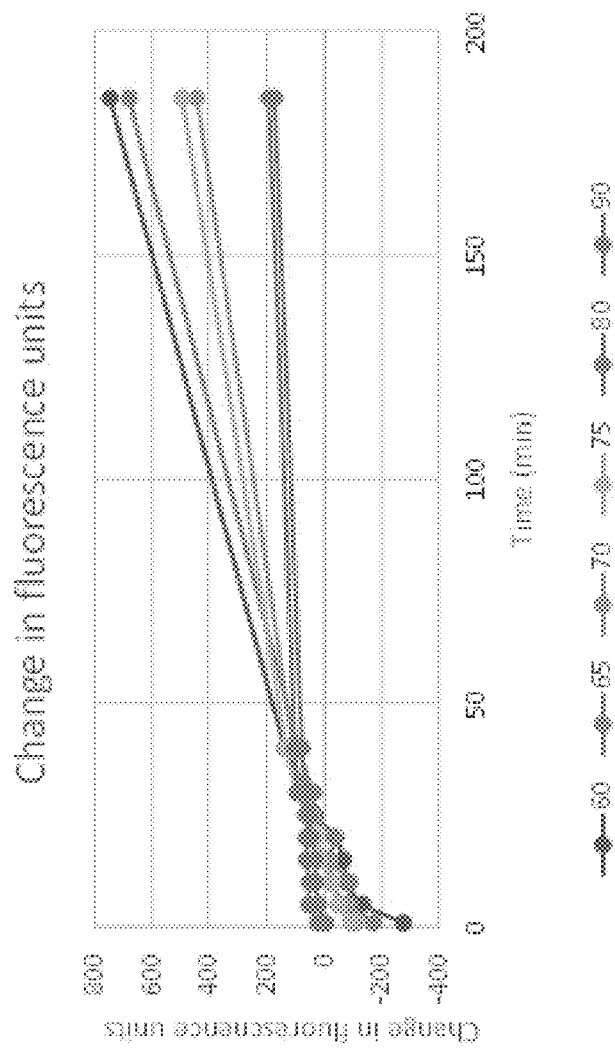
FIG. 31 is a graph of the change in fluorescence units versus time for different GO concentrations (in ng/µL).
Figure 32:
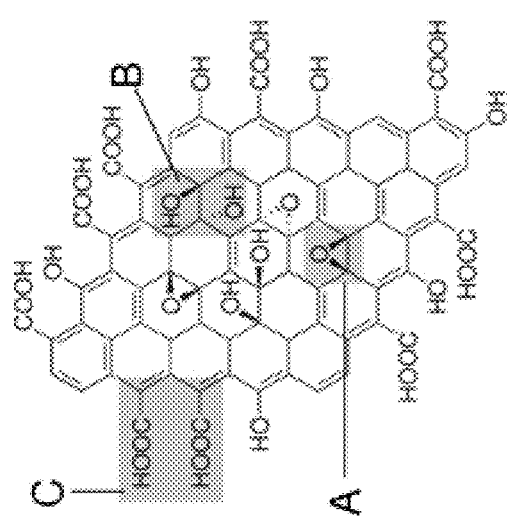
FIG. 32 shows the proposed structure of graphene oxide/graphene with different functional groups A: Epoxy bridges, B: Hydroxyl groups, C: Pairwise carboxyl groups.

FIG. 31 provides the increase in fluorescence units over a longer period (185 min). As the concentration of GO increased, the change in fluorescence units as measured in relative units decreased in the presence in of CdeM protein, while the proportional increase in fluorescence increased. In conclusion, the response in terms of change in fluorescence units was higher with less quenching.

Example 10: Direct Detection on Surface

Aptamers that bind to *C. difficile* exosporium proteins have been labeled with a FAM fluorophore for visualization. A no-wash detection method using graphene oxide (GO) is provided. In some embodiments, the aptamers adhere to graphene oxide (GO) resulting in a quenching of fluorescence. In some embodiments, when the mixture of aptamers+GO is added to spores on a surface an increase in fluorescence is observed, as the aptamers are displaced from the GO as a function of binding to the spores. This proof of concept is shown with specific exosporium proteins from *C. difficile*.

The objective was to visually detect the presence of *C. difficile* spores on a stainless-steel surface with the application of the aptamer(s)/GO complex. The visual detection can be recorded in a video.

Step 1: Adherence of Spores to Surface.

In some embodiments, the following spores are provided.
$5 \times 10^9$ strain 630 erm
$\sim 1 \times 10^{10}$ strain 027
$\sim 2 \times 10^8$ strain 078

Strain 078 is the base strain. The initial experiments began with applying the spores on circular surface spot (cm$^2$) at a concentration of 1000 spores (high), 100 spores (medium) and 10 spores (low).

The spores are in a form of a liquid suspension (stock solutions). The surface of a stainless-steel bench was cleaned and disinfected. The spore solution was loaded onto the stainless-steel bench. Using a cell spreader, the solution was spread on the surface, for even drying of the spore solution, which was allowed to dry on the steel bench, by incubating it for overnight (~12 h) at RT.

Step 2: Set Up Video Recording Equipment

Figure 48:
FIG. 48 illustrates positioning of the camera and special flashlight relative to the spots on the surface.

A camera as described below was used to capture images along with a special flashlight (505 nm) and protective goggles. Both the camera and special flashlight were mounted on tripods. The camera was focused as close to the surface as possible, while still retaining the capacity to observe all spots. FIG. 48 illustrates positioning of the camera and special flashlight relative to the spots on the surface. To operate the camera, the power switch was turned to "Record" and the Manual Focus switch on the lens was turned to "MF". At this point, the small ring was used to focus the camera on the field, with the lens zoomed in fully (completely extended from the camera). Recording was started and ended by pressing the Record button. The camera was set for optimal video through the Menu settings, selecting "Movie rec. size" to "FHD 59.94P IP8". A polarization filter (Filter ONE circular polarizing filter, Hoya) was installed in front of the camera lens. There were two filters stacked in front of the lens: BP590 bandpass filter (MidOpt). For example, the polarizing filter contained two rings, one to tighten the filter, and one to rotate the filter.

The camera and light source were set up as follows. The maximum field of vision was 9 cm×9 cm with the optimal area being no larger than 5 cm×5 cm as indicated by the blue square in the picture. The orange safety eye shields were in place before turning on the light source, then the light was turned on by rotating the ring in the direction of the arrow and released. The light source was turned off by turning the ring in the same direction and released. The battery was returned to the camera as soon as possible after it finished charging so that the pre-set recording settings were not lost.

Step 3: Visualization

A mark was made on the surface with a sharpie and the camera was focused on that mark. Video recording began and then the solutions were applied to the spots. The room was not dark, but the lights were dimmed.

The aptamer/graphene oxide (GO) mixture used was 1 mM aptamer+80 ng/mL GO, in water, which was loaded onto the stainless-steel bench with a spray bottle/assembly. The sprayer was primed, with at least 3 full pumps by squeezing the trigger all the way in until the spray was complete, with no sputtering. At this point, the spray assembly was held approximately 40 cm away from the region on the intended surface. To start, the solution was sprayed by squeezing the trigger roughly "halfway" to allow the solution to come out as droplets and cover the intended region on the surface including the area where the virus-containing solution was dried. At this point, the goggles were employed and the flashlight was turned on (505 nm wavelength). Data acquisition was obtained by recording the video on the camera and capturing the subsequent images. The signal emanating from the region of the steel bench, where virus-containing solution was present was observed, and was compared to the region with no virus-containing solution. After five minutes, the flashlight was turned off, then switched back on when 20 minutes had elapsed since the aptamer+GO was applied onto the spots. The samples were then observed and then the flashlight was switched off. After 30 minutes had elapsed since the aptamer+GO was applied, the flashlight was turned on again and the samples were observed, and then the flashlight was switched off Example 11: Visualization of Spores Reagents:
*Clostridium difficile* spores (ribotype 027) in water at 1E10 spores per mL were supplied by Sporogen.

Integrated DNA Technologies supplied the aptamer labeled at 5' end with 6-carboxyfluorescein (FAM). Following is the sequence of the aptamer:

```
                                              (SEQ ID NO: 55)
5'- FAM/CTC AAT GCC TTC CAT TCA CCT ACC GAG

CTA AGC GTT CGA CTT AGG TCT GTA CT/- 3'.
```

Graphene oxide resuspension in water at 4 mg/mL was purchased from Sigma Aldrich.

Optical Equipment:
Rofin's Polilight Flare PLUS2 was used as an excitation light source (505 nm).
PPE used were Rofin's standard orange goggles.
Canon EOS Rebel SL3 camera was used.
BP590 from MidOpt, was used as optical bandpass filter.

The circular polarization filter used was Fusion One CIR-PL from Hoya.

Frames extracted from video using Kdenlive version 18.12.3 running on Debian 10.5

Method:

The spore solution was loaded on a clean stainless-steel bench in evenly spread manner, and was allowed to air dry at room temperature for overnight. The optical bandpass filter and polarization filter were assembled onto the camera. The camera and the flashlight were mounted appropriately so that the region containing the dried spores was in the field of view of camera and was under the incident light from excitation source (flashlight). The aptamer/GO mixture (referred herein as "aptamer/GO formulation") to detect the dried spores was prepared by mixing FAM-labelled aptamers with graphene oxide, as follows:

1 mM of FAM-labelled aptamer (Em2.1) were mixed with 80 ng/mL of graphene oxide (GO), in de-ionized (DI) water The aptamer/GO formulation was equilibrated by incubating at room temperature, in the dark for overnight.

The equilibrated aptamer/GO formulation was sprayed on the dried spores.

Orange goggles were put on to protect eyes, and the flashlight was then switched ON intermittently for short durations to record the response from the dried spores on camera while the video recording continued from the start of the experiment for approximately 30 minutes.

Where there was no appreciable signal to observe, identical time points were used for both aptamer/GO formulation on bare steel and water on dried spores to roughly correspond with time points for aptamer/GO formulation on dried spores Detection of the presence of spores was observed when the 505 nm light source was turned on in the aptamer/GO formulation-on-bare-steel experiment, but no fluorescence was detectable with the negative control of water on dried spores. The images were processed using GiMP 2.10.0, were cropped and the color data was removed by setting Chroma to −100. No other filters were applied to the images. Spore ribotype 027 used for both dried spots.

Example 12: Cocktail of Aptamers

In some embodiments, are provided aptamers for several different proteins from *C. difficile* wherein the aptamers are combined together in a composition useful for the detection of *C. difficile* on surfaces. For example, a cocktail of different aptamers can be used to detect different proteins on the surface of *C. difficile*.

In some embodiments, are provided aptamers targeting protein aggregate balls. These protein balls can be used to test and optimize the fluorescence response of live spores. it should be noted that these protein balls can quench fluorescence when they are added to a solution due to their capacity to physically block excitation and emission light paths. This fluorescence quench can be reduced by using live spores because live spores can adhere to a surface and the light is observed from above. In some embodiments, are provided the use of soluble proteins that do not interfere with the subsequent fluorescence measurement.

Four optimized aptamers were used: CotE H2.1.2 (SEQ ID NO: 30); CotE D2.1 (SEQ ID NO: 31); CotA C1.1 (SEQ ID NO: 33); and CotEC Chitinase (SEQ ID NO: 36).

Figure 49:
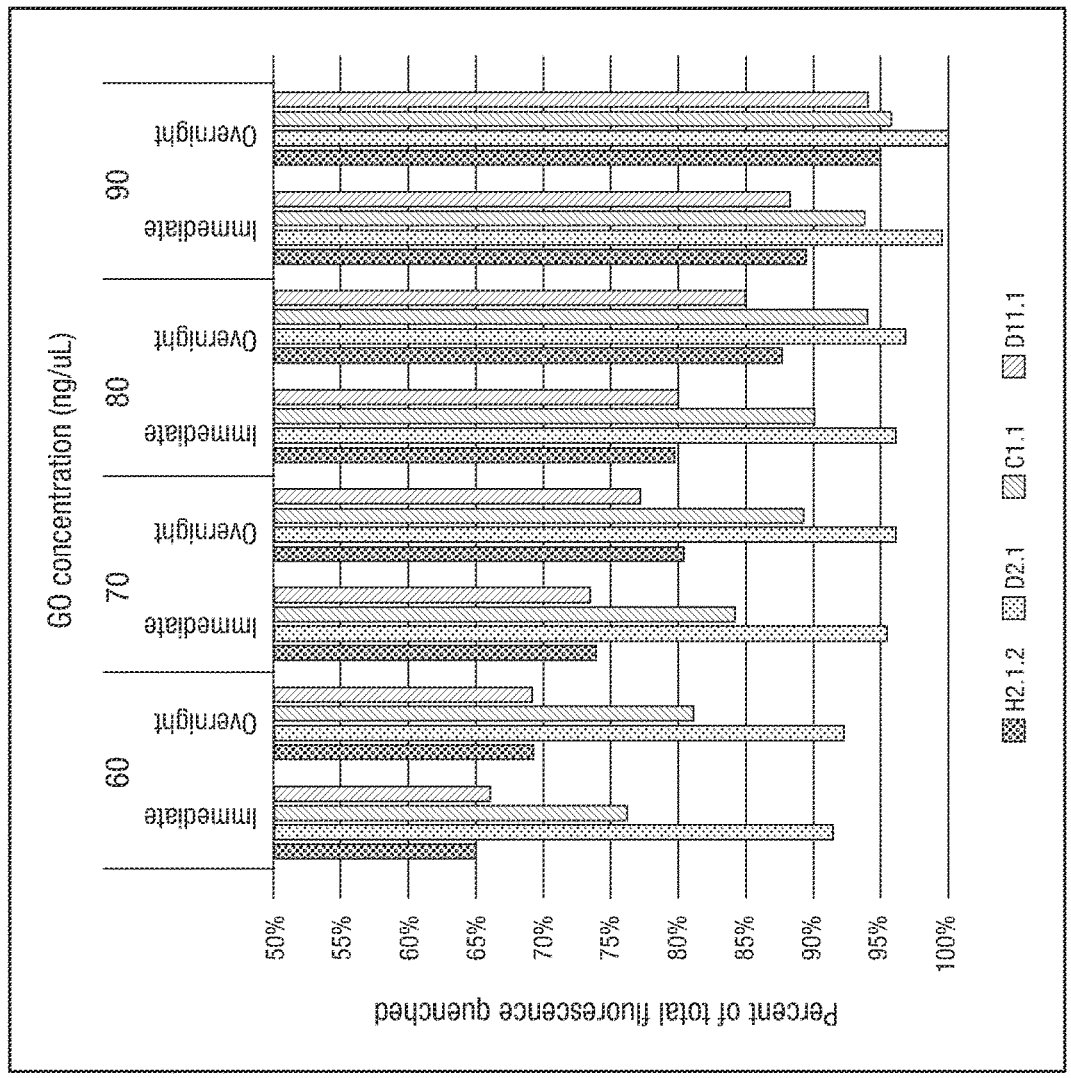
FIG. 49 shows the effect of varying graphene oxide concentration and time on quenching of fluorescence of various C. difficile aptamers.

In the first experiment, the quenching capacity for each aptamer was determined individually with varying amounts of graphene oxide (GO). A 1 mM concentration of each aptamer was exposed to a range of GO concentrations in buffer (50 mM Tris pH 7.6, 2.5 mM MgCl$_2$, 2.5 mM CaCl$_2$), 85 mM NaCl). Quenching of fluorescence was measured over a 24 hour period. FIG. 49 shows the effect of varying graphene oxide concentration and time (immediate and overnight) on quenching of fluorescence (% of total fluorescence quenched) of various *C. difficile* aptamers.

For all GO concentrations, an immediate apparent quenching activity was observed that was attributed to a function of light blockage by the GO particles. This effect was positively related to the GO concentration. A further quenching effect was observed that occurred as a function of the aptamer adhering to the GO particles. This further quenching effect was manifested by the increase in quenching observed between immediate and overnight measurements.

The direct detection of *C. difficile* on a surface in that the fluorescence was quenched at a very high level>99%. The total fluorescence measured when quenching was equilibrated was in the range of 160 to 190 RFU, with a GAIN setting of 118, on a Tecan, Sapphire II fluorometer with excitation at 495 nm, and emission at 517 nm, with a band width of 5 nm, 10 reads, with an integration of 2000 us, and a Z position set optimally in the first read and fixed at that position for subsequent reads.

In some embodiments, this was achieved for the D2.1 aptamer as shown in Table 9, which shows the relative fluorescence units prior to the addition of protein for 90 ng/mL GO with various aptamers (average over two wells).

TABLE 9

|  | 90 |
|---|---|
| H2.1.2 | 2407.5 |
| D2.1 | 167.5 |
| C1.1 | 1661 |
| D11.1 | 3318 |

A 1 mM concentration of the appropriate soluble protein for each aptamer was added to one well, while an equal amount of buffer was added to the other well. The effect of both treatments for each aptamer in terms of fluorescence response was tracked every five minutes for 30 minutes in total.

The relative fluorescence response was calculated for each well by dividing the fluorescence for that well recorded at a given time interval by the original fluorescence recorded prior to the addition of protein or buffer. Unity was subtracted from this dividend.

Figure 50:
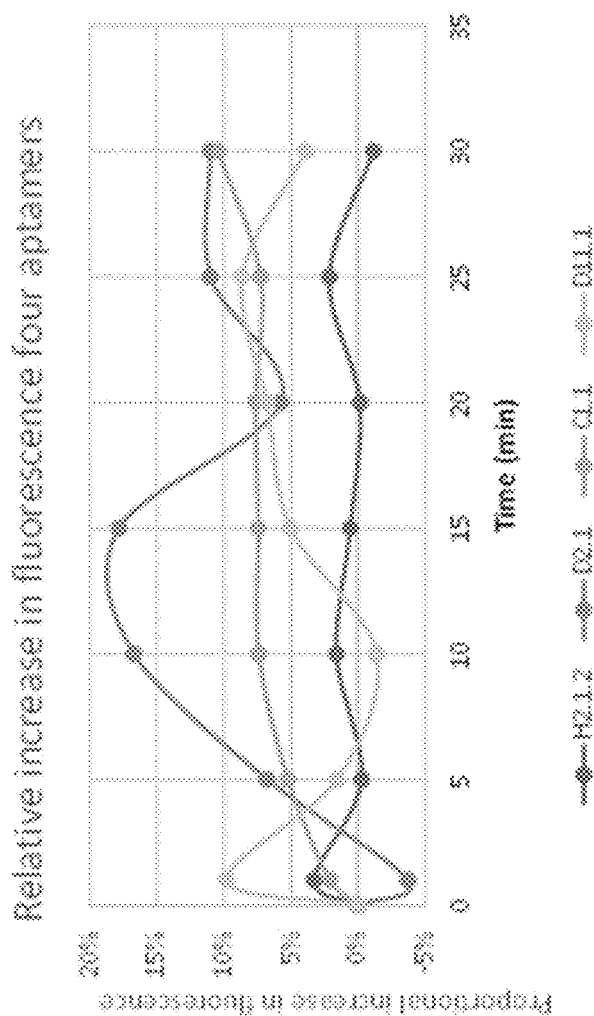
FIG. 50 is a graph showing the proportional increase in fluorescence in % versus time for four different aptamers (CotE H2.1.2, CotE D2.1, CotA C1.1, Chitinase D11.1).

The buffer alone values were then subtracted from the protein added values, as shown in FIG. 50.

Figure 51:
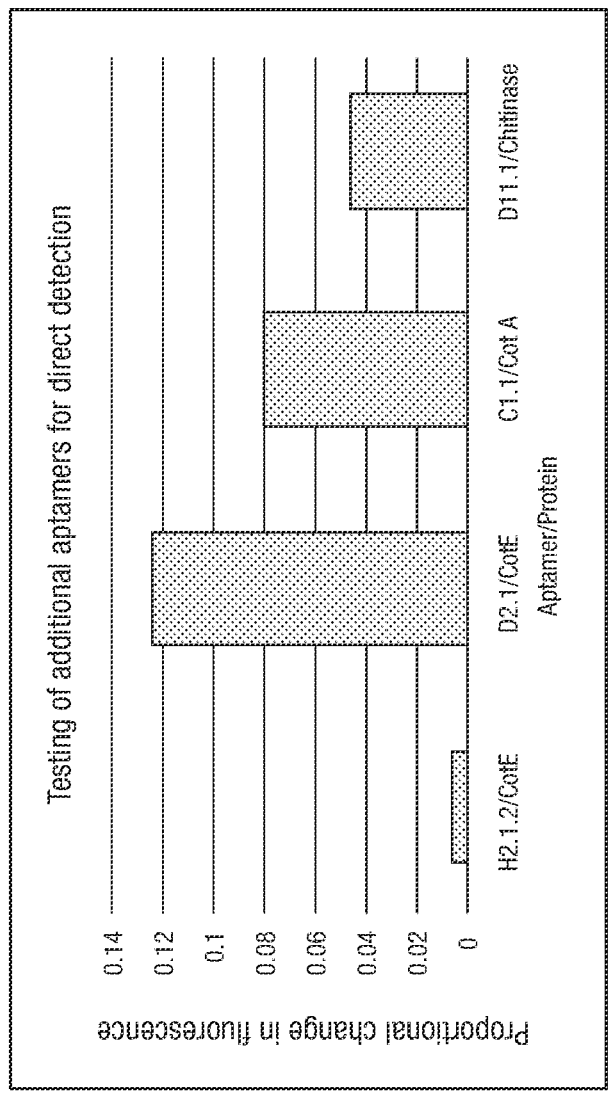
FIG. 51 is a graph showing the proportional change in fluorescence for four different aptamers (CotE H2.1.2, CotE D2.1, CotA C1.1, Chitinase D11.1).

The response varied for each aptamer as a function of time. FIG. 51 provides the average increase in fluorescence across all time points for each aptamer/protein combination.

These experiments showed that under these conditions the H2.1.2 aptamer with CotE was not exhibiting a strong fluorescence response. Low fluorescence response can be caused by a lower level of quenching with GO for this aptamer compared to the other aptamers.

In a subsequent experiment three of these aptamers D2.1, C1.1 and D11.1 were combined, each at a concentration of 333 nM for a total aptamer concentration of 1 µM. This solution was quenched with 110 ng/µL GO overnight. A quenching level of 98.4% was achieved overnight with a total RFU of 821 at the standard settings referred to above. A mixture of the soluble proteins was prepared such that each protein (CotE, CotA, and chitinase) would be present in a well at a concentration of 100 nM. An equal volume of buffer was also added to a well with the three aptamers quenched to the same level.

Figure 52:
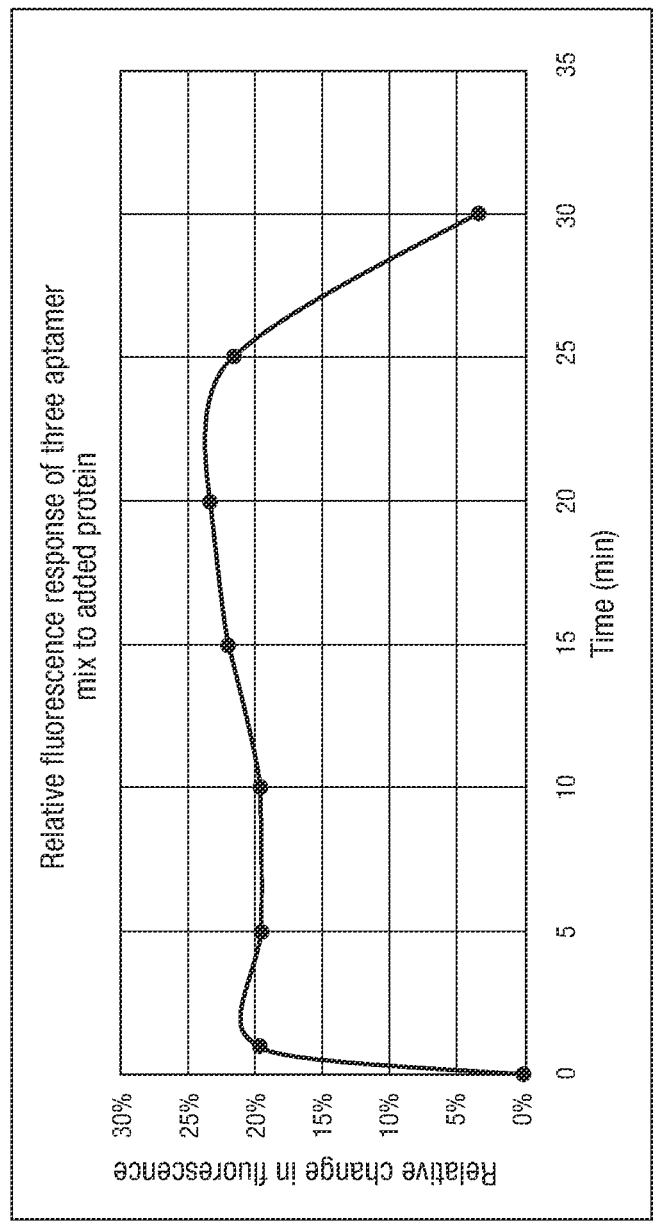
FIG. 52 is a graph showing the relative change in fluorescence versus time for a three aptamer mix added to protein.

Fluorescence was measured immediately after the addition of soluble protein and at 5 min intervals thereafter. Proportional change in relative fluorescence was determined as described above (FIG. 52).

Figure 53:
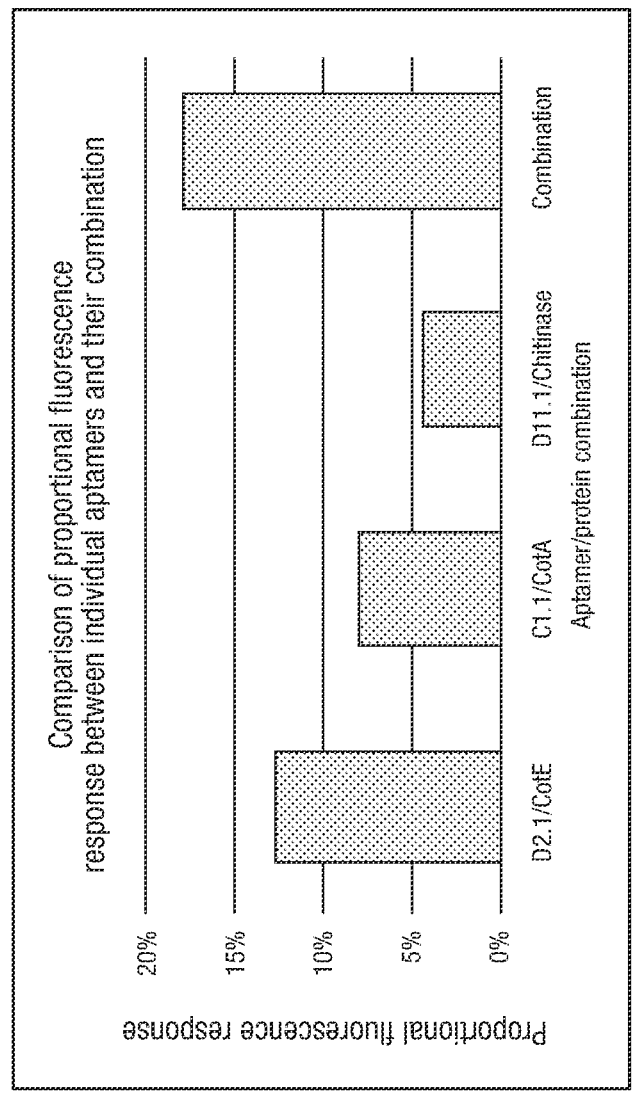
FIG. 53 is a graph showing the proportional fluorescence response for three individual aptamers (CotE D2.1, CotA C1.1, Chitinase D11.1), and the combination thereof.
Figure 54:
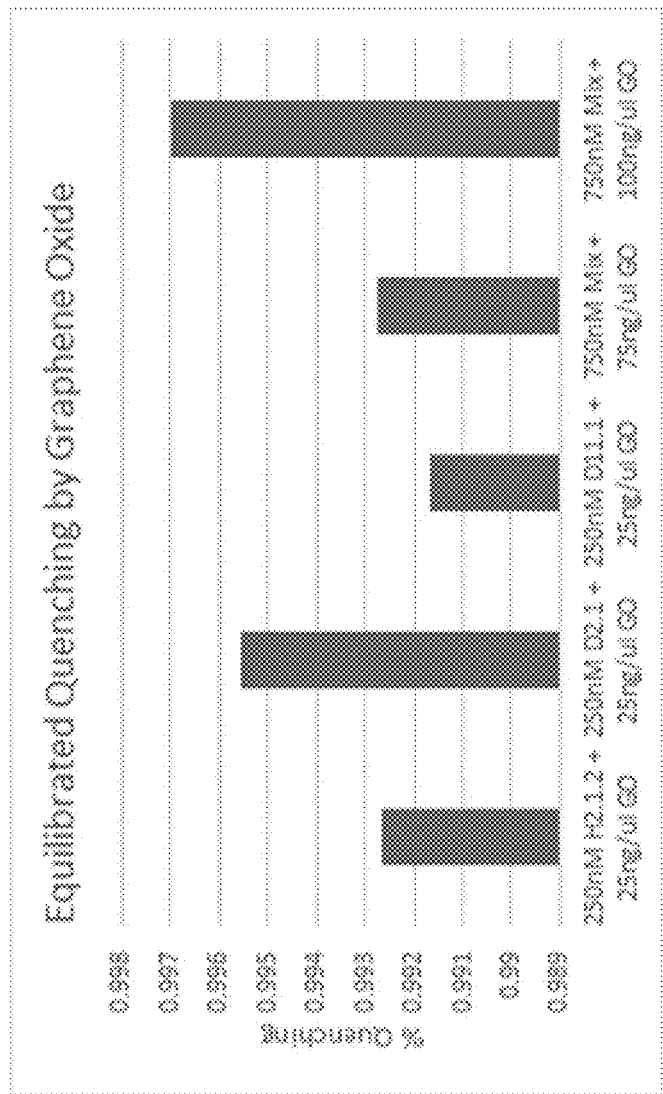
FIG. 54 shows the percent of FAM-labeled aptamer fluorescence quenched by graphene oxide, by comparing the fluorescence of aptamer-GO formulations to the fluorescence of aptamer alone at the same concentration after equilibrating for 2 days.
Figure 55:
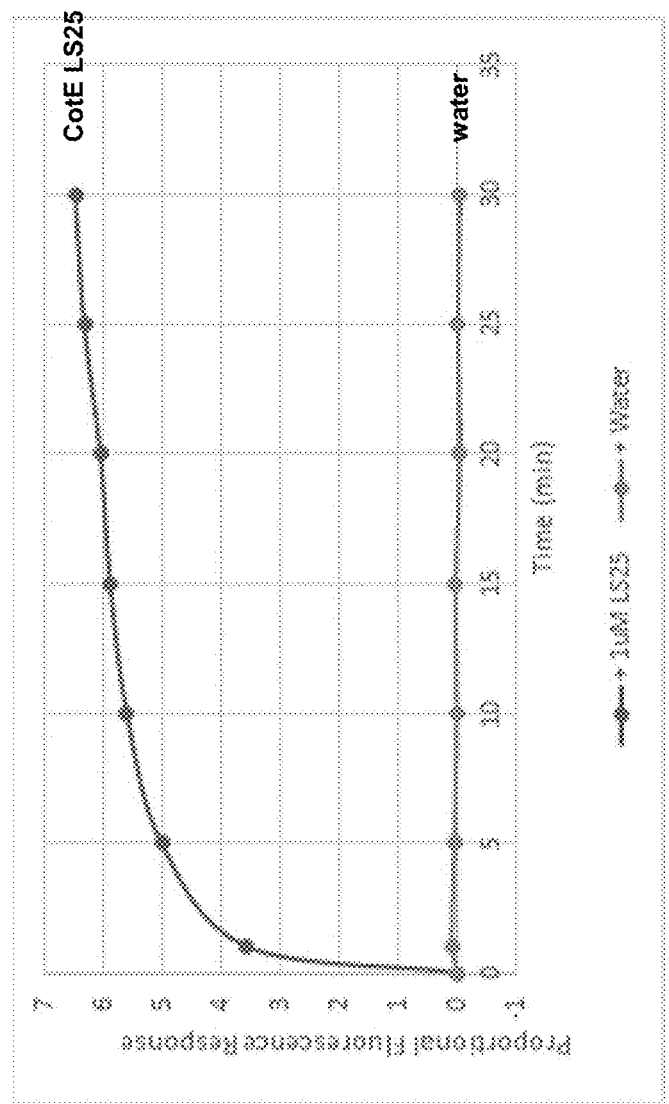
FIG. 55 shows that the fluorescence of FAM-H2.1.2 in GO increases in the presence of protein, for example, the change in fluorescence over time of 250 nM FAM-H2.1.2 in 25 ng/μL GO with the addition of 1 mM CotE LS25 (blue) and water (orange).
Figure 56:
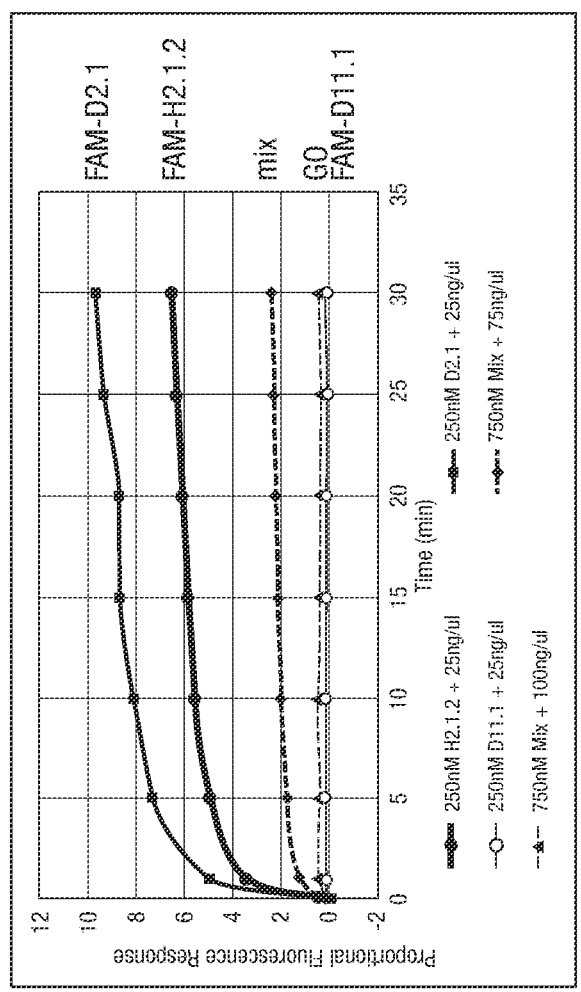
FIG. 56 shows the fluorescence response of aptamer-GO formulations in the presence of protein. For example, the change in the proportional fluorescence, relative to the baseline fluorescence (t0) of the individual aptamer-GO formulations—FAM-H2.1.2 (blue), FAM-D2.1 (orange), and FAM-D11.1 (grey)—and the aptamer-GO cocktail—75 ng/ml GO (yellow), 100 ng/ml GO (light blue). The corrected response is shown with the water response for each aptamer formulation subtracted from the protein response.

The comparison to the response of each aptamer on an individual protein can be seen in FIG. 53.

It should be noted that 100 nM of each individual protein was added to the individual aptamer/protein treatments, and 100 nM of each protein to the combination response. Thus, the results show that the combination of aptamers provided a synergistic proportional fluorescence response. That is, the combination of aptamers provided a stronger proportional fluorescence response than would be expected based on the sum of the proportional fluorescence response exhibited by each aptamer by itself. The only explanation is that the aptamers are working within this system cooperatively to produce a response that is beyond what would be expected additively.

Example 13: Multi-Aptamer Cocktail

In some embodiments, is provided a multi-aptamer cocktail for the detection of *C. difficile* spores.
Materials and Methods
Aptamer and Protein Selection In this experiment three optimized aptamers for the soluble CotE spore coat protein were used. Two recombinant proteins spanning specific segments of the *C. difficile* CotE protein were obtained from Sporogen. One protein, designated LS25, spans amino acids 281-712 and the other designated AB45 spans the chitinase region (aa381-712). Binding kinetics of two of the optimized aptamers, H2.1.2 and D2.1 to LS25, and binding kinetics of the aptamer D11.1 to AB45, have been previously characterized. For this experiment each of the aptamers were synthesized with a 5' FAM label for fluorescence detection.
Preparation of Aptamer-GO Formulation Previous experiments showed that in solution, graphene-oxide (GO) was able to quench the fluorescence of FAM-labeled aptamers. Individual aptamer-GO formulations were prepared for the aptamers H2.1.2, D2.1, and D11.1. The formulations were made up to 250 nM FAM-labeled aptamer, in buffer (50 mM Tris pH 7.6, 2.5 mM $MgCl_2$, 2.5 mM $CaCl_2$), and 85 mM NaCl) with GO at 25 ng/μL. Aptamer cocktails were formulated with 250 nM of each FAM-labeled aptamer (750 nM total aptamer) in buffer with 75 ng/μL GO and 100 ng/μL GO. For each of the aptamer-GO formulations, solutions of aptamer in buffer were made up to equal concentrations without GO. The formulations were left in the dark at room temperature for 3 days to equilibrate.
Fluorescence Analysis Samples (85 μl) of aptamer in buffer and aptamer-GO for each individual aptamer and aptamer cocktail were pipetted into the wells of a 96-well, half-area, black-bottomed microplate (Corning, #3686). Fluorescence was measured using a Tecan Safire² Microplate Reader. Fluorescence intensity was read using a 495 nm excitation wavelength and 517 nm emission wavelength with a 5 nm bandwidth. The gain and Z-position were manually set to 118 and 7520 μm (based on previous optimized settings). A baseline fluorescence of each aptamer and aptamer-GO solution was determined in relative fluorescence units (RFUs) (t=0). Protein solutions of LS25 (18 μM), AB45 (18 μM), and LS25+AB45 (36 μM; 18 μM each) were prepared in water. Proteins (5 μl) were added directly to the wells with the respective aptamers and mixed. The fluorescence intensity was read immediately after the addition of protein (t1). The fluorescence intensity was measured every 5 minutes after the addition of protein for 30 minutes. Samples were analyzed in duplicate. Water (5 μl) was added to additional wells of aptamer and aptamer-GO as a negative control. Negative samples were analyzed in duplicate.
Results
Graphene Oxide Quenches Fluorescence of FAM-Labeled Aptamers After the formulations were equilibrated, a baseline fluorescence was determined for each aptamer and aptamer-GO formulation. Graphene oxide quenched over 99% of the fluorescence measured by the aptamer alone in buffer. This was determined by the signal measured with aptamer+GO relative to the signal produced by the FAM-labeled aptamer alone.

$$1 - \frac{RFU \text{ of Aptamer} + GO(t_0)}{RFU \text{ of Aptamer } (t_0)}$$

Two concentrations of GO were used to quench the signal of the aptamer cocktail. Greater quenching was observed with 100 ng/μL GO than with 75 ng/μL GO, as shown in Table 10.

TABLE 10

| Aptamer | Fluorescence (RFUs) Aptamer Alone | Aptamer + GO |
|---|---|---|
| H2.1.2 | 11648 | 86 (a) |
| D2.1 | 10507 | 47 (a) |
| D11.1 | 14239 | 119 (a) |
| Mix | 36123 | 261 (b) |
| | | 108 (c) |

(a) 25 ng/μL GO; (b) 75 ng/μL GO; (c) 100 ng/μ GO.

FIG. 54 shows the percent of FAM-labeled aptamer fluorescence quenched by GO, by comparing the fluorescence of aptamer-GO formulations to the fluorescence of aptamer alone at the same concentration after equilibrating for 2 days.

Fluorescence Increases in the Presence of Target Protein

Protein detection was observed as an increase in fluorescence of the aptamer-GO formulations. The proportional fluorescence response was calculated as a function of the RFU signal at a given time after the addition of protein (tx) relative to the initial RFU signal before the addition of protein (t0).

$$\frac{RFU t_x}{RFU t_0} - 1$$

Fluorescence of the FAM-H2.1.2 aptamer in GO increased with the addition of 1 mM CotE LS25. The same increase in fluorescence was not observed with the addition of water to the aptamer-GO (FIG. 55).

The proportional fluorescence response to the addition of water was subtracted from the proportional fluorescence response to the addition of protein to obtain a response corrected for the change in volume (FIG. 56). FAM-H2.1.2+

25 ng/μL GO and FAM-D2.1+25 ng/μL GO showed a positive response in the presence of protein (>1). The aptamer-cocktail (H2.1.2+D2.1+D11.1)+75 ng/μL GO had a greater proportional response than the cocktail+100 ng/μL GO. The cocktail+100 ng/μL GO had a greater % Quenching than the cocktail+75 ng/μL GO.

Figure 57:
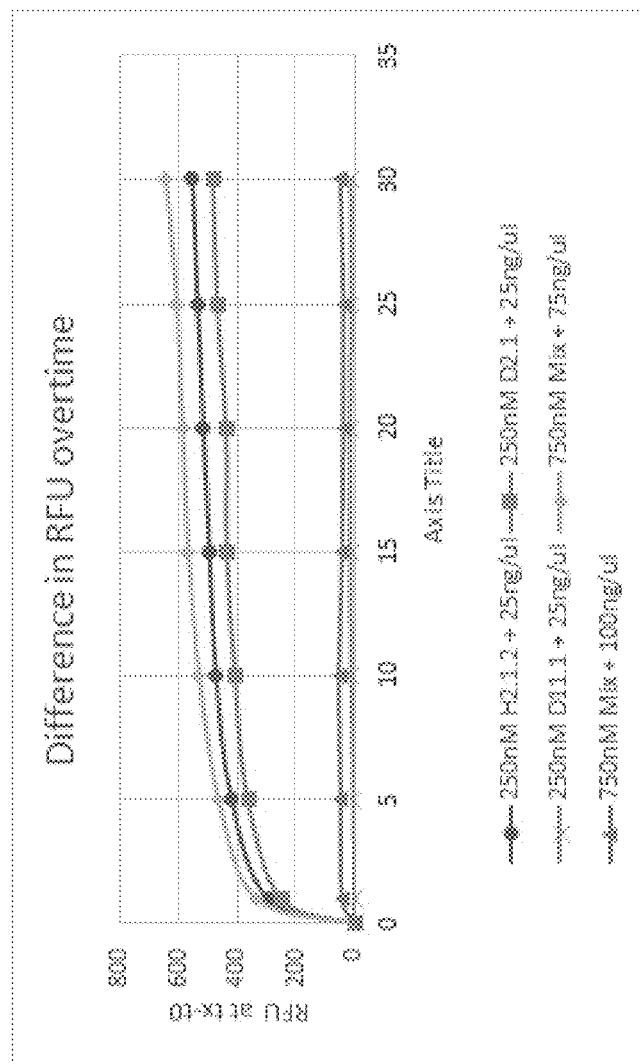
FIG. 57 shows the overall difference in RFU in the presence of protein.

As shown in FIG. 57, fluorescence of FAM-H2.1.2 in GO increases in the presence of protein, for example, the change in fluorescence over time of 250 nM FAM-H2.1.2 in 25 ng/μL GO with the addition of 1 mM CotE LS25 (blue) and water (orange) is shown.

Figure 58:
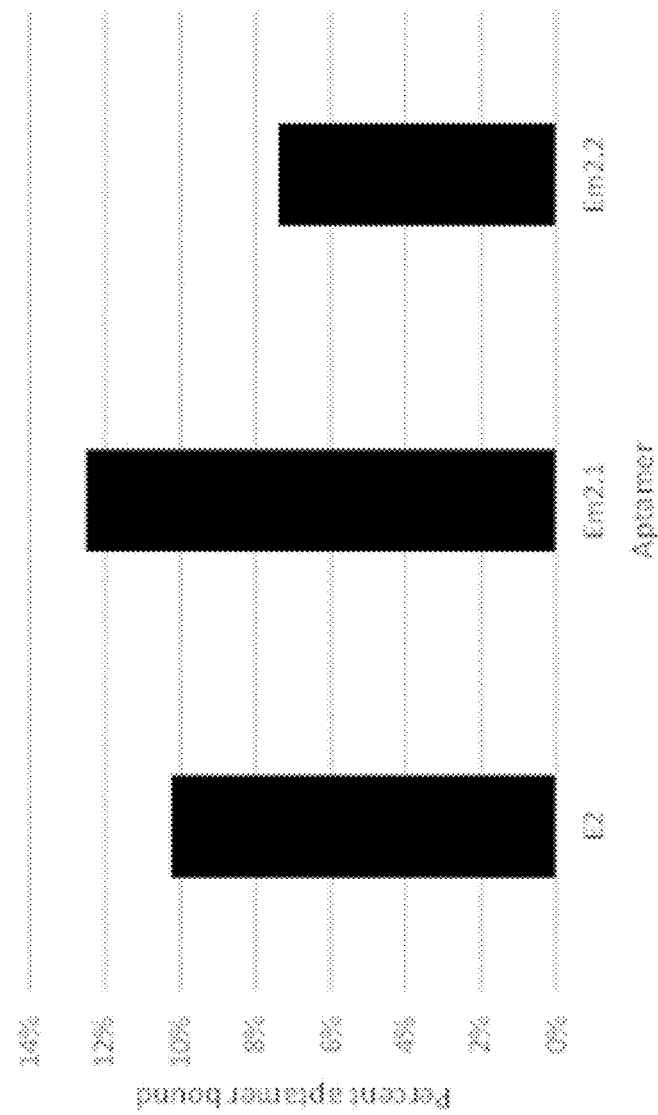
FIG. 58 is a bar graph of percent aptamer bound for the E2, Em2.1, and Em2.2 aptamers.

FIG. 58 shows the fluorescence response of aptamer-GO formulations in the presence of protein. For example, the change in the proportional fluorescence, relative to the baseline fluorescence (t0) of the individual aptamer-GO formulations—FAM-H2.1.2 (blue), FAM-D2.1 (orange), and FAM-D11.1 (grey)—and the aptamer-GO cocktail—75 ng/μL GO (yellow), 100 ng/μL GO (light blue) are shown. The corrected response is shown with the water response for each aptamer formulation subtracted from the protein response.

Aptamer Cocktail Increases Detection Signal

The aptamer cocktail with 75 ng/μL GO produced the highest RFU signal at 30 minutes after the addition of protein (RFU=907). The initial RFU signal is subtracted from the RFU signal at a given time after the addition of protein to give the overall difference in RFU.

$$RFU\ t_x - RFU\ t_0$$

Following the immediate addition of protein (t1) the difference in RFU increased over time for H2.1.2, D2.1, and the aptamer cocktail with 75 ng/μL GO. The aptamer cocktail showed a greater ΔRFU than any of the individual aptamers. A greater ΔRFU means a greater difference between the positive and negative response of the aptamer-formulation.

Conclusion

The combination of the aptamers H2.1.2 and D2.1 resulted in a higher accumulation of actual relative fluorescence units in the presence of added protein than the fluorescence signal achieved with either of these aptamers alone, thus provided a demonstration of the following: (a) the two aptamers are not competing with each other for binding sites on this protein; (b) the combination of the two aptamers in one formulation led to a synergistic effect, i.e. a higher level of fluorescence increase in the presence of protein than was observed with the either aptamer by itself.

It is important to note that in both the mix and in the individual aptamer treatments there was the same amount of overall protein (1 mM of the target protein).

Example 14: Em2.1 Aptamer

The structure formed starting with a double-stranded stem at position 17 and ending with another double-stranded stem at position 63 is thought of being the core structure (FIG. 13) enabling this aptamer to bind to the CdeM target. This structure could be described as: Stem(4f)/Loop(5)/Stem(4r)/Loop(5)/Stem(2f)/Loop(1)/Stem(2f)/Loop(1)/Stem(5f)/Loop(7)/Stem(5r)/Loop(1)/Stem(2r)/Loop(1)/Stem(2r), where the term "stem" refers to a double-stranded structure and "loop" refers to a single-stranded structure, the terms 'f' and 'r' refer to 5' side of a double stranded structure and the 3' side respectively.

Two truncated, optimized aptamers were created—one starting at position 14 and ending at position 66 (named Em2.1), and one starting at position 32 and ending at position 66 (named Em2.2).

The aptamer Em2.1 assumes that all of the stem and loop structures described above are necessary for binding to CdeM protein.

The aptamer Em2.2 was designed based on the assumption that only the following substructure was necessary for binding to CdeM protein: Stem(2f)/Loop(1)/Stem(2f)/Loop(1)/Stem(5f)/Loop(6)/Stem(5r)/Loop(1)/Stem(2r)/Loop(1)/Stem(2r).

Binding of Sequences to Targets

The CdeM protein is similar to the CdeC protein in that it forms aggregated balls when purified. An amount of protein equivalent to 1E8 particles with 1 μM of each of the Em2, Em2.1 and Em2.2 aptamers in a total volume of 50 μL in the CdeM buffer was used. The mixture was allowed to incubate for 15 min at room temperature, then centrifuged. The supernatant was removed, and the pellet resuspended in CdeM buffer. This was centrifuged again and the wash process repeated once more. The bound aptamer was then eluted with exposure to 6M urea and 85° C. This was centrifuged again and the supernatant retained. This elution process was repeated three times and the three elutions were pooled. The urea was removed with a PCR cleanup column and the fluorescence retained was compared to the initial fluorescence of the aptamer applied to each treatment.

FIG. 58 shows that the retention of the entire structure represented by the aptamer Em2.1 was necessary to obtain optimum binding results to the CdeM protein.

Surface Detection

It was possible to fluorescently label an aptamer and to detect the binding of such an aptamer to the target that it binds by partitioning the unbound aptamer from the bound aptamer. Aptamer binding to a target can be observed as a function of a change in a signal including but not limited to methods such as the use of a conjugated methylene blue moiety and measurement of a change in redox potential, or the expression of fluorescence from an aptamer that is otherwise quenched. These methods are applicable if the base level (the amount of signal observed in the absence of target) does not need to be a fixed value as long as the signal in the presence of target is larger or smaller than the base level.

The surface detection methods and compositions described herein allow for the following criteria: detection of a signal upon binding without a need to partition bound from unbound aptamers; and a lack of visual observation of the signal in the absence of the target, and the presence of a visual signal in the presence of the target. There is a need for aptamer/target protein binding to modulate the expression of a signal, and the base level of this signal must be determined such that it is not observable, visually, in the absence of the target. In some embodiments, "visually" shall be taken to mean by the human eye directly, with the aid of appropriate filters.

The Phospho505 flashlight is capable of exciting a fluorophore with an excitation spectrum below 505 nm, while orange goggles that filter out light between 190 and 540 nm can be used to greatly reduce the observation of light directly from the flashlight. Aptamers labeled with the FAM fluorophore, which has an excitation peak of 497 nm and an emission peak of 517 nm, were observed to fluoresce more brightly when the Phospho505 flashlight was used to excite them and were observed visually with the use of the orange goggles.

As described herein, an aptamer labeled with a FAM fluorophore with a certain level of fluorescence was not visible once the solution was dried on a surface. This level of fluorescence was quantified as between 150 and 190 relative fluorescence units (RFU) with a TECAN Safire II monochromatic fluorometer with a GAIN setting 118, excitation of 497 nm, emission of 517 nm, with a band width of 5 nm. In some embodiments, a fluorescence of 170 RFU at these setting can be employed.

As described herein, the aptamer Em2.1, at a concentration of 1 µM in water, in the presence of 80 ng/µL of graphene oxide had 99.5% of its fluorescence quenched, such that it was only emitting fluorescence of approximately 170 RFU in a TECAN Safire II instrument with the specification provided above.

In some embodiments, the optics of the system can be further improved by adding a circular polarizing filter to the image capture side, resulting in a reduction in the amount of fluorescence observed in the absence of spores.

When applied to live *C. diff* spores on a surface, the formulation exhibited visual fluorescence with the lighting source and goggles used once the solution containing the aptamer had dried, while no fluorescence was observed in the absence of spores with the same lighting and observation systems.

The process for Em2.1 with *C. diff* ribotype 027 at various concentrations is shown. The aptamer/GO formulation was applied as a 20 µL solution with a pipettor. CdeM protein was included as a positive control, Aptamer+GO on steel is the formulation applied to a spot that does not have spores on it. Spores were applied at the concentrations indicated in 1 cm spots and allowed to dry overnight prior to this experiment.

Figure 59:
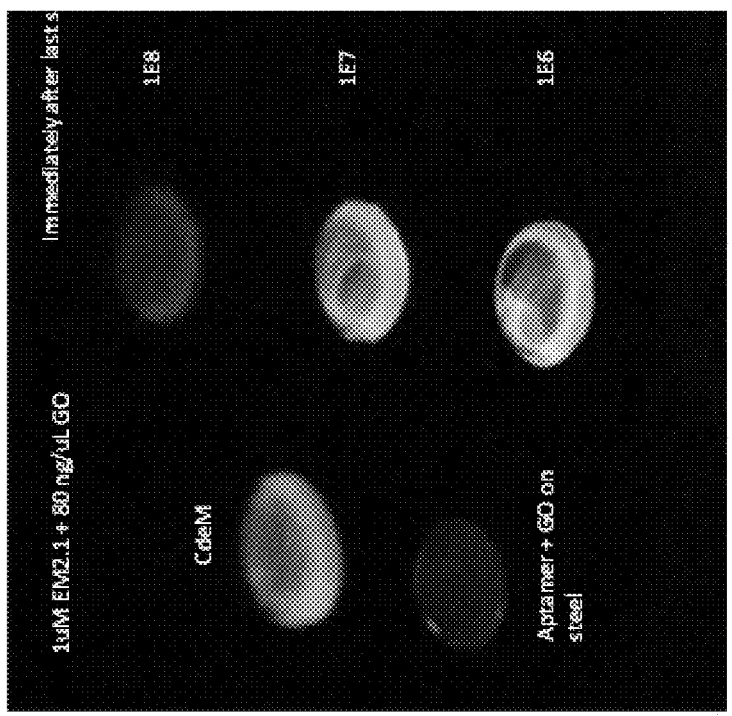
FIG. 59 is an image of Em2.1 at various concentrations, immediately after application.
Figure 60:
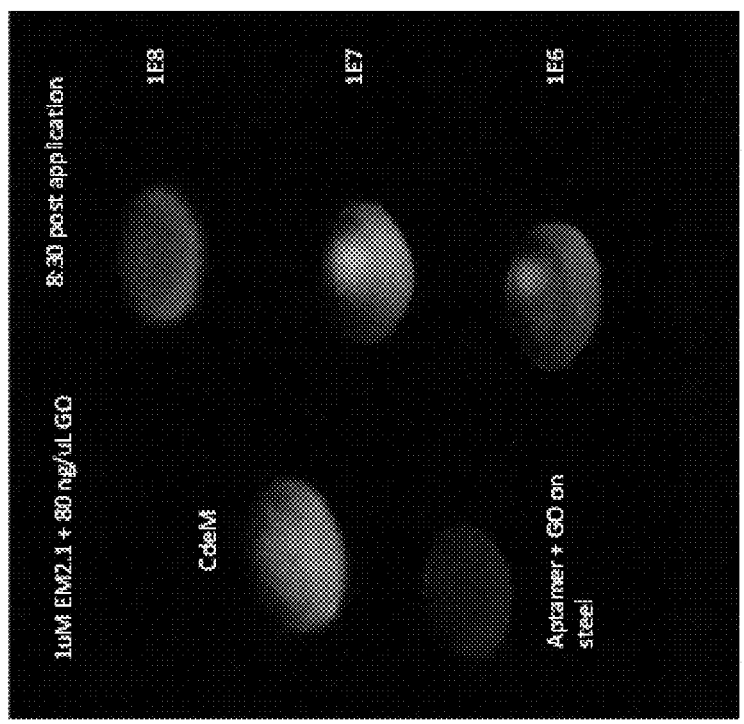
FIG. 60 is an image of Em2.1 at various concentrations, 8:30 minutes after application.
Figure 61:
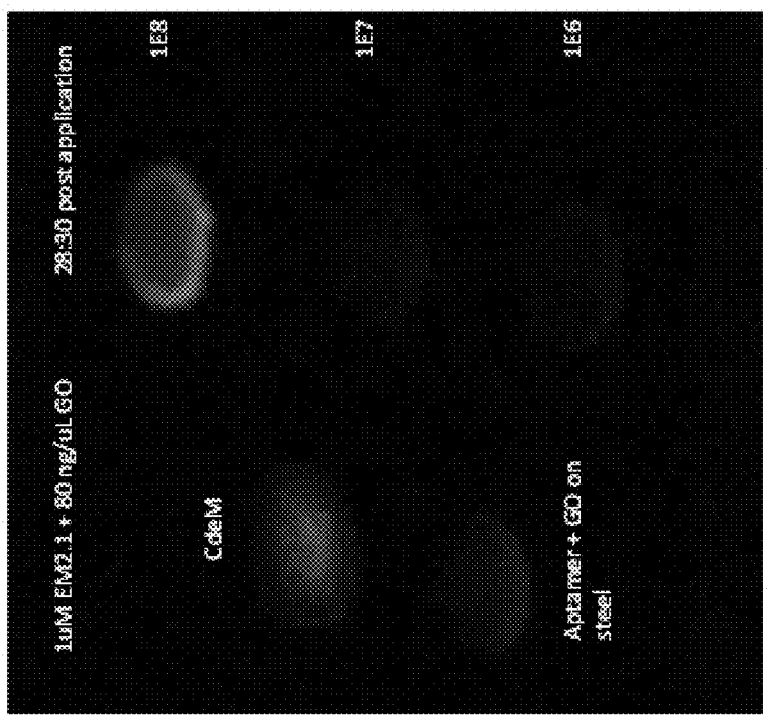
FIG. 61 is an image of Em2.1 at various concentrations, 28:30 minutes after application.

FIG. 59 shows the spots immediately after application, FIG. 60 shows the spots 8:30 minutes after application, and FIG. 61 shows the spots 28:30 minutes after application. Thus, the higher the concentration of spores the longer the fluorescence effect lasts.

The formulation can be applied as a spray. A total of 10 mL of formulation (1 µM Em2.1 quenched with 80 ng/µL GO) was prepared and loaded into a 15 mL Falcon tube. The head of a mechanical spraying device was detached and the straw was cut to reduce the need for excessive volume of formulation. The sprayer was primed with approximately 5 mL of formulation. Then, a half spray of formulation was released on 5 cm spots of spores (ribotype 027, 1E9 spores/mL) spread on a stainless steel surface and on a bare stainless steel surface from a distance of 20 cm. The spray was repeated 1 min later. The spots were illuminated with the Phospho505 flashlight and the images recorded through the goggles and a circular polarizing filter.

Figure 62:
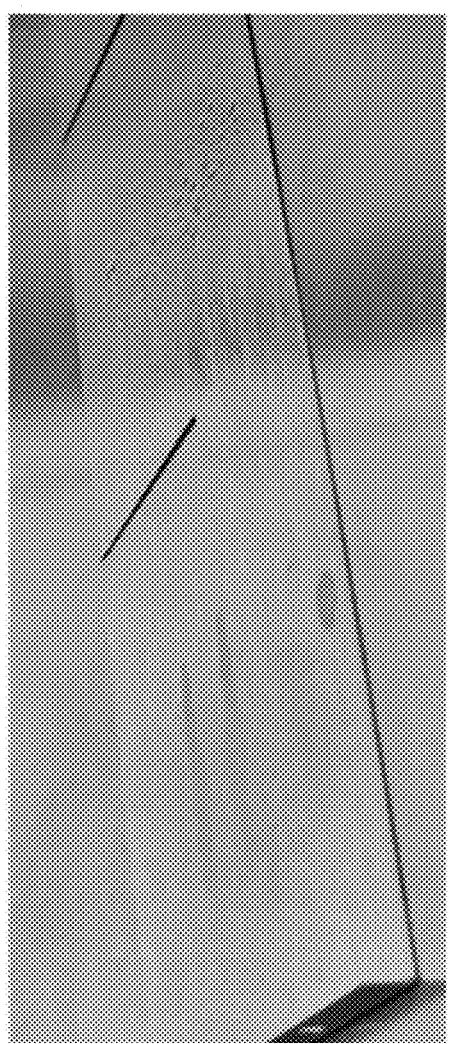
FIG. 62 is a photograph showing the layout of the spraying experiment on stainless-steel.
Figure 63:
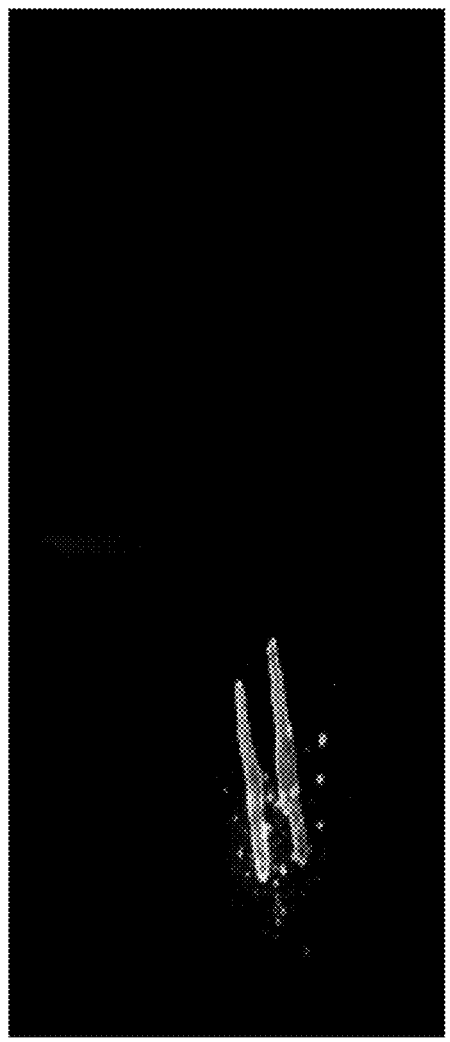
FIG. 63 is an image of the surface, 1 minute after the Em2.1/GO formulation was s megacolon, perforation of the bowel and even death if the infection is not controlled quickly.
Figure 64:
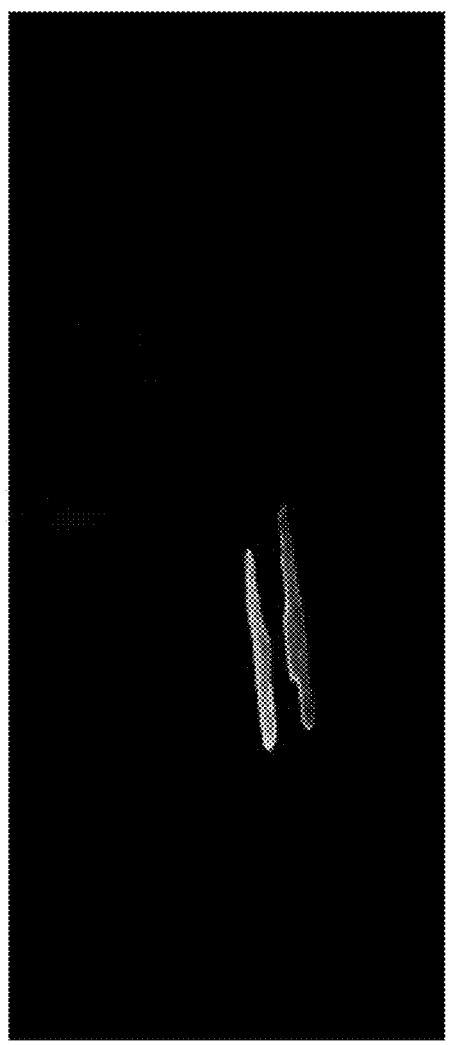

FIG. 62 shows the layout of the experiment. On the right hand side, the darker streaks represent spores (1E9) spread on a stainless steel surface. The left side of the image does not have spores. This image was taken immediately after the Em2.1/GO formulation was sprayed on the surface. FIG. 63 shows the surface 1 minute after application of Em2.1/GO formulation, FIG. 64 shows the surface 10 minutes after application of Em2.1/GO formulation, captured with a webcam through the orange goggles. The webcam had its own filter adjustments so the circular polarizing filter was not used.

Example 15: Cocktail of Aptamers

Figure 65:
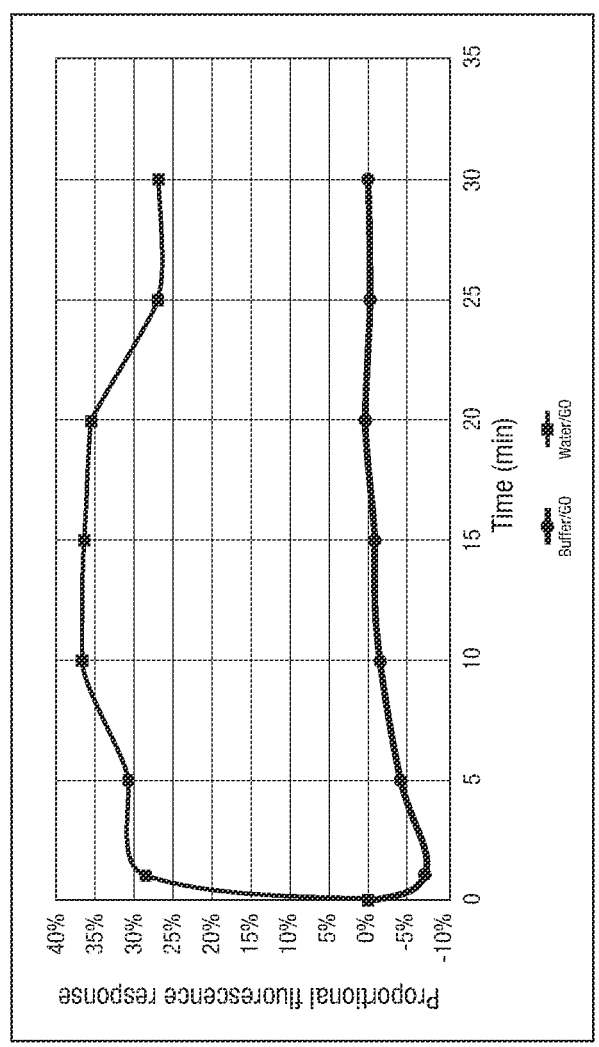

In some embodiments, multiple aptamers can be combined together in a formulation. In some embodiments, the multiple aptamer formulation can result in improved detection. In some embodiments, water can be used as the solvent for the formulation. In some embodiments, buffer can be used as the solvent for the formulation. FIG. 65 shows that for the Em2.1 aptamer, the response with the GO solution was not as strong against CdeM proteins in the CdeM buffer as it was in water. Buffer/GO refers to 1 µM Em2.1 aptamer with 100 ng/µL GO in CdeM buffer. Water/GO refers to 1 µM Em2.1 aptamer with 100 ng/µL GO in water.

It is possible that certain ribotypes of *C. diff* could have low amounts of a specific target protein (CdeM in the case of Em2.1) or have a variant form of the protein such that the epitope recognized by the Em2.1 aptamers is less well recognized. In some embodiments, a cocktail of aptamers for a variety of *C. diff* aptamers can improve the consistency of detection of *C. diff* spores regardless of the ribotype present, or the growing conditions of the spores. In some embodiments, improved performance of a mix of aptamers in one formulation over the activity of each individual aptamer can be demonstrated.

Figure 66:
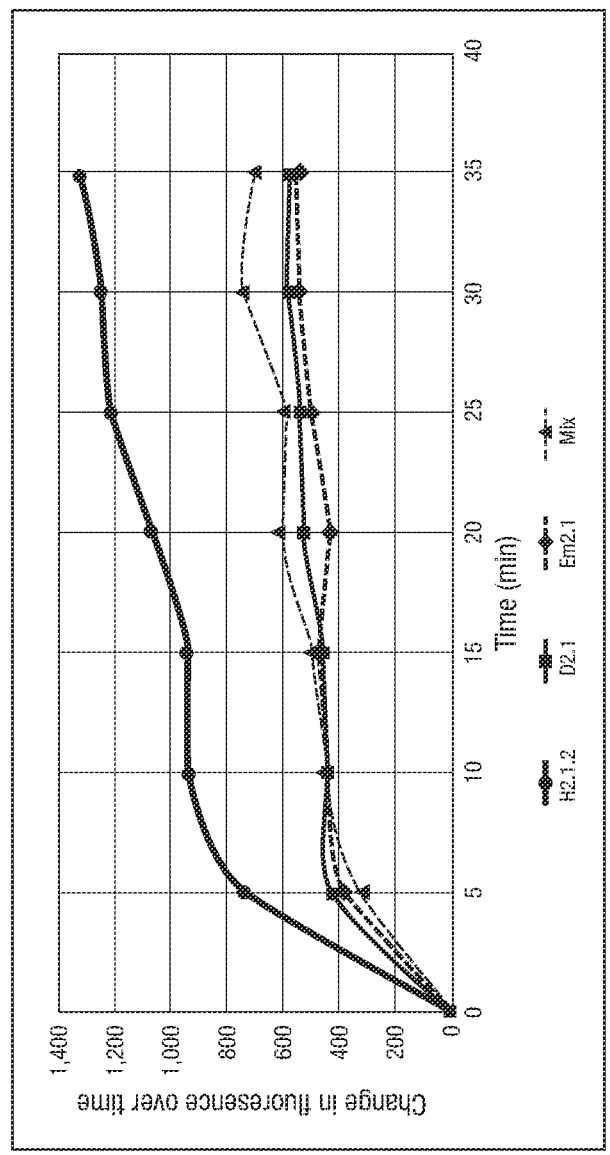

In an initial experiment, each of three aptamers individually at a concentration of 250 nM each with 25 ng/µL GO and in a mixture of 250 nM each and 75 ng/µL GO were tested. As shown in FIG. 66, it appeared that the H2.1.2 aptamer alone outperformed a mix of any of the aptamers. However, in this case, the H2.1.2 and D2.1 aptamers were quenched to a lower level than was desired.

TABLE 11

| PERCENT QUENCHING | | | |
|---|---|---|---|
| H2.1.2 | D2.1 | Em2.1 | Mix |
| 0.940625 | 0.972772 | 0.98764 | 0.986012 |

Figure 67:
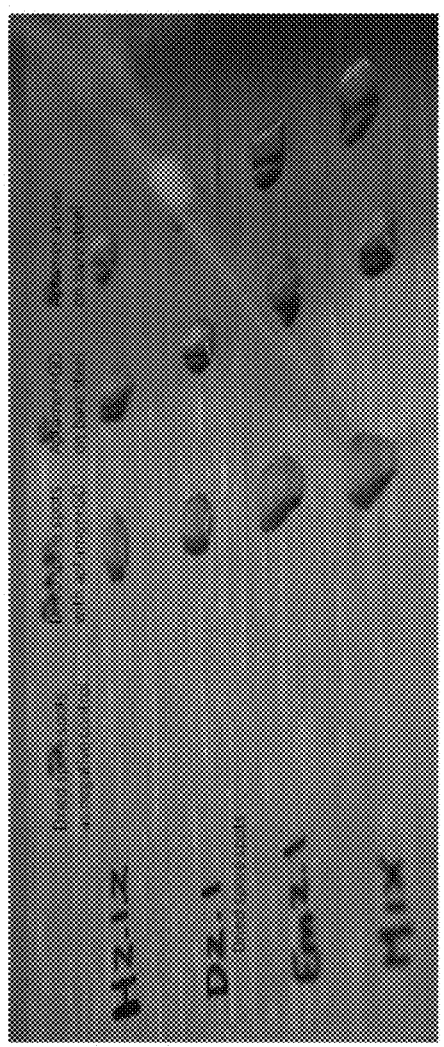
Figure 68:
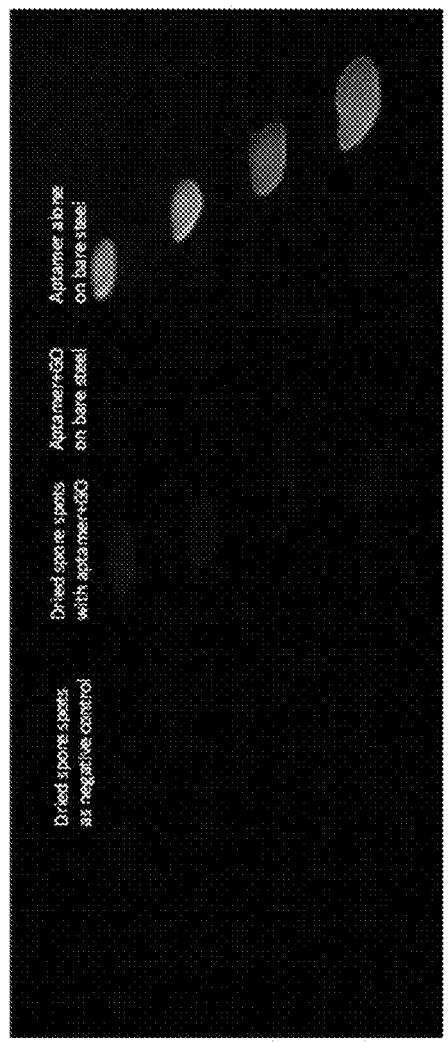
Figure 69:
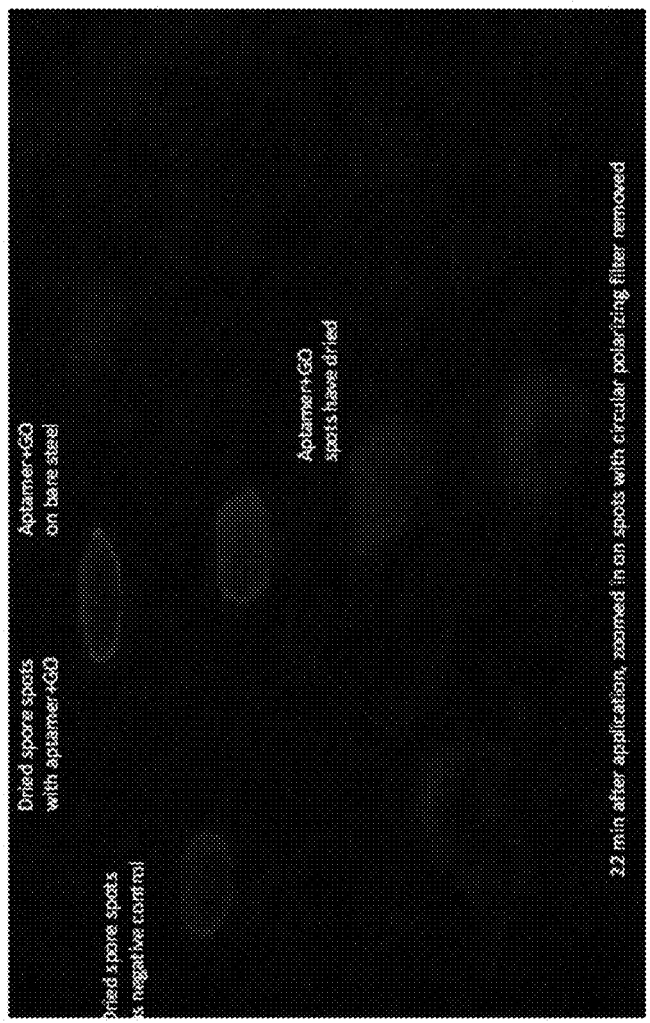

The aptamer/GO formulations were also applied to spores spotted on a surface and to a surface without spores. As a positive control the aptamers were also spotted on the surface without GO quenching. FIG. 67 shows the experimental layout with the formulation being added to the spots. The legend on the left describes which aptamer formulation was applied to the surface, H2.1.2, D2.1, Em2.1, and the mixture, respectively. FIG. 68 was taken with the flashlight and camera with appropriate filters immediately after the last formulation was applied. FIG. 69 was taken 22 minutes after application of the formulation with the polarizing filter removed.

FIG. 69 shows the direct fluorescence measurements of the individual aptamers, giving the appearance that the individual aptamers were performing better than would be expected based on the direct fluorescence measurements. However, it was realized that GO quenches all the aptamers in a cocktail. In some embodiments, the amount of each aptamer in such cocktail can be optimized in order to obtain the maximum potential effect from each aptamer within a mixture.

In some embodiments, five different formulations as described in Table 12, can be employed.

TABLE 12

| FIVE FORMULATIONS | | | |
|---|---|---|---|
| | Em2.1 | H2.1.2 | D2.1 |
| A | 600 | 200 | 200 |
| B | 200 | 400 | 400 |

TABLE 12-continued

FIVE FORMULATIONS

| | Em2.1 | H2.1.2 | D2.1 |
|---|---|---|---|
| C | 333 | 333 | 333 |
| D | 200 | 600 | 200 |
| E | 200 | 200 | 500 |

Three different aptamers (H2.1.2, D2.1 and Em2.1) were combined in different ratios all leading to a total aptamer concentration of 1 µM. The values within the table are in nM for each aptamer.

Figure 70:
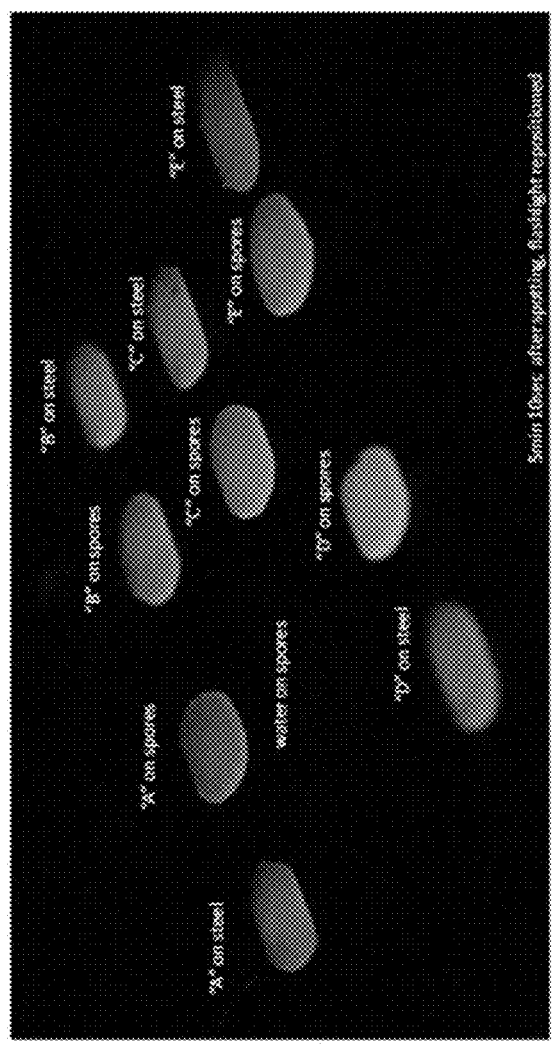
Figure 71:
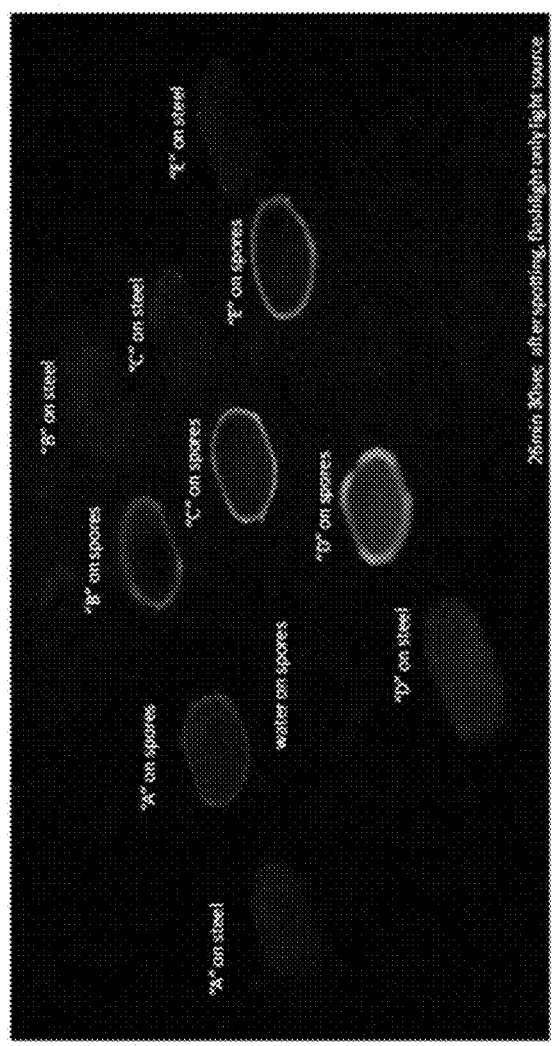

The formulations were applied to 10 µL spots of 1E9 spores/mL ribotype 027 spores on the surface in an identical manner. FIG. 70 shows that while the formulation remained undried on the spots there was not a discernible difference between the presence and absence of spores. This image was recorded 5:10 minutes after the application of the last formulation. FIG. 71 was recorded once the formulations had dried on the spots, 26:30 minutes after the application of the last formulation. It is clear that the mixtures of formulations on live spores exhibited an enhanced fluorescent signal in the presence of spores versus the absence. The mixture exhibiting the strongest fluorescent response was mixture D. This mixture contained a higher amount of the aptamer H2.1.2 for the protein CotE relative to the other aptamers.

The observation that the mixtures with the highest amount of Em2.1 did not exhibit the strongest fluorescence response to spores on a surface indicates that the mixtures with the appropriate calibration between aptamers in terms of concentration are not dependent on this aptamer for their response.

Figure 72:
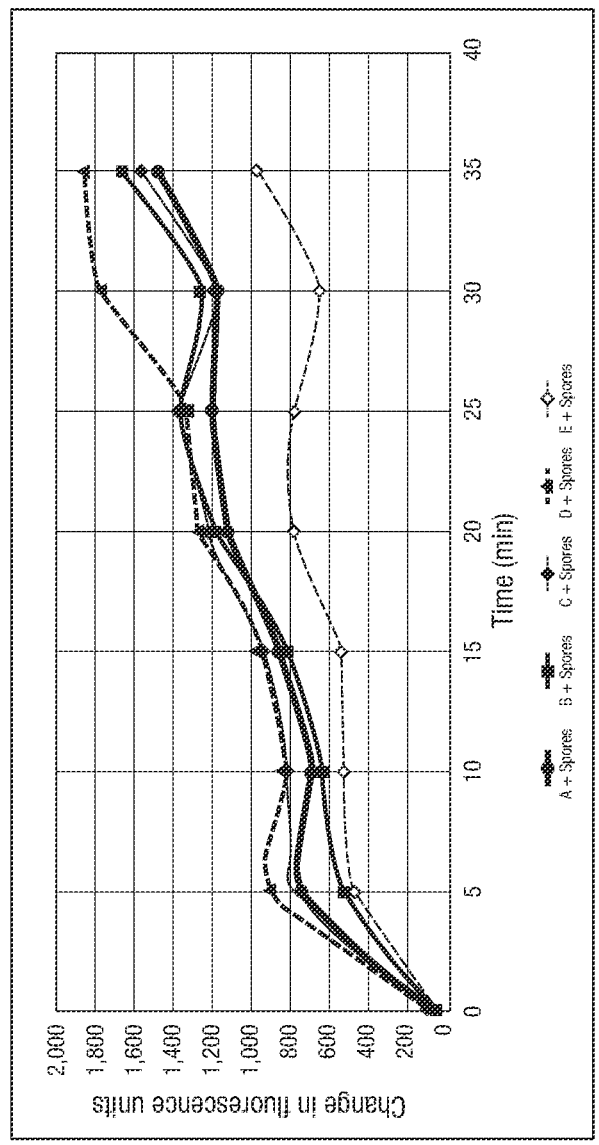

FIG. 72 shows the change in fluorescence in the presence and absence of spores (ΔRFU) in solution in an Omega Fluostar fluorometer. These measurements align well with the observations of the performance of the formulations on the spores on the surface, with mixture D performing the best over time.

The references cited throughout this application, are incorporated herein in their entireties for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this disclosure is not limited to the particular embodiments disclosed but is intended to cover all modifications which are within the spirit and scope of the disclosure as defined by the appended claims; the above description; and/or shown in the attached drawings.

What is claimed is:

1. A method of visualizing *Clostridium difficile* spores on a surface, comprising:
   contacting a surface with a liquid composition comprising (a) at least one aptamer conjugated to a fluorophore, wherein the at least one aptamer has a stem-loop structure having a specific binding affinity for a surface protein of *Clostridium difficile* spore, wherein the at least one aptamer comprises a nucleic acid sequence having at least 90% identity with any one of the nucleic acid sequences as set forth in any of SEQ ID NOs: 43-55 wherein the surface protein is a spore coat surface protein or an exosporium layer protein; and (b) graphene oxide, wherein fluorophore is quenched by the association with the graphene oxide; and visualizing the presence or absence of *Clostridium difficile* spores on the surface, wherein fluorescence is visible when the at least one aptamer is bound to the surface protein of *Clostridium difficile* spores.

2. The method of claim 1, wherein when the at least one aptamer is not bound to the surface protein, the fluorophore is quenched and wherein when the aptamer binds to the surface protein, the fluorophore is not quenched.

3. The method of claim 1, wherein the surface protein is CdeM, or CotE Chitinase.

4. The method of claim 1, wherein the at least one aptamer comprises a nucleic acid sequence that selectively binds to surface protein CdeM of the *Clostridium difficile* spores, the aptamer having a stem-loop structure comprising Loop(3)/Stem(4f)/Loop(5)/Stem(4r)/Loop(5)/Stem(2f)/Loop(1)/Stem(2f)/Loop(1)/Stem(5 f)/Loop(5)/Stem(5r)/Loop(1)/Stem(2r)/Loop(1)/Stem(2r)/Loop(3).

5. The method of claim 1, wherein the composition comprises two or more aptamers having a binding affinity to two or more epitopes of a surface protein of the *Clostridium difficile* spores or to two or more surface proteins of the *Clostridium difficile* spores.

6. The method of claim 1, wherein the graphene oxide is in the form of nanoparticles.

7. The method of claim 1, wherein the fluorophore emits at a wavelength of between about 510 nm and about 520 nm.

8. The method of claim 1, further comprising illuminating the surface with a light source.

9. The method of claim 8, wherein light from the light source has a predetermined wavelength, and the predetermined wavelength is different than a wavelength of light emitted by the fluorophore of the aptamer conjugate.

10. The method of claim 8, wherein the light source is configured to produce light at a wavelength of between about 485 nm and about 515 nm.

11. The method of claim 8, further comprising filtering the light produced by the light source such that light at a wavelength emitted by the fluorophore is visually detected.

12. The method of claim 8, comprising passing the light produced from the light source through a bandpass filter such that light at a wavelength emitted by the fluorophore is visually detected.

13. The method of claim 8, comprising passing the light produced from the light source through a circular polarizing filter such that light at a wavelength emitted by the fluorophore is visually detected.

14. The method of claim 1, wherein the contacting comprises spraying.

15. A method of visualizing *Clostridium difficile* spores on a surface, comprising:

contacting a surface with a liquid composition comprising (a) at least one aptamer conjugated to a fluorophore, wherein the at least one aptamer has a stem-loop structure having a specific binding affinity for a surface protein of *Clostridium difficile* spore, wherein the at least one aptamer comprises a nucleic acid sequence as set forth in SEQ ID NO: 55, wherein the surface protein is a spore coat surface protein or an exosporium layer protein; and (b) graphene oxide, wherein fluorophore is quenched by the association with the graphene oxide; and visualizing the presence or absence of *Clostridium difficile* spores on the surface, wherein fluorescence is visible when the at least one aptamer is bound to the surface protein of *Clostridium difficile* spores.

16. The method of claim 15, wherein when the at least one aptamer is not bound to the surface protein, the fluorophore is quenched and wherein when the aptamer binds to the surface protein, the fluorophore is not quenched.

17. The method of claim 15, wherein the at least one aptamer comprises a nucleic acid sequence that selectively binds to surface protein CdeM of the *Clostridium difficile* spores, the aptamer having a stem-loop structure comprising Loop(3)/Stem(4f)/Loop(5)/Stem(4r)/Loop(5)/Stem(2f)/Loop(1)/Stem(2f)/Loop(1)/Stem(5 f)/Loop(5)/Stem(5r)/Loop(1)/Stem(2r)/Loop(1)/Stem(2r)/Loop(3).

18. The method of claim 15, wherein the composition comprises two or more aptamers having a binding affinity to two or more epitopes of a surface protein of the *Clostridium difficile* spores or to two or more surface proteins of the *Clostridium difficile* spores.

19. The method of claim 15, wherein the graphene oxide is in the form of nanoparticles.

20. The method of claim 15, wherein the fluorophore emits at a wavelength of between about 510 nm and about 520 nm.

21. The method of claim 15, further comprising illuminating the surface with a light source.

22. The method of claim 21, wherein light from the light source has a predetermined wavelength, and the predetermined wavelength is different than a wavelength of light emitted by the fluorophore of the aptamer conjugate.

23. The method of claim 21, wherein the light source is configured to produce light at a wavelength of between about 485 nm and about 515 nm.

24. The method of claim 21, further comprising filtering the light produced by the light source such that light at a wavelength emitted by the fluorophore is visually detected.

25. The method of claim 21, comprising passing the light produced from the light source through a bandpass filter such that light at a wavelength emitted by the fluorophore is visually detected.

26. The method of claim 21, comprising passing the light produced from the light source through a circular polarizing filter such that light at a wavelength emitted by the fluorophore is visually detected.

\* \* \* \* \*

SEQUENCE LISTING

```
<160> NUMBER OF SEQ ID NOS: 55

<210> SEQ ID NO 1
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccagtgtaga ctactcaatg ctcttacgat cctcacctgc tagcacaccc atatcccatg      60
cgtactatcc acaggtcaac c                                               81

<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccagtgtaga ctactcaatg cgggttgcga catggtggta agagctcagc ccgttcccat      60
agtactatcc acaggtcaac c                                               81

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
```
ccagtgtaga ctactcaatg cacggcctgt tcgtaagacc cttacagact agtttttccc    60
tgtactatcc acaggtcaac c                                              81

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccagtgtaga ctactcaatg ccctattagc tgtatcgatc cgtttagtcg ctcctccgat    60
agtactatcc acaggtcaac c                                              81

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccagtgtaga ctactcaatg cctggtaaat cgatgaccgc tgcctcgcct gagtaatcat    60
cgtactatcc acaggtcaac c                                              81

<210> SEQ ID NO 6
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccagtgtaga ctactcaatg ccgtggactg gtcgggtttg gattcggcag atgaatcagt    60
agtactatcc acaggtcaac c                                              81

<210> SEQ ID NO 7
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccagtgtaga ctactcaatg ccttgtaaga agaacaatcg ccgcttcgcc tgaataggtt    60
cgtactatcc acaggtcaac c                                              81

<210> SEQ ID NO 8
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccagtgtaga ctactcaatg cggaccgttg cctcgcccga gtaatccgcc atcgcctttc    60
cgtactatcc acaggtcaac c                                              81

<210> SEQ ID NO 9
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccagtgtaga ctactcaatg cttaagttct ggggacacgt gatgaacgca tttaatgggg    60
cgtactatcc acaggtcaac c                                              81

<210> SEQ ID NO 10
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccagtgtaga ctactcaatg ccgtggactg gtcgggtttg gattcggcag atgaatcact    60
agtactatcc acaggtcaac c                                              81

<210> SEQ ID NO 11
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccagtgtaga ctactcaatg cggctgtgtg acttgacctt tggaatgggt gggagggatg    60
ggtactatcc acaggtcaac c                                              81

<210> SEQ ID NO 12
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccagtgtaga ctactcaatg cggtgtggtg accttgacct atggaacctg gttgtagtac    60
tatccacagg tcaacc                                                    76

<210> SEQ ID NO 13
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccagtgtaga ctactcaatg ctcgacattt ccgccccgac ggccctccta gtgatgggga    60
gagtactatc cacaggtcaa cc                                             82

<210> SEQ ID NO 14
<211> LENGTH: 81

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccagtgtaga ctactcaatg ccttccattc acctaccgag ctaagcgttc gacttaggtc    60
tgtactatcc acaggtcaac c                                              81

<210> SEQ ID NO 15
<211> LENGTH: 305
<212> TYPE: PRT
<213> ORGANISM: Clostridium difficile

<400> SEQUENCE: 15
```

| Met | Glu | Asn | Asn | Lys | Cys | Arg | Glu | Asp | Phe | Arg | Phe | Thr | Gln | Glu | Tyr |
|---|---|---|---|---|---|---|---|---|---|---|---|---|---|---|---|
| 1 | | | | 5 | | | | | 10 | | | | | 15 | |

| Glu | Glu | Asp | Tyr | Pro | Asn | Thr | Asn | Glu | Arg | Tyr | Tyr | Glu | Asn | Tyr | Gln |
|---|---|---|---|---|---|---|---|---|---|---|---|---|---|---|---|
| | | | 20 | | | | | 25 | | | | | 30 | | |

| Val | Ala | Asp | Arg | Tyr | Tyr | Asn | Tyr | Pro | Asn | Lys | Tyr | Lys | Glu | Pro | Lys |
|---|---|---|---|---|---|---|---|---|---|---|---|---|---|---|---|
| | | 35 | | | | | 40 | | | | | 45 | | | |

| Ile | Lys | Gln | Cys | Cys | Lys | Lys | Ser | Met | Arg | Glu | Ala | Leu | Glu | Leu |
|---|---|---|---|---|---|---|---|---|---|---|---|---|---|---|
| 50 | | | | | 55 | | | | | 60 | | | | |

| Leu | Arg | Tyr | Asp | Ala | Leu | Arg | Pro | Phe | Val | Asn | Phe | Asn | Gln | Phe | Ala |
|---|---|---|---|---|---|---|---|---|---|---|---|---|---|---|---|
| 65 | | | | 70 | | | | | 75 | | | | | 80 | |

| Phe | Ile | Ser | Asp | Phe | Phe | Ile | Val | Gly | Ala | Asn | Leu | Val | Gly | Ile | Asp |
|---|---|---|---|---|---|---|---|---|---|---|---|---|---|---|---|
| | | | 85 | | | | | 90 | | | | | 95 | | |

| Leu | Ser | Ala | Pro | Pro | Lys | Asp | Asn | Leu | Ser | Gly | Leu | Asp | Gly | Thr | Phe |
|---|---|---|---|---|---|---|---|---|---|---|---|---|---|---|---|
| | | 100 | | | | | 105 | | | | | 110 | | | |

| Glu | Arg | Phe | Ser | Ala | Cys | Asn | Cys | Asp | Leu | Ile | Asp | Ile | Ala | Gly | Arg |
|---|---|---|---|---|---|---|---|---|---|---|---|---|---|---|---|
| | | 115 | | | | | 120 | | | | | 125 | | | |

| Val | Ser | Tyr | Pro | Ile | Pro | Val | Pro | Leu | Thr | Leu | Glu | Gly | Leu | Ile | Asn |
|---|---|---|---|---|---|---|---|---|---|---|---|---|---|---|---|
| | 130 | | | | | 135 | | | | | 140 | | | | |

| Thr | Ile | Gly | Thr | Ile | Pro | Gly | Val | Ala | Glu | Leu | Ile | Ala | Leu | Ile | Asp |
|---|---|---|---|---|---|---|---|---|---|---|---|---|---|---|---|
| 145 | | | | | 150 | | | | | 155 | | | | | 160 |

| Ala | Val | Ile | Pro | Pro | Thr | Ile | Asp | Leu | Gly | Ala | Ile | Leu | Asp | Ala | Ile |
|---|---|---|---|---|---|---|---|---|---|---|---|---|---|---|---|
| | | | 165 | | | | | 170 | | | | | 175 | | |

| Leu | Ala | Ala | Ile | Ile | Asp | Phe | Ile | Leu | Ala | Ala | Ser | Thr | Pro | Leu | Ala |
|---|---|---|---|---|---|---|---|---|---|---|---|---|---|---|---|
| | | | 180 | | | | | 185 | | | | | 190 | | |

| Asn | Val | Asp | Leu | Ala | Ser | Leu | Cys | Asn | Leu | Lys | Ala | Val | Ala | Phe | Asp |
|---|---|---|---|---|---|---|---|---|---|---|---|---|---|---|---|
| | 195 | | | | | 200 | | | | | 205 | | | | |

| Ile | Thr | Pro | Ala | Asp | Tyr | Glu | Asp | Phe | Ile | Ala | Ser | Leu | Gly | Tyr | Tyr |
|---|---|---|---|---|---|---|---|---|---|---|---|---|---|---|---|
| | 210 | | | | | 215 | | | | | 220 | | | | |

| Leu | Asp | Lys | Lys | His | Tyr | Lys | Glu | Cys | Asn | Cys | Asn | Cys | Asp | Cys | Asp |
|---|---|---|---|---|---|---|---|---|---|---|---|---|---|---|---|
| 225 | | | | | 230 | | | | | 235 | | | | | 240 |

| Asp | Cys | Cys | Cys | Asn | Lys | Gly | Ile | Leu | Asp | Asn | Leu | Tyr | Met | Ser | Asn |
|---|---|---|---|---|---|---|---|---|---|---|---|---|---|---|---|
| | | | | 245 | | | | | 250 | | | | | 255 | |

| Ile | Asn | Asn | Gln | Val | Thr | Val | Val | Ala | Gly | Ser | Leu | Val | Leu | Thr | Gly |
|---|---|---|---|---|---|---|---|---|---|---|---|---|---|---|---|
| | | | 260 | | | | | 265 | | | | | 270 | | |

| Val | Glu | Val | Leu | Gly | Lys | Lys | Asn | Asp | Val | Ile | Val | Leu | Gly | Asn | Ser |
|---|---|---|---|---|---|---|---|---|---|---|---|---|---|---|---|
| | 275 | | | | | 280 | | | | | 285 | | | | |

| Asn | Asp | Ser | Arg | Ile | Tyr | Phe | Val | Cys | Val | Asp | Ser | Ile | Asp | Tyr | Ile |
|---|---|---|---|---|---|---|---|---|---|---|---|---|---|---|---|
| | 290 | | | | | 295 | | | | | 300 | | | | |

| Ala |
|---|
| 305 |

<210> SEQ ID NO 16
<211> LENGTH: 712
<212> TYPE: PRT
<213> ORGANISM: Clostridium difficile

<400> SEQUENCE: 16

```
Met Ile Tyr Met Pro Asn Leu Pro Ser Leu Gly Ser Lys Ala Pro Asp
1               5                   10                  15

Phe Lys Ala Asn Thr Thr Asn Gly Pro Ile Arg Leu Ser Asp Tyr Lys
            20                  25                  30

Gly Asn Trp Ile Val Leu Phe Ser His Pro Gly Asp Phe Thr Pro Val
        35                  40                  45

Cys Thr Thr Glu Phe Leu Cys Phe Ala Lys Tyr Tyr Asp Glu Phe Lys
    50                  55                  60

Lys Arg Asn Thr Glu Leu Ile Gly Leu Ser Val Asp Ser Asn Ser Ser
65                  70                  75                  80

His Leu Ala Trp Met Tyr Asn Ile Ser Leu Leu Thr Gly Val Glu Ile
                85                  90                  95

Pro Phe Pro Ile Ile Glu Asp Arg Asp Met Arg Ile Ala Lys Leu Tyr
            100                 105                 110

Gly Met Ile Ser Lys Pro Met Ser Asp Thr Ser Thr Val Arg Ser Val
        115                 120                 125

Phe Ile Ile Asp Asn Asn Gln Ile Leu Arg Thr Ile Leu Tyr Tyr Pro
    130                 135                 140

Leu Thr Thr Gly Arg Asn Ile Pro Glu Ile Leu Arg Ile Val Asp Ala
145                 150                 155                 160

Leu Gln Thr Ser Asp Arg Asp Asn Ile Val Thr Pro Ala Asn Trp Phe
                165                 170                 175

Pro Gly Met Pro Val Ile Leu Pro Tyr Pro Lys Asn Tyr Lys Glu Leu
            180                 185                 190

Lys Asn Arg Val Asn Ser Cys Asn Lys Lys Tyr Ser Cys Met Asp Trp
        195                 200                 205

Tyr Leu Cys Phe Val Pro Asp Asn Tyr Asn Asp Glu Glu Val Ser Lys
    210                 215                 220

Lys Ile Asp Asn Thr Cys Ser Trp Lys Lys Glu His Thr Lys Asn Ile
225                 230                 235                 240

Glu Asn Glu Cys Asn Cys Glu His Glu His His Asp Tyr Leu Asn Lys
                245                 250                 255

Ala Leu Asp Cys Lys Gln Glu His Lys Thr Asp Ile Lys Asp Asp Cys
            260                 265                 270

Asn His Glu Lys Lys His Thr Lys Asn Thr Asn Lys Val His Asn Ser
        275                 280                 285

Lys Gln Asp Lys Phe Lys Asp Lys Ser Cys Asp Glu Met Asn Phe Asn
    290                 295                 300

Tyr Asp Lys Asp Glu Ser Cys Asp Lys Ile Asn Ser Ser Tyr Asn Lys
305                 310                 315                 320

Glu Asp Ser Ser Tyr Glu Asp Phe Tyr Lys His Asn Tyr Lys Asn Tyr
                325                 330                 335

Asp Tyr Thr Ser Glu Lys Asn Thr Lys Ile Ala Met Lys Thr Leu
            340                 345                 350

Lys Asp Ser Lys Lys Leu Val Arg Pro Gln Ile Thr Asp Pro Tyr Asn
        355                 360                 365

Pro Ile Val Glu Asn Ala Asn Cys Pro Asp Ile Asn Pro Ile Val Ala
```

```
                370                 375                 380
Glu Tyr Val Leu Gly Asn Pro Thr Asn Val Asp Ala Gln Leu Leu Asp
385                 390                 395                 400

Ala Val Ile Phe Ala Phe Ala Glu Ile Asp Gln Ser Gly Asn Leu Phe
                405                 410                 415

Ile Pro Tyr Pro Arg Phe Leu Asn Gln Leu Leu Ala Leu Lys Gly Glu
            420                 425                 430

Lys Pro Ser Leu Lys Val Ile Val Ala Ile Gly Gly Trp Gly Ala Glu
        435                 440                 445

Gly Phe Ser Asp Ala Ala Leu Thr Pro Thr Ser Arg Tyr Asn Phe Ala
    450                 455                 460

Arg Gln Val Asn Gln Met Ile Asn Glu Tyr Ala Leu Asp Gly Ile Asp
465                 470                 475                 480

Ile Asp Trp Glu Tyr Pro Gly Ser Ser Ala Ser Gly Ile Thr Ser Arg
                485                 490                 495

Pro Gln Asp Arg Glu Asn Phe Thr Leu Leu Leu Thr Ala Ile Arg Asp
            500                 505                 510

Val Ile Gly Asp Asp Lys Trp Leu Ser Val Ala Gly Thr Gly Asp Arg
        515                 520                 525

Gly Tyr Ile Asn Ser Ser Ala Glu Ile Asp Lys Ile Ala Pro Ile Ile
    530                 535                 540

Asp Tyr Phe Asn Leu Met Ser Tyr Asp Phe Thr Ala Gly Glu Thr Gly
545                 550                 555                 560

Pro Asn Gly Arg Lys His Gln Ala Asn Leu Phe Asp Ser Asp Leu Ser
                565                 570                 575

Leu Pro Gly Tyr Ser Val Asp Ala Met Val Arg Asn Leu Glu Asn Ala
            580                 585                 590

Gly Met Pro Ser Glu Lys Ile Leu Leu Gly Ile Pro Phe Tyr Gly Arg
        595                 600                 605

Leu Gly Ala Thr Ile Thr Arg Thr Tyr Asp Glu Leu Arg Arg Asp Tyr
    610                 615                 620

Ile Asn Lys Asn Gly Tyr Glu Tyr Arg Phe Asp Asn Thr Ala Gln Val
625                 630                 635                 640

Pro Tyr Leu Val Lys Asp Gly Asp Phe Ala Met Ser Tyr Asp Asp Ala
                645                 650                 655

Leu Ser Ile Phe Leu Lys Thr Gln Tyr Val Leu Arg Asn Cys Leu Gly
            660                 665                 670

Gly Val Phe Ser Trp Thr Ser Thr Tyr Asp Gln Ala Asn Ile Leu Ala
        675                 680                 685

Arg Thr Met Ser Ile Gly Ile Asn Asp Pro Glu Val Leu Lys Glu Glu
    690                 695                 700

Leu Glu Gly Ile Tyr Gly Gln Phe
705                 710

<210> SEQ ID NO 17
<211> LENGTH: 332
<212> TYPE: PRT
<213> ORGANISM: Clostridium difficile

<400> SEQUENCE: 17

Pro Ile Val Ala Glu Tyr Val Leu Gly Asn Pro Thr Asn Val Asp Ala
1               5                   10                  15

Gln Leu Leu Asp Ala Val Ile Phe Ala Phe Ala Glu Ile Asp Gln Ser
            20                  25                  30
```

```
Gly Asn Leu Phe Ile Pro Tyr Pro Arg Phe Leu Asn Gln Leu Leu Ala
            35                  40                  45

Leu Lys Gly Glu Lys Pro Ser Leu Lys Val Ile Val Ala Ile Gly Gly
 50                  55                  60

Trp Gly Ala Glu Gly Phe Ser Asp Ala Ala Leu Thr Pro Thr Ser Arg
 65                  70                  75                  80

Tyr Asn Phe Ala Arg Gln Val Asn Gln Met Ile Asn Glu Tyr Ala Leu
                 85                  90                  95

Asp Gly Ile Asp Ile Asp Trp Glu Tyr Pro Gly Ser Ser Ala Ser Gly
            100                 105                 110

Ile Thr Ser Arg Pro Gln Asp Arg Glu Asn Phe Thr Leu Leu Leu Thr
            115                 120                 125

Ala Ile Arg Asp Val Ile Gly Asp Asp Lys Trp Leu Ser Val Ala Gly
130                 135                 140

Thr Gly Asp Arg Gly Tyr Ile Asn Ser Ser Ala Glu Ile Asp Lys Ile
145                 150                 155                 160

Ala Pro Ile Ile Asp Tyr Phe Asn Leu Met Ser Tyr Asp Phe Thr Ala
                165                 170                 175

Gly Glu Thr Gly Pro Asn Gly Arg Lys His Gln Ala Asn Leu Phe Asp
            180                 185                 190

Ser Asp Leu Ser Leu Pro Gly Tyr Ser Val Asp Ala Met Val Arg Asn
            195                 200                 205

Leu Glu Asn Ala Gly Met Pro Ser Glu Lys Ile Leu Leu Gly Ile Pro
210                 215                 220

Phe Tyr Gly Arg Leu Gly Ala Thr Ile Thr Arg Thr Tyr Asp Glu Leu
225                 230                 235                 240

Arg Arg Asp Tyr Ile Asn Lys Asn Gly Tyr Glu Tyr Arg Phe Asp Asn
                245                 250                 255

Thr Ala Gln Val Pro Tyr Leu Val Lys Asp Gly Asp Phe Ala Met Ser
            260                 265                 270

Tyr Asp Asp Ala Leu Ser Ile Phe Leu Lys Thr Gln Tyr Val Leu Arg
            275                 280                 285

Asn Cys Leu Gly Gly Val Phe Ser Trp Thr Ser Thr Tyr Asp Gln Ala
290                 295                 300

Asn Ile Leu Ala Arg Thr Met Ser Ile Gly Ile Asn Asp Pro Glu Val
305                 310                 315                 320

Leu Lys Glu Glu Leu Glu Gly Ile Tyr Gly Gln Phe
                325                 330

<210> SEQ ID NO 18
<211> LENGTH: 405
<212> TYPE: PRT
<213> ORGANISM: Clostridium difficile

<400> SEQUENCE: 18

Met Gln Asp Tyr Lys Lys Asn Lys Arg Met Met Asn Gln Pro Met
 1               5                  10                  15

Ser Thr Met Asn Glu Glu Glu Val Tyr Thr Asp Glu Ile Asn Ser Glu
                 20                  25                  30

Asp Met Arg Gly Phe Lys Lys Ser His His Asn Gly Cys Asn Thr
            35                  40                  45

Asp Asn Lys Cys Glu Cys His Asp Asp Cys Asn Pro Cys Asn Pro Cys
 50                  55                  60

Asn Pro Cys Lys Pro Asn Pro Cys Asn Pro Cys Lys Pro Asn Pro Cys
 65                  70                  75                  80
```

```
Asp Asp Asn Cys Gly Cys His Asp Asn Cys Lys Cys Asp Cys Glu Pro
            85                  90                  95

Cys Glu Met Asp Ser Asp Glu Cys Phe Glu Asn Lys Cys Gly Pro Glu
            100                 105                 110

Cys Cys Asn Pro Ile Ser Pro Arg Asn Phe Ser Val Ser Asn Ala Val
            115                 120                 125

Pro Phe Ala Ile Glu Ala Asn Arg Ile Phe Asp Thr Met Gln Phe Gln
            130                 135                 140

Thr Phe Thr Asp Ala Thr Gly Pro Asn Gly Glu Pro Leu Thr Phe Glu
145                 150                 155                 160

Thr Glu Val Val Glu Val Phe Gly Ser Val Pro Ser Ala Gly Gln Ala
                165                 170                 175

Ser Val Thr Ile Glu Lys Ile Cys Leu Ser Asn Asp Gly Ile Val Ile
            180                 185                 190

Asp Thr Gly Met Thr Thr Leu Glu Asp Phe Asp Leu Asp Pro Leu Gly
            195                 200                 205

Asp Ile Val Gly Arg Asn Cys Glu Thr Thr Phe Glu Phe Ala Val Cys
            210                 215                 220

Gly Glu Arg Asn Ser Glu Cys Cys Arg Gln Gly Lys Gly Lys Ser Val
225                 230                 235                 240

Ala Tyr Lys Gln Arg Gly Leu Thr Val Ala Val Arg Asn Leu Val Leu
                245                 250                 255

Glu Leu Arg Gly Arg Cys Gly Cys Thr Glu Phe Val Ala Leu Ala Phe
            260                 265                 270

Pro Ala Val Arg Ala Gly Gly Cys Lys Arg Arg Val Asp Tyr Val
            275                 280                 285

Glu Phe Thr Phe Asn Thr Leu Ser Ala Pro Ile Cys Leu Pro Ala Asp
            290                 295                 300

Gly Arg Ala Val Thr Leu Arg Gln Glu Tyr Gln Thr Asn Leu Thr Val
305                 310                 315                 320

Asp Cys Ile Gly Lys Ser Ile Leu Lys Leu Glu Cys Asn Glu Cys Cys
            325                 330                 335

Glu Pro Phe Tyr Glu Leu Ile Ile Pro Asn Asp Ile Asp Leu Val Leu
            340                 345                 350

Cys Leu Gln Glu Thr Val Ser Thr Leu Ile Ser Glu Gln Ile Val Val
            355                 360                 365

Leu Ala Ser Pro Asn Pro Ile Gln Pro Arg Leu Val Asp Thr Phe Ser
            370                 375                 380

Lys Val Cys Asp Phe Ser Gln Cys Gly Pro Asn His Gly Ser Gly Lys
385                 390                 395                 400

Pro Ser Cys His Arg
            405

<210> SEQ ID NO 19
<211> LENGTH: 157
<212> TYPE: PRT
<213> ORGANISM: Clostridium difficile

<400> SEQUENCE: 19

Met Glu Asn Lys Lys Cys Tyr Ser Glu Asp Trp Tyr Glu Arg Gly Glu
1               5                   10                  15

Ser Thr Ala Lys Trp Phe Gln Asn Asp Arg Glu Glu Tyr Glu Arg Glu
            20                  25                  30

Ala Tyr Asp Glu Asp Arg Glu Arg Arg Gly Ser Asn Cys Gly Cys Ser
```

```
              35                  40                  45
Asp Ser Gly Glu Asn Arg Pro Arg Asn Cys Glu Arg Phe Arg Arg Glu
 50                  55                  60

Ala Glu Ile Arg Glu Arg Glu Ala Arg Glu Ala Phe Cys Glu Ser Ser
 65                  70                  75                  80

Glu Lys Lys Lys Glu Ala Leu Ala Tyr Glu Cys Glu Ala Arg Lys Leu
                     85                  90                  95

Trp Glu Glu Ala Glu Lys Tyr Trp Asp Glu Tyr Ser Lys Tyr Asn Tyr
                    100                 105                 110

Lys Gly Ile Glu Tyr Leu Ala Glu Ala Arg Leu Phe Asp Glu Gly
                    115                 120                 125

Met Glu Cys Glu Ala Arg Arg Asn Gly Asn Asn Gly Gly Asn Asn Asn
                    130                 135                 140

Asn Cys Cys His Lys Cys Asn Cys Asn Cys Cys Arg Lys
145                 150                 155
```

<210> SEQ ID NO 20
<211> LENGTH: 432
<212> TYPE: PRT
<213> ORGANISM: Clostridium difficile

<400> SEQUENCE: 20

```
Asn Thr Asn Lys Val His Asn Ser Lys Gln Asp Lys Phe Lys Asp Lys
 1               5                  10                  15

Ser Cys Asp Glu Met Asn Phe Asn Tyr Asp Lys Asp Glu Ser Cys Asp
                 20                  25                  30

Lys Ile Asn Ser Ser Tyr Asn Lys Glu Asp Ser Ser Tyr Glu Asp Phe
                 35                  40                  45

Tyr Lys His Asn Tyr Lys Asn Tyr Asp Tyr Thr Ser Glu Lys Asn Thr
 50                  55                  60

Lys Lys Ile Ala Met Lys Thr Leu Lys Asp Ser Lys Lys Leu Val Arg
 65                  70                  75                  80

Pro Gln Ile Thr Asp Pro Tyr Asn Pro Ile Val Glu Asn Ala Asn Cys
                 85                  90                  95

Pro Asp Ile Asn Pro Ile Val Ala Glu Tyr Val Leu Gly Asn Pro Thr
                100                 105                 110

Asn Val Asp Ala Gln Leu Leu Asp Ala Val Ile Phe Ala Phe Ala Glu
                115                 120                 125

Ile Asp Gln Ser Gly Asn Leu Phe Ile Pro Tyr Pro Arg Phe Leu Asn
130                 135                 140

Gln Leu Leu Ala Leu Lys Gly Glu Lys Pro Ser Leu Lys Val Ile Val
145                 150                 155                 160

Ala Ile Gly Gly Trp Gly Ala Glu Gly Phe Ser Asp Ala Ala Leu Thr
                165                 170                 175

Pro Thr Ser Arg Tyr Asn Phe Ala Arg Gln Val Asn Gln Met Ile Asn
                180                 185                 190

Glu Tyr Ala Leu Asp Gly Ile Asp Ile Asp Trp Glu Tyr Pro Gly Ser
                195                 200                 205

Ser Ala Ser Gly Ile Thr Ser Arg Pro Gln Asp Arg Glu Asn Phe Thr
210                 215                 220

Leu Leu Leu Thr Ala Ile Arg Asp Val Ile Gly Asp Lys Trp Leu
225                 230                 235                 240

Ser Val Ala Gly Thr Gly Asp Arg Gly Tyr Ile Asn Ser Ser Ala Glu
                245                 250                 255
```

```
Ile Asp Lys Ile Ala Pro Ile Ile Asp Tyr Phe Asn Leu Met Ser Tyr
            260                 265                 270

Asp Phe Thr Ala Gly Glu Thr Gly Pro Asn Gly Arg Lys His Gln Ala
        275                 280                 285

Asn Leu Phe Asp Ser Asp Leu Ser Leu Pro Gly Tyr Ser Val Asp Ala
    290                 295                 300

Met Val Arg Asn Leu Glu Asn Ala Gly Met Pro Ser Glu Lys Ile Leu
305                 310                 315                 320

Leu Gly Ile Pro Phe Tyr Gly Arg Leu Gly Ala Thr Ile Thr Arg Thr
                325                 330                 335

Tyr Asp Glu Leu Arg Arg Asp Tyr Ile Asn Lys Asn Gly Tyr Glu Tyr
            340                 345                 350

Arg Phe Asp Asn Thr Ala Gln Val Pro Tyr Leu Val Lys Asp Gly Asp
        355                 360                 365

Phe Ala Met Ser Tyr Asp Asp Ala Leu Ser Ile Phe Leu Lys Thr Gln
    370                 375                 380

Tyr Val Leu Arg Asn Cys Leu Gly Gly Val Phe Ser Trp Thr Ser Thr
385                 390                 395                 400

Tyr Asp Gln Ala Asn Ile Leu Ala Arg Thr Met Ser Ile Gly Ile Asn
                405                 410                 415

Asp Pro Glu Val Leu Lys Glu Glu Leu Glu Gly Ile Tyr Gly Gln Phe
            420                 425                 430

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccagtgtaga ctactcaatg c                                              21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtactatcca caggtcaacc                                                20

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atcgatgacc gctgcctcgc ctgagtaatc atcgta                              36

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 24
ccatactcaa tgctcttacg atcctcatca acc        33

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccagtgtaga ctactcaatg ctcttacgat cctcatcaac c        41

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agtgtagact actcaatgcg gctggccaca ggtcaacc        38

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cttgaccttt ggaatgggtg ggagggatgg gtactatcca caggtcaacc        50

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aatgggtggg agggatgggt acta        24

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cttgaccttt ggaatgggta gggagggagg gatactatcc acaggtcaac c        51

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cttgaccttt ggaatgggtg ggagggaggg tatccacagg tcaacc            46

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
actactcaat gctcgacatt tccgccccga cggccctcct agtgagggga gagtaga      57

<210> SEQ ID NO 32
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
actactcaat gctcgacatt tccgccccga cggccctcct agtgatgggg agagtaga     58

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
actcaaggcc gtggactggt cgggtttgga ttcggcagat gaatcact               48

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actcaaggcc gtggactggt cgggtttgga t                                 31

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
acccgtggga ctgggtcggg tcggg                                        25

<210> SEQ ID NO 36
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aactgcctgg taaatcgatg accgctgcct cgcctgagta atcatcgtac tatccacagg    60
tc    62

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtaaatcgat gaccgctgcc tcgcctgagt aatcatcgta c    41

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
actactcaaa cccgtggact ggtcgggttt ggattcggca gatgaatcag tagaaa    56

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
actactcaat gccgtggact ggtcgggttt ggaatcggca gatgaatcag tagtaaa    57

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cattccaaag gtcaag    16

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cacacattcc aaaaggtcaa g    21

<210> SEQ ID NO 42
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctcaatgcct tccattcacc taccgagcta agcgttcgac tta                43

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cctaccgagc taagcgttcg acttaggtct gtact                         35

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctcacctgct agcacaccca tatcccatgg gtacaatcca caggtcaa            48

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctcacctgct agcacaccca catcccgtgc gtgctatcca caggtgaa            48

<210> SEQ ID NO 46
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agtgcagact actcaatgca cggccggttc ggaagaccct tccagactag ttttccctg   60 tactagtcca ccggcta                                                77

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agtgcagact actcaatgca cggcctggtt cgtaagaccc ttaccagact            50

<210> SEQ ID NO 48
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
cggttgcgac atggtggtaa gagctcagcc cgttcccata gtactatcca caggtcaacc    60
t                                                                    61

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cggttgcgac atggtggtaa gagctcagcc cgttcccata gtactatcca caggtcgcaa    60
cct                                                                  63

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cccgtgtaga ctactcaatg cgggctgcga catggtggta agagctcagc ccgttcccat    60
agtactatcc acgggt                                                    76

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cccgtgtaga ctattttagt actatccacg gg                                  32

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tgcgggctgc gacatggtgg taagagctca gcccgtt                             37

<210> SEQ ID NO 53
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
acccaggtgt aggacgactc aatgccctat tagctgtatc gatccgttta gtcgctcctc    60
cgatagtacc ctatccacca ggga                                           84

```
<210> SEQ ID NO 54
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
accaggtggt agacctactc acatgcccta ttagcgtgta tcgatccggt ttagtccgct      60
tcgatagtag ucccaccagg a                                              81

<210> SEQ ID NO 55
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctcaatgcct tccattcacc taccgagcta agcgttcgac ttaggtctgt act           53
```